United States Patent

Benner

[11] Patent Number: 5,958,784
[45] Date of Patent: Sep. 28, 1999

[54] PREDICTING FOLDED STRUCTURES OF PROTEINS

[76] Inventor: Steven Albert Benner, Hadlaubstrasse 151, CH-8006 Zürich, Switzerland

[21] Appl. No.: 07/857,224

[22] Filed: Mar. 25, 1992

[51] Int. Cl.$^6$ .............................. G01N 33/00; G06F 15/00
[52] U.S. Cl. .............................. 436/86; 436/89; 364/413.1
[58] Field of Search ......................... 436/86, 89; 364/496, 364/497, 413.1

[56] References Cited

U.S. PATENT DOCUMENTS

| | | | |
|---|---|---|---|
| 5,265,030 | 11/1993 | Skolnick et al. | 364/496 |
| 5,436,850 | 7/1995 | Eisenberg et al. | 364/496 |

Primary Examiner—David A. Redding

[57] ABSTRACT

A method is presented for predicting the folded structure of proteins that comprises obtaining an alignment of the sequences of a set of homologous proteins, using patterns of conservation and variation of the sequence between proteins with clearly defined evolutionary relationships to assign positions in the alignment to the surface of the folded structure, the inside of the folded structure, active site, or parsing segments, assigning secondary structures by identifying periodicity in said assignments, and then assembling the secondary structural units into a globular form using distance constraints imposed by disulfide bridges, active site assignments, and covariation analysis.

2 Claims, 28 Drawing Sheets

Benner, Fig.1
Predicting Folded Structure of Proteins
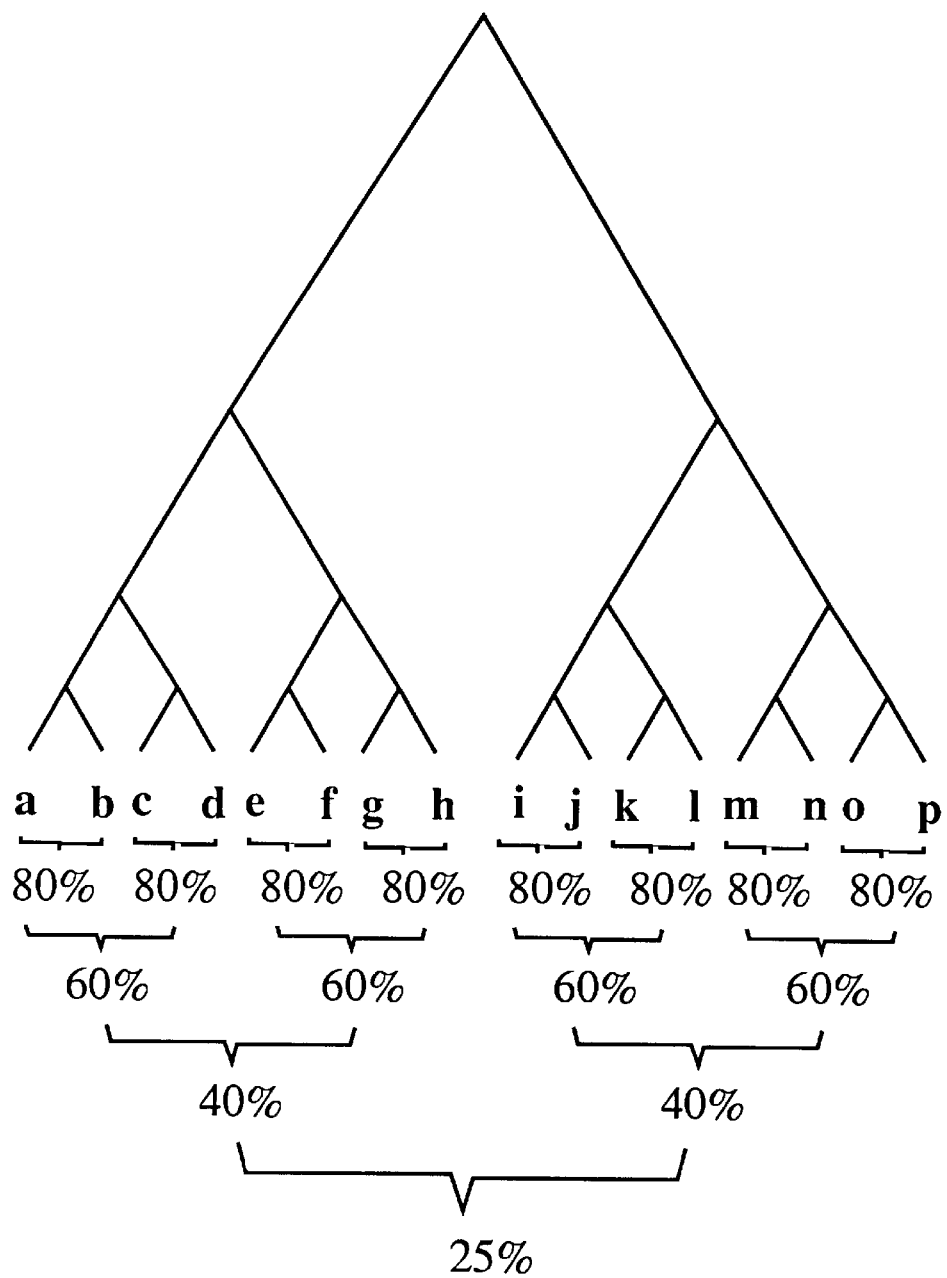

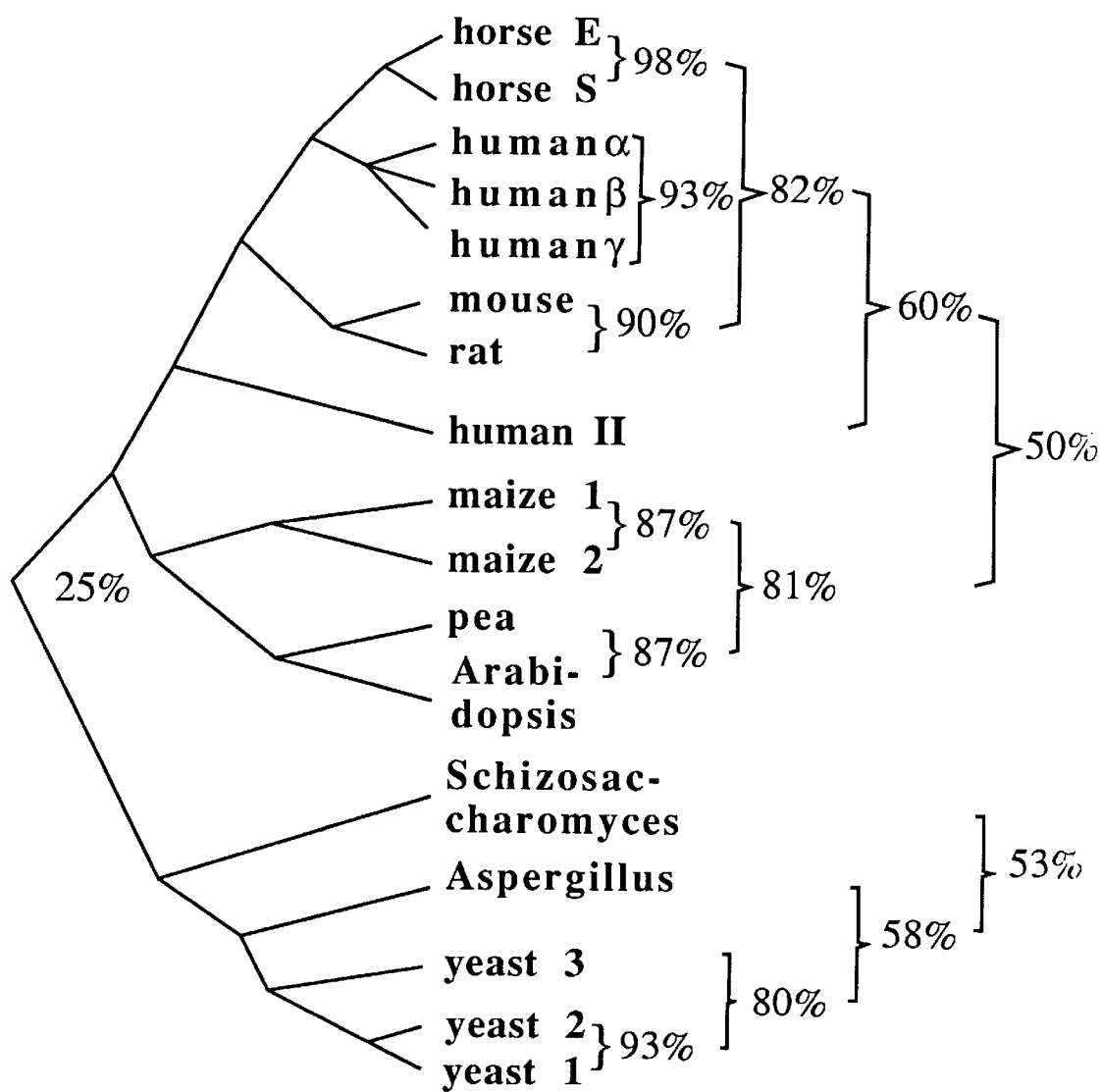
Benner, Fig. 2
Predicting Folded Structure of Proteins

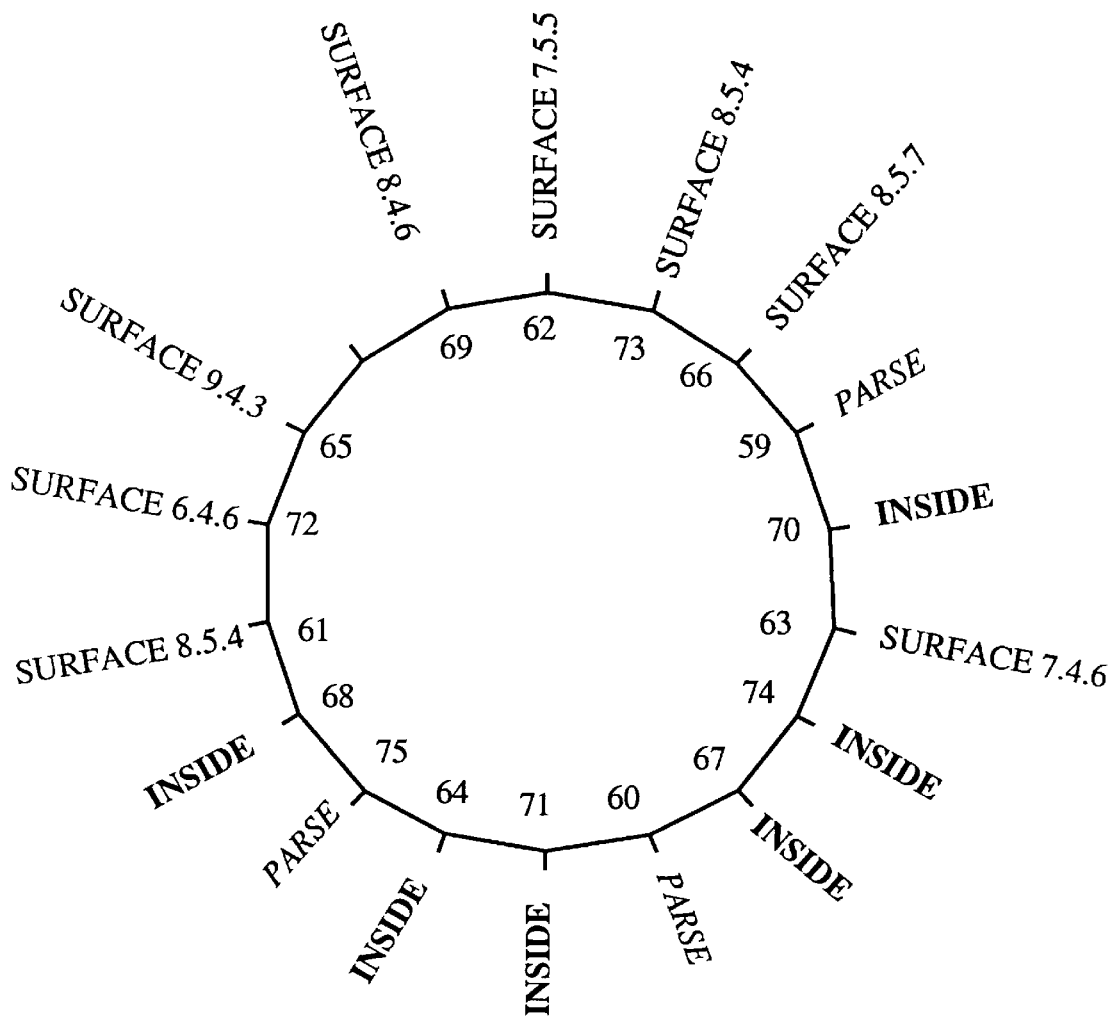
Benner, Fig.3a
Predicting Folded Structure of Proteins

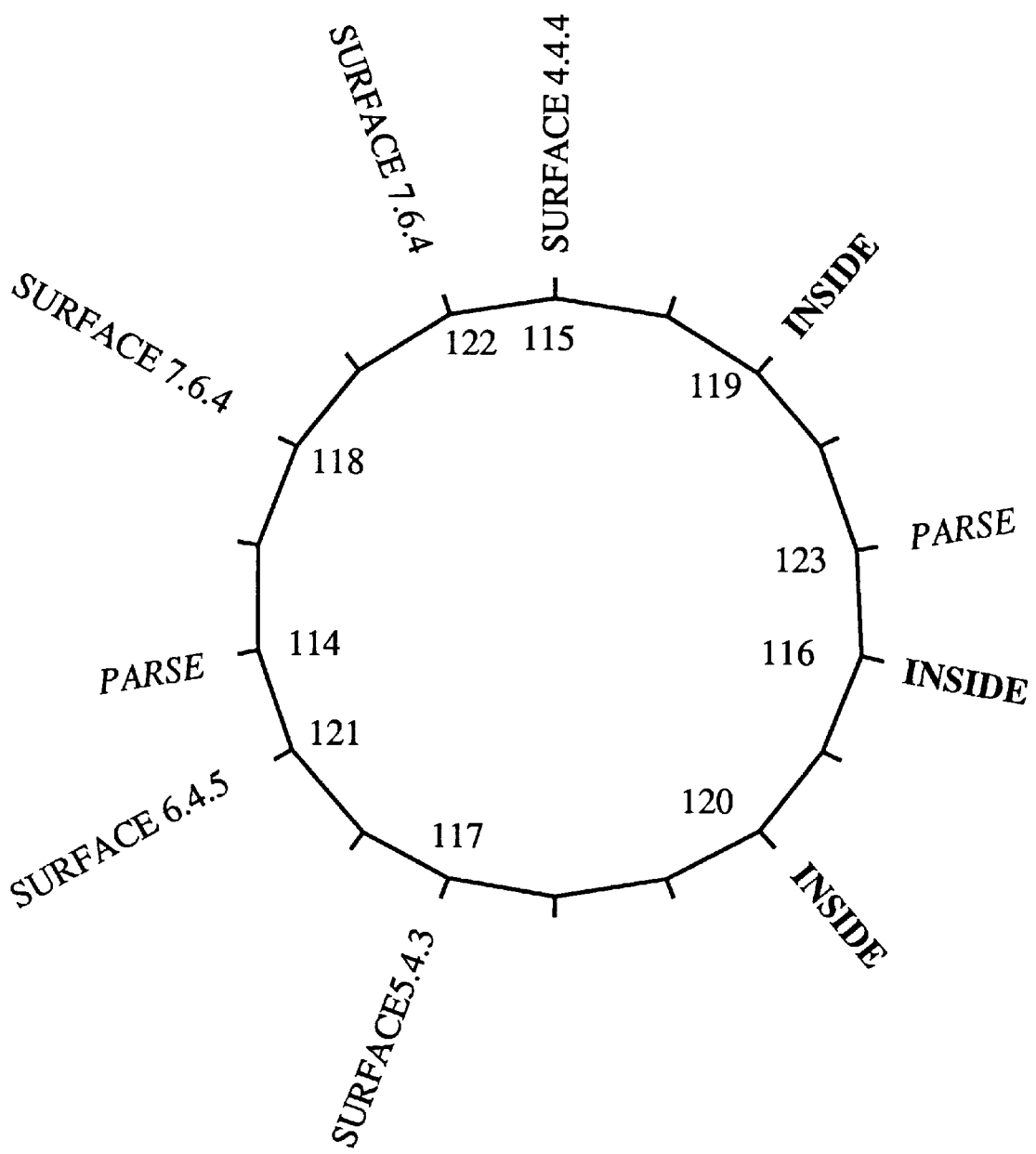
Benner, Fig.3b
Predicting Folded Structure of Proteins

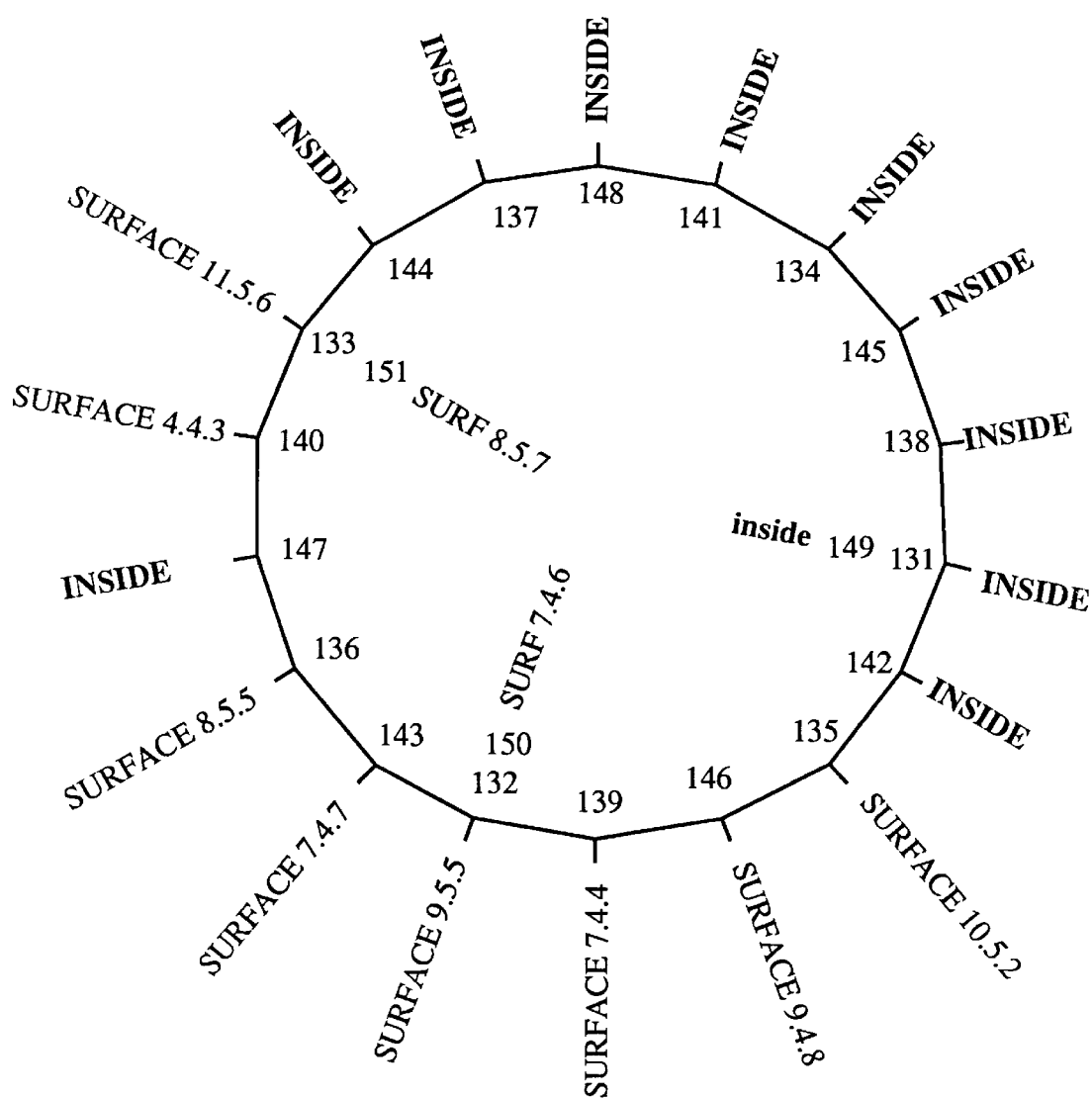
Benner, Fig.3c
Predicting Folded Structure of Proteins

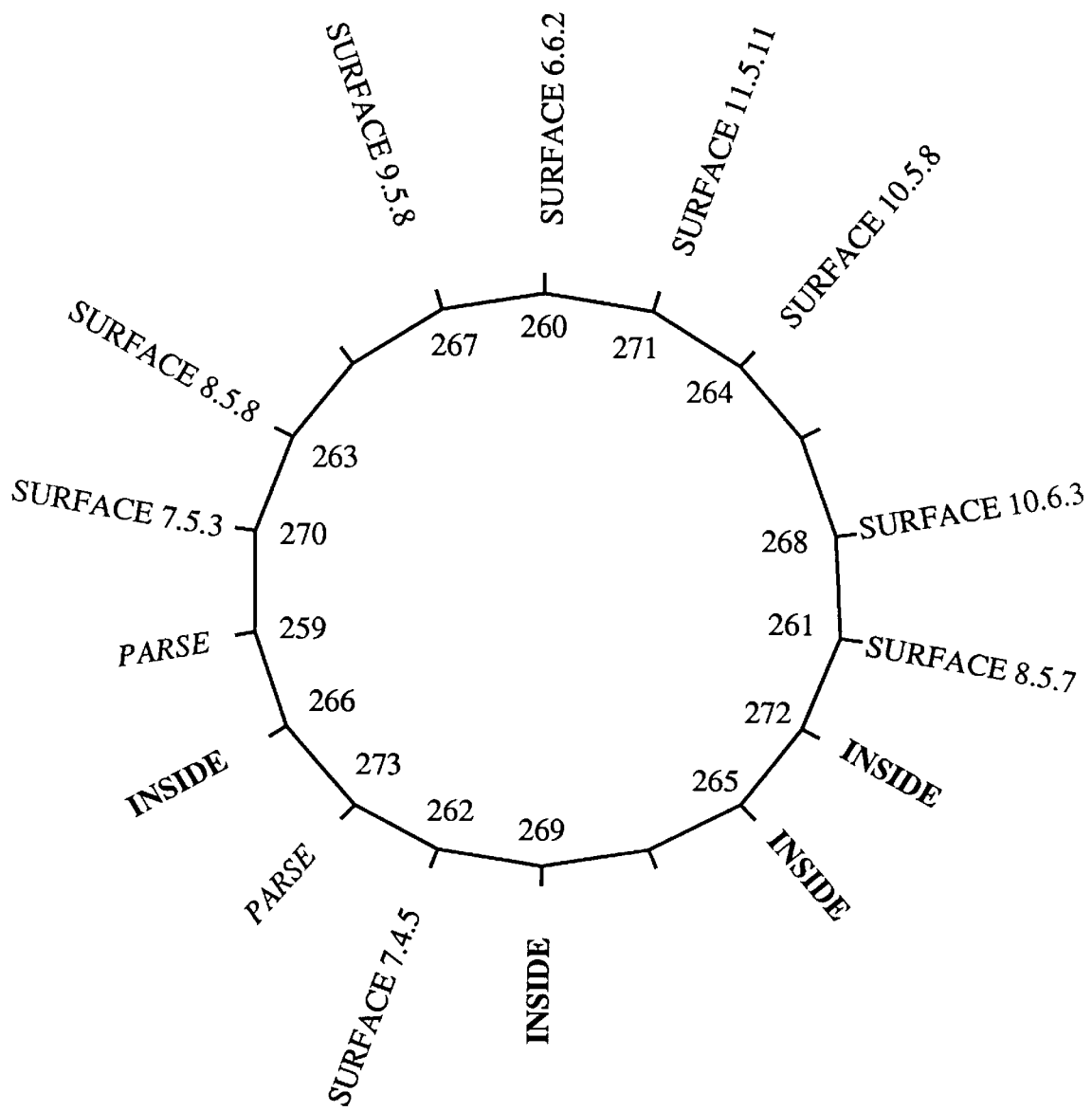
Benner, Fig.3d
Predicting Folded Structure of Proteins

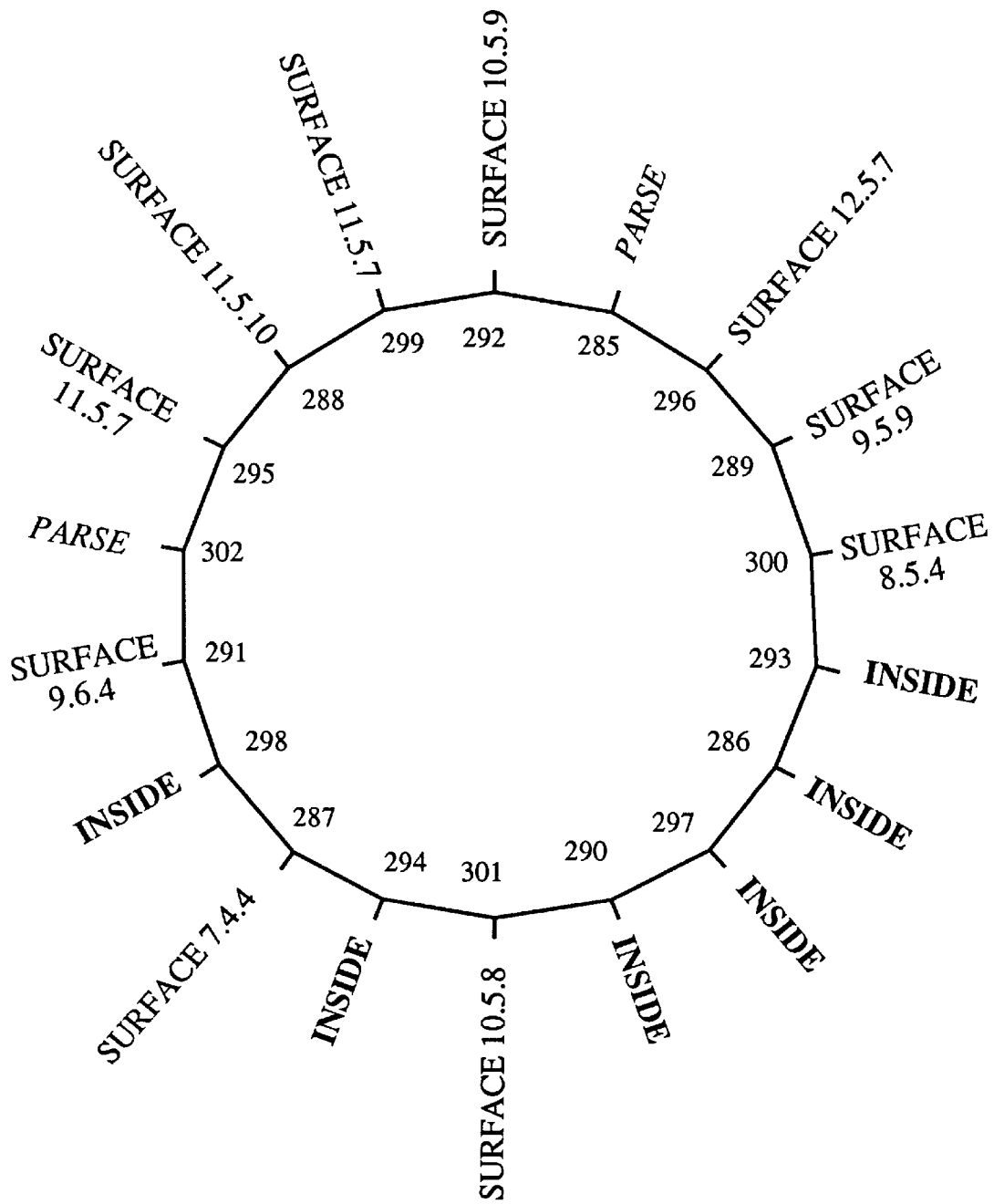
Benner, Fig.3e
Predicting Folded Structure of Proteins

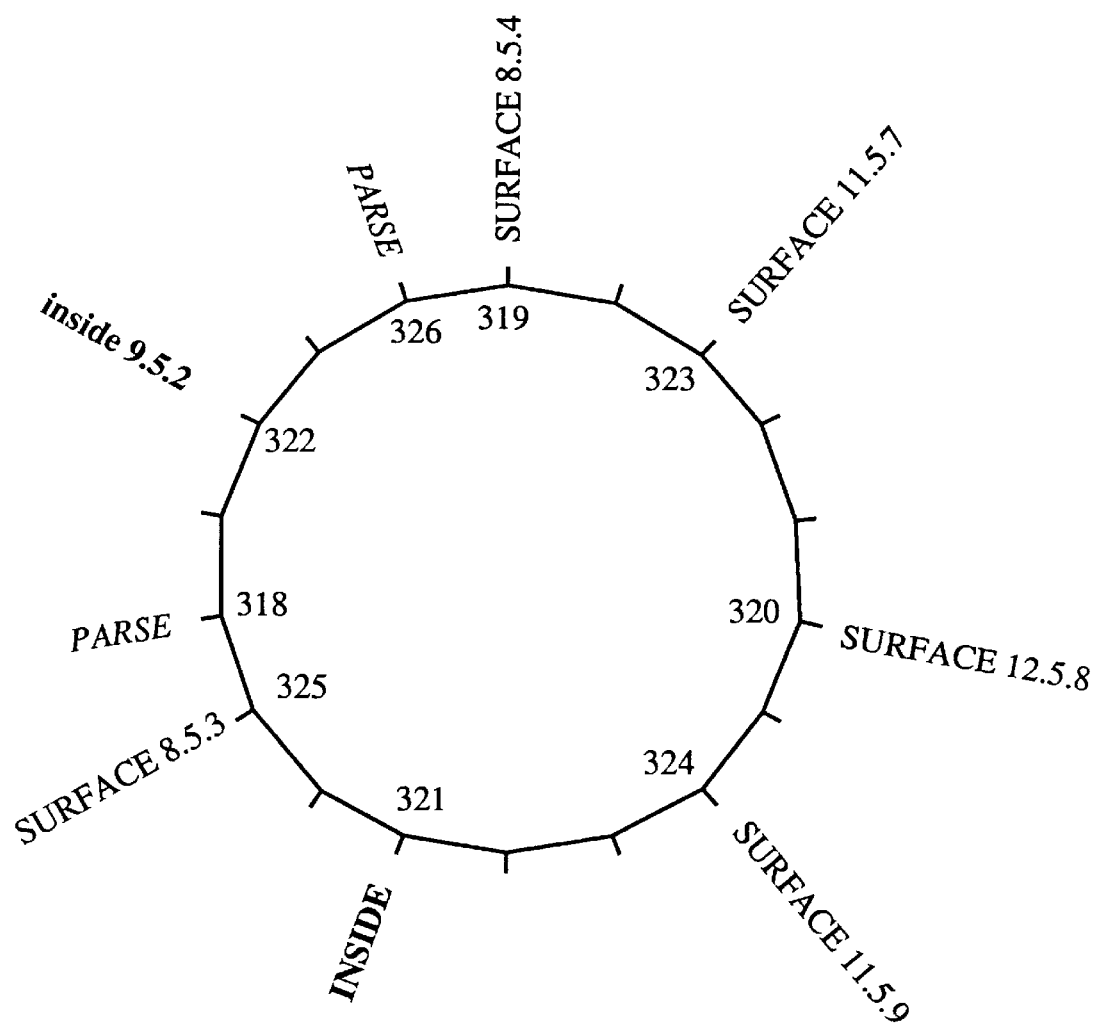
Benner, Fig.3f
Predicting Folded Structure of Proteins

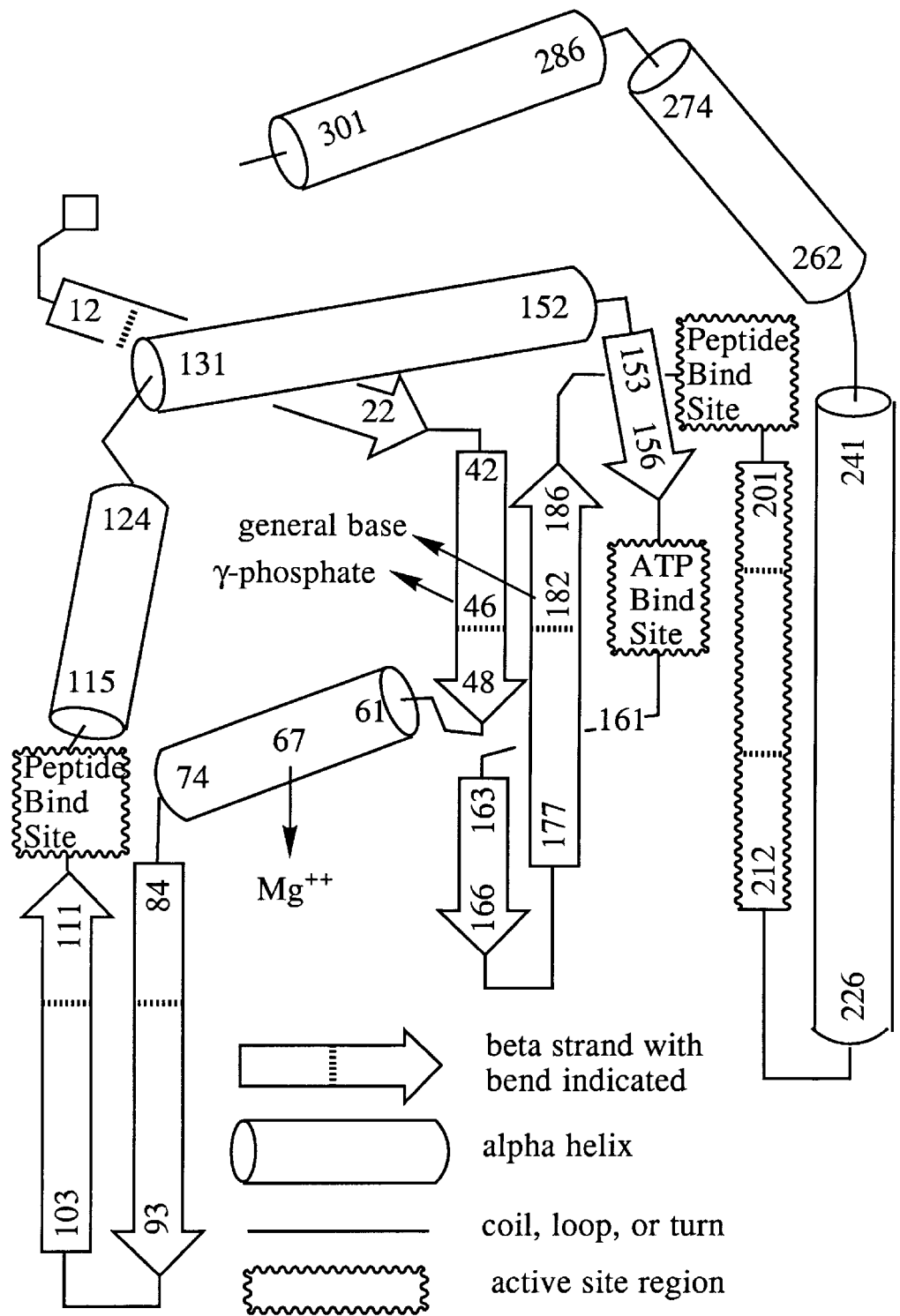
Benner, Fig.4
Predicting Folded Structure of Proteins

Benner, Fig.5
Predicting Folded Structure of Proteins
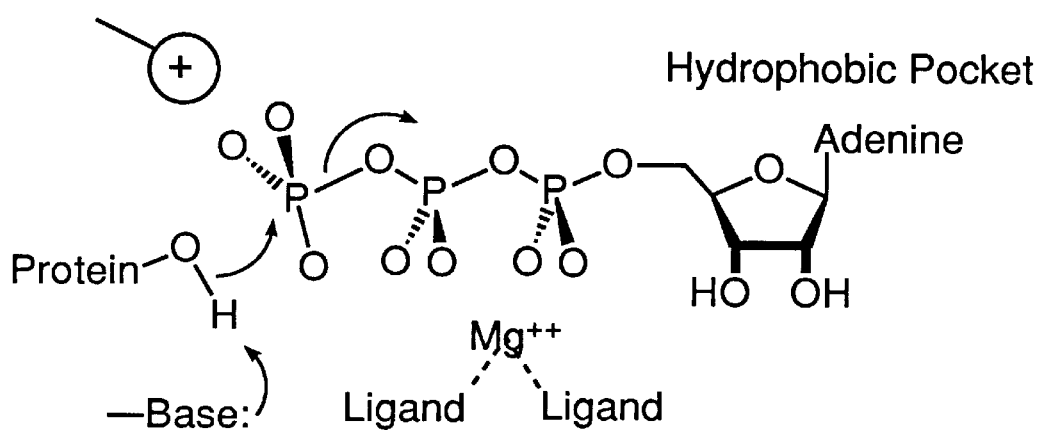
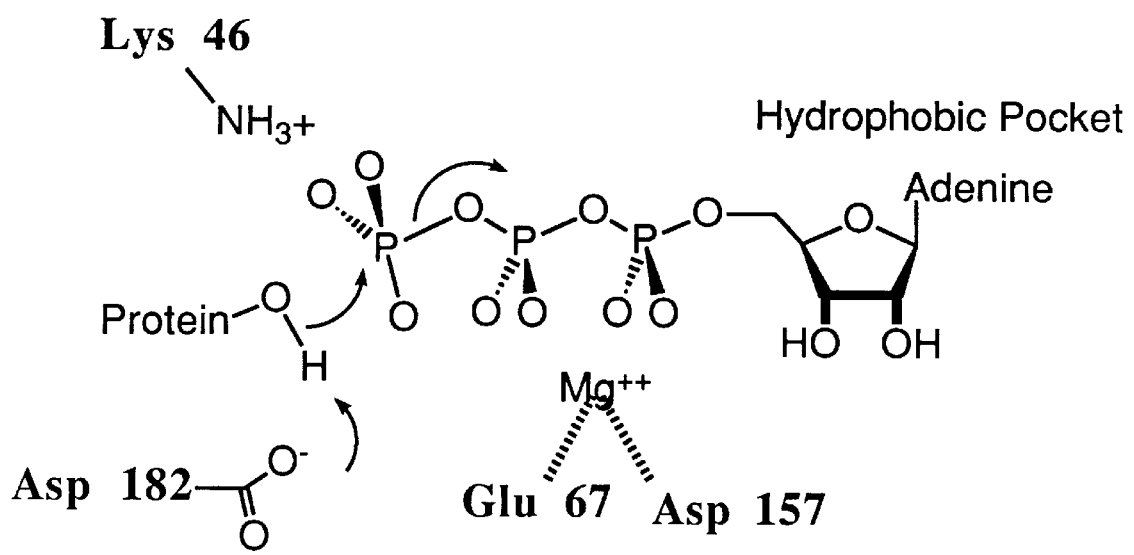

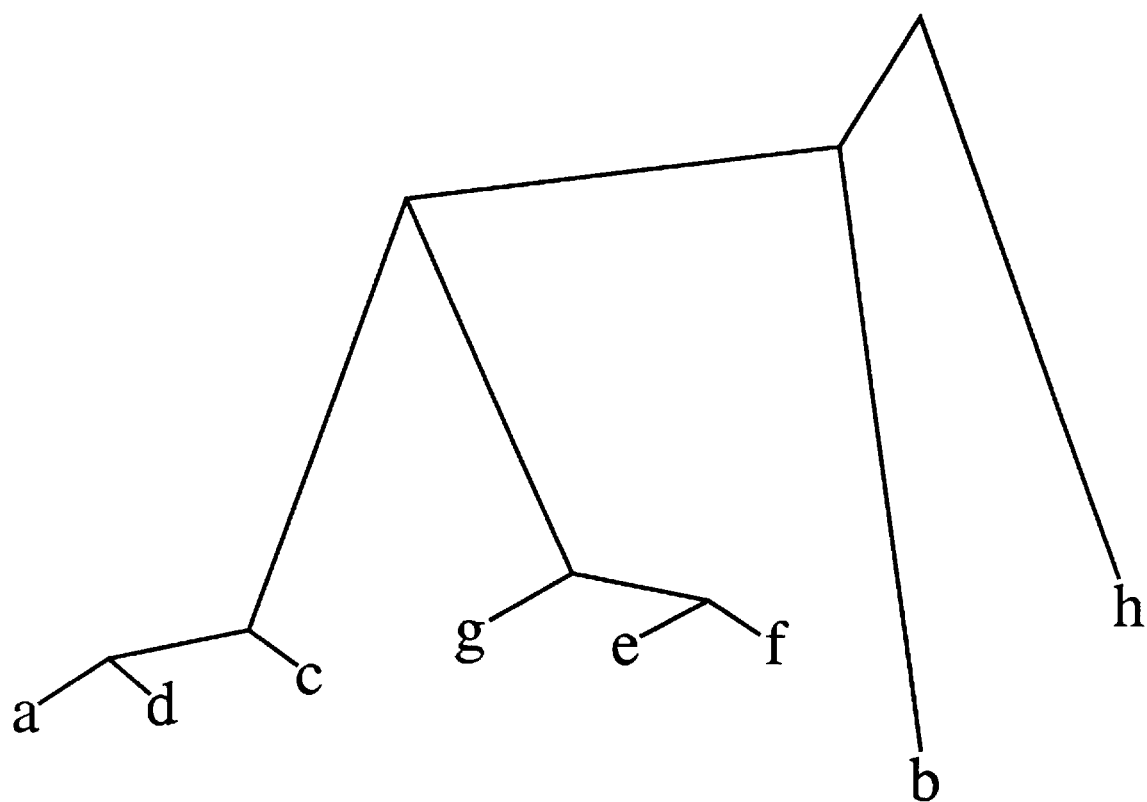
Benner, Fig. 6a
Predicting Folded Structure of Proteins

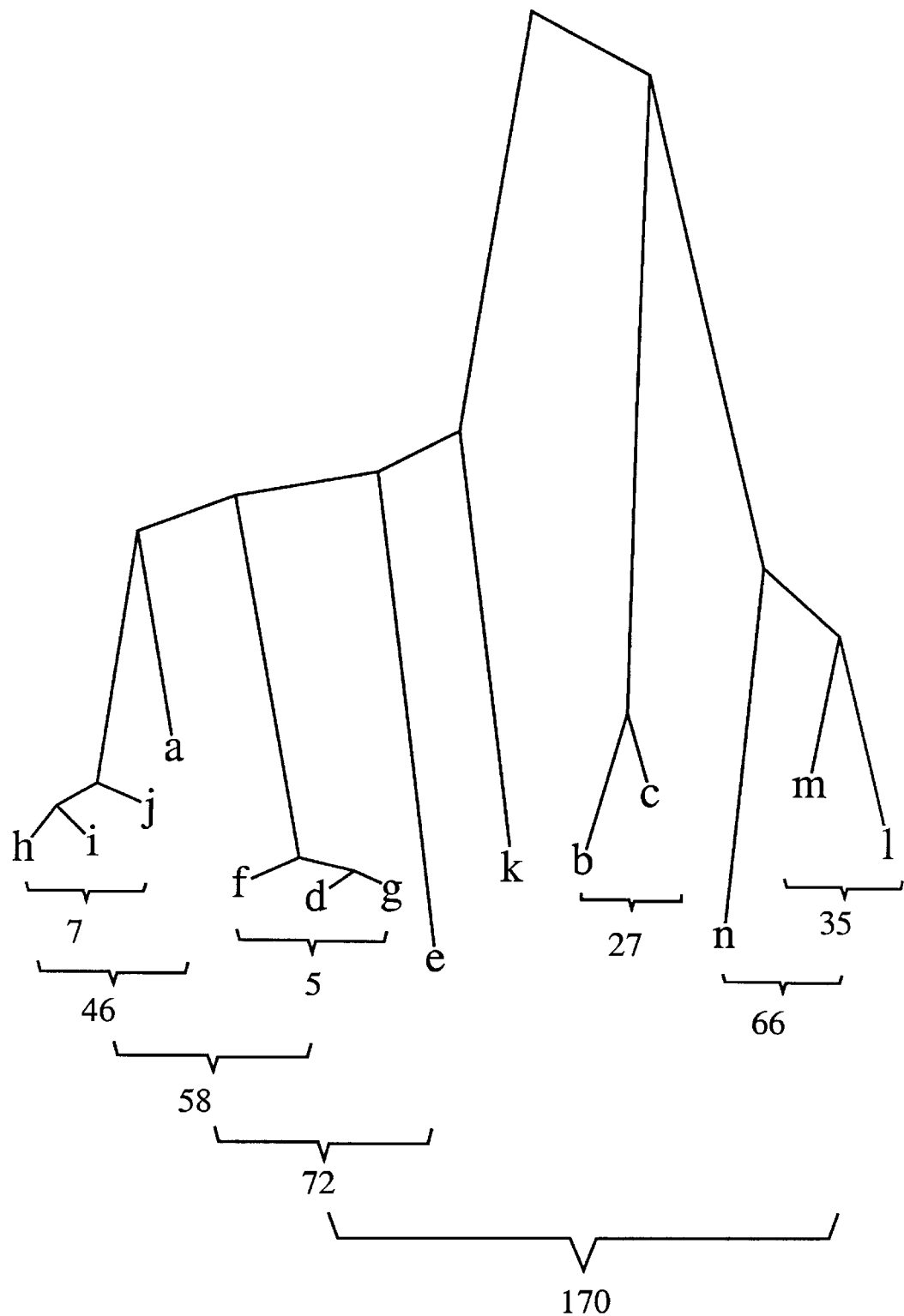
Benner, Fig. 6b
Predicting Folded Structure of Proteins

Benner, Fig.7a
Predicting Folded Structure of Proteins
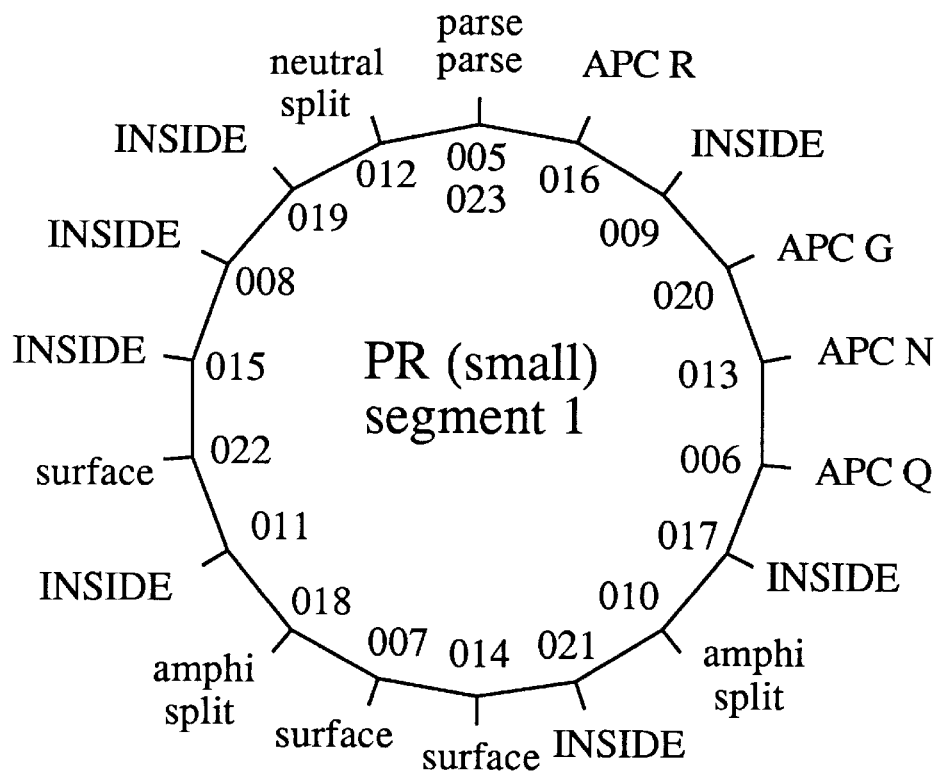
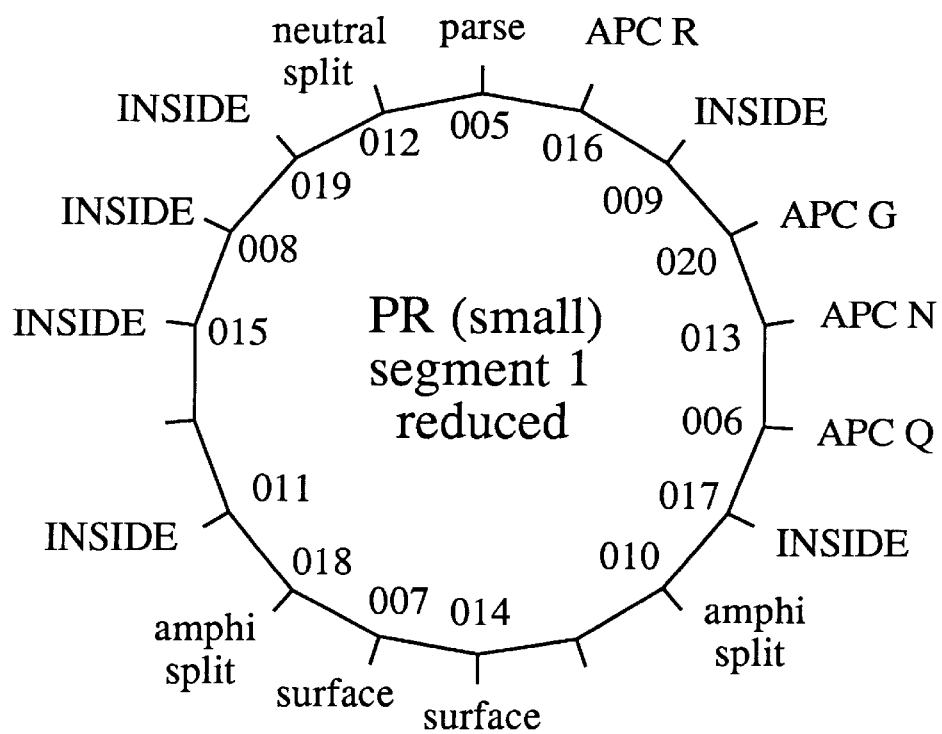

Benner, Fig.7b
Predicting Folded Structure of Proteins
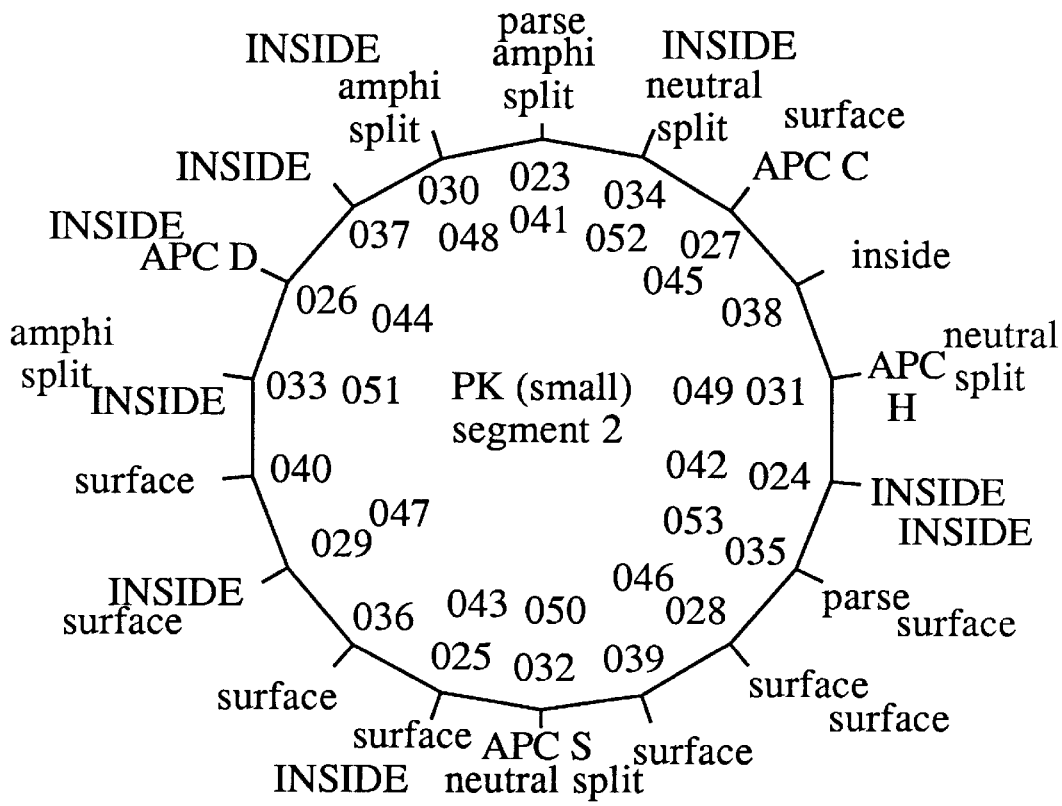
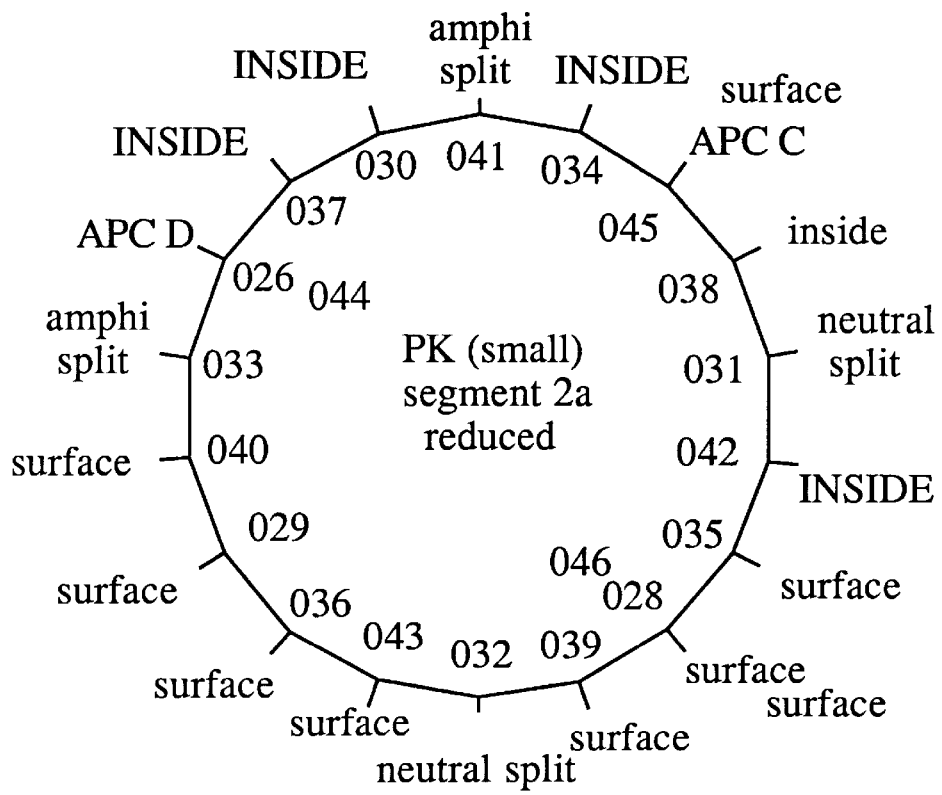

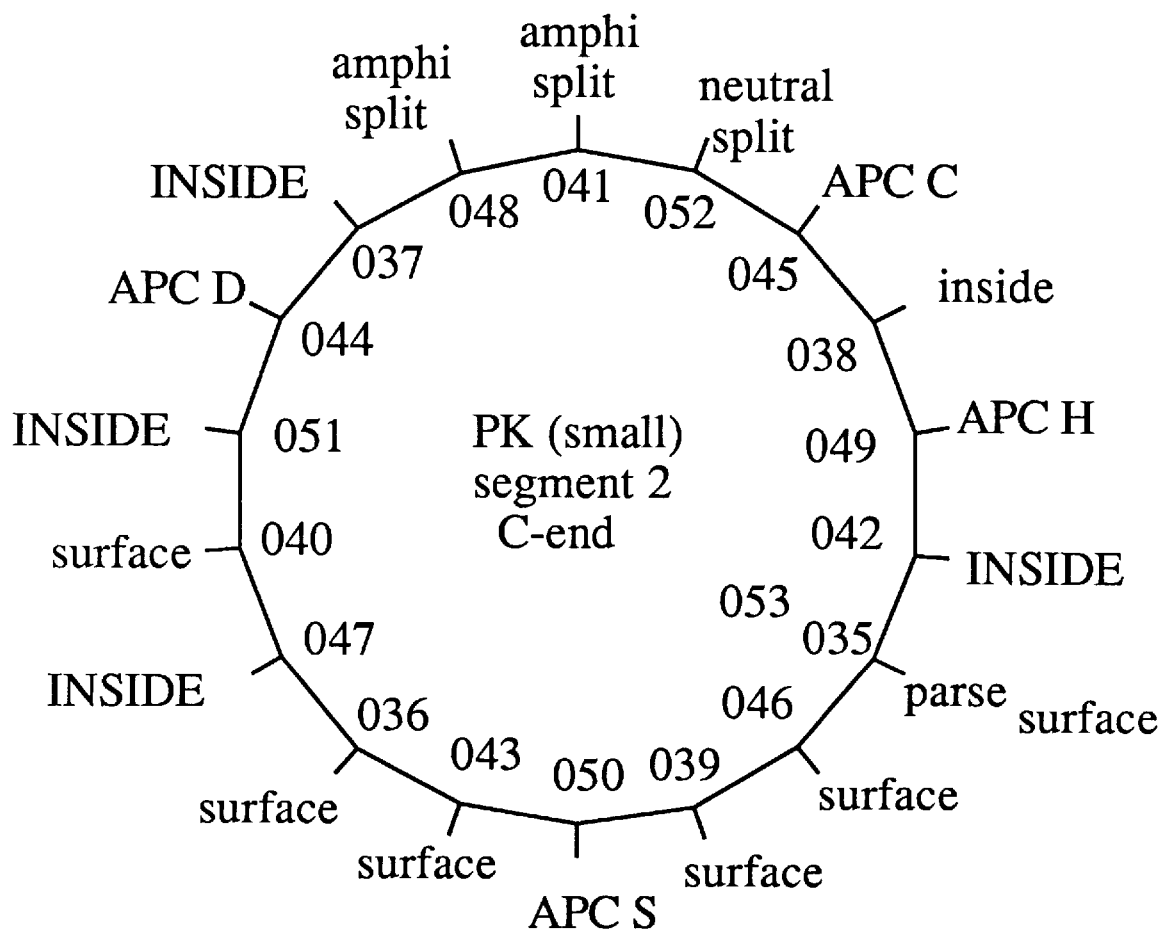
Benner, Fig.7c
Predicting Folded Structure of Proteins

Benner, Fig.7d
Predicting Folded Structure of Proteins
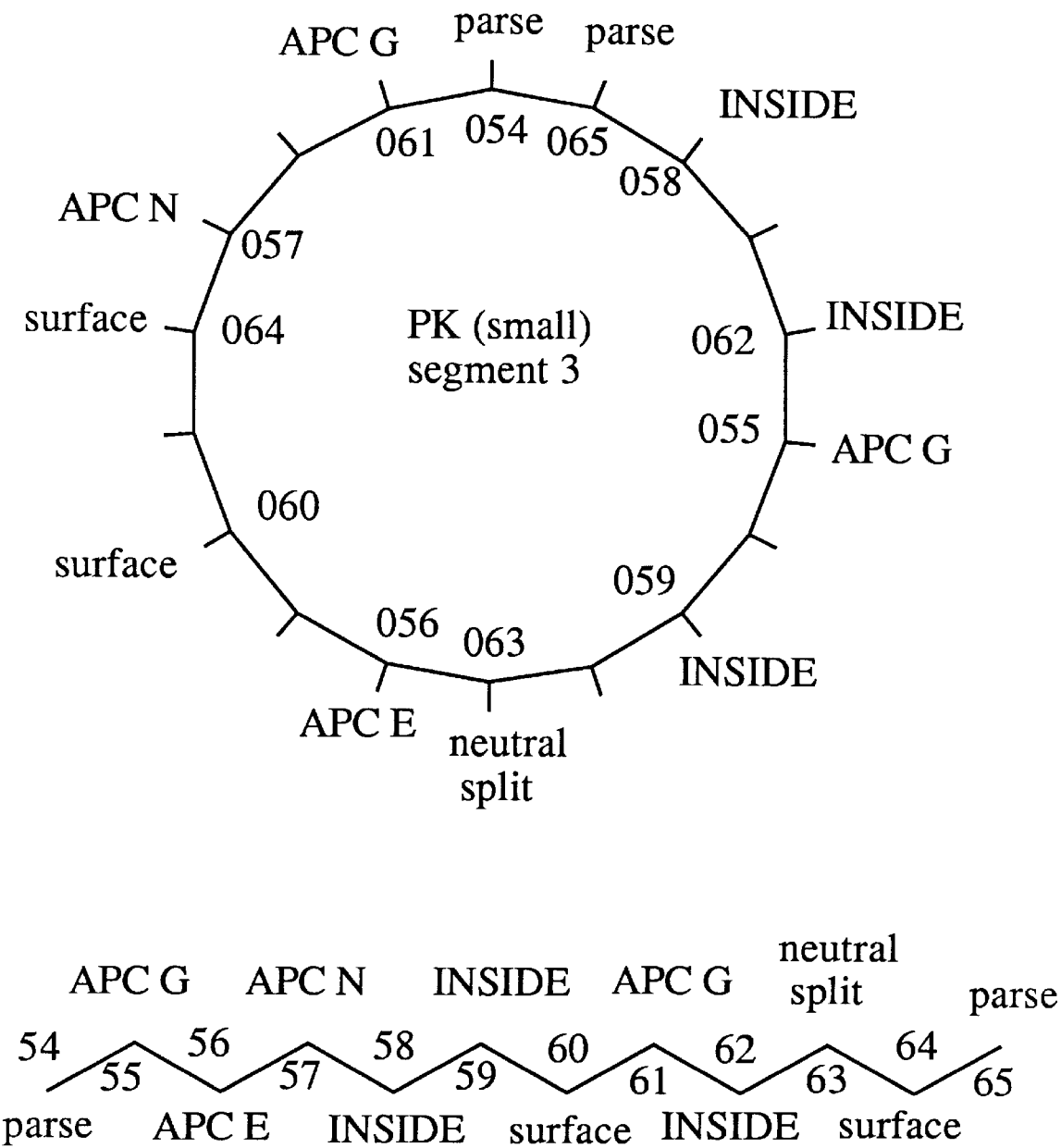

Benner, Fig.7e
Predicting Folded Structure of Proteins
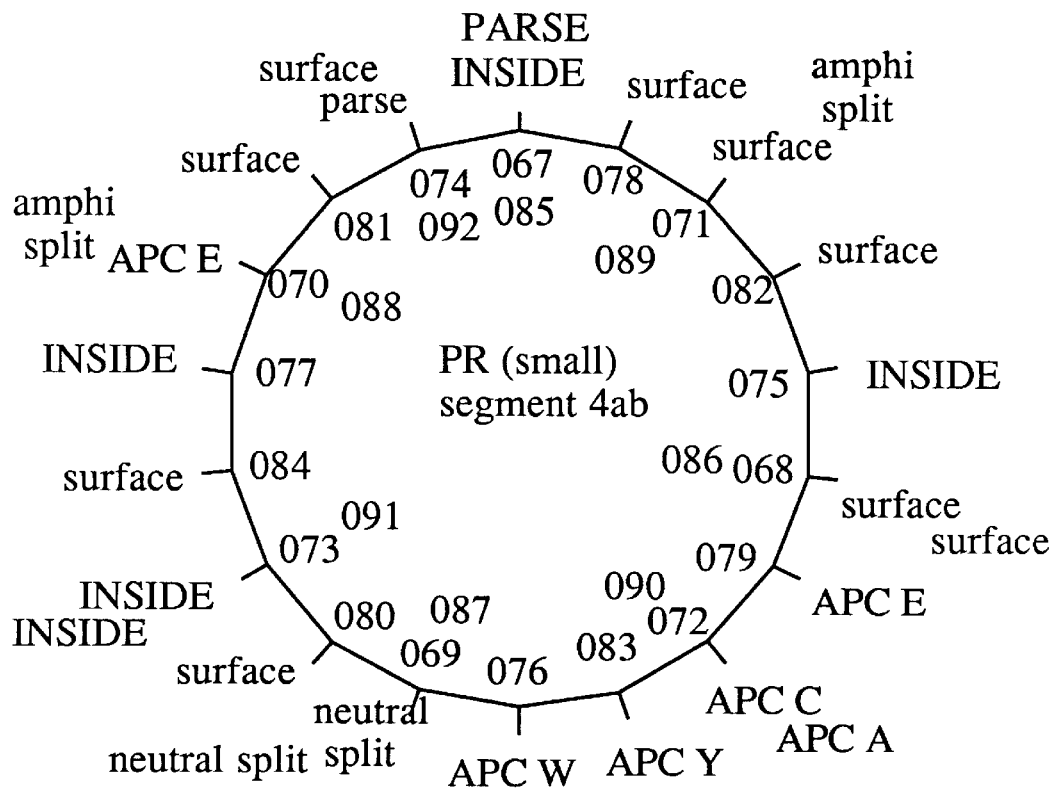
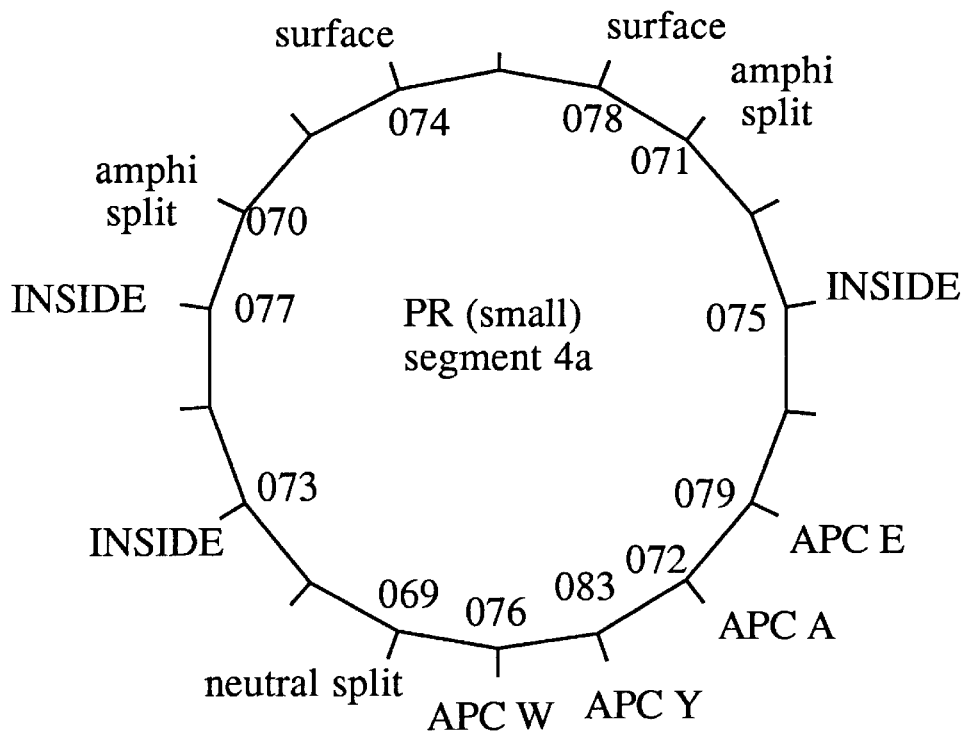

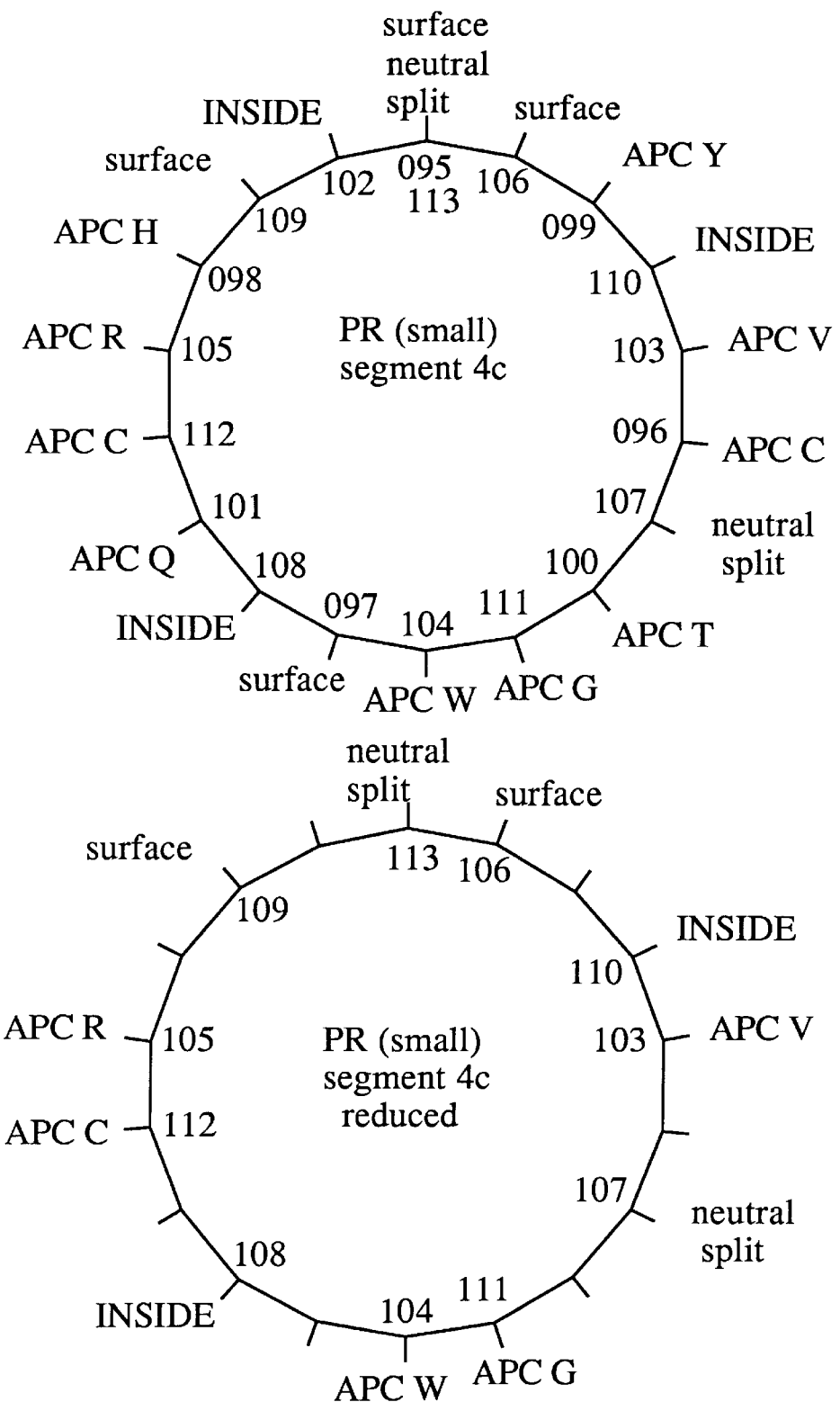
Benner, Fig.7f
Predicting Folded Structure of Proteins

Benner, Fig.7g
Predicting Folded Structure of Proteins
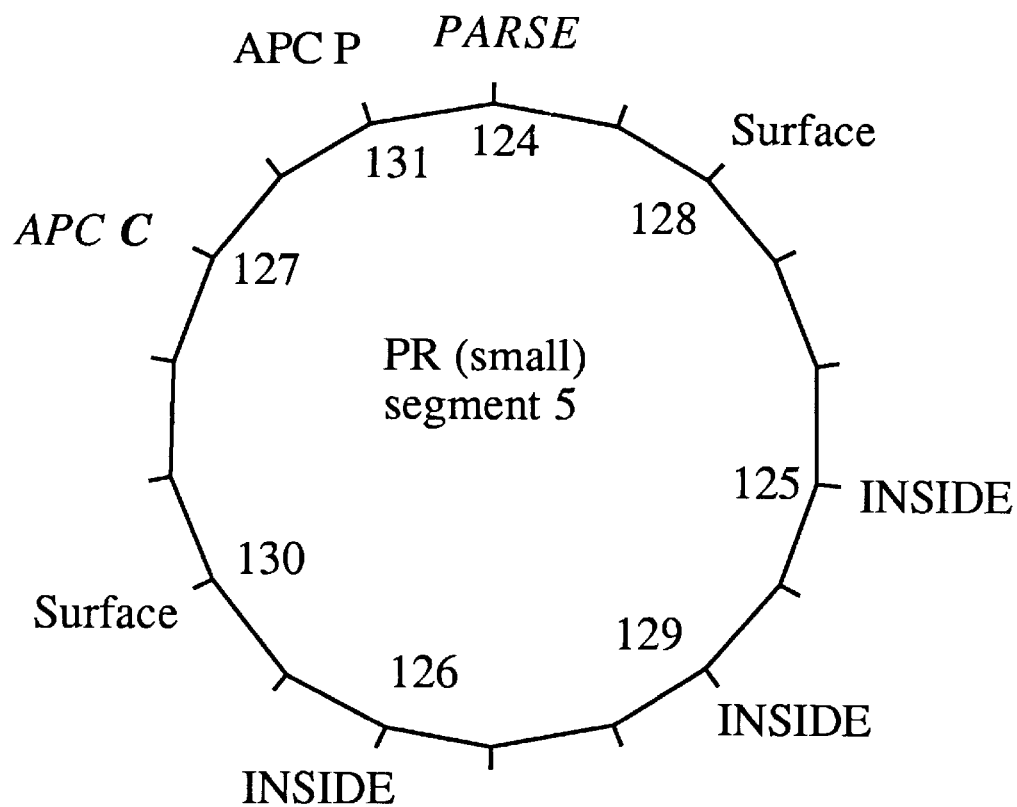
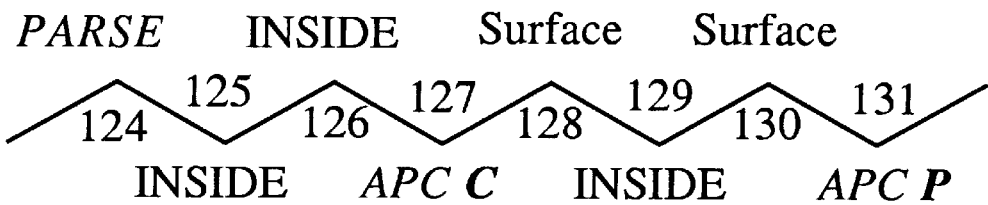

Benner, Fig. 7h
Predicting Folded Structure of Proteins
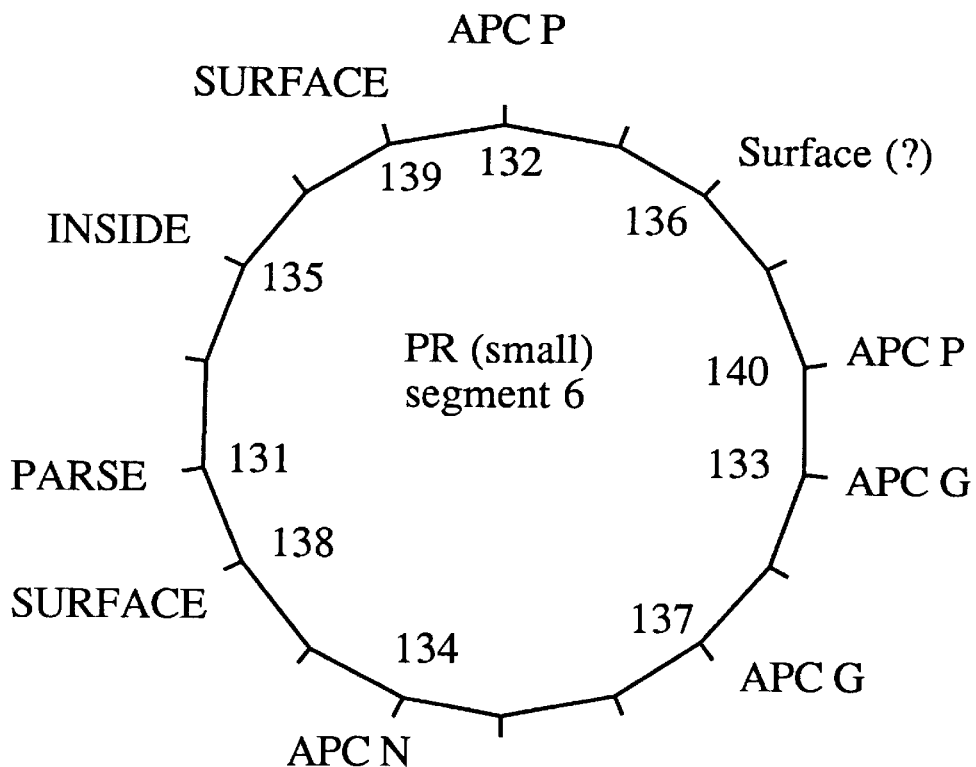
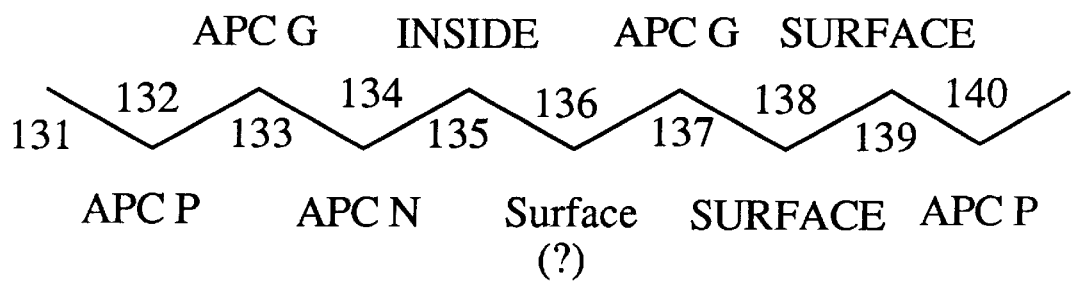

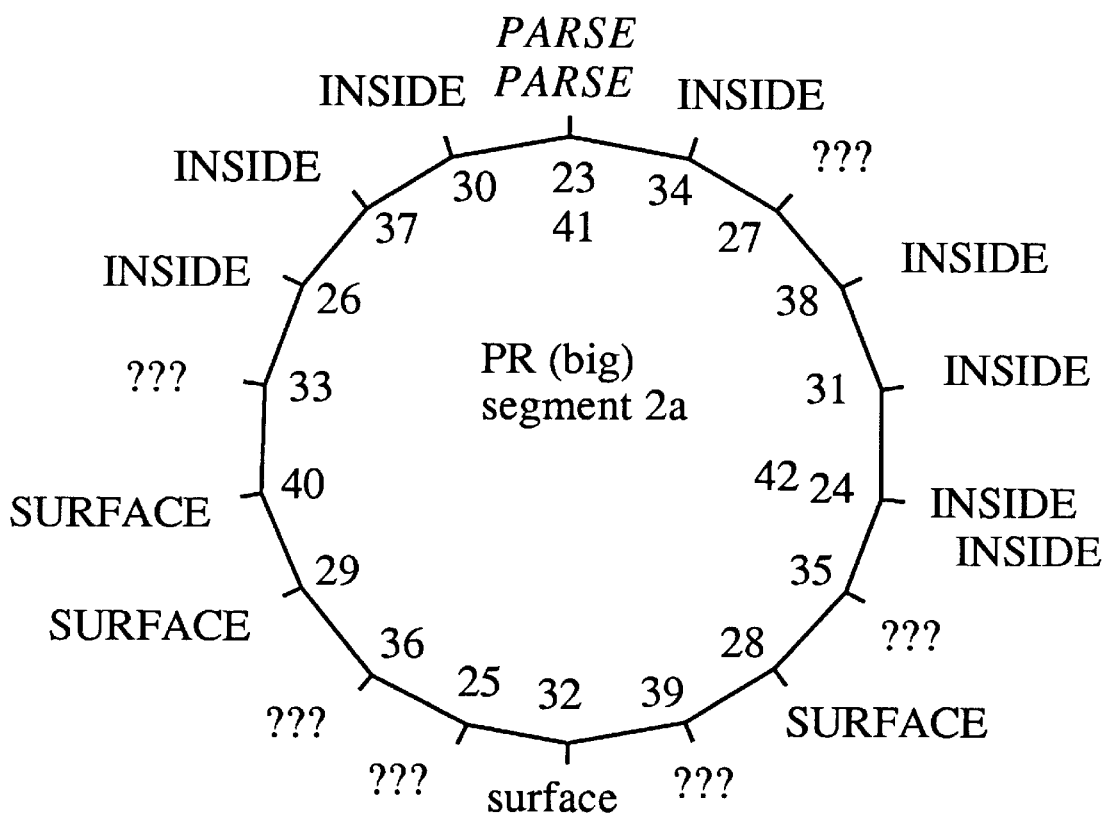
Benner, Fig. 8a
Predicting Folded Structure of Proteins

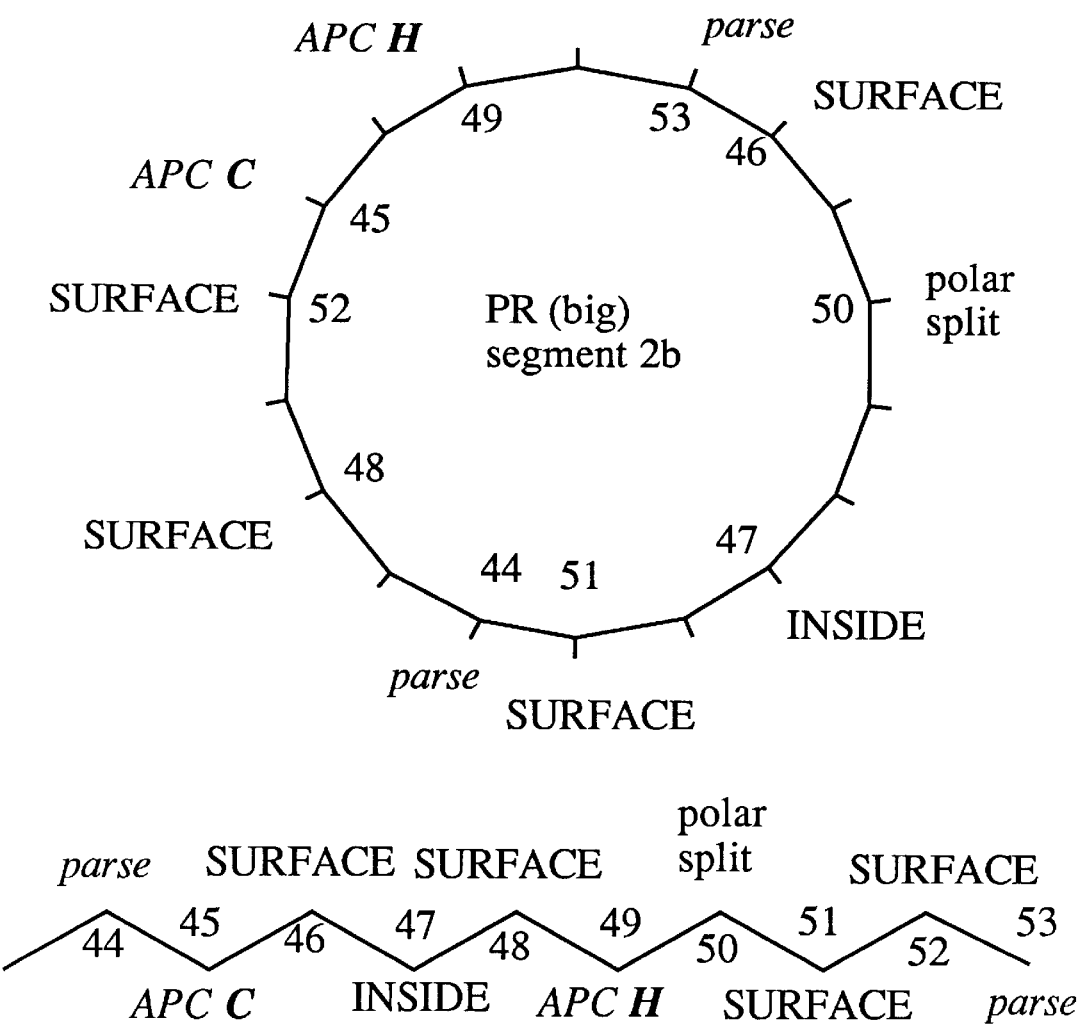
Benner, Fig. 8b
Predicting Folded Structure of Proteins

Benner, Fig. 8c
Predicting Folded Structure of Proteins
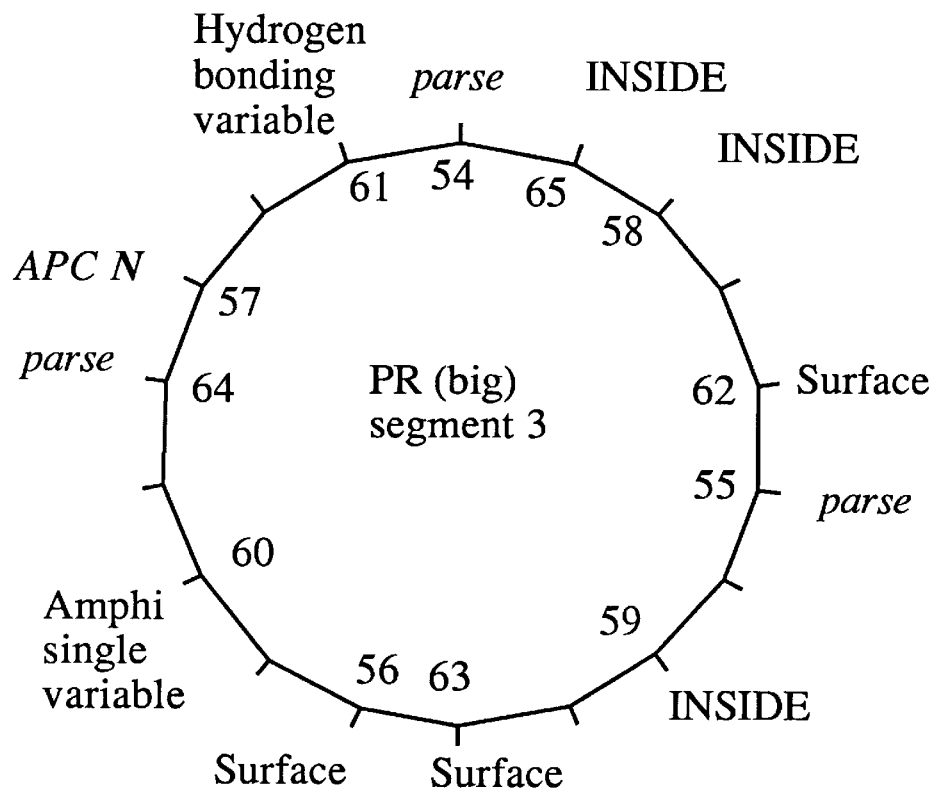
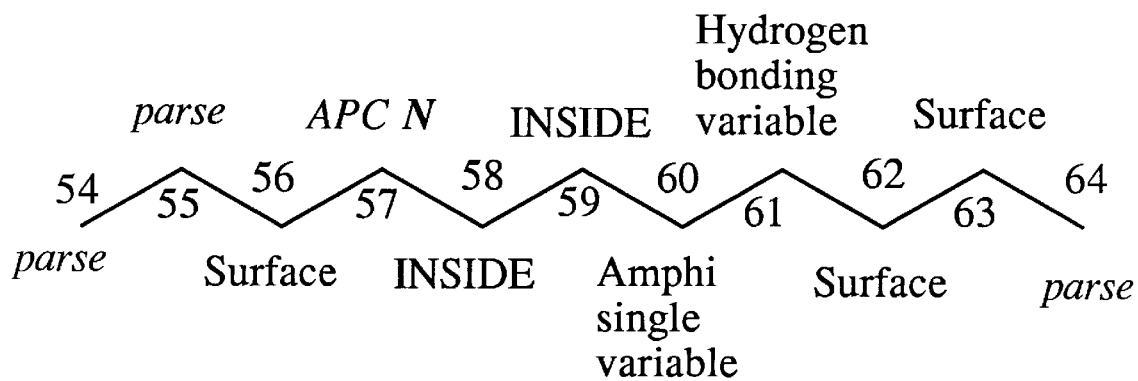

Benner Fig. 8d
Predicting Folded Structure of proteins
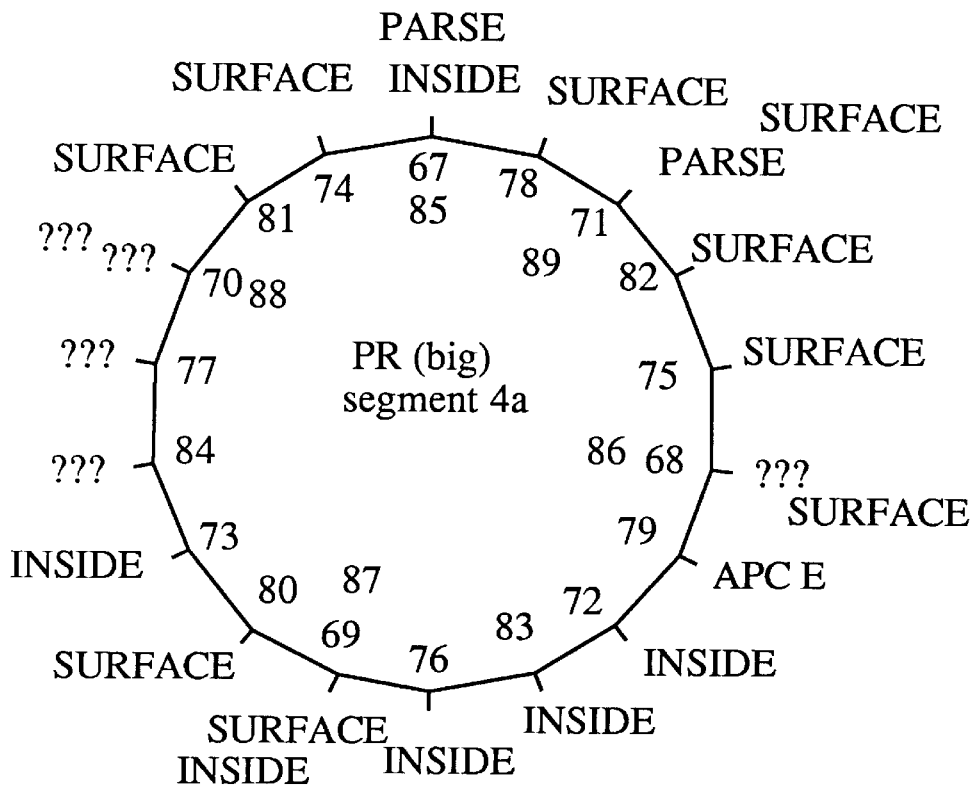
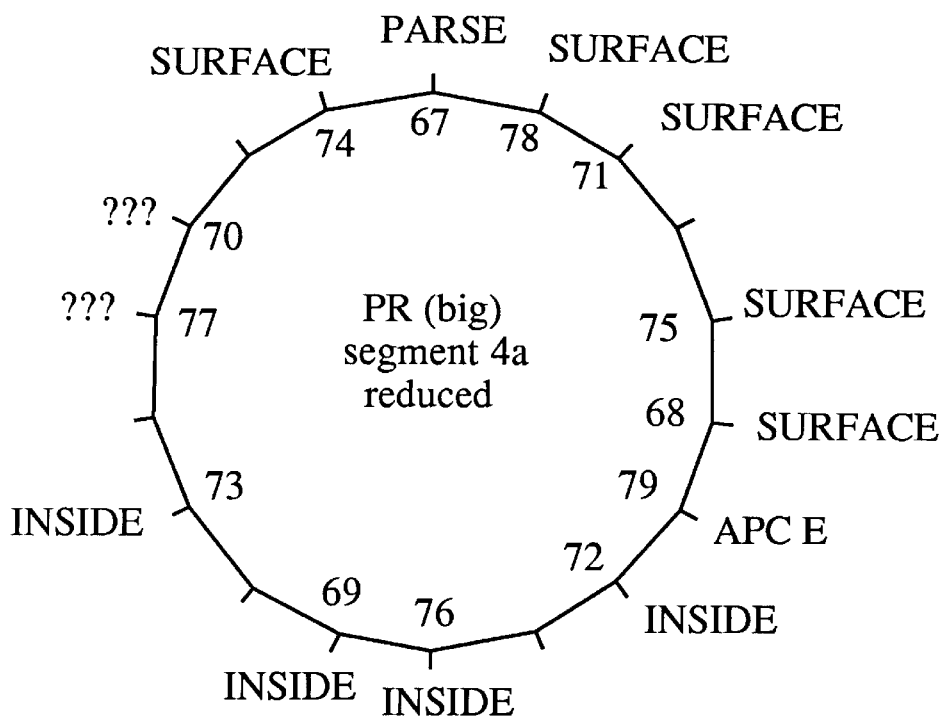

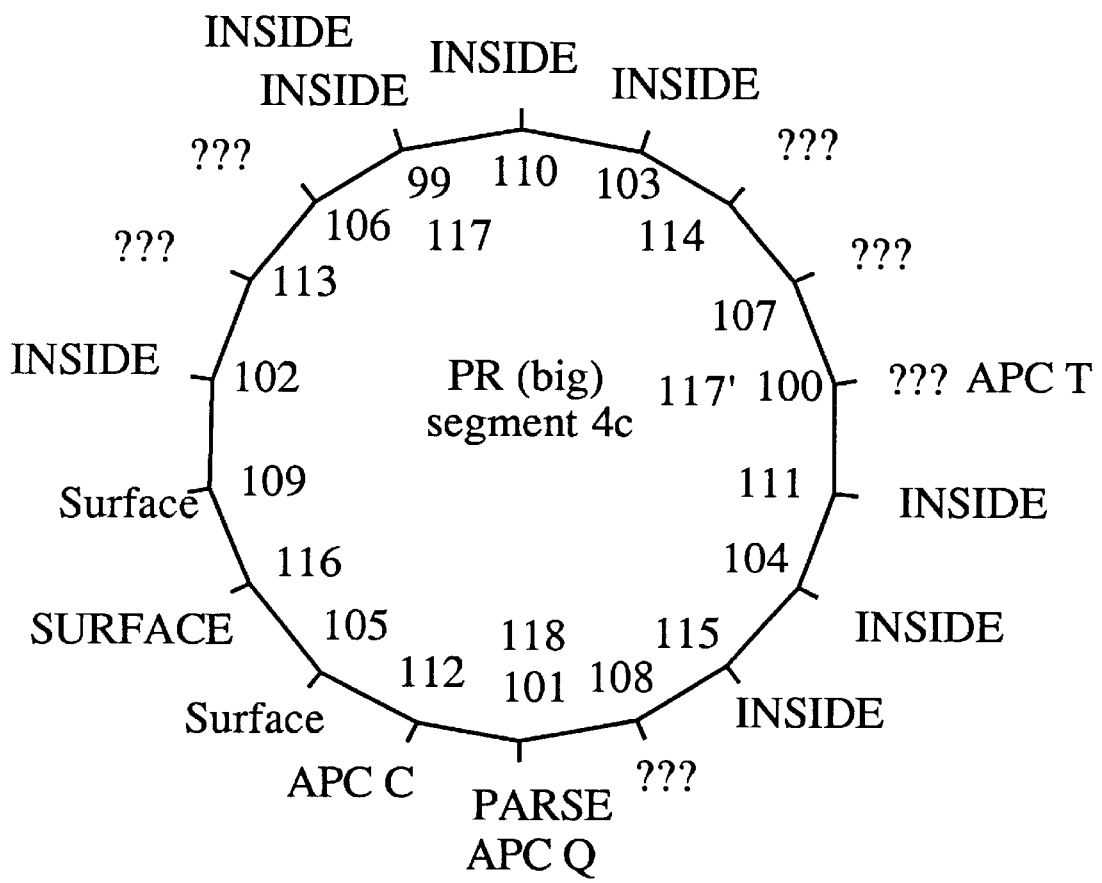
Benner, Fig. 8e
Predicting Folded Structure of Proteins

Benner, Fig. 8f
Predicting Folded Structure of Proteins
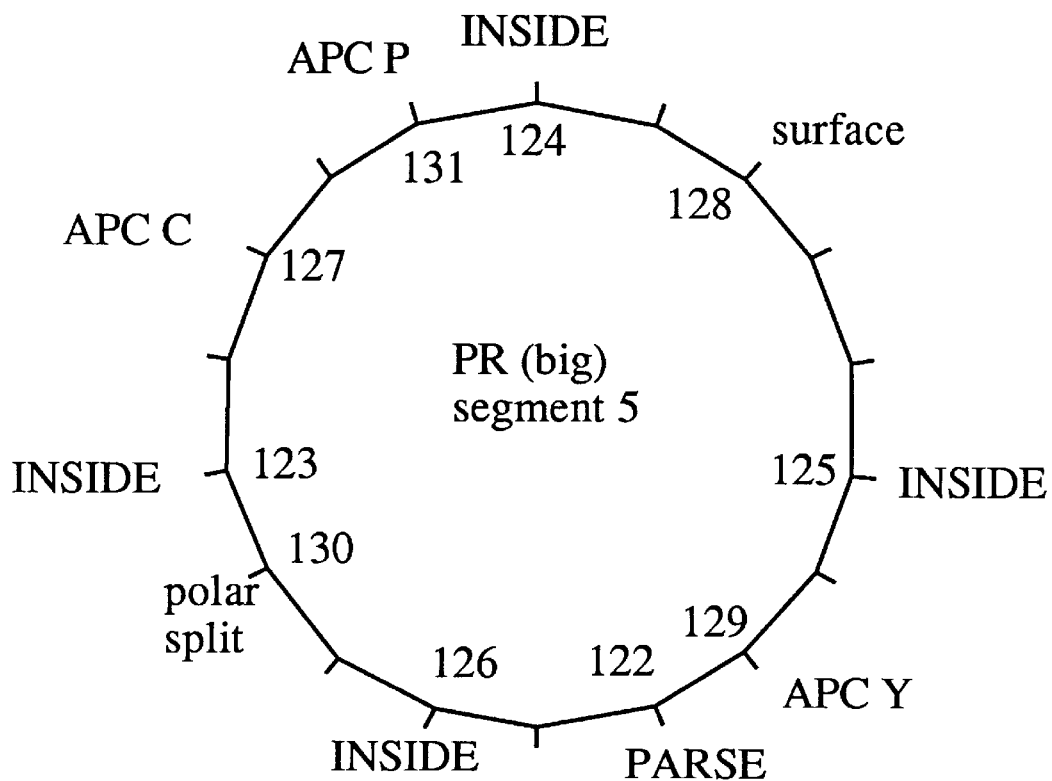
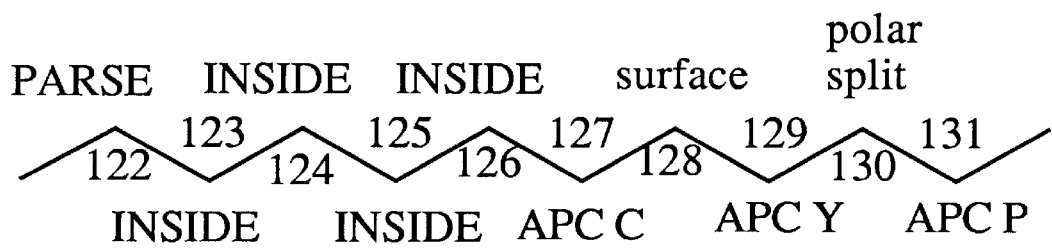

Benner, Fig. 8g
Predicting Folded Structure of Proteins
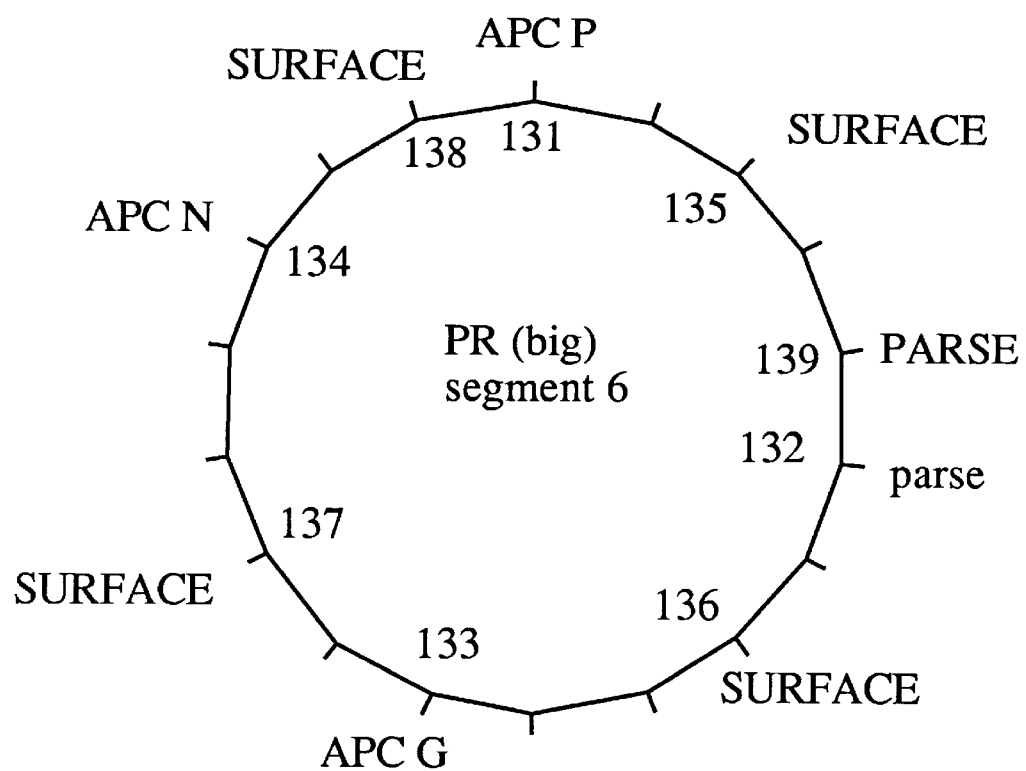
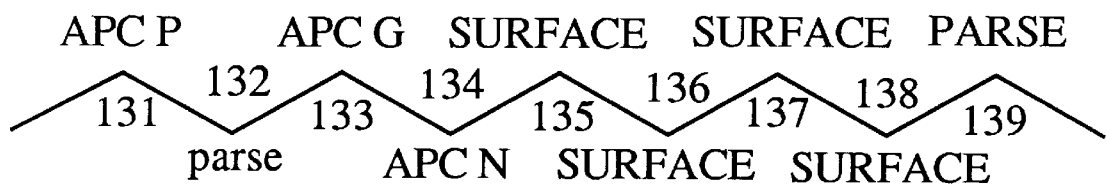

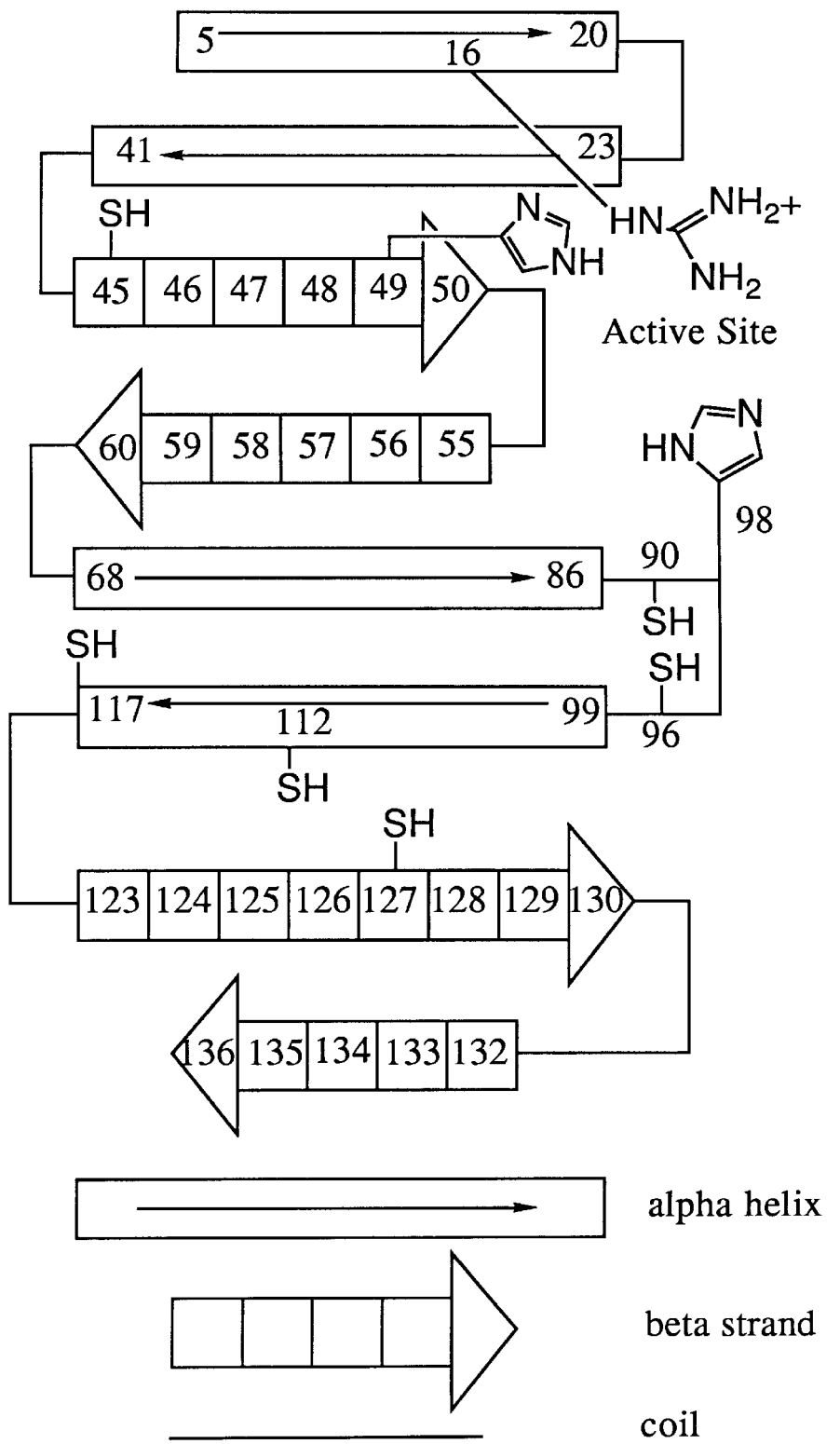
Benner, Fig.9
Predicting Folded Structure of Proteins

PREDICTING FOLDED STRUCTURES OF PROTEINS

CROSS REFERENCES TO RELATED APPLICATIONS

None

STATEMENT OF RIGHTS TO INVENTIONS MADE UNDER FEDERALLY-SPONSORED RESEARCH

None

BACKGROUND OF THE INVENTION

1. Field of the Invention

This invention relates to methods for constructing models for the secondary structure, supersecondary structure, and tertiary structure of proteins in the absence of any crystallographic information for any member of the protein family. More particularly, the present invention pertains to methods for extracting structural information from a set of aligned sequences of homologous (related by common ancestry) proteins for these purposes. More particularly, the present invention pertains to methods that extract structural information concerning a protein fold from the patterns of conservation and divergence of amino acid sequence within a set of homologous protein sequences, where this information is extracted using algorithms that reflect the evolutionary processes by which the protein family emerged.

2. Description of the Related Art

Proteins are linear polypeptide chains composed of 20 different amino acid building blocks. Determining the sequence of amino acids in a protein is now experimentally routine, both by direct chemical analysis of the proteins themselves, or by translation of a gene that encodes the protein. Existing data bases contain over 10 million amino acids.

The linear polypeptide sequence provides only a small part of the structural information that is important to the biochemist, however. The polypeptide chain folds to give secondary structural units (most commonly alpha helices and beta strands) which then fold to give supersecondary structures (for example, beta sheets) and a tertiary structure. Most of the behaviors of a protein are determined by its secondary and tertiary structure, including those that are important for allowing the protein to function in a living system. Further, the folded structure must be known before pharmaceuticals can be designed to bind to the protein.

The utility of methods able to predict secondary structure of a protein from sequence data alone is obvious to any individual ordinarily skilled in the art. High quality secondary structure predictions are useful for identifying antigenic sites on a protein molecule, as guides for site directed mutagenesis studies, and for understanding the interaction of a protein with other molecules. Further, high quality secondary structure predictions are prerequisites for building tertiary structural models for proteins.

The importance of methods for predicting the folded structure of proteins from sequence data has been appreciated by biochemists for over 30 years, and a corresponding three decades of labor have been devoted to efforts to develop such methods. The problem has proven to be extremely difficult to solve. In the process, a very large number of publications have appeared describing approaches towards solution to the structure prediction problem. Many of the classical approaches attempting to develop methods for predicting the folded structure of proteins from sequence data are summarized in a book [G. Fasman, editor, *Prediction of Protein Structure and the Principles of Protein Conformation,* NY Plenum (1989)], which is incorporated herein by reference.

It is clearly impossible to provide in this disclosure a complete description of the entire body of classical work in the field of protein structure prediction. What is presented is a summary of these classical methods, together with a brief comment on their efficacy, the prior art known to the Applicant that serves as the closest precedent for the method of the present invention, and criteria that allow the present invention to be distinguished from all aspects of the prior art known to the Applicant.

First, the method of the present invention is de novo, that is, it allows the prediction of the folded structure of a protein without the need for any crystallographic data. De novo predictive methods are distinct from other methods that rely on crystallographic information to be useful, in particular, "knowledge based" method, where a structural model for a protein whose structure is unknown is built by extrapolation from a structure of a homologous proteins whose crystal structure has already been solved [T. L. Blundell, B. L. Sibanda, M. J. E. Sternberg, J. M. Thornton: "Knowledge-based Prediction of Protein Structures and the Design of Novel Molecules", *Nature* 1987, 326: 347–352].

De novo methods in the prior art that attempt to predict the folded structure of proteins from sequence data fall into three general categories:

(i) Computational methods attempt to model the folded structure of proteins by calculating the relative energies of various possible conformations of the polypeptide chain in the search for the accessible conformation with the lowest energy. This method has been largely unsuccessful due to the large conformational space that a polypeptide chain can occupy, and difficulties in modeling the interaction of the protein with the solvent, water.

(ii) Statistical methods examine the proteins whose folded structures are known, and tabulate from these structures the probability that each of the 20 proteinogenic amino acids occurs in a particular secondary or supersecondary structure. In predictive work, these statistical structural propensities can be influenced by the sequence of the protein immediately before or after the amino acid residue in question, and can be averaged over an alignment of homologous protein sequences. Such methods normally are only partly successful, in part because the statistical preferences for individual amino acids to occupy particular secondary structures is small.

(iii) Methods based on physical chemical properties of the side chains of different amino acids place amino acid side chains that are hydrophilic outside the folded protein structure, where they are presumed to interact with solvent water, and hydrophobic side chains inside the folded structure. Secondary structures are assigned by patterns in the hydrophobicity or hydrophilicity of the side chains. For example, 3.6 residue periodicity is indicative of an alpha helix, while alternate periodicity is indicative of a beta strand. Such methods are only partly successful because evolutionary forces tend to introduce amino acid residues into polypeptide sequences that violate the 3.6 residue periodicity to achieve proteins with the desired level of conformational instability [S. A. Benner, "Patterns of Divergence in Homologous Proteins as Indicators of Tertiary and Quaternary Structure," *Adv. Enzym. Regulation,* 28, 219–236 (1989)].

From the large body of classical work, it is worth noting the classical work of Lim and of Schiffer and Edmundson, as the method of the present invention derives considerable inspiration from these authors. Schiffer and Edmundson [M. Schiffer, A. B. Edmundson, "Use of helical wheels to represent the structures of proteins and to identify segments with helical potential", *Biophys. J.* 7, 121–135 (1967)] was the first to use helix wheels to illustrate the properties of alpha helices. Lim [V. I. Lim, "Structural principles of the Globular organization of proteins chains: A stereochemical theory of globular protein secondary structure", *J. Mol. Biol.,* 88, 857–872 (1974); V. I. Lim, "Algorithms for prediction of α-helical and β-structural regions in globular proteins", *J. Mol. Biol.,* 88, 873–894 (1974)] was one of the first to formalize a method for identifying alpha helices in proteins structures that searches for a property of a polypeptide sequence that displays 3.6 residue periodicity.

In recent years, a number of papers appeared that transcended classical approaches, in that they have examined the sequences of more than one homologous protein in an effort to extract structural information. These papers have focused on the fact that homologous proteins have similar folded structures [Chothia & Lesk, *EMBO J.* 5, 823 (1986); N. L. Summers, W. D. Carlson, M. Karplus, *J. Mol. Biol.* 196, 175 (1987)].

For example, Crawford et al. [I. P. Crawford, T. Niermann, K. Kirschner, "Prediction of Secondary Structure by Evolutionary Comparison: Application to the α Subunit of Tryptophan Synthase", *Proteins,* 2, 118–129 (1987)] examined a set of aligned homologous sequences of tryptophan synthase, and predicted that this protein folded to yield an eight fold alpha-beta barrel. This is, to the Applicant's knowledge, the first time that a correct de novo prediction has been made for the folded structure of a protein in advance of crystallographic data. Further, Crawford et. al. [(1987) op. cit.] used gaps in the alignment to separate individual secondary structural elements. To assign secondary structure to each of these elements, Crawford et al. used a classical statistical algorithm developed by Gamier et al. [J. Gamier, D. J. Osguthorpe, B. Robson, "Analysis of the Accuracy and Implications of Simple Methods for Predicting the Secondary Structure of Globular Proteins", *J. Mol. Biol.,* 120, 97–120 (1978)], assigned secondary structures to each homologous sequence individually, and then averaged the secondary structural assignments over all of the protein sequences to give an average secondary structure prediction. The secondary structure prediction had eight alpha helices interspersed with eight beta strands, a pattern well known in one class of protein fold, the eight fold alpha-beta barrel fold. This pattern was used by Crawford et al. to build a corresponding tertiary structure model for tryptophan synthase.

Zvelebil et al. [M. J. Zvelebil, G. J. Barton, W. R. Taylor, M. J. E. Sternberg, "Prediction of Protein Secondary Structure and Active Sites using the Alignment of Homologous Sequences", *J. Mol. Biol.,* 195, 957–961 (1987)] proposed a similar approach of averaging secondary structure predictions made by the method of Gamier et al. [(1978) op. cit.], but did not attempt to predict any unknown structures with this approach. Likewise, Taylor and Green [W. R. Taylor, N. M. Green, "The predicted secondary structures of the nucleotide-binding sites of six cation-transporting ATPases lead to a probably tertiary fold", *Eur. J. Biochem.* 179, 241–248 (1989)] average secondary structure predictions made individually for each of a set of protein sequences to obtain a consensus secondary structure prediction, and use a knowledge-based approach to model a tertiary structure.

The main disadvantage of the method advocated by Crawford et al., Zvelebil et. al., and Taylor and Green is that it does not work well on a wide range of protein structures.

Patthy also suggested that gaps in an alignment of several homologous protein sequence can indicate which residues form surface loops [L. Patthy, "Prediction of surface loops of protein-folds from multiple alignments of homologous sequences," *Acta Biochim. Biophys. Hung.* 24, 3–13 (1989)], but did not attempt to predict any surface loops in any unknown structures with this approach.

Further, it is generally appreciated in the art that certain residues at the active site of an enzyme are highly conserved during divergent evolution. Zvelebil and Sternberg [M. J. Zvelebil, M. J. E. Sternberg, *Prot. Eng.* 2, 127–138 (1988)] have reported an algorithm that scans for conserved polar residues in regions of high conservation in a multiple alignment as an indicator of active site residues. Of 16 active site residues in a test sample of alignments, 13 were correctly predicted, with an overprediction of 50 positions. This level of success is inadequate to permit a prediction of a structure using this algorithm as a component of the predictive method.

Overington et al. [J. Overington, M. S. Johnson, A. Sali, T. L. Blundell, "Tertiary Structural Constraints on protein evolutionary diversity: Templates, key residues, and structure prediction" *Proc. Roy. Soc. B..* 241, 132–145 (1990)] have studied patterns of sequence divergence in proteins with known crystal structures. Depiereux and Feytmans [E. Depiereux, E. Feytmans, "Simultaneous and multivariate alignment of protein sequences: Correspondence between physicochemical profiles and structurally conserved regions", *Prot. Eng.,* 4, 603–613 (1991)] have also noticed patterns in conservation of individual residues during divergent evolution. Neither have provided a method for predicting secondary or tertiary structure.

SUMMARY OF THE INVENTION

In the method of the present invention, a model for the folded structure of a set of proteins is built from a set of aligned homologous protein sequences. The method of the present invention is characterized by several operational features, each of which is essential for the method to be efficacious:

(i) The method of the present invention examines aligned sequences of a set of homologous proteins, rather than a single sequence of a single protein.

(ii) The method of the present invention extracts information concerning the three dimensional structure of the protein family from patterns of conservation and variation within a set of homologous sequences, not by a simple averaging of a property of the sequences taken individually.

(iii) The method of the present invention combines algorithms that assign positions in the alignment to the surface of the folded structure, to the interior of the folded structure, and to the active site, as a first step for predicting secondary structural elements.

(iv) The method of the present invention identifies separate secondary structural elements in the alignment using parsing algorithms that identify gaps in the alignment and specific parsing sequence motifs.

(v) The algorithms used by the method of the present invention are applied to subgroups of proteins with clearly identified evolutionary relationships, in particular, a clearly specified sequence identity and evolutionary distance.

(vi) The algorithms are designed to reflect how natural selection and neutral drift, two evolutionary processes, influence the divergent evolution of protein sequences.

(vii) The method of the present invention assembles the secondary structural elements to form supersecondary and tertiary structural models by orienting these elements using disulfide bridges, active site assignments, and covariation analysis.

Some aspects of the method covered by this application were discussed in an article published on Mar. 27, 1991 by the Applicant and a coworker who worked at the Applicant's direction [S. A. Benner and D. Gerloff, "Patterns of Divergence in Homologous Proteins as Indicators of Secondary and Tertiary Structure: The Catalytic Domain of Protein Kinases," Adv. Enzyme Regulat., 31, 121–181 (1991)]. The publication date is less than one year prior to the date that this application is being filed.

The general philosophy underlying the method of the present approach was outlined in an earlier publication [Benner (1989) op. cit.]. However, this publication covers only the preliminary work leading to the method of the present invention, was written prior to the reduction to practice, and neither makes obvious to nor enables one of ordinary skill in the art to practice the method of the present invention.

What allows the de novo predictive method that forms the present invention to be most clearly distinguished from the prior art is its efficacy. Specifically, the method disclosed here has been shown to provide remarkably reliable predictions for the folded structures of proteins whose structures are not known at the time that the prediction is made, but subsequently become known. Methods known in the prior art have not.

Illustrating the inefficacy of methods known in the prior art was a contest sponsored recently by the Protein Club. In this contest, laboratories developing and using classical methods for predicting the folded structure of proteins were invited to predict the folded structure of protein whose structures had been solved, but where the solution was withheld from the contestants. No de novo method successfully allowed the prediction of the folded structure. Wrote the workshop organizer, "The answer to the question 'Structures from Sequences?' is 'Not yet, unless you know what the structure looks like'" [D. C. Rees, "Three-dimensional Protein Structure Prediction Workshop: Overview and Summary", Curr. Res. in Prot. Chem., NY, Academic Press, 551–556 (1990)].

The efficacy of the method of the present invention was demonstrated by the prediction of a secondary structure for protein kinase in advance of any information regarding the crystal structure. The prediction was submitted for publication by Benner and Gerloff [(1991) op. cit.] on Sep. 21, 1990, well in advance of the solution of the crystal structure by Sowadski, Taylor and their colleagues. The results of the crystal structure were published in July, 1991 [D. R. Knighton, J. Zheng, L. F. Ten Eyck, V. A. Ashford, N. H. Xuong, S. S. Taylor, J. M. Sowadski: "Crystal Structure of the Catalytic Subunit of Cyclic Adenosine Monophosphate-dependent Protein Kinase", Science, 253, 407–414 (1991)]. The crystal structure showed that the prediction was remarkably accurate. Knighton et al. [(1991) op. cit.] wrote:

"Although most of the predictions of secondary structure in the C subunit have been quite inaccurate and do not correlate well with the actual structure, the recent prediction by Benner and Gerloff is an exception. Their prediction of the secondary structure . . . is remarkably accurate, particularly for the small lobe"

Another indication of the inefficacy of the prior art and the efficacy of the method of the present invention comes from the paper of Thornton et al. [J. M. Thornton, T. P. Flores, D. T. Jones, M. B. Swindells: "Prediction of Progress at Last", Nature, 354, 105–106 (1991)] published in Nature shortly after the prediction for protein kinase was confirmed by Knighton et al. [(1991) op. cit.]. Thornton et al. noted that:

"Benner and Gerloff tackled secondary-structure prediction; this was essentially a case study of the catalytic domain of the protein kinases, the structure of which was then unknown. The cause for excitement is that the structure has since been solved by X-ray crystallography, and Benner and Gerloff's prediction of the core secondary structures was much better than that achieved by standard methods."

Another indication of the efficacy of the method of the present invention comes from Table 1, which summarizes the prediction for the catalytic domain of protein kinases. The details of the predictive success are reviewed by Benner [Benner, "Predicting de novo the Folded Structure of Proteins", Curr. Opin.. Struct.. Biol., in press (1992), copy enclosed], and by Thornton et al. [(1992) op. cit.].

The method is also operationally distinct from the prior art. Although Crawford et. al. [(1987) op. cit.] made a prediction based on an analysis of an alignment of homologous sequences, they predict secondary structure by averaging secondary structural predictions made on individual sequences, rather than by extracting information concerning the three dimensional fold of the protein family from patterns of conservation and variation within the set of homologous sequences. This is the same approach advocated by Zvelebil et al. [(1987) op. cit.] This approach has a particularly important disadvantage: it has been shown not to work well for many classes of protein fold other than the 8-fold alpha-beta barrel class.

Further, although Zvelebil and Sternberg [(1988) op. cit.] extract information concerning the position of active site residues within a protein family from patterns of conservation and variation within a set of homologous sequences, their algorithms make no effort to to initially understand the evolutionary relationship between the sequences themselves as a precondition for interpreting patterns of conservation and variation in a fashion. This deficiency is responsible in part for the low reliability of the algorithms that these investigators have produced. In particular, missing from all of the prior art is operational feature (v). Those who analyze variation and conservation within a family of protein sequences seem universally to have overlooked the need to understand in a systematic way the evolutionary relationship between the sequences themselves as a precondition for interpreting conservation and variation in a fashion that is likely to be predictively useful. Also missing from all work in the prior art is operational feature (vi), a recognition that competing evolutionary processes, natural selection and neutral drift, will complicate the analysis of patterns of structural divergence in a protein family. Also missing from all work in the prior art is operational feature (vii), an approach towards building a model for the supersecondary and tertiary structure for a family of proteins. Although such model building is an art that is slightly different for each protein family examined, the method of the present invention did yield a correct model for the first domain of protein kinase [Benner (1992) op. cit.; Thornton et al. (1991) op. cit.], again before any crystallographic information was available.

BRIEF DESCRIPTION OF THE DRAWINGS

FIG. 1. Evolutionary tree describing the evolutionary relationship for a preferred set of proteins for implementing the method of the present invention for predicting the folded structure of proteins from a set of aligned homologous sequences. The idealized set of 16 proteins has 8 pairs of proteins, each pair 80% sequence identical. Numbers indicate the pairwise identity of the designated subgroups of proteins.

FIG. 2. The evolutionary tree relating the alcohol dehydrogenases whose sequences are aligned in Table 3. Numbers indicate the minimum pairwise identity of the designated subgroups of proteins.

FIG. 3. Helix wheels for segments of protein kinase: (a) Helix wheel covering positions 59–75 of protein kinase; (b) Helix wheel covering positions 114–123 of protein kinase; (c) Helix wheel covering positions 131–151 of protein kinase; (d) Helix wheel covering positions 259–273 of protein kinase; (e) Helix wheel covering positions 285–302 of protein kinase; (f) Helix wheel covering positions 318–326 of protein kinase.

FIG. 4. The predicted secondary, supersecondary, and tertiary structure for protein kinase.

FIG. 5. A model for the active site of protein kinase.

FIG. 6.(a) Evolutionary tree for the pathogenesis related proteins from plants;

a. PR14 pathogenesis-related protein from tobacco
   b. Arabidopsis thaliana pathogenesis-related protein 1 (PR-1) gene
   c. Lycopersicon esculentum PR (pathogenesis related) protein (P4)
   d. Lycopersicon esculentum PR (pathogenesis related) protein (P6)
   e. Tobacco PR-1a gene for pathogenesis-related proteins
   f. Tobacco gene for pathogenesis-related protein 1b (PR1b)
   g. Tobacco mRNA fragment for pathogenesis-related protein PR1c
   h. Maize PRms gene for a pathogenesis-related protein (b) Evolutionary tree for pathogenesis related proteins from plants and their homologues, the sperm coating and testis specific (TPX) proteins from mammals, and venom allergens from insects. The numbers indicate the approximate PAM distance between the evolutionarily most distant members of the indicated subgroups [Gonnet et al. (1992) op. cit.], that is, the number of accepted point mutations per 100 residues separating the most distant protein sequences.

a. Pathogenesis related leaf protein P14
   b. Pathogenesis related protein 1A precursor (PR-1A).
   c. Pathogenesis related protein 1B precursor (PR-1B).
   d. Pathogenesis related protein 1C precursor (PR-1C).
   e. Basic form of Pathogenesis related protein 1 precursor (PRP 1)
   f. Sperm coating glycoprotein (SCP)
   g. Testis specific protein TPX-1 precursor (gene name: TPX1)
   h. Testis specific protein TPX-1 precursor
   i. Venom allergen 5 form 2 precursor (AG5-2).
   j. Venom allergen 5 form 3 precursor (AG5-3)

FIG. 7. Helix wheels for segments of the pathogenesis related proteins from plants, derived from the alignment in Table 16. (a) Helix wheel covering segment 1 of PR proteins; (b) Helix wheel covering segment 2a of PR proteins; (c) Helix wheel covering segment 2b of PR proteins; (d) Helix wheel and beta template covering segment 3 of PR proteins; (e) Helix wheel covering segment 4ab of PR proteins; (f) Helix wheel covering segment 4cd of PR proteins; (g) Helix wheel and beta template covering segment 5 of PR proteins; (h) Helix wheel and beta template covering segment 6 of PR proteins.

FIG. 8. Helix wheels for segments of the pathogenesis related proteins from plants and their homologues, derived from the alignment in Table 17. (a) Helix wheel covering segment 2a of PR proteins; (b) Helix wheel and beta template covering segment 2b of PR proteins; (c) Helix wheel and beta template covering segment 3 of PR proteins; (d) Helix wheel covering segment 4a of PR proteins; (e) Helix wheel covering segment 4c of PR proteins; (f) Helix wheel and beta template covering segment 5 of PR proteins; (g) Helix wheel and beta template covering segment 6 of PR proteins.

FIG. 9. The predicted secondary structure for pathogenesis related proteins from plants and their homologues.

DETAILED DESCRIPTION OF THE INVENTION AND PREFERRED EMBODIMENTS

A glossary of abbreviations and terms is given below.

Alignment Anchor: A position in an alignment that is sufficiently conserved across the entire alignment, or undergoes only conservative substitution, such that the alignment of the sequences at this position is highly reliable.

Amphiphilic split in a cluster of subgroups with MPI of X: Designates a position in an alignment where none of the subgroups in the cluster of subgroups at MPI=X is variable, where at least one subgroup contains a hydrophobic residue and at least one subgroup contains a hydrophilic residue.

APC (all proteins conserved): Designates a position in an alignment where all of proteins being considered have the same amino acid at that position.

Clusters of subgroups with an MPI=X: The proteins in the alignment are divided into subgroups with different overall levels of sequence identity. All subgroups with a particular MPI belong to a particular cluster of subgroups.

CMX Y (Count minus X): Designates a position in the alignment where all but X proteins have amino acid Y.

Distributed parse: A parse built from parsing elements that appear in different subgroups of the alignment at neighboring position numbers.

Functional subgroups: The proteins in the alignment are divided into 12 functional subfamilies, where members of each functional subgroup (or subfamily) share among themselves, and are distinct from members of other functional subgroups, a particular biological function or catalytic behavior.

Helix Wheel: A projection of a helix down its long axis, showing the directions that side chains at different positions along the helix protrude [Schiffer & Edmundson (1967) op. cit.]

Hydrogen bonding variable at MPI=X: Designates a position in an alignment with more than one variable subgroup in the cluster of subgroups with MPI=X, where at least some amino acids in the subgroups have an indifferent residue at this position (C, H, Q, S, T), but no subgroups have a polar residue at this position (D, E, K, N, R).

Hydrophilic split in a cluster of subgroups with MPI of X. Designates a position in an alignment where the each subgroup displays no variation within subgroup, and all amino acids in each subgroup are either hydrophilic or indifferent.

Hydrophobic anchor for an external loop: A position with a hydrophobic amino acids in most proteins appearing in a segment that is a parse or otherwise assigned as a surface loop.

Hydrophobic residue: An amino acid selected from the group consisting of Phe, Ile, Leu, Met, Val, Trp, and Tyr.

Hydrophobic split in a cluster of subgroups with MPI of X. Designates a position in an alignment where none of the subgroups in the cluster of subgroups at MPI=X is variable, and all amino acids in each subgroup are either hydrophobic or indifferent.

Hydrophobic variable in a cluster of subgroups with MPI of X: Designates a position in an alignment where none of the subgroups in the cluster of subgroups at MPI=X is variable, but where none of the subgroups has either an indifferent or a polar residue (C, H, Q, S, T, D, E, K, N, R).

Indifferent residue: An amino acid selected from the group consisting of Ala, Cys, Gly, His, Pro, Gln, Ser, and Thr.

Inside arc: The side of a helix wheel from which protrude side chains of residues assigned to the inside of the folded protein structure.

MPI=Minimum pairwise identity. The MPI value for a subgroup of proteins in the alignment is the percent sequence identity of the two least similar proteins in the subgroup. Increasing MPI corresponds to decreasing PAM distance connecting the most distantly related proteins the subgroup.

Neutral split in a cluster of subgroups with MPI of X: Designates a position in an alignment where none of the subgroups in the cluster of subgroups at MPI=X is variable, where every subgroup contains an indifferent residue.

Non-standard secondary structure: All secondary structures other than an alpha helix or a beta strand (e.g., a $3_{10}$ helix or a collagen helix).

PAM distance (accepted point mutations): A measure of the evolutionary distance between two proteins, where the PAM distance is the most probable number of accepted point mutations separating the two sequences per 100 amino acid residues, corresponding to the number of times the first sequence must be transformed by a 1% mutation matrix (a mutation matrix where the sum of all off diagonal elements is such that transformation of a sequence by this matrix yields a protein with 1 mutation per 100 amino acids) to yield the second protein with the highest probability.

Parse: A segment that divides the alignment into segments whose secondary structure is considered separately.

Parsing string: A sequences of consecutive amino acids in a single protein that indicates that the segment lies between standard secondary structural units (e.g., GG, PP, PG, GP, NN, NS, etc.).

Polar residue: An amino acid selected from the group consisting of Asp, Glu, Arg, Lys, and Asn.

Reflexivity: Designates a position in an alignment where patterns of variation among the proteins being examined suggests a tree-like relationship between these proteins that is different from the evolutionary tree derived from examination of the entire sequences of the proteins. Most commonly, a position displays reflexivity when the pattern of variation involving particular amino acids is the same in two distant subgroups.

Split at MPI=X: Designates a position in an alignment where none of the subgroups in the cluster of subgroups at MPI=X is variable.

Standard secondary structural elements: an alpha helix or a beta strand.

String: A set of consecutive positions in the alignment

Subgroup with an MPI=X: A subset of the proteins in an alignment that bears a specified evolutionary relationship, that the sequences have a minimum pairwise identity of X percent.

Surface arc: The side of a helix wheel from which protrude side chains of residues assigned to the surface of the protein.

Variable subgroup: At a position in an alignment, a subgroup of proteins in the alignment where more than one kind of amino acid is present.

Throughout this discussion, the one letter code for amino acids is used (Table 2).

Step 1. Obtain an Alignment

Sequences of a set of homologous proteins must be obtained and aligned. Alignments of the sequences of homologous proteins may be obtained using one of many algorithms well known to those skilled in the art, and summarized in volume 183 of Methods in Enzymology [R. F. Doolittle, editor, *Methods Enzymol.* 183, 1–736 (1990)].

To be useful in structure prediction work, the alignment must meet a simple criterion: The alignment should match as much as possible homologous amino acid residues in different proteins, that is, amino acids from two proteins placed in apposition in the alignment must be descendents of a single codon in the most recent common ancestral protein. This criterion is easily met in proteins having high sequence similarity. For proteins with lower sequence similarity, this normally requires accurate placement of gaps in an alignment. Operationally, this requirement can normally be met with classical alignment algorithms by incorporating into an alignment only protein pairs that have a minimum pairwise identity of at least 35%. More divergent proteins can be aligned successfully using a deletion gapping penalty derived from an exhaustive matching of the protein sequence data base [G. H. Gonnet and S. A. Benner, "Computational Biochemistry Research at ETH", *Technical Report I54, Departement Informatik,* March (1991); G. H. Gonnet, M. A. Cohen, S. A. Benner, "Exhaustive Matching of the Entire Protein Sequence Database", *Science* in press (1992), copy enclosed]. However, when pairwise identity falls below ca. 25%, the reliability of an alignment drops below the point where is is useful in the method of the present invention.

Further, to be useful, an alignment must contain at least 4 homologous protein sequences, and include some pairs that are closely similar in sequence (more than 80% identical in sequence), some pairs that are moderately similar in sequence (40–80% pairwise identity), and some that have distant similarity (less than 40% pairwise identity). More preferably, an alignment should contain at least 8 homologous protein sequences, which consist of 4 subgroups of proteins consisting of pairs of sequences with 80–85% minimum pairwise identity, where these subgroups pairwise form two subgroups with an intersubgroup pairwise identity of 45–55%, and with the subgroup containing all of the protein sequences having a minimum pairwise identity of 25–35% (FIG. 1). Most preferably, the alignment should be as large as possible, and the evolutionary tree relating the proteins in the alignment should be highly branched. For example, with protein kinase (Example 1), a successful prediction was made with over 70 proteins in the alignment.

Should the appropriate homologous sequences not be available in sequence databases, they can be obtained by molecular biological methods well known to those skilled in the art, using one of the available sequences as a probe for new homologous sequences in appropriately chosen libraries. Branches are added at the appropriate positions to an evolutionary tree by selecting the organisms from which additional sequences are cloned, based on the estimated rate of divergence of the protein sequence, and the estimated time of divergence of the organisms that provide the additional sequences.

Step 2. Divide the alignment into subgroups with different overall sequence similarity.

A key element of the method of the present invention is based on the recognition that information regarding folding patterns appears and disappears at different points during the divergent evolution of a set of proteins. Thus, variation and conservation in a set of homologous protein sequences can be interpreted only in the context of the overall sequence similarity of the proteins being examined. Thus, the "minimum pairwise identity" (or MPI) within a subgroup of proteins must be known to evaluate the significance of any conservation or divergence seen within the subgroup. The structural significance of the similarities and differences between the sequences of a pair of homologous proteins depends on the overall sequence divergence of the pair, according to simple rules. For two closely homologous proteins that are similar in sequence, the differences in the sequences are most significant. For two distantly homologous proteins that are different in sequence, the similarities in the sequences are most significant. Thus, before structural information can be extracted from an alignment, it must be divided into subgroups with different minimum pairwise identities (MPI).

For example, a set of sequences of homologous alcohol dehydrogenases contains 17 proteins. An alignment of these sequences is shown in Table 3; an evolutionary tree relating these sequences is shown in FIG. 2. At MPI=85%, there is a cluster of 10 subgroups of proteins in the alignment. At MPI=50%, however, there are only 2 subgroups.

Step 3. Divide the sequence into segments using parsing algorithms

The core of any structural analysis is a discussion that, from the beginning to the end of an alignment, examines every structural feature of the protein family, one position at a time. To simplify the discussion, the alignment is divided into manageable pieces using "parsing elements", or "parses". Parsing algorithms are intended to identify segments that lie between standard secondary structural units (e.g., alpha helices or beta strands), allowing the biological chemist to consider the secondary structure of the segments between parses individually.

Parsing algorithms have different degrees of reliability. The parsing algorithms find the positions in the alignment that have following structural features, and assign breaks in the secondary structure at these positions. The algorithms are illustrated in Table 4, and listed below in order of decreasing reliability:

(i) Gap parse. The strongest algorithm parses the alignments at points whether there is a gap, that is, at position where the alignment shows that one or more proteins in the family of homologous proteins has undergone an insertion or deletion during divergent evolution. As a rule, insertions and deletions are generally not accepted by natural selection within standard secondary structural elements (alpha helices and beta strands). Thus, the presence of a gap in an alignment indicates that this region is not part of one of these secondary structural units. Some precedence for this parsing algorithm can be found in the literature [Crawford et al. (1987) op. cit.]. In the cases where there is a parse via a gap, it is occasionally useful to have an assignment (surface or inside) for those sequences that are present (vide infra).

(ii) APC P parse. While a proline present in a single sequence is not a good indicator of a break in a secondary structural unit, a proline that is conserved in a set of proteins having an MPI below 40% is a strong indicator of a break in standard secondary structure.

(iii) Distributed parse. When parsing elements (e.g., a Pro or a Gly) is not conserved at a single position in all of a set of proteins having an MPI below 40%, but is found at adjacent or closely adjacent positions in these proteins, this is also a reliable indicator of a break in standard secondary structure.

(iv) APC G parse. While a glycine present in a single sequence is not a good indicator of a break in a secondary structural unit, a proline that is conserved in a set of proteins having an MPI below 40% is an indicator of a break in standard secondary structure. The parsing element is not absolute. APC G can be found as an inside residue in a standard secondary structure as well.

(v) Combination parse. A combination of Pro, Gly, Asn, Ser, or Asp conserved across the entire alignment.

(vi) Distributed combination parse: A distributed combination of Pro, Gly, Asn, Ser, or Asp.

(vii) String parse. Certain dipeptides (GG, GP, PG, PP) almost always indicate parses, especially if conserved in subgroups with an MPI of 85% or lower. Other dipeptides (NN, SS, NS, SN, NG, GN, GS, SG, PN, NP, PS, SP) occasionally indicate parses, especially if conserved in subgroups with an MPI of 70% or lower.

Depending on the size of the alignment, it is often possible to use only the strongest parsing algorithms to assign breaks in secondary structure. This is the case with Example 1. With alignment containing only a few proteins, weaker parsing units must be considered, at least tentatively. This is illustrated in Example 2. In every case, parsing decisions can be revised in light of data collected at later stages in this procedure; occasionally, the alignment is also slightly modified, as alignments are generally least accurate near regions of gaps (Example 2). This revision is necessary because, although the parsing algorithms are highly accurate, they are not perfectly accurate. Approximately once every 400 positions in a typical alignment, a deletion occurs within a secondary structural element. For example, in alcohol dehydrogenase (ADH), a deletion position 256 in the horse liver enzyme, in a helical region. Finally, the alignment is the weakest in regions of surface loops (which are normally the most rapidly diverging segments of a protein). Thus, refinement of the assignments of parses involves three issues:

(i) Where are the beginning and end of the parse?
(ii) Is the parse confirmed by segments within the insertion?
(iii) Can the deletion or insertion be removed by shifting of the alignment itself?

To confirm a gap parse, the segments of the sequences of proteins that do not have a deletion are examined for weaker parsing elements, for example, consecutive G's, PXP motifs, and PG strings, which are common in external loops that are prone to deletion during divergent evolution.

Point (iii) addresses features of the alignment itself. The most preferable alignment programs have a deletion penalty obtained by an exhaustive matching of the entire protein sequence data base [Gonnet et al. (1992) op. cit.], which places a high cost on deletions.

Finally, errors in an alignment can juxtapose amino acids in different proteins that are not true homologs, that is, are not descendent from the same codon in a common ancestor. These errors create problems at several levels of the analysis, and the alignment therefore must be reevaluated throughout the structural modelling. Examination of the alignment focuses on alignment anchors, positions where the conservation across the entire alignment is sufficiently high that there can be no question that the alignment is correct at this position. The alignment is then built out from the anchors towards other anchors, as exemplified below.

Step 4. Assign Surface Positions

Positions in the alignment that contain amino acids whose side chains lie on the surface of the folded structure are identified by surface algorithms. The development of surface algorithms requires a sophisticated understanding of the processes by which protein sequences divergently evolve, and it is instructive at this point to consider both an evolutionarily naive and an evolutionarily sophisticated approach to constructing such algorithms.

In a naive approach, variation of the amino acid side chain at a position in an alignment can be taken as an indication that the side chain at that position protrudes into solvent (water). The logic is straightforward. A residue that protrudes into solvent can be more easily changed without disrupting the function of the protein, because it does not form contacts with other protein residues whose position might be disrupted by a change in the size or functionality of the residue in question.

This approach is naive at two levels. First, the significance of variation in an alignment depends, as noted above, on the overall divergence of the protein sequences being examined. The more sequence divergence that has taken place between two proteins, it is less likely that this variation is an indicator of a surface position, as it is more likely that internal variation is compensated by other internal variation.

Obviously, the most reliable surface assignments are based on variation between two proteins that have an high overall level of sequence simliarity.

Simple empirical evaluation demonstrates that even if adjusted for overall variation among the proteins being examined, an algorithm that assigns positions to the surface based simply on variation is unreliable. For example, in alcohol dehydrogenase, if one assigns a position in the alignment to the surface if it displays variation in a subgroup of proteins with an MPI=85%, of 174 positions assigned to the surface, only 106 (61%) are correctly assigned; 68 (39%) of the positions do not in fact lie on the surface. In this protein, if assignments were made at random, they would be 50% correct. Thus, the predictive power of the naive algorithm is little better than random.

It is easy to explain why this algorithm is bad: It is based on an incorrect understanding of how proteins evolve. During divergent evolution, two types of variation can occur. The first is neutral variation, substitutions of one amino acid by another that do not alter the behavior of a protein to an extent sufficient to influence the ability of a host organism to survive and reproduce. The second is adaptive variation, substitution of one amino acid by another that is selected for precisely because it does alter the behavior of a protein to an extent sufficient to influence the ability of a descendent organism to survive and reproduce in a new environment. Neutral variation and adaptive variation have exactly opposite implications, both in terms of impact on the behavior of a protein, and its position in the folded structure.

Neutral variation lies predominantly on the surface of the protein, where it does not influence the behavior of a protein to an extent that will influence survival. However, adaptive variation is supposed to alter the behavior of a protein. Therefore, it does not necessarily occur on the surface. Adaptive variation can occur anywhere in the folded structure, including inside the folded structure, or at the active site.

The naive algorithm fails because it treats all variation in an alignment as neutral variation. Indeed, a key teaching of the present invention is that for a method to successfully extract structural information from an alignment of homologous sequences, algorithms must be constructed to distinguish neutral and adaptive variation.

The discovery that underlies the surface predictions used by the method of the present invention distinguishes neutral variation from adaptive variation by patterns of concurrent polar variation. As with parsing algorithms, surface algorithms have different degrees of reliability. The surface algorithms find the positions in the alignment that have following structural features, and assigns the side chains of amino acids at these positions to the surface of the proteins. The algorithms are illustrated in Table 5, and listed below in order of decreasing reliability:

(i) Surface Algorithm 1: Concurrent polar variation in n subgroups: In a cluster of subgroups with a defined MPI, variation at a position concurrently in n subgroups at a defined MPI, where n is two or greater, when at least one of the variable subgroups contains a hydrophilic amino acid (Arg, Lys, Asp, Glu, Asn). The reliability of the algorithm increases with increasing n, increasing MPI, and increasing number of polar residues. Preferably n is 2 or greater, and MPI is 80% or greater. The larger the number of sequences in the alignment (other factors being equal), the greater the fraction of the surface positions that are assigned using this algorithm.

(ii) Surface Algorithm 2: Concurrent variation in n subgroups matched against a polar residue: In a cluster of subgroups with a defined MPI, variation at a position concurrently in n subgroups at a defined MPI, where n is two or greater, when at least one of the nonvariable subgroups contains a hydrophilic amino acid (Arg, Lys, Asp, Glu, Asn). The reliability of the algorithm increases with increasing n, increasing MPI, and increasing number of polar residues. Preferably n is 2 or greater, and MPI is 80% or greater. The larger the number of sequences in the alignment (other factors being equal), the greater the fraction of the surface positions that are assigned using this algorithm.

(iii) Surface Algorithm 3: Polar single variable: In a cluster of subgroups with a defined MPI, variation in one subgroup, where the variable subgroup contains at least one a hydrophilic amino acid side (Arg, Lys, Asp, Glu, Asn), and the non-variable subgroups contain no amino acids other than (Ala, Cys, Asp, Glu, Gly, His, Lys, Asn, Pro, Gln, Arg, Ser, or Thr). The reliability of the algorithm increases with increasing n, increasing MPI, and increasing number of polar residues. The larger the number of sequences in the alignment (other factors being equal), the greater the fraction of the surface positions that are assigned using this algorithm.

(iv) Surface Algorithm 4: Polar Split: In a cluster of subgroups with a defined MPI, all subgroups are non-variable, all subgroups contain no amino acids other than (Ala, Cys, Asp, Glu, Gly, His, Lys, Asn, Pro, Gln, Arg, Ser, or Thr), and at least one subgroup containing one of the amino acids (Arg, Lys, Asp, Glu, Asn).

Depending on the branching of the evolutionary tree of the proteins in the alignment, it is often possible to use only the strongest surface algorithms to identify a majority of the positions that lie on the surface of the folded structure. This is the case with Example 1. With alignment containing only a few proteins, weaker surface algorithms must be used. This is illustrated in Example 2. In every case, surface assignments can be revised in light of information developed at later stages in this procedure. This revision is necessary because, although the surface algorithms are highly accurate, they are not perfectly accurate. For example, Table 6 shows data for estimating the quantitative reliability of Surface Algorithm 1 for the protein alcohol dehydrogenase (Adh)

Step 5. Assign interior positions

Positions in the alignment that contain amino acids whose side chains lie inside the folded structure are identified by interior algorithms. These algorithms are in many respects the converse of surface algorithms. They identify conservation (rather than variation), and hydrophobic residues (rather than polar residues). The significance of conservation is greater in subgroups with lower MPI values than with high MPI values. As with other algorithms, interior algorithms have different degrees of reliability. The surface algorithms find the positions in the alignment that have following structural features, and assigns the side chains of amino acids at these positions to the surface of the proteins. The algorithms are illustrated in Table 7, and listed below in order of decreasing reliability:

(i) Interior Algorithm 1: APC hydrophobic. A hydrophobic residue (A,F,I,L,M,V,W,Y) conserved in all proteins in an alignment. The reliability of this algorithm decreases with increasing MPI.

(ii) Interior Algorithm 2: Hydrophobic variable. In a cluster of subgroups with a defined MPI, variation at a position concurrently in n subgroups at a defined MPI, where n is two or greater, when no subgroup contains a hydrophilic amino acid (Arg, Lys, Asp, Glu, Asn) or a neutral amino acid (C,H,Q,S,T). The reliability of this algorithm increases with decreasing MPI for all proteins in the alignment.

(iii) Interior Algorithm 3: Hydrophobic split. In a cluster of subgroups with a defined MPI, a position where no subgroup displays variability, and where all subgroups contain either hydrophobic or neutral residues at this position. The reliability of this algorithm increases with decreasing MPI, and with increasing numbers of proteins in the alignment.

(iv) Interior Algorithm 4: Hydrophobic single variable. In a cluster of subgroups with a defined MPI, variation in one subgroup, where all subgroups contain only hydrophobic residues.

(v) Interior Algorithm 5: Preponderance of hydrophobic residues. In all proteins at this position, a high percentage (>85%) contain a hydrophobic amino acid. The reliability of this algorithm increases with decreasing MPI for all proteins in the alignment, and with increasing percentage of hydrophobic residues.

Step 6. Assign active site residues

Side chains bearing functional groups (C,D,E,H,K,N,Q, R,S,T,Y) that are conserved across the entire alignment are tentatively assigned to an active site. Cysteines involved in the formation of disulfide bridges are excluded in this analysis. This assignment is rigorous only when the overall divergence of the family of proteins contains pairs of sequences with a pairwise identity of less than 50%, more preferably less than 35%. The assignment is most reliable for C, H, and S. Charged side chains (D, E, K, and R) are often conserved during divergent evolution because they play a structural role in the folding of the polypeptide chain. T and Y are only occasionally at the active site; they are often highly conserved when they are part of a core structure. Thus, all active site assignments must be confirmed.

Confirmation of active site assignments involves identifying conserved strings in subgroups of proteins with different overall minimum pairwise identities. In subgroups with a MPI of 30–45%, APC dipeptide strings are indicators of an active site; APC tripeptides are strong indicators. In subgroups with a MPI of 45–60%, APC tripeptide strings are indicators of an active site; APC tetrapeptides are strong indicators. In subgroups with a MPI of 60–70%, APC tetrapeptide strings are indicators of an active site. The conserved strings can be broken by 1 or 3 interspersed non-conserved positions; in these cases, an active site beta strand and an active site helix are indicated, respectively. In subgroups of proteins having higher MPI values, longer conserved strings can occasionally be used to confirm an active site assignment. However, in these cases, conservation is often so widespread in such subgroups as to make such an analysis not particularly valuable. The strongest active site assignments are those based on an APC functional residue embedded in an APC dipeptide in a subgroup with MPI=30–45%, which is in turn embedded in a APC tripeptide in other subgroups of the same alignment with a MPI of 45–60%, which is in turn embedded in a APC tetrapeptide in other subgroups of the same alignment with a MPI of 60–70%.

Active sites create problems in assigning secondary structures, as the constraints on divergence arising from a catalytic or binding role are generally greater than those that manifest themselves in the patterns of conservation and variability that indicate a particular standard secondary structural element. Thus, active site segments are generally assigned an active site coil designation, unless the pattern of active site assignments themselves indicates a 3.6 residue or 2 residue periodicity.

Occasionally special circumstances in a family of proteins can be used to assign active site positions. This is especially the case when the function of members of a protein family has diverged, and patterns of variation in sequences can be detected that are responsible for this divergence of function can be identified. While these assignments are normally unique for each class of protein studied, and are illustrated for alcohol dehydrogenase in Benner [(1989), op. cit.].

Finally, knowledge of the catalytic function of an enzyme can suggest to one skilled in the art particular catalytic roles for individual active site residues. Often, these roles imply a relative spatial arrangement of these residues, and hypotheses concerning this spatial arrangement can help constrain the folding of a polypeptide chain.

Step 7. Assign secondary structure.

If a secondary structural unit sits in the folded form asymmetrically with respect to functional or structural features, then alpha helices and beta strands will make themselves apparent by 3.6 and 2 residues periodicity in the patterns of conservation and variation. The strongest assignment is made when the functional constraints on sequence divergence are the most asymmetrically disposed with respect to the two sides of the secondary structural unit. Thus, alpha helices that lie in the folded structure at the interface between the solvent and the core of the protein are essentially completely found by the method of the present invention, and no segments that are not surface helices are assigned as surface helices by this method.

In this approach, a dialectic method is used. First, a "canonical" assignment of secondary structure is made using simple rules. Other assignments are then said to have the burden of proof, meaning that the canonical designation is accepted unless the alternative designation is supported by the preponderance of evidence. In attempting to have other assignments meet this burden, the biological chemist is expected to construct as strong an argument as possible to set in opposition to the canonical assignment. This includes making ad hoc assumptions, restructuring the alignment, and questioning the assignments of positions to the surface and the interior of the protein.

Standard procedure in attempting to detect a helical segment involves mapping the surface/interior positions on a helix wheel. Should a pattern of amphiphilicity not be seen, positions are dropped from the ends of the segment, working towards the center, to determine whether the segment contains a subsegment that does display a 3.6 residue periodicity in conservation or variation. A canonical helix is assigned if amphiphilicity is seen over a segment 6 positions or longer. The effect of this procedure is to drop surface assignments at the ends of a helix when they fall in the "inside" face of the helix; this is not irrational, as many positions on the hydrophobic side of an amphiphilic helix lie on the surface when they are at the end of the helical structure. Further, this procedure has the effect of dropping loops with hydrophobic anchors at the end of helical segments.

If the pattern remains non-amphiphilic, the helical wheel is examined to identify assignments that, if changed, would create an amphiphilic helix. This provides a set of ad hoc assumptions (e.g., the helical assignment can be made if a particular assignment is incorrect). Then, the procedure is begun again, but this time beginning with the strongest assignments and working towards the weakest. The goal of this process is to find the strongest possible argument that the segment is helical. Quite often, the segment will be assigned to some other structure canonically, and this argument will serve only to establish a dialectic with respect to the canonical assignment.

There are several reasons why positional assignments might be incorrect. For example, in multimeric proteins, the most common interior misassignments are positions that lie on the surface of a subunit but form a subunit-subunit contact. The biological chemist must be aware of these complications when building models. Indeed, in alcohol dehydrogenase, such ambiguities can be used to advantage, as subgroups within the protein family are dimers while others are tetramers, and contact sites can be predicted based on patterns of sequence divergence and conservation (Benner (1989) op. cit.). Analogous problems are also expected when the protein interacts with a membrane.

The standard procedure for assigning a beta strand is to map a segment on an alternating template. Beta strands are rarely as obvious as alpha helices by this process when the entire alignment (with MPI<40%) is examined. Therefore, several expedients are adopted.

First, beta strands are often internal structures, and therefore appear as strings 2–8 positions long with consecutive interior assignments. [M. J. E. Sternberg and J. E. Thornton, "On the conformation of proteins: An analysis of beta-pleated sheets", *J. Mol. Biol.* 110, 285–296 (1977)]. A hydrophobic stretch of this length is canonically assigned as an interior beta strand. Further, the pattern of variability of a putative internal beta segment is apparent as a progression from less conserved to more conserved to less conserved, with this pattern superimposed on an alternating pattern. Such structures are normally highly ordered, with splits at MPI>50%, and are not easily mistaken for surface helices or coils and loops.

Nevertheless, two major ambiguities remain in our approach in assigning beta strands. First, very short beta segments (2 amino acids) are generally difficult to assign correctly. Second, surface beta strands are often confused with surface coils. The latter may be an intrinsic limitation of any method that builds structural models from a set of homologous proteins, as the conformation of surface beta strands is not necessarily conserved during divergent evolution.

A string of four consecutive surface assignments is canonically assigned as a surface loop, an assignment that is rationalized by the classical argument that four consecutive polar amino acids in a single protein sequence indicates a surface loop or turn [F. E. Cohen, R. M. Abarbanel, I. D. Kuntz, and R, J. Fletterick, Secondary structure assignment for alpha/beta proteins by a combinatorial approach, *Biochemistry* 22, 4894–4904 (1983); F. E. Cohen, R. M. Abarbanel, I. D. Kuntz, R, J. Fletterick, "Turn prediction in proteins using a pattern-matching approach", *Biochemistry* 25, 266–275 (1986)]. Often a surface loop is observed to have a single position where a hydrophobic amino acid is found (often hydrophobic variable). This is termed a "hydrophobic anchor for the loop, and serve as indicators of short loops.

In assigning secondary structures to parsed segments that are not coils, it is useful to classify the segment by the number of surface and interior assignments that it contains. This is done below.

Segments containing both surface and inside assignments. Such structures can be surface helices, surface beta strands, or surface coils. If the segment is longer than 6 positions, the possibility that it forms a surface helix is first considered. The entire segment is diagrammed onto a helix wheel. Then, subsegments are sought where the surface and inside assignments are rigorously amphiphilic. The positions at the beginning and end of the subsegment that break amphiphilicity (position $i_N$ and $i_C$) are then identified. A helix is tentatively assigned between positions $i_N$ and $i_C$, with the "inside arc" being that side of the helix wheel from which protrude positions assigned to the inside, and the "surface arc" being that side of the helix wheel from which protrude positions assigned to the surface protrude. This is the primary tentative helix assignment.

To generate the secondary tentative helical assignments, the positional assignments that break amphiphilicity are assumed to be incorrect. Starting with the helix wheel generated above, two helical wheels are constructed, one continuing towards the amino terminus, the other continuing towards the carboxyl terminus. The next assignments that break amphiphilicity next found. If these amphiphilicity breakers are at position $i_N-1$ or $i_N-2$ (continuing towards the amino terminus), or at position $i_C+1$ or $i_C+2$ (continuing towards the carboxyl terminus), the tentative helix is terminated at positions $i_N$ and $i_C$, and no secondary tentative helix assignments are made. If an amphiphilicity breaker is at position $i_N-3$ or $i_N-4$ (continuing towards the amino terminus), or $i_C+3$ or $i_C+4$ (continuing towards the carboxyl terminus), a second, longer tentative helix is also tabulated beginning and ending at these positions.

Should the pattern of amphiphilicity not be broken a positions $i_C-1$, $i_C-2$, $i_C-3$ or $i_C-4$ (continuing towards the amino terminus), or $i_C+1$, $i_C+2$, $i_C+3$ or $i_C+4$ (continuing towards the carboxyl terminus), the helix diagrams are extended in both directions until another amphiphilicity breaker is encountered, and the process repeated.

The tentative helix assignments are confirmed and refined based on the fact that during divergent evolution, helices can undergo partial reorientation with respect to the folded structure. This reorientation occasionally manifests itself in the pattern of conservation and divergence in the alignment, and when such manifestations are observed, they can confirm a helix assignment, and allow the biological chemist to refine the extent of the helix assignment.

This process focuses on assignments that break amphiphilicity (inside assignments that fall in the surface arc, or surface assignments that fall in the inside arc), and assignments that lie in the two boundary regions between the surface arc and the inside arc, especially amphiphilic splits in these regions. The alignment is divided into subgroups, and inside and surface assignments are made for the subgroups of proteins individually where those assignments are consistent within the subgroup. Then, helix wheels are constructed to determine whether the misassignments apply to only some subgroups of proteins in the alignment and whether the misassignments can be reconciled with different helix orientations and/or different helix lengths in different subgroups of proteins in the alignment.

In some cases, a single turn at the end of a helix has been deleted during divergent evolution. A gap of 3 or 4 amino acids at the end of a putative helix can support a helix assignment.

Should a 3.6 residue amphiphilicity not be observed, and if the segment is shorter than 7 amino acids, an assignment as a coil or a beta strand is plausible. Each segment is also diagrammed on an alternating strand template to detect patterns of 2 residue periodicity that indicates a beta strand. Alternating inside and surface assignments that continue for 4 or more positions are assigned a surface beta structure.

More common with beta strands is a subsegment of 3 or more internal residues embedded in a parsed segment 10 positions or shorter. Again if no 3.6 residue periodicity is observed, a beta strand is assigned to the subsegment. This assignment can be confirmed by looking for 2 position periodicity in the parts of the segment flanking the subsegment.

Segments that have no surface assignments. Consecutive internal positions 3–6 amino acids long are assigned as beta strands, with the assignment confirmed as noted above.

Extended internal segments are either internal helices or a set of internal internal beta strands. The simplest approach for identifying internal helices is 3.6 position periodicity, especially that involving APC positions, splits, or active site residues. Alternatively, internal beta strands often manifest 2 position periodicity in this respect.

The most difficult important problem arises when an extended internal structure displays neither periodicity with statistical significance. The key to distinguishing between an internal alpha helix and an internal beta strand in this case comes from an estimate of the dimensions of the folded structure of the domain. This information can be obtained experimentally for single domain proteins, by sedimentation, diffusion, viscosity, or other methods known to those in the art. In the absence of experimental data, a single domain protein is assumed to be spherical, and the size of the core structure estimated from the length of the core sequence. For multidomain proteins, or in the absence of experimental information, domain size is assumed to be 20–30 Å across.

Underlying the assignment of internal structures is the generalization that secondary structural elements (alpha helices, beta strands) do not end in the middle of a folded structure. A beta strand traverses 3.2 to 3.4 Å per residue; an alpha helix traverses 1.5 Å per residue. A typical domain size is 20–30 Å across. Thus, a helix that traverses the domain must be no shorter than 13 amino acids. In contrast, an beta strand that traverses the domain is no longer than ca. 10 amino acids. A shorter helix can, of course, traverse a domain obliquely. However, amphiphilicity is generally seen with such helices at the ends.

Thus, if the extended internal segment is 13 amino acids or longer, an internal helix is assigned. If it is less than 13 amino acids, an internal beta strand is assigned. These assignments are canonical, and alternative assignments can be made if they meet a burden of proof. The most plausible alternative assignment for an extended internal segment longer than 13 positions is a set of bent beta strands. In these cases (Example 1), secondary parses are sought that might break the beta strand. Further, in cases where the segment passes near the active site, parsing elements are possibly obscured. In this case, the structure may be bent at the active site position.

Extended segments that have no inside assignments. Extended stretches having no inside assignments are assigned as surface coils [Cohen et al. (1983) op. cit.]. Usually such an assignment is confirmed by a deletion in one position of the alignment. Often, such coils have a single inside assignment that serves as a hydrophobic anchor.

Step 8. Orient secondary structural elements with respect to each other

Secondary structural predictions based on the assignments described above typically identify better than 90% of the secondary structural units in a protein, with the residue-by-residue assignments of secondary structure correct over 70% of the time. The principal shortcomings of the method of the present invention are occasional misassignments of surface beta strands as surface coils (and vice versa), difficulties in assigning a conformation to strings near the active site (where functional conservation and adaptive variation often obscure patterns of conservation and variation that might otherwise indicate a particular secondary structure), difficulties defining precisely the beginnings and ends of the secondary structural elements, and difficulties distinguishing long internal bent beta strands from internal helices.

The first three difficulties do not as a rule obstruct the building of a supersecondary or tertiary structural model. Homologous proteins have similar, but not identical structures. Among homologous proteins, the beginnings and ends of secondary structural elements are not normally conserved during divergent evolution more precisely than ±1 amino acid. With the de novo prediction of protein kinase, the ends of the secondary structural units were predicted to ca. ±1.5 residues, perhaps the best that can be obtained using a method based on a comparison of homologous sequences [Benner (1992) op. cit.]. Similarly, missing non-core structures does not normally obstruct the building of a supersecondary or tertiary structural model.

Only the last difficulty seriously hinders the assembly of a supersecondary or tertiary structure, as a mistake in assigning a core secondary structure almost always prevents the building of a tertiary structural model for a protein domain.

Assembling a supersecondary or tertiary structure is simplified if the secondary structural units form a recognizable supersecondary pattern, or fall into a particular taxonomical class of protein fold [J. S. Richardson, "Anatomy and Taxonomy of Proteins", Adv. Prot. Chem. 34, 167–339 (1981)]. Further, if the protein contains disulfide bonds, or if chemical modification studies suggest that certain parts of the chain are close in three dimensions, this constrains the number of different types of folded structure that the protein can adopt.

However, the most general method for assembling a supersecondary or tertiary structure involves bringing the active site positions, scattered throughout the alignment, together in a way that is mechanistically plausible. This process also constrains the number of different types of folded structure that the protein can adopt. While each protein family is individual in this process, Example 1 shows how this can be done.

Step 9. Covariation analysis

Once a tentative model of the supersecondary or tertiary structure is in hand, it can be examined by looking for covariation, a pattern of conservation and variation that suggests that amino acid substitutions at distant parts of the alignment are not occurring independently. This in turn suggests that in the folded structure, these positions are not distant in space.

Scope of This Invention

For reasons that will be readily appreciated by those skilled in the art, the method of the present invention is most generally applicable to monomeric enzymes that are water soluble. The method is less satisfactory for enzymes that aggregate, or form multimers in solution, although predictions for dimeric and tetrameric enzymes are still quite reliable using this method. The method is still less applicable to enzymes that reside under physiological conditions bound within membranes.

EXAMPLES

Examples are provided concerning three proteins to illustrate how to make structure predictions.

The first, for protein kinase, is an example where an abundance of sequence information is available. This is the case where a secondary structure prediction was made before crystallographic information was available, and where a subsequently obtained crystal structure showed the prediction to be remarkably accurate.

The second, concerning pathogenesis related proteins from plants, considers a case where relatively little sequence information is available. At the present time, no crystallographic information is available for any member of this protein family.

Example 1

Predicting the Structure of Protein Kinase

The protein kinases form a large family of homologous proteins, with sequences of nearly 100 protein kinase catalytic domains available from work in many laboratories [S. K. Hanks, A. M. Quinn, and T. Hunter, "The protein kinase family: Conserved features and deduced phylogeny of the catalytic domains", Science 241, 42–52 (1988)]. Thus, this example serves to illustrate the application of the method of the present invention to an extremely large alignment, the most preferred embodiment of the method of the present invention.

It is worth noting at this point that several groups have attempted to predict the folded structure of the catalytic domain of protein kinases using classical approaches, and that all of these predictions have been far from the mark. For example, a prediction by Shoji et al. [S. Shoji, D. C. Parmelee, R. D. Wade, S. Kumar, L. H. Ericsson, K. A. Walsh, H. Neurath, G. L. Long, J. G. Demaille, E. H. Fischer, and K. Titani, "Complete amino acid sequence of the catalytic subunit of bovine cardiac muscle cyclic AMP-dependent protein kinase", Proc. Nat. Acad. Sci. 78, 848–851 (1981)] using a Chou-Fasman algorithm found three regions of the catalytic domain with different secondary structures, the first (positions 1–98 in the alignment discussed here) being highly (79%) helical, the second consisting of 3 "subdomains" (positions 99–146, 147–188, and 189–251) each consisting of a beta strand followed by two alpha helices and separated by two beta turns, and the third (252-end) being highly aperiodic (only 18% alpha helix and 20% beta strand). Other predictive work has focused on the fact that the amino terminal portion of the domain has the sequence GXGXXG, a sequence that is conserved in most members of the family. Such a sequence is also found in the "Rossmann fold", an α-β-α supersecondary structural unit that is present in several proteins that bind nucleotides and dinucleotides. Thus, several authors have suggested that this supersecondary structural unit is formed by the catalytic domains of protein kinases.

The typical protein kinase is expected to fold to give a globular structure, with a mean radius of ca. 26 Å. [E. A. First, S. S. Taylor, "Selective modification of the catalytic subunit of cAMP-dependent protein kinase with sulfhydryl-specific fluorescent probes", *Biochemistry* 28, 3598–3605 (1989).]

Step 1: Obtain an alignment: An alignment of the sequences of the catalytic domains of a set of protein kinases was constructed [Benner and Gerloff (1991) op. cit.]. The alignment is shown in Table 8, where individual protein sequences are read vertically downwards. The first column of numbers in Table 8 are the alignment numbers. These are used throughout this example to designate specific positions in the protein alignment. The second column of numbers contains the sequence number from mouse recombinant cAMP-dependent protein kinase. This is the enzyme for which a crystal structure was solved subsequent to this prediction. Further, the proteins in the alignment have been divided into 12 "functional subfamilies", sets of enzymes performing analogous functions, as indicated in the caption to the Table. Each column in Table 8 (including the gaps) has a "protein number" (from 1 through 90) which is used throughout the text to designate specific proteins.

Step 2: Divide Alignment into Subgroups: A matrix showing the pairwise identity of each sequence used here is shown in Table 9. The MPI values for the individual functional subfamilies is given in the caption to Table 9.

Steps 3–6: Assign parses, surface positions, interior positions, and active site positions. Table 10 shows, by alignment number, the surface, interior, hydrogen bonding variable, and parsing assignments made for the positions in this alignment.

Step 3: Divide the sequence into segments using parsing algorithms. Given the large number of sequences in the alignment, the first phase of the parsing can be executed using only the strongest parsing algorithm. Weaker parses are used when the individual segments are analyzed while assigning secondary structure.

It should be noted that in most of the proteins examined here, position 1 is not the first in a separate polypeptide chain, but is normally fused to a transmembrane region, from which it can be released by proteolysis. Such proteolysis often occurs in coils or loops, providing independent support for the canonical assignment. In the cAMP-dependent kinases specifically, the polypeptide chain begins 30–40 amino acids before the beginning of the alignment. It is conceivable that this leading segment adopts a standard secondary structure. If so, this structure is almost certainly broken by a distributed parse at positions −7 to −5 (where the alignment in Table 8 starts at position 1).

Primary Parse 1: 23-25-41-42. The first deletion parse is associated with a major insertion at positions 25–38. The parse is confirmed by parsing strings in some of the inserted sequences. For example, in protein 80, there is a PPNG sequence. The parse is reinforced at its amino end by P scattered in positions 23 and 24 in proteins where there is no insertion. It is reinforced at its carboxyl end by scattered P and deletions at positions 39–42. Further, alignment anchors at positions 44 (CM1 A) and 46 (APC K) make the alignment here indisputable.

Primary Parse 2: 49-50-59-61. There is a major insertion at positions 54–59. The parse is confirmed by parsing strings within several insertion. For example, protein 36 has a GGGGGGG string at positions 53–59. The region of disrupted secondary structure extends strongly on the amino end of the deletion. Scattered P's are found starting at position 49. Residues are deleted as early as position 49 (in protein 44), and a PP sequence is found at position 53–54 in proteins 70–72 (MPI=80%), and a PG at 50–51 (proteins 56–60, 63, MPI=70%). The parse cannot be extended on the carboxyl terminus. The single deletion in protein 29 at position 60 is probably a misalignment; an R can be moved from position 51. There are scattered P's in positions 60–65, but not sufficient to extend the parse in this direction. Alignment anchors at positions 47 and 67 (APC E) make the alignment here secure.

Primary Parse 3: 74-75-80-83. There is a major insertion at positions 75–80. The parse is confirmed by parsing strings within the insertion. For example, protein 17 has the sequence GGRGPGG at positions 74–80. The parse might be weakly extended on the amino terminus by a deletion at position 74 in proteins 52–54 which is not easily realigned, but no further. There are scattered P at positions 81 and 82, and a widely distributed P at position 83. The deletions in protein 14 at positions 81–83 are probably an alignment error; a KPP sequence can be moved down from positions 76–78 moving the deletion to these positions.

Primary Parse 4: 94-95-100-103. There is a major insertion at positions 96–100. The parse is confirmed by parsing strings within the insertion. For example, protein 52 has the sequence PAGSN at positions 96–100. The parse might be weakly extended on the amino terminus by a deletion in only one protein at position 94 (a deletion that cannot be accounted for by an alignment error), but no further. There are scattered P at positions 101–103; this segment is PP in two proteins (67 and 68, MPI=80%).

Primary Parse 5: 111-113-114-114. There is a 1-2 amino acid insertion at positions 113–114. The parse might be weakly extended on the amino terminus back to position 108, where the first P's are found. However, the P's do not appear to be significant before position 111. The parse cannot be extended on the carboxyl terminus. If the proteins containing the insertion are removed from the alignment, a secondary parse (a conserved GG string) would remain, thus confirming the parse.

Primary Parse 6: 123-126-128-132. There is a 3 amino acid insertion at positions 126–128. The parse is weakly confirmed by parsing strings within the insertion. For example, protein 36 has the sequence PPPG at positions 124–127. The parse might be extended on the amino terminus by a deletion at position 123, supported by P an G. However, as the preceding segment is assigned as a helix (vide infra), and a 3 amino acid deletion is found in proteins 39 and 40, this could indicate the loss of a single turn of a helix. There are scattered P at positions 129–132; the distribution does not make a strong case for an extension of the parse, however.

Primary Parse 7: 167-170-176-176. There is a major insertion at positions 170–176. The parse is only weakly confirmed, however, by structure disrupters within the insertion (a lone P in protein 81 at position 173). The parse might be weakly extended on the amino terminus by scattered P at positions 167–169. The sequences NG (proteins 5–8), PG (protein 26) and a deletion (protein 76) at position 169 make this extension at least plausible for a single position. However, the parsing element cannot be extended on the carboxyl side.

Primary Parse 8: 190-194-197-200. There is a 2 to 4 amino acid insertion at positions 194–197. The parse is weakly confirmed by P's scattered within the insertion, including a weak distributed parse in functional group 7 (MPI=35%) (positions 196–197). The parse might be extended on the amino terminus by a scattered P's back to position 190. Further, P's are scattered throughout the next segment leading to Primary Parse 9. Especially notable is a strong secondary parse at position 209, a conserved P. A PP sequence is found in proteins 46, 65, 80, and 84 (MPI <35%). Thus, it is difficult to terminate this parsing region at the carboxyl end.

Primary Parse 9: 213-213-216-220. There is a major insertion at positions 213–216. The parse is not confirmed, however, by parsing strings within the insertion. The parse cannot be extended on the amino terminus. Thus, it is appropriate to examine the alignment in this region. The APC E (position 210) and CM3 P (position 209) firmly anchor the alignment on the amino end. The APC E is normally an indicator of an active site residue, as is the presence of conserved strings 4 positions (and longer) in length in subgroups with MPI values below 50%. The alignment is solidly anchored on the carboxyl side of this parse by positions 227, 228, and 229. There is, a highly conserved P at position 209 which may indicate a secondary parse (see above). Scattered P's are found at position 218 and 220; none are found at 217 or 219. Thus, it is difficult to extend the parse in the carboxyl direction.

Primary Parse 10: 223-224-224-225. There is a 1 amino acid insertion at position 224 in proteins 28–31(MPI=50%). However, if the sequences of proteins 28–31 is shifted up by one position in the alignment between positions 217–224, the gap disappears. In its place remains a distributed parse extending from position 218–225 in the serine protein kinases (functional groups 1–7), but not in the tyrosine protein kinases. This parsing element is strong. A single deletion is found in protein 36 at position 220.

Primary Parse 11: 241-241-241-241. There is an insertion of a single amino acid at position 241. The parse is not confirmed by parsing strings in this insertion, nor is it confirmed on either side. The insertion might be an alignment problem; shifting the sequences of proteins 1–54 up by one position would move this deletion down to the major deletion that follows. However, the two plausible alignment anchors at positions 245 and 246 would be disrupted by this shift.

Primary Parse 12: 244-249-259-263. There is a major insertion at positions 249–259. The parse is confirmed by structure disrupters within the insertion. For example, protein 44 has the sequence PRGP at positions 250–253. The parse can be extended on the amino terminus by a deletion at positions 247–248, and scattered P back to position 244, with a highly conserved P at position 245. Widely scattered P's are present at positions 260–263, although the fact that the following segment is possibly an alpha helix could indicate that this segment involves the presence or absence of a single turn of a helix.

Primary Parse 13: 272-280-285-289. There is a single amino acid insertion at position 273. The parse is confirmed by 2 P's in the insertion. There are also 5 P's at position 272, and protein 36 has a PP sequence in this segment. On the carboxyl end, P's are scattered all of the way until position 276. Thus, it is difficult to end the parse. Position 275 may be a hydrophobic anchor for an external loop. Further, and most seriously, the parse might be collapsed by shifting the residues in functional subfamilies 1–4 up by one position. For this discussion, the alignment has therefore been realigned to remove the deletion at position 273.

There is a major insertion at positions 280–285. The parse is confirmed by scattered P's within the insertion. For example, protein 26 has the sequence PWPS at positions 281–284. The parse is almost certainly extended on the amino terminus by a deletions up to position 276; these cannot be accounted for by a misalignment. Further, P's are densely scattered back to position 276. Finally, disrupting sequences can be found in this region; a PPP is found in protein 42 at positions 276–278. On the carboxyl end, scattered P's are found from positions 286–289. However, the fact that the following segment is possibly an α helix could indicate that this segment involves the presence or absence of a single turn of a helix.

Primary Parse 14: 314-314-318-320. There is a major insertion at positions 314–318. The parse is only weakly confirmed by parsing strings within the insertion. The parse cannot be extended on the amino terminus. However, a few P's at position 320 might weakly extend the parse to this position.

It is worth noting that the end of this alignment does not correspond to the end of many of these proteins. It is, however, the end of the alignable catalytic domains. Thus, the end of the protein is not necessarily a strong parsing element in these cases. In functional subgroups 2, the sequence extends 12 positions before an apparent parse. An apparent parse is found in functional group 8 only two positions past the end of the alignment.

The regions of the alignment included in the deletion parses are assigned as surface coils, loops, and turns. Such structures are strongly indicated for the alignment numbers indicated in bold face. The extent of these structures is determined in part by the secondary structures assigned to the parsed segments that lie between them. These are considered below.

Step 4: Assign surface positions: Surface positions are identified by the presence of variation in more than one subgroup at different levels of minimum pairwise identities. These are tabulated in Table 10. The column in which an entry is made indicates the number of variable subgroups in a particular cluster of subgroups with a particular MPI, with the MPI of the subgroups designated by the first number in the entry, followed by a period and a number indicating the number of these subgroups that contain at least one polar residue (D, E, K, N, R). Due to the large number of aligned sequences, the assignments should be quite accurate (>95%) and relatively complete (>95% of all surface residues identified). On helix wheels, surface positions are followed by x.y.z, where x is the number of variable subgroups in cluster y, with z the number of subgroups with a polar residue (D, E, K, N, R).

Step 5: Assign interior positions: Interior positions assigned using the algorithms given above are listed in Table 10. Upper case INSIDE assignments are reserved for the more reliable assignments, while lower case Inside" assignments indicate less reliable assignments. On helix wheels, inside positions are indicated boldface.

Step 6: Assign active site positions: Active sites are assigned to every position in the alignment where a functionalized side chain (C,D,E,H,K,N,Q,R,S,T) is conserved across the entire alignment. These are listed in Table 10. Conserved strings are discussed in the appropriate segments.

These assignments can be combined with experimental work that uses chemical modification to identify regions of the protein that are involved in binding ATP and protein substrates. This experimental information is often redundant. However, as certain assignments of active site residues (in particular, assignments to the active site of highly conserved charged residues) are not highly reliable, this extra information is valuable to confirm active site assignments made by our approach.

Step 7: Assign secondary structure. These data are used to construct secondary structural hypotheses for parsed segments of the alignment. A complete secondary structural assignment is presented in Table 11. The segments are designated by the alignment position numbers that they encompass. As noted above, the parses comprise different segments in different branches of the evolutionary tree. Normally, the ends of secondary structural units are expected to be different by one or two residues in different proteins. Therefore, the segments are designated by position number, with the bold face numbers inside the minimum extent of the segment, and the outside number (plain type) the greatest extension of the segment. This is the origin of the maximum and minimum lengths reported in Table 11. The preferred length is tailored to the cAMP-dependent subfamily, as this is the subfamily presently being studied crystallographically. Normally, parses are included as the last position of a helix unless the parse is a deletion.

This variation in lengths presumably represents the fact that the structures of homologous proteins whose sequences have diverged by over 70%, although similar overall, are different in detail. This is, of course, a limitation on any method that builds models from a set of homologous proteins.

Detailed discussions for each of the 15 segments of the alignment created by the primary parses are given below. Helix wheels for these segments can be found in FIG. 3.

Segments 1 and 2. This segment is longer than might be expected for a single secondary structure unit. Further, the second part is largely hydrophobic, the first part largely hydrophilic, and no pattern of amphiphilicity can be found to indicate that it forms a helix. A secondary parse is therefore sought to break the segment into two or more shorter segments. The APC G at position 12 and the CM1 G at position 10 are individually secondary parse; together they make a strong secondary parse. This suggests a break at positions 10 or 12. There are some strings in individual protein sequences that confirm a parse in this region. For example, proteins 67–69 conserve (in a subgroup with an MPI=70%) a GGG string at positions 10–12. GG strings in position 12–13 are found in proteins 9, 46, and 52–55. Further, in protein 44, the T at position 10 that substitutes for an otherwise conserved G is complemented by a P at position 11. Thus, the first segment is parsed into two smaller segments, positions 1–10 (Segment 1) and 12–24 (Segment 2), and the secondary structure of these segments considered separately.

The first segment contains both surface and inside assignments. A helix wheel shows no obvious amphiphilicity across the entire segment. An amphiphilic helix can be built from position 1–14 only if position 8 is regarded as a surface (K=5, 6 variable subgroups, 5 with polar residues), the surface assignment at position 2 is ignored (perhaps justified by the generalization that positions "inside" but at the ends of an amphiphilic helix often lie on the surface), and the surface assignments at positions 5 and 6 are treated as weak. These ad hoc assumptions are weak. For example, the surface assignments for position 6 (13 variable subgroups, 4 with polar residues) and position 11 (10 variable subgroups, 5 with polar residues) are of essentially identical strength. Yet in the amphiphilic helix, position 6 is in the middle of the "interior" region, while position 8 is in the middle of the "surface" face of the helical projection. On these grounds, the assignment as a helix is rejected.

The remaining two possibilities are as a surface coil or as a end beta. As noted above, the method of the present invention often cannot distinguish between these two structures, although the distinction is not particularly critical, as end beta strands do not form the core of a tertiary structure. The scattered P's at positions 5 and 7 and the consecutive surface assignments at positions 4–8 favor assignment as a coil.

The surface assignments in the second segment are weak, especially compared with those that are made elsewhere with such a large alignment. It has a low fraction of surface assignments, a large number of splits, no pattern of helical amphiphilicity, and APC residues (or nearly APC residues) at positions 12, 15, and 17. Thus, the segment from positions 12–20 is treated therefore as an internal segment, and it must be decided whether it is an internal beta strand or an internal helix. With only 9 amino acids (one being a parse), the segment length indicates a beta assignment. Looking to the ends of the strand, one finds alternating patterns of periodicity. In particular, the strongest surface assignments are at positions 19, 21, and 23, an alternating pattern that indicates canonically that this is a beta structure. Essentially no evidence suggests that this segment is an internal helix.

At its greatest extent, the beta strand might begin at position 10, and end at position 23 (14 amino acids). This beta strand is longer than typically found in folded proteins. The strand can be shortened by removing the parsing positions at the beginning of the segment (certainly to position 12, possibly to position 15). Alternatively, the beta strand can be bent at position 15–16 (secondary parse) to form two shorter beta strands, the first 4 positions in length, the second 7.

We have no grounds for preferring a start of the strand at position 12 or 13. The choice of the end point at position 22 is based on the alternating pattern observed in some subgroups of the alignment, and the need to have a sufficient number of filled positions in functional subfamily 7 to execute a standard turn before the next secondary structural segment (vide infra).

This secondary assignment, classed as "moderately reliable", is controversial. This segment contains the string GXGXXG, well-known in proteins that bind ATP and adenine dinucleotides [R. K. Wierenga and W. G. J. Hol, "Predicted nucleotide-binding properties of p21 protein and its cancer-associated variant", *Nature* 302, 842–844 (1983).]. Thus, several investigators, using classical methods, predicted that this segment indicates that the catalytic domain of protein kinases is homologous to other kinases and, in particular, this first region is a strand-turn-helix structure. A particularly convincing case for this is made by Sternberg and Taylor, who compared this region with the NAD+ binding regions of glyceraldehyde-3-phosphate, lactate and alcohol dehydrogenase, and the FAD binding regions of glutathione reductase and p-hydroxybenzoate hydroxylase [M. J. E. Sternberg and W. R. Taylor, "Modelling the ATP-binding site of oncogene products, the epidermal growth factor receptor and related proteins", *FEBS Lett.* 175, 387–392 (1984).]. In these proteins, the GXGXXG sequence lies between a beta strand and an alpha helix (a beta-turn-alpha structure), and Sternberg and Taylor concluded that this region had a similar conformation in the protein kinases discussed here. Thus, the prediction made by classical methods is different from the prediction made by the method of the present invention.

There are no assignments of active site residues in this segment. The absence of active site assignments in this region contradicts an experimental fact, that Lys 7 is protected from modification by acetic anhydride in the presence of Mg-ATP and an inhibitory peptide [J. A. Buechler, T. A. Vedvick, S. S. Taylor, "Differential labeling of the catalytic subunit of cAMP-dependent protein kinase with acetic anhydride: Substrate-induced conformational changes", *Biochemistry* 28, 3018–3024 (1989)], which may indicate that this segment is near the active site.

Segment 3. The proteins of functional subfamily 7 have a gap in the alignment that extends fully from position 25 to position 41. This fact implies that positions 24 and 42 lie close together in space in the other proteins, suggesting that if the beta strands assigned to positions 12–22 and positions 42–48 are part of the same beta sheet, they lie antiparallel. Further, it leads us to terminate the preceding beta strand one residue sooner and start the following beta strand one position later than would be done based on analysis of the first segment alone. There is no evidence for active site residues in the coil.

Segment 4. The dominant feature of this segment are the interior assignments to positions 43 to 46 and 48. Further, there are several hydrophobic splits throughout the alignment, indicating an ordered structure (rather than a coil). This is an internal segment (43–46); from its length, the canonical assignment for this segment is a beta strand. This assignment is confirmed by the alternating pattern at both ends, and is strongly confirmed within the strand by the two-position periodicity in the pattern of conservation and variation, especially evident in subgroups of the alignment with MPI values near 60%. For example, functional group 11 (MPI=50%) has the string 43 (V or C); 44 (conserved A); 45 (I or V); 46 (conserved K); 47 (surface); 48 (V or L); 49 (surface). Thus, this secondary assignment is classed as "very strong".

The most significant evidence for a 3.6 residue periodicity that might suggest an internal helix is the 3 amino acid deletion at the beginning of the segment (positions 39–41) in functional subfamily 7, and the deletion of three amino acids at positions 49–52 with respect to protein 29, and four amino acids (49–53) in protein 44. The strong alignment anchors at positions 44 and 46 fix this deletion. However, these deletions are also consistent with a coil structure at the ends of this segment, and no other evidence appears to suggest a helical assignment for this region.

Position 46 (APC K) is strongly assigned to the active site. This assignment is consistent with experimental data. Lys 46 is modified by fluorosulfonylbenzoyladenine, a substrate analog. Further, when cAMP-dependent protein kinase is treated with dicyclohexylcarbodiimide, it appears that a major product is an intrachain crosslink with Asp 182. Both residues are absolutely conserved, and the modification is blocked by the presence of Mg-ATP [ M. J. Zoller, N. C. Nelson, S. S. Taylor, "Affinity labeling of cAMP-dependent protein kinase with p-fluorosulfonylbenzoyl adenosine", *J. Biol. Chem.* 256, 10837–10842 (1981)].

Segment 5. This segment contains both deletions and parsing elements, and therefore is assigned a coil structure. Protein 44 has the entire region from position 49–59 deleted, implying that positions 48 and 60 lie close together in space in the other proteins. Functional subfamily 8 also deletes much of this region, with parsing indicators present as late as position 63. Functional subfamily 10 (MPI=65%) shows covariation between positions 50 (EEK) and 55 (KKE), consistent with an interaction between these two residues in this subgroup of proteins. The parse in this region has some noteworthy features. Protein 36 has a string of 7 consecutive glycines (positions 53–59). Also, there are 3 consecutive D's in functional subfamily 2 (positions 56–60). The scattered P's at positions 60–63 suggest that the parse might extend as far as position 63. There is no evidence for active site residues in the coil. However, the segment 52–57 could adopt a standard secondary structure in functional subfamilies 1 and 2; a helix is consistent with the sequences in these proteins.

Segment 6. The alignment is well-anchored in this region by the APC E at position 67. On the amino end, the alignment is secure at position 46 (APC K).

From position 64 to 73, the interior and surface assignments map well on a helical wheel (FIG. 3a). Therefore, this segment is canonically assigned as an a helix. This assignment is initially classed "moderately strong", as it involves relatively weak surface assignments. Indeed, the strongest surface assignment based on variable subgroups is at position 65 (9 variable subgroups, K=4). However, only 3 of the variable subgroups at this position have a polar residue (DEKRN). Indeed, the amino acids found at position 65 are largely hydrophobic, and it is also worthy of note that proteins 46 and 61 have P at this position. Position 66 has the largest number of variable subgroups (8) where the variable subgroup also includes a polar residue (7). Position 64 is a functional variable (7 variable subgroups), a strong indicator of an inside position in an alignment this large. This position is also listed as a hydrophobic variable (4 variable subgroups, K=5). Position 65 is also listed as a hydrophobic variable, 2 variable subgroups (K=9,8). The rather weak assignments of positions to the surface suggest that this helix is partly buried, especially when compared with other helices (e.g. the helical conformation assigned to segment 14.

To strengthen (or possibly weaken) the assignment, other indicators are examined. Covariation analysis identifies a few interesting residues that are consistent with a helical assignment in this position. For example, in the three proteins in functional subfamily 10, the residues at position 62 are KKE, while the residues at position 66 are DDR. This pattern of covariation is consistent with an intrahelical contact between the side chains at these positions in these proteins, and provides further support for extending this helix to position 61 in at least some of the functional subfamilies.

The first four positions of this segment (positions 60–63) are assigned to the surface, canonically indicating a coil. Scattered P's in this segment (e.g., conserved in proteins 33–36, MPI=50%, 56–59, MPI=80%) and the parsing string PXP (protein 62) confirm this assignment as a coil. However, a dialectic position is possible that the helix extends another full turn, starting from position 60. In this extra turn, position 63 falls on the inside of the helical projection. As this position lies at the end of the helix, this assignment is not entirely incompatible with the moderate surface assignment at this position (Table 10). However, it is conceivable that the first turn of the helix is missing in proteins in functional subfamily 8 (for example), where the preceding coil is short.

In the preferred assignment (Table 11), the last position is position 74 due to the inside assignment. The choice of position 61 as the first position of the helix is somewhat arbitrary; it was made because the cAMP-dependent protein kinases have a hydrophobic residue at this position, and the parses at positions 60 and 75 match.

Especially noteworthy about this segment is the absolutely conserved E at position 67. This is a glutamate in the middle of the hydrophobic region. Canonically, one assigns an APC E as an active site residue, which would place this helix at the active site. There are, of course, other roles for amino acids with functionalized side chains that are sufficiently important that the residue at that position is highly conserved. For example, in lactate dehydrogenase, an APC E (311) is found in the middle of the final helix, where it forms a hydrogen bond to W 203 (which is also conserved). Likewise, an APC E in alcohol dehydrogenase is found at position 35 in a beta strand not at the active site. In the putative helix in the protein kinase family, there is little to indicate that this segment is at the active site; for example, there is no string of conserved residues at low MPI (compare, for example, the pattern of conservation in the active site helix between positions 46 and 55 in the ADH family). Thus, for future assembly of the secondary structural elements into a folded structure, this helix need not end up at the active site.

In this context, several experimental facts are valuable. First, Glu 67 is especially reactive with carbodiimides, implying that it lies in a hydrophobic region, and the reactivity is diminished in the presence of Mg-ATP ([J. A. Buechler, S. S. Taylor, "Identification of aspartate-184 as an essential residue in the catalytic subunit of cAMP-dependent protein kinase", *Biochemistry* 27, 7356–7361 (1988)], implying that it lies near the active site. Further, the lysine at position 68 appears to be inside the protein fold based on its slow reaction with acetic anhydride.

Segment 7. In functional subfamily 7, all amino acids are deleted from position 74 to 80, indicating that positions 73 and 81 are close in space in the remaining proteins. There is no evidence for active site residues in the coil.

Segment 8 This is the first of several beta-like segments that are broken by secondary parsing segments at several places throughout. Only two strong surface assignments are made after position 84 in this segment, at positions 87 and 94. A third, at position 90, is weak enough to be indecisive. The remaining positions are hydrophobic splits (e.g., at positions 86 and 90, the splits are perfect at MPI=70%). Thus, the canonical assignment for this segment is a beta strand from position 84 to position 93. However, the assignment is classified only as "strong" because it is difficult to confirm this assignment by alternating patterns in the alignment.

Central to this difficulty is the fact that prolines are found scattered throughout this segment, at position 87, and at position 91. These secondary parses are potentially valuable as the beta strand is long, and is probably bent. Position 87 is interesting in this regard. Positions displaying variability of this sort are often found in beta strands that emerge above the surface of the globular protein at a point where the beta strand bends and then continues, in this case until position 93 or 94. The fact that isolated P's are found in proteins 40, 44, 50, and 57 at position 87 supports this picture, as does covariation analysis with the following segment (vide infra). It is worth noting that the lysines at position 87 and 93 appear to be inside the protein fold based on reaction with acetic anhydride [J. A. Buechler, S. S. Taylor, "Differential labeling of the catalytic subunit of cAMP-dependent protein kinase with a water-soluble carbodiimide: Identification of carboxyl groups protected by Mg-ATP and inhibitor peptides", *Biochemistry* 29, 1937–1943 (1990)]. Finally, the carboxyl side chains of E 89 is especially reactive with carbodiimide, and is not protected by substrate, suggesting that it is inside the folded structure but not at the active site.

The parse at the amino end extends strongly to position 83, suggesting that any beta-like structure begins only at position 84. The segment is ended at position 93 in the cAMP-dependent protein kinases (Table 11) because of the deletion in protein 39. The two amino acid deletion could, however, indicate that in the remaining proteins, the beta strand continues two positions further.

Dialectically, one can attempt to assign this segment a helical structure. Positions 84, 87, and 94 can be assigned to the surface with varying degrees of reliability. These map on one side of a helical wheel. Position 90 maps extremely weakly on the surface, and appears on the correct side of the helix. Position 91 violates the amphiphilic helical pattern. Based on the assignments at positions 90 and 91, it is unlikely that this segment is a surface helix; however, a helical assignment might be made if the assignments at positions 90 and 91 were in error. Therefore, the possibility that it is an internal helix, or a helix forming a contact with a membrane or another protein subsegment cannot be ruled out.

However, "functional variable" assignments at positions 85, 86, 91, and 92 are distributed evenly around the helical projection, and offer no support for a helical assignment. Further, none of the 12 helical wheels for the functional subfamilies show convincing patterns of amphiphilicity, either in the pattern of variation or in the polarity of the amino acid residues themselves, largely because position 86 remains firmly inside. Thus, a helical assignment is rejected.

Segment 9. Positions 94–100 contain no amino acids in protein 39, suggesting that positions 93 and 99 are close in space in the remaining proteins. However, protein 39 is among the most structurally divergent in from the bulk of the alignment, and a more reliable hypothesis is that positions 95 and 99 are close together in the folded structures. This implies that if the preceding and following beta strands belong to the same beta sheet, they reside antiparallel. Covariation analysis (vide infra) suggests that this is the case. There is no evidence for active site residues in the coil.

Segment 10. This segment appears to be another long broken beta strand. The alignment is anchored in this region at position 108. Especially unusual is the 2 residue deletion (positions 108 and 109) in protein 5, which is 90% sequence identical with proteins 6 and 8. This deletion corresponds to a single P in functional group 11 (protein 85), and two P's in functional group 6 in proteins 40 and 44. Position 108 is unusual; it is a highly conserved E in the middle of a hydrophobic stretch. This deletion can be moved down in the alignment by realigning the segment; the alignment anchors in this region are not decisive, and this realignment is the basis for the analysis that follows.

The segment forms part of the interior core of the protein, with positions 103–110 all assigned to the inside (position 105 has 5 variable subgroups, K=4, with a single variable subgroup with a polar residue). This is canonically assigned as a beta strand.

Again, the beta strand is rather long, and probably bent at position 108. This notion has an interesting consequence in the context of the assignment of Segment 8. There is substantial covariation between position 87, which has a high proportion of basic residues, and position 108, which has a high proportion of acidic residues. In particular, in proteins 40, 44 and 85, the E at position 108 is replaced by a P, and in all three cases, the basic residue at position 87 is replaced either by a P (proteins 40 and 44) or by an S (protein 85). The covariation is striking in functional group 7, where position 87 has LLPLRRR matched against QQQQEEE at position 108. Thus, it seems to be a reasonable working hypothesis that these beta strands are in close proximity, with the bend at position 87 matched to the break at position 108, with a contact formed between the side chains of the amino acids at these two positions.

Covariation analysis is one of the most problematic ways of finding contacts between distant points in a polypeptide chain. We do not yet have programs to do covariation analysis on an alignment as large as protein kinase. Further, covariation is rarely perfect. However, in the absence of disulfide bonds, it is the only way to constrain the distance between portions of the chain that do not lie at the active site. In any case, it seems certain that covariation analysis is most useful when one already has a structural hypothesis, as is the case here.

Segment 11. This coil has little variability in length, with 2–4 positions. There is some experimental evidence that this coil lies near the active site. When the phosphorylatable serine in the peptide LRRASLG is replaced by the photo-affinity agent, p-benzoylphenylalanine, Gly 113 and Met 116 are modified [W. T. Miller, E. T. Kaiser, "Probing the peptide binding site of the cAMP-dependent protein kinase by using a peptide-based photoaffinity label", *Proc. Nat. Acad. Sci.*, 85, 5429–5433 (1988)].

Segment 12. Positions 115–123 of this segment show a 3.6 residue periodicity indicative of a helix (FIG. 3b). However, the assignment classified only as "strong". A plot of the surface/interior assignments on a helical wheel shows only weak amphiphilicity. Positions 115, 117 and 119 are assigned only weakly to the surface (only 5 variable subgroups K=4). The strongest surface assignment is at position 118, and at 122, but here the amino acid is at the end of a secondary structural element (given the parse that follows), making it unlikely that a surface assignment here would be definitive in ruling in or out a particular assignment.

As shown below, there is reason to believe that the serine and tyrosine kinases are not perfectly aligned in this region. A misalignment has two implications. First, it is difficult to identify secondary structure from an examination of the entire alignment. Second, examining fragments of the alignment should be a more productive way to assign secondary structure.

The segment is flanked on both sides by deletion/insertions of varying lengths. Second, there are no anchors for the alignment within the segment. Indeed, there are essentially no anchors for some distance outside the segment. The Gly at position 113 might be considered as an alignment anchor, but it comes in a loop region. The substitutions at position 106 provide a weak anchor, as might the scattered P in the two main classes of kinases at position 132. However, on the amino end of the segment, the last completely solid anchor is at position 67, although weaker anchors might be found at position 108 (where the ancestral residue is presumably E) and perhaps the hydrophobic element at positions 103–107 (although alignments based on such an orientation can be plus or minus a single residue). The next completely solid anchor on the carboxyl side comes at 155–157 to the carboxyl side, although weaker anchors exist at positions 144, 140 (where Q might be reconstructed as the primitive residue in the common ancestral sequence), and 139 (with A as the common ancestor). Clearly, in between, the alignment is unreliable.

However, when the segment is divided into the 12 functional classes and the data replotted, the helical ambiguity goes away. For example, functional subfamily 3 at position 119 has either the hydrophilic D (proteins 20 and 21) or R (proteins 24, 25, and 26), while the position is the hydrophobic Y in proteins 22 and 23. The distribution is tree-like based on the overall sequence identities of the proteins. The situation is mirrored on the other side of the putative helix. Position 121 has either the hydrophobic V (proteins 20, 21, and 24) or I (proteins 25 and 26), while the position is the more hydrophilic T in proteins 22 and 23. Thus, it appears that in proteins 22 and 23, the helix is rotated a bit "clockwise" with respect to the folded structure of the protein. Table 12 lists the borders of the helix in the different functional subfamilies.

This region illustrates also how information appears at different levels of sequence divergence. Group 2 does not obviously show an amphiphilic helix, and a helical assignment of this segment would not be secure if these were the only sequences available to the biological chemist.

When a helix has become "reoriented" by a residue (a statement that, at the present level of analysis, is equivalent to a statement that the alignment is misconstructed due to a shift of one position), the assignments made across the shift become confused, and assignment of secondary structural elements becomes weaker. However, if a helical pattern is strengthened by assignments based on a partitioning the alignment to avoid including shifted (or misaligned) structures within a single alignment, a "very strong" assignment of secondary structure can be obtained.

For the cAMP-dependent kinases, the preferred helix extends from position 115 to position 124. The fact that position 123, assigned to the surface, appears on the inside face of the helix is acceptable as it is at the end of the helix. The last turn of the helix is probably missing in members of functional subfamily 6.

Segment 13. In proteins 39 and 40, positions 123–128 are deleted, suggesting that positions 127 and 129 are close in space in the remaining proteins. Further, this suggests that the parse extends until position 132, although it can be argued (vide infra) that the following helix begins as early as position 131. There is no evidence for active site residues in the coil.

Segments 14–17. This is the longest unparsed segment in the alignment (41 positions with no insertions or deletions). A helix of this length would have 11 turns, and be approximately 60 Å in length; a single beta strand would, of course, be longer. 60 Å is considerably longer than the expected diameter of a spherical globular protein of this length, implying that there should be an internal parse. The first four positions (129–132) are plausibly coil structures (note the parsing string PXP conserved in part of functional group 1, MPI=80%). A secondary parse is present at position 160. These potentially divide or shorten standard secondary structures that might be assigned to this segment.

However, the most striking features of this segment are the highly conserved strings RDLK and RDLA at positions 155–157. Such strings are assigned canonically to the active site, and are often found in loops or coils, making plausible a break in a helical structure up to this point. Further, the reaction of E 161 with water-soluble carbodiimide is partially by Mg-ATP, and fully blocked in the presence of both Mg-ATP and peptide substrate [J. A. Buechler, S. S. Taylor, "Identification of the peptide recognition site in the catalytic subunit of cAMP-dependent protein kinase", *J. Cell Biol.* 107, 491a (1989)], experimental evidence favoring an active site assignment for this segment.

The segment has the most distinctive alpha helical pattern in the protein, with amphiphilicity extending in a "textbook" fashion from position 131 until 151, over 5 turns (FIG. 3c). Textbook surface helices of this length are essentially never misassigned, making this among the strongest secondary assignments in this alignment.

It is worth a few words to examine the extent to which this helix is confirmed by the details of the pattern of conservation and variation. Position 135 at the boundary between the surface and inside faces of the helical projection is rather weakly assigned to the surface. Although there are 10 variable subgroups at MPI=60%, only 2 contain a polar amino acid. Closer inspection of the alignment shows that the surface assignment comes from subgroups in the serine/threonine kinase functional class; the sequences of the tyrosine kinases alone would yield an interior assignment.

It then remains to determine how far this helix can be extended in either direction. The amphiphilic pattern is disrupted in the amino direction by the surface assignment at position 130 (which is on the inside face of the helix) and by the inside assignment at position 129 (which is on the surface face of the alignment. Position 130 may still be a part of the helix, of course; as noted previously, "inside" amino acids at the end of amphiphilic helices are often found on the surface. However, this implies that the helix does not extend more than a half turn further in the amino direction. This notion is confirmed by the scattered P's at position 132. Again, P can be in a helix, but normally within one turn of the amino end. Based on this reasoning, the amino terminus of the helix is designated as position 131.

The carboxyl end of the helix is more difficult to assign. Position 149 technically breaks the amphiphilic pattern of the helix, but with only 3 variable subgroups (MPI=50%), and only 2 of these having polar residues, this is a weak surface assignment and is not decisive. Positions 150 and 151 are assigned to the surface and appear correctly on the helical wheel. Position 152 is a surface assignment appearing on the "inside face" of the projection, 153 an "inside" assignment on the inside face, and position 154 an inside assignment on the surface face of the helix. These positions mark the end of the amphiphilicity in the helix.

Attempts to extend the helix further are problematic, as the segment now becomes highly conserved and highly functionalized. Consecutive conserved functional residues are strongly assigned to the active site, and functional constraints and adaptive variation often obscure patterns that would otherwise be good indicators of secondary structure.

The helix is rather long (22 amino acids, a bit over 6 turns), with a total length of ca. 33 Å. Thus, it traverses the entire globular structure of the protein, and it is difficult to imagine the active site perched on the end should we extend the helix much farther than position 153. The implication is that the helix must end here, that the parse at position 160 must be a real break in secondary structure, and that the secondary structure of the segment that follows (from position 161–169) must be considered separately.

The remainder of the segment is divided into three segments. The first reflects the possibility that there is a short beta strand at the end of the helix (positions 153–156). This canonical assignment is based on the large number of splits. Unfortunately, this assignment is classified as "weak" because splits near an active site are also indicative of coil structures.

The next subsegment (segment 16) is clearly an active site coil based on the APC D at position 157 and the APC N at position 162.

The following subsegment (segment 17), a string (positions 163–165) of interior assignments, is canonically assigned as a beta strand.

The lysine at position 159 appears to be inside the protein fold based on reaction with acetic anhydride. Further, the carboxyl side chains of E 161 is especially reactive with water-soluble carbodiimide; it is completely protected by Mg-ATP and an inhibitory peptide. This confirms the assignment of this region to the active site [Buechler & Taylor, 1988, op. cit.].

Segment 18. The four consecutive surface positions (166–169) at the end of the previous segment are canonically assigned as a coil. As the deletion in protein 76 starts at position 169, and the alignment is well-anchored in this region, the minimum length of the parsing segment is 2 amino acids, and position 168 is likely to be near position 177 in the remaining proteins. There is no evidence for active site residues in the coil.

Segments 19 and 20. Problems arise because within this segment, differences in the sequences of the different subgroups of the kinases make the alignment difficult to construct reliably. However, these differences cannot be explained as the random variation expected for a segment that lies far from the active site as their is an absolutely conserved triplet DFG at positions 182–184. The conserved triplet is an extremely strong indicator of a segment near the active site.

It is worth noting here is that it is the conserved string of three residues that makes this assignment strong. APC D is known at positions other than the active site, and APC G is often simply a parse. APC F is occasionally found in the center of hydrophobic cores. Thus, each conserved amino acid alone would not be a strong indicator that this segment lies near the active site. Further, nearby positions display reflexivity. For example, at position 186, functional subfamilies 1–7 have A, S, and C, while functional subfamilies 8–12 have A, S, and T. Such reflexivity often indicates a purely structural constraint on divergence. However, a conserved string such as the one present here is essentially never found far from the active site.

Chemical modification studies also suggest that this segment is at the active site. Treatment of a cyclic AMP-dependent protein kinase with carbodiimide yields a protein crosslinked between the side chains of Asp 182 and Lys 46 [J. A. Buechler, S. S. Taylor, "Dicyclohexylcarbodiimide cross-links two conserved residues, Asp- 184 and Lys-72, at the active site of the catalytic subunit of cAMP-dependent protein kinase", Biochemistry 28, 2065–2070 (1989)]. Mg-ATP blocks this reaction. Chemical modification studies support the notion that K 46 lies at the active site, implying that the pair is at the active site.

Extreme variation in sequence near an active site is, of course, anticipated for a set of homologous proteins whose function has undergone divergent evolution. This is a strength of the approach used here, as neither variation nor hydrophilicity is automatically assigned to the surface, but rather only specific types of variation and hydrophilicity. Thus, the variation in this region is interpreted as evidence that this segment forms a structure at the active site that is important for binding the protein substrate. As the structure of the natural protein substrate is quite different for different functional subfamilies, one expects both the sequence and the folded structure of this region to be different in different proteins, meaning that the assumption central to our approach is probably not entirely true in this region of the alignment.

Canonically, a string of inside residues and splits (e.g. positions 177–186; note that the surface assignment at position 177 is weak) is assigned a beta strand structure. Here, it seems plausible to associate the strand at position 182 with the beta strand assigned between positions 42 and 48, primarily on experimental data obtained by crosslinking experiments. As discussed below, these two beta strands appear to be aligned antiparallel to each other. Further, if the first beta strand is bent at position 46, so would the second (at position 182).

Positions 190–193 are assigned to the surface, position 90 strongly in all subgroups of kinases. Four consecutive surface assignments are canonically assigned as a coil. In functional subfamilies 1–6, these positions also contain scattered P's throughout. Thus, the canonical assignment of this subsegment is a coil in this subfamily. However, in other functional subfamilies, other secondary structural assignments are possible, especially as no P's are found at this position in functional subfamilies 7–12. It is important to look closely at these, starting with the functional subfamily with the lowest MPI, as this is the subgroup that retains the most information, provided that the tree within is appropriately branched.

Functional subfamily 7 has a MPI=35%, and is divided into two subgroups (proteins 48–51 and 52–54 respectively) with MPI=80%. Thus, the extent and distribution of diversity of the proteins in functional subfamily 7 is nearly satisfactory for this functional subfamily to serve (by itself) as the basis for an application of our structural prediction method. Indeed, did we not have the other sequences, we would attempt to assign a structure from these 7 proteins alone, although the reliability of the structural assignments would, of course, be much lower than the ones presented here.

The segment in functional subfamily 7 between positions 184 (APC G, viewed as a parse for this discussion) and 191 maps as an amphiphilic helix. At positions 188 and 189, the apparently contradictory assignments (surface and inside) in fact divide exactly according to the two subgroups of functional subfamily 7. Proteins 48–51 are "inside" at position 188 and "outside" at position 189, while proteins 52–54 are "outside" at position 188 and "inside" at position 189. This suggests that the helix is turned slightly in proteins 48–51 in comparison with proteins 52–54, and the pattern strengthens what would otherwise be a weak helical assignment. The segment also contains charge variation at position 191 (R or D) and at position 188 (V or K); this could be covariation indicating a helical structure, but analogous indicators in proteins with known structures are not highly reliable. Nevertheless, the assignment of a helix in this region is satisfactory for us to make it the preferred assignment in this region for this subfamily of proteins.

Two functional subfamilies, 3 and 5, have MPI=45%. In functional subfamily 3, the segment 185–190 could map as an amphiphilic helix, but the clarity of the map is compromised by uncertain assignments at positions 186 and 187. In functional subfamily 5, a helix is possible from positions 185–189, but the number of positions assigned is too small for the amphiphilicity to be significant.

Functional subfamily 1 has a higher MPI (50%), meaning that still more information is lost in the subalignment. Nevertheless, a pattern of amphiphilicity resembling a helix from position 85 to position 189, and possibly to position 193, is observed. The parse at position 190 is preferred based on a comparison with other subgroups, but is not absolute.

It is worth noting that surface assignments made for these subfamilies, are weaker than those made when the entire alignment is considered. For example, position 187 has an APC K (MPI=50%). With a subalignment of so few proteins and such little overall divergence in sequence, it is difficult to tell whether the conservation indicates a functional constraint on drift, or whether it merely indicates that insufficient sequence divergence has taken place for us to have (fortuitously) found a protein where the codon corresponding to this position had undergone mutation. For our purposes here, the position has been assigned as the weakest surface, simply based on the polarity. However, it is worth noting that K 187 is less reactive with acetic anhydride than other lysines in the protein, and therefore appears to be inside the protein fold.

To search for secondary patterns of conservation that might indicate that the active site segment exists in a particular standard secondary structure, the number of conserved subgroups in clusters of subgroups with different minimum pairwise were examined (Table 13). The data show a general trend; conservation falls off in both directions as one proceeds away from positions 182–184. However, in the amino direction, there is a pronounced increase in the conservation at position 179. In the carboxyl direction, the amino acids at position 187 are disproportionately conserved. Notably, these flank the CM1 F at position 183 in a helical projection, not the APC D. This is not unusual in active site helices, where the contact of the helix with the bulk of the protein is the most highly conserved, while the active site residues conserved in a portion of the helix "fade" in one direction as the active site helix moves away from the critical section. Remarkably, at both positions, the predominant amino acid is basic; at position 179 is a Lys, and at position 187 an Arg or Lys. Thus, there is weak evidence for a helical structure here.

The functional subfamilies can also be mapped out on a beta strand template to look for patterns of alternating properties. The underside of the beta strand is clearly more variable than the upper side. This is most evident in functional subfamily 6. but also in functional subfamilies 3, and particularly at positions 177–181. Further, the pattern of alternation from positions 177–181 is evident, making the beta structure more plausible for this segment. Thus, a weak case can also be made that this segment adopts a beta structure.

An expedient that has been used to resolve uncertain cases has been to reconstruct the sequences of ancient proteins using a rule of parsimony and examine their structures. By this process, weak evidence for helix can be found in this region; in the tyrosine kinases, positions 177, 181, and 188 are all indeterminate, and all lie on one side of a helical wheel. However, this region in the reconstructed protein is highly hydrophobic. Still stronger evidence for beta strand comes in subgroup 6, where 177, 179, and 185 are indeterminate, 181 nearly so; 183 is an APC F.

Segment 21. The deletion at positions 194–197 in functional subfamily 1 indicate that positions 193 and 198 are close in the remaining proteins. This region contains the autophosphorylation site for the tyrosine kinases (position 194), a site that may be near the active site. However, there is no evidence from the alignment that this segment is at the active site. Here again, this is most likely because of substantial functional adaptation that has led to sequence divergence within different functional subfamilies of proteins. Notably, the autophosphorylation site in the serine-threonine kinases (at position 199 in the next segment) does not align with the autophosphorylation site in the tyrosine kinases (position 194) in the alignment prepared by Hanks et al. (1988).

Segment 22. This segment appears to be another long broken beta strand. The alignment is not well anchored in this segment. Mobashery and Kaiser [S. Mobashery, E. T. Kaiser, "Identification of amino acid residues involved in substrate recognition by the catalytic subunit of bovine cyclic AMP dependent protein kinase: Peptide-based affinity labels", *Biochemistry* 27, 3691–3696 (1988)] aligned the TWTLC segment against the NEYTA segment in the tyrosine kinases, based on the fact that the middle residue in both is the autophosphorylation site. The change in the alignment is extremely significant. If the residues from the tyrosine kinases presently matched with positions 198–204 remain, the conformation of the segment would be assigned as an active site coil. If not, it would be assigned as an active site beta strand from position 198–203.

The alignment from position 191–228 is heavily laden with parsing elements. Nine of the 29 positions involve deletion/insertions, and 18 of the 29 positions have P in at least one protein. Thus, a full 24 of the 29 positions (83%) are candidates of varying strengths for parses. There are several strong active site assignments. Position 209 is a CM6 P, canonically assigned as a secondary parse; a PP parsing sequence is found in proteins 46, 65, 80, and 84 (MPI<35%) confirms the assignment of a parse at this position. This parse is adjacent to an APC E, canonically designated an active site residue. A distributed parse is found at positions 203–204. Further, in positions 190–201, every residue is assigned to the surface, although the assignments at positions 200 and 201 are relatively weak. Likewise, the segment from 217–225 is largely assigned to the surface.

The pattern of variation and conservation suggests that this segment lies near the active site. From position 202–216, there are no surface assignments, and extremely little variability. Conserved strings and an APC E at position 210 support more strongly an assignment of this segment to the active site. There is ample experimental evidence to confirm this suggestion [H. N. Bramson, N. Thomas, R. Matsueda, N. C. Nelson, S. S. Taylor, E. T. Kaiser, "Modification of the catalytic subunit of bovine heart cAMP dependent protein kinase with affinity labels related to peptide substrates", *J. Biol. Chem.* 257, 10575–10581 (1982); N. C. Nelson, S. S. Taylor, "Differential labeling and identification of the cysteine-containing tryptic peptides of the catalytic subunit of porcine heart cAMP-dependent protein kinase", *J. Biol. Chem.* 256, 3743–3750 (1981)]. As noted above, position 194 is the autophosphorylation site of several tyrosine kinases. Short peptides (e.g. LRRASLG) are phosphorylated by the catalytic subsegment of bovine cyclic AMP dependent protein kinase. When these are modified to introduce reactive groups, Thr 199 (alignment number) and Cys 201 are modified, and these residues are protected by substrate.

The principal difficulty in assigning conformations to segments such as these is to chose between an assignment as an active site coil, or as a set of short beta strands separated by bulges or turns. The first is favored in this case, as there are a large number of parsing elements in this segment. There is a conserved string in subgroup 2 (MPI=50%) (VTLWYR), a canonical indicator of an active site string. We have assigned an active site coil from position 201 to position 212, with the bent or broken at position 203–204 and again at position 209.

Segment 23: Positions 213–216 are deleted in most of the proteins in the alignment. Further, there is a deletion at position 224, a deletion that possibly can be moved by readjusting the alignment. The issue regarding the intervening segment (positions 217–223) is whether or not it adopts a standard secondary structure. Four consecutive surface assignments (positions 217–220) are canonically designated as a coil. Further, parsing elements are found at positions 218, 219, 220, and 223. A coil is the canonical assignment, with position 221 serving as its hydrophobic anchor, a residue that points inside to hold the otherwise external loop in a defined conformation. There is a string SSS in protein 45 (positions 217–219) is also suggestive of a coil.

This conformational assignment may not hold for tyrosine kinases (functional subfamilies 8–12), which do not contain parsing strings or deletions in this region, and otherwise do not appear to be as non structured in this region as the serine-threonine kinases. However, given the problems with the alignment noted above, this matching may be deceptive.

Segment 24: The segment from 226–240 is entirely assigned to the inside; only at position 237 is there an extremely weak surface assignment (two variable subgroups MPI=50% with only one having a polar residue). The region has a large number of splits at low MPI's. Thus, this is an example of an example of an extended internal segment. Thus, the segment is either an internal beta strand or an internal helix. From the length of the segment, the internal helix assignment is canonical, although as indicated above, assigning internal segments is difficult for the method of the present invention.

The alternative assignment is a beta strand much too long to form a single secondary structural unit. For this assignment to be correct, the strand must be broken. The APC G at position 232 is a secondary parse, indicating one break. This creates a beta strand (7–8 residues, positions 225–232) followed by another beta strand (8 residues, positions 233–240), as both internal segments are now too short to be internal helices. Further, the first hypothetical beta strand might be broken by the APC D at position 227.

The patterns at the ends of the segment offer no confirmation for either assignment. Thus, as the beta strand has not met a burden of proof, the segment is canonically assigned a helical structure.

Segment 25. This segment is assign a coil conformation because of the distributed parse at positions 244–245, a presumed hydrophobic anchor at position 246, and the conserved G (secondary parse) at position 242. There is no evidence for active site residues in the coil. Positions 246 and 260 are close in space, as indicated by the deletion in protein 46. There is no evidence for active site residues in the coil.

Segment 26. This segment is not well anchored, and the single amino acid insertion at position 273 might well be collapsed by a shift of the alignment. This would move the beginning of the parse to position 276, possibly adding 2 more positions to the helix in the previous segment. This revised alignment is used in the analysis here.

There is textbook amphiphilicity from positions 260 to 272, suggesting an assignment of a 10 residue helix in this region (FIG. 3d). Helices of this type are only rarely misassigned, making this one of the strongest predictions in this structure. It then remains to determine how far this helix can be extended in either direction. The amphiphilic pattern is disrupted in the amino direction by the surface assignment at position 262 (which is on the inside face of the helix). Position 262 therefore may still be a part of the helix; as noted previously, amino acids on the inside ends of amphiphilic helices are often assigned to the surface. However, this implies that the helix does not extend more than a half turn further in the amino direction. This notion is confirmed by the scattered P's at positions 262, 261, and 260. Further, there is a parsing string PXP in positions 260–262 of protein 9, and the parsing string PP in positions 261–262 of protein 90. Based on this reasoning, the assigned helix begins at position 262.

The carboxyl end of the helix is more difficult to assign. Position 273 breaks the amphiphilic pattern of the helix, but the assignment is generated for the alignment with the deletion at position 273. This alignment is modified to remove the deletion in our final analysis. Likewise, the "correct" (presuming the helical wheel) assignment of position 274 to the surface is less strong in the realigned segment. To match parses (often in surface helices, the parses at the beginning and ends of the helix fall on the same side of a helical projection), there are several choices, as the potential parses at the beginning of the helix at positions 61, 62, and 63 each match with potential parses at the end (261 matches with 272; 262 matches with 273, and 263 matches with 274 in the rearranged alignment). Nevertheless, it is clear that the helix does not extend past position 275 (note the PPP parsing string in protein 42). Thus, positions 262–273 are assigned a helical structure, with a coil extending from 274 until the next parse.

Buechler and Taylor [(1988) op cit.] found that the carboxyl side chains of D 260 is especially reactive with water-soluble carbodiimide. However, the side chain is not protected by substrate.

Segment 27: Positions 276–285 are deleted in protein 46, indicating that positions 275 and 286 are close in space in the folded structure in the remaining proteins. A large number of parsing strings within the region make the canonical assignment a coil for this segment. There is no evidence for active site residues in the coil.

Segments 28, 29, and 30. There is textbook amphiphilicity from positions 288 to 300, suggesting a 15 residue helix (a bit over four turns) in this region (FIG. 3e). Helices of this type and length are almost never misassigned, making this a "very strong" assignment. It remains to determine how far this helix can be extended in either direction. A deletion parse ending at position 285 suggests that the helix begins exactly at position 286. However, some of the amino acids can be moved from above the deletion to position 285 without significantly altering the significance of the alignment in this region. Indeed, in some proteins (e.g. proteins 52–54), the pattern of amphiphilicity appears to extend in this direction. Extending the helix back by one amino acid also superimposes the parses at each end of the helix. On these grounds, the amino end of the helix is extended to position 284 in the maximum helix (Table 11) in a readjusted alignment (some residues from positions 279 and 280 of proteins in functional subfamilies 1 and 2 are moved to position 284 in the alignment).

At the carboxyl end of the helix, amphiphilicity is broken at position 301. Further, a secondary parse at position 302 provides a plausible point to end the helix. Positions 299 to 304 are also a string of 6 consecutive surface assignments. Thus, positions 286–301 are assigned a helical structure in the preferred assignment for cAMP-dependent protein kinases (Table 11).

The conformations of the subsegments that immediately follow (positions 303–313) are difficult to assign. Positions 303, 304, 307, 309, 310, 313, and 314 are all assigned to the surface. Positions 306, 308, 311, and 312 are assigned to the inside. The most distinctive feature of this segment is the APC R at position 305. This is canonically assigned to the active site (although again, such assignments are only ca. 70% accurate).

Secondary parses at position 302 and 306 separated by 2 surface residues are canonically assigned as a loop. There are no active site strings that would confirm the APC R as an active site residue, even at relatively high MPI values. Thus, it might be argued that the APC R is an "anchor" for a loop not at the active site. However, in view of the wide range of functions performed by different members of this family of proteins, it is important to reexamine this point by functional class, assuming that the variation that is seen is adaptive in a substrate binding segment of the kinases. For example, in functional group 1 (50% MPI), one does not find the amount of variation that one would expect in a surface loop far from the active site. Thus, this is assigned as an active site coil.

The conformation of the following segment is especially problematic. Canonically, the presence of parsing strings (e.g., in functional subfamily 2, GSGPDGEP) and weak secondary parsing elements at positions 307, 309, 310, and 312 suggests that this segment is a coil with hydrophobic anchors at positions 308 and (in some subfamilies) 311 and 312.

Segment 31. Positions 314–318 are deleted in functional subgroups 3–6, implying that positions 313 and 319 are close together in space in the remaining proteins. There is no evidence for active site residues in the coil.

Segment 32. It is important to note that the sequences in this alignment are truncated; they continue past this point, often for some length. However, these carboxyl terminal extensions in the different proteins cannot be aligned. Canonically, it is simplest to assign this segment simply as an coil, as lies largely on the surface (all positions are assigned to the surface). However, the strength of the assignments varies as expected for an alpha helix. So does the hydrophobicity of the segment. Thus, it is possible that this segment is the beginning of a helix that will extend into the next section of the protein. It is important to test this by looking at the extended sequences of proteins, where they can be aligned.

In functional group 1, 2 and 8, the amphiphilic helix can be extended by one position (to 326). Group 8 has a secondary parse at what would be position 327 in the alignment. In the serine kinase groups, this position is occupied by a conserved W, a W that breaks the amphiphilic helix at this position. The sequence that follows also does not fit on the amphiphilic wheel; the next parsing segment in this class is at positions 337. While the method cannot discuss these structures without an alignment, there is no reason not to accept in this segment a short helix (7 amino acids, 319–325, with 319 being a weak surface). The P scattered in functional groups 1–5 either indicate that the helix is shorter in these groups (which makes the (in ADH, phospholipase, and other proteins, there are analogous single turn helices that show amphiphilicity) or, more probably in our opinion, a P in the first turn of an alpha helix.

Step 8: FIG. 4 contains a summary of the secondary structure predicted for protein kinase, together with those elements of the supersecondary and tertiary structure obtained in this example. Assembly of the secondary structural elements to form supersecondary structures requires that distant positions in the polypeptide chain be brought together in three-dimensional space. One way of obtaining information to assemble these elements comes from assignments of certain positions in the alignment to the active site, as these must be brought together in the folded protein. Unfortunately, the active site of protein kinase is quite large; therefore, these distance constraints are not very demanding. Nevertheless, active site assignments at positions 46, 113, 116, 156–162, 182, 199, 201, 210, and 305 have been used to assemble proposals for the folded structure shown in FIG. 4.

Unfortunately, protein kinases lack sulfide bonds that might be used to provide distance constraints connecting positions of the polypeptide chain that do not lie at the active site. Finally, no knowledge of the biochemistry of protein kinases has been used to constrain distances in this protein. Thus, the structural model shown in FIG. 4 is not complete.

Assembling the Secondary Structural Elements

To assemble the secondary structural units, positions 46, 67, 113, 116, 156–162, 182, 199, 201, 210, 237, and 305 are tentatively assigned as lying at or near the active site, suggesting that these points in the polypeptide chain come together in three dimensional space. Position 305 only weakly is assigned to the active site, however, and alternative models that place this residue at a position removed from the active site must also be considered.

The beta strands that are connected by short loops are then examined to see if evidence can be found that they lie antiparallel in a beta sheet. As discussed above, covariation analysis suggests that the two strands 84–93 and 103–111 lie antiparallel, with the side chain of the amino acid at position 87 of the first beta strand on the same side of the sheet as the side chain of the amino acid at position 108, and these two side chains in close proximity.

Further, based on active site assignments, beta strand 201–212 is arranged antiparallel to beta strand 226–240, although these long strands are almost certainly discontinuous, implying that this antiparallel arrangement need not extend along the entire strand.

Chemical crosslinking experiments suggest that the side chain of the amino acid at position 46 in the beta strand 43–48 is in close proximity to the side chain at position 182 in the beta strand 177–185; covariation analysis suggests that these these strands lie antiparallel (based on functional variation at positions 47 and 181, and the hydrophobic variable position 85 and the APC F at position 198). In contrast, no evidence can be found for any association of beta strand 12–22 with beta strand 43–48.

These considerations lead to the minimal structure shown in FIG. 4. It should be noted that in this Figure, the long beta strands are almost certainly bent. Further, constraints imposed by a need for a two dimensional representation distort the picture. Thus, as indicated on the Figure, the structure is further folded to bring together the active site residue at position 67 (near the ATP binding site) and att 113–116 (near the peptide binding site.

This picture can be modified by inferences drawn from chemical considerations of the reaction being catalyzed. First, the nucleophilic displacement is "in-line" with a trigonal bipyramidal phosphorus in the transition state lying between an attacking nucleophile and the departing beta-phosphate of ATP. The nucleophile (a serine, threonine, or tyrosine) must lose a proton to a basic residue at the active site. The pentacoordinate phosphate with additional negative charge must be stabilized by a positively charged residue on the protein. Finally, the Mg-ATP must be bound on the distal side of the phosphorus, with the divalent magnesium cation coordinated to the alpha and beta phosphates of ATP and to ligands on the enzyme. Finally, groups on the enzyme must form hydrogen bonds to the ribose ring hydroxyl groups, and present a hydrophobic pocket to hold the purine ring with a hydrogen bond to N(6).

What sorts of residues might one expect the enzyme to contribute for this sort of a catalytic effect? Some information bearing on this question can be obtained from the crystal structures of phosphoglycerate kinase [R. D. Banks, C. C. F. Blake, P. R. Evans, R. Haser, D. W. Rice, G. W. Hardy, M. Merrett, A. W. Phillips, "Sequence, structure, and activity of phosphoglycerate kinase: A possible hinge-bending enzyme", Nature 279, 773–777 (1979)], phosphofructokinase [Y. Shirakihara, P. R. Evans, "Crystal structure of the complex of phosphofructokinase from Escherichia coli with its reaction products", J. Mol. Biol. 204, 973–994 (1988)] adenylate kinase [D. Dreusicke, P. A. Karplus, G. E. Schulz, "Refined structure of porcine cytosolic adenylate kinase at 2.1 Å resolution", J. Mol. Biol. 199, 359–371 (1988)], and pyruvate kinase [H. Muirhead, D. A. Clayden, D. Barford, C. G. Lorimer, L. A. Fothergill-Gilmore, E. Schlitz, W. Schmitt, EMBO J. 5, 475–481 (1986)].

Consider first the coordination of magnesium. In pyruvate kinase, the magnesium coordinates to the side chain of Glu 271 and two main chain carbonyl residues. Glu 271 is conserved in enzymes from cat, chick, rat, and yeast, is part of a conserved string of three, and lies in a turn at the end of a beta strand and two positions before the start of an alpha helix. In adenylate kinase, the side chain of Asp 93 (in the middle of a beta strand) appears to coordinate the magnesium. In phosphofructokinase, Asp 103 (in a conserved heptapeptide at the start of an alpha helix) coordinates magnesium. Asp 129 appears to bind water coordinated to magnesium in this protein. In phosphoglycerate kinase, Asp 374 (at the start of an alpha helix in a GGGD conserved string) coordinates the magnesium. Thus, we can expect that Asp and Glu residues (with perhaps a slight preference for the former) will also be involved in the coordination of magnesium in protein kinase, and that these residues can be identified by their pattern of conservation.

Interactions with the phosphate groups involves, not surprisingly, Arg and Lys residues, with perhaps a preference for the former. For example, in pyruvate kinase, Lys 114 and Arg 119 form salt bridges to the phosphate groups of the substrates. Arg 72 (in a beta strand) and Arg 293 (in a coil between a beta strand and an alpha helix) appear to be near the phosphorus electrophile. Both are completely conserved, the second in a string many amino acids long. In adenylate kinase, Lys 21 (in a turn or at the beginning of a helix) may be near the gamma-phosphate group. The residue is conserved in five sequences with pairwise identities from 24% to 52%. Arg 44, Arg 97, Arg 128, Arg 138, and Arg 149 are all conserved, and all point towards the active site cleft in this enzyme, not surprising considering the number of negatively charged groups that are brought together in the active site. In phosphofructokinase, Arg 72 seems to bind to the alpha-phosphorus of ATP as well as the phosphorus being transferred. In phosphoglycerate kinase, Lys 219 (at the start of an alpha helix) appears to bind the alpha-phosphate of ATP. The beta and gamma phosphates are found on the amino terminal end of a helix.

Coordination to ribose is varied. In phosphofructokinase, Tyr 41 (in a conserved dipeptide at the start of an alpha helix) provides the contact. In phosphoglycerate kinase, Glu 343 ( in a coil at the end of a GVFE conserved sequence)) appears to make a hydrogen bond with the ribose hydroxyl groups. In alcohol dehydrogenases, the ribose is hydrogen bonded to an APC Asp 223 (at the end of a beta strand).

Similar roles may be assigned to various positions in protein kinase. In addition to the sequences themselves, information is available from chemical modification studies involving carbodiimide (for acidic residues), acetic anhydride (for Lys), and peptide analogs, summarized in Table 14.

There are only two candidates for a side chain to provide the positive charge to the gamma phosphate, K 46 and R 305. The chemical modification experiments with reactive analogs of ATP place the side chain K 46 near the gamma-phosphorus of ATP, and it seems not unreasonable to assign tentatively this role to this residue.

Identifying roles for the individual carboxyl groups is more difficult, as they can presumably serve to coordinate magnesium, or bind to the ribose, or act as a base abstracting a proton from the nucleophilic center of the protein substrate. Acidic residues under consideration here are of three types. First, there are two residues that are conserved, reactive with carbodiimide, and are protected by Mg-ATP (E 067 and D 182). Second, there are two residues that are conserved and do not react with carbodiimide (D 157 and E 210). Then there are two acidic residues that are not conserved, react with carbodiimide, but require both Mg-ATP and peptide to protect them (E 161 and E 237). Finally, there are two acidic residues that are not conserved, reactive, and are not protected by any sort of substrate combination (E 089 and D 260).

The last pair, E 089 and D 260, can be presumed not to lie at the active site, and therefore to be uninteresting for the present discussion. E 161 and E 237 might be presumed to lie between the substrate peptide binding site and the Mg-ATP binding site. Because they are not conserved, they presumably play no role in catalysis. However, these positions in the polypeptide chain should lie between positions 113–116 and 199–201 (the peptide binding site) and positions 157–160 and 67 (the Mg-ATP binding site).

In contrast, both D 157 and E 210 are absolutely conserved. Both do not react with carbodiimide, suggesting either that they are buried, or that they are for chemical reasons unreactive. The assignment of E 210 to the active site is not extremely strong. It is in a beta strand that appears to be inside the folded structure, but displays few of the sequence characteristics expected for a string at the active site. As noted above, absolutely conserved charged residues appear only ca. 70% of the time at the active site. It is possible that E 210 is one of the 30% of this type of position that does not.

In contrast, there is no question from the pattern of conservation in the region that D 157 lies at the active site. It must therefore be accessible to solvent under some conditions. We cannot say why it fails to react with carbodiimide. However, it is worth noting that the reaction with carbodiimide proceeds from the protonated form of a carboxyl group. A carboxyl group with a low pKa might not be expected to react. This is a behavior exactly opposite that expected for a carboxylate involved as a general base catalyst, suggesting that the residue at position 157 does not play this role. Presumably E 067 acts either as a ligand for magnesium or to form hydrogen bonds with the hydroxyl groups on the ribose ring.

The conservation of E 067 and D 182 indicates that these residues do play critical roles. However, in contrast to D 157, D 182 is extremely reactive with carbodiimide, suggesting that the side chain carboxylic acid has a high pKa. This implies, of course, that the conjugate base is relatively strong, as would be expected were this carboxylate to act as a base to deprotonate the nucleophile in the reaction. In this role, D 182 should be close enough to the position where the gamma-phosphate would bind in the enzyme-substrate complex that it forms a crosslink with K 46 when no substrate is present.

In this context, it is worth noting that the pKa values of the hydroxyl groups of serine and tyrosine are different by some six orders of magnitude. Thus, it is not expected a priori that the same basic group will abstract a proton from each. We had hoped to find in the protein kinase alignment a basic residue conserved in each functional subfamily but different between the two (a "functional split"), and use this pattern to identify the residue that acts as a base. Unfortunately, no such residue appears to exist in the alignment. Closest are positions 149 (mostly His in the serine/threonine kinases, and mostly Glu in the tyrosine kinases), but the conservation in each functional subfamily is not perfect. Thus, our preferred candidate for a residue that acts as a general base in the catalytic reaction is Asp 182.

These conclusions can be summarized in a model of the active site (FIG. 5) showing the transition state for the reaction and the presumed orientation of reactions involved in catalysis. While both E 67 and D 157 are shown coordinating magnesium, one of these two side chains might instead be forming hydrogen bonds to the hydroxyl groups of the ribose ring.

The models shown in FIGS. 4 and 5 are not, of course, complete representations of the conformation of the folded protein. However, provided that the two peptide binding sites are brought together in three dimensions, positions 67 and 157 brought to within bonding distance of a single magnesium, positions 161 and 237 placed between the peptide binding site and the ATP binding site, and positions 46 aligned with the gamma phosphate and 182 placed to abstract a proton from the reactive nucleophile, only a small number of folded forms are consistent with the constraints imposed by the assignments of secondary structure, the assignments of inside and surface positions (Table 10), and the covalent links of the polypeptide backbone. Further constraints are introduced if position 7 is placed near the active site.

Step 9: Using covariation analysis to help assemble supersecondary structure. In FIG. 4, the two beta strands (84–93 and 103–111) are oriented antiparallel to each other. This supersecondary structural assignment is based on covariation analysis, which suggested that positions 87 and 108 in protein kinase underwent variation that was not independent. The covariation is shown in Table 15. In particular, within functional subgroups 7 and 11, whenever position 87 suffers a substitution that lead to a loss of a charge, position 108 suffers the complementary substitution:

Remarks:

The key elements of the supersecondary and tertiary structure prediction are as follows:

(i) Protein kinase does not contain a domain that folds to give a Rossmann fold.

(ii) Rather, the cores structure of one domain contains consecutive β strands, aligned to form an antiparallel beta sheet.

(iii) Further, the distribution of helices does not follow the pattern suggested by the classical algorithms. These contrasts between predictions made by our method and by other methods is, of course, a point where the merits of the various approaches can be critically compared.

Example 2

Prediction of the Structure of Pathogenesis Related (PR) Proteins

Pathogenesis related (PR) proteins from plants come in several families. One family, often referred to as the PR1 family, has no known catalytic or physiological function. It is synthesized when the plant is subjected to environmental stress [J. F. Bol, J. M. Linthorst, B. J. C. Cornelissen, "Plant pathogenesis-related proteins induced by viral infection", *Ann. Rev. Phytopathology*, 28, 113–138 (1990)].

This example is provided to show the scope of the predictive method when only a very few sequences are available, and where the pairwise identity of the sequences is sub-optimal. There are far fewer sequences of homologous pathogenesis-related proteins than there are for protein kinases (Example 1). Further, the distribution of sequences on an evolutionary tree is far less satisfactory than with protein kinase. Finally, extremely little is known about the catalytic or physiological function of pathogenesis related proteins. The structure prediction in this example is developed in two steps, first with a small alignment of PR proteins alone (Table 16), and then with a larger alignment that includes the homologous TPX proteins from mammals and venom allergens from insects (Table 17). to show how the addition of sequences to an alignment can resolve ambiguities in assignments made from an alignment of only a few protein sequences.

Step 1: A set of sequences of homologous pathogenesis related proteins were found by searching the MIPS and SwissProt data bases. Errors in the sequences were corrected where necessary. An alignment was constructed using the DARWIN system from those sequences that were from plants.

Step 2: Two alignments are used in this example. Table 16 shows a small alignment of the sequences of the pathogenesis related proteins from plants. Table 17 shows a larger alignment of the sequences of the pathogenesis related proteins from plants together with their homologues, the TPX proteins from mammals and venom allergens from insects. Evolutionary trees showing the evolutionary relation between the proteins in the two alignments is given in FIG. 6. The evolutionary distance in the small alignment overall is only approximately 75 accepted point mutations per 100 amino acid residues, meaning that the strongest surface algorithms will not cover much of the surface. The evolutionary distance is larger in the big alignment, but the branching is still not as much as would be desired in the most preferable case. As is evident from the tree, the collection of sequences is rather small, and not optimally distributed in terms of evolutionary distance. Proteins a, d, and c form one subgroup with and MPI of greater than 90%, proteins g, e, and f form another subgroup with a similar MPI, and proteins b and h each stand alone in the tree.

Step 3. Divide the alignment into segments using parsing algorithms. Parses can be assigned based on gaps at positions 001–004, 053–054, 065–067, and 124. APC P's are present at positions 023, 131, and 140. Thus, the alignment is divided into 6 segments (excluding parsing segments): segment 1 (006–023), segment 2 023–052, segment 3 (055–064), segment 4 (068–123), segment 5 (125–131), and segment 6 (131–140).

Steps 4–6: When so few sequences are involved, the surface assignments made by the most reliable algorithms are few; surface assignments must therefore be made using less reliable algorithms to get adequate coverage of the alignment. Conservation of hydrophobic and functional amino acids is less significant with less overall sequence divergence; thus, the respective inside and active site assignments are less reliable. In this analysis of the PR proteins, it is understood that most assignments are weak. When strong assignments are made, they are capitalized.

In this example, it is recognized that the MPI values for subgroups that are examined concurrently are not uniform. In the first part of this example, there are only 3 subgroups that can be used. The first includes proteins a, b and c, the second proteins d, e, and f, and the third proteins g and h. This does not imply that a systematic understanding of the evolutionary relationship between the proteins in these subgroups can be ignored. Rather, this understanding is used to evaluate the reliability of the assignments made in Steps 4–6. Indeed, this example is intended to illustrate how to apply the method of the present invention when tidy subgroups with consistent MPI values cannot be obtained because of the small number of sequences in the alignment, and how, despite these constraints, useful assignments can be made with identified strengths. For example, surface assignment at position 013 is stronger than at position 007, as the former has 4 different polar residues, the latter only two.

Table 18 shows the residue by residue assignments for the PR proteins alone. In this Table, amphiphilic single variable positions are assigned to the surface if the variability occurs in the polar subgroup.

Step 7: Assign secondary structure.

An analysis of the secondary structure proceeds with each segment being examined individually. In this analysis, parsing segments are assigned as coils, and not discussed in detail.

Segment 1. Segment 1 starts at position 005 and ends at position 023. It contains both inside and surface assignments, and a helix wheel is shown in FIG. 7a. Amphiphilicity is found for positions 5–20, and a helix can be assigned tentatively to this segment.

Segment 2: Segment 2 starts at position 023 and ends at position 053. It is too long (31 residues) to form a single secondary structural unit. Indeed, a helix wheel covering the entire segment (FIG. 7b) shows consistent pattern of amphiphilicity over the entire length. Therefore, it might be subdivided using weaker parsing algorithms. A candidate for a secondary parse is found at position 039/040 (the NS dipeptide is a weak parse).

To find evidence for a helical structure in the first subsegment, a reduced helix wheel is plotted (FIG. 7b), where assignments are removed from the helical wheel from each end to search for a core segment that displays 3.6 position periodicity. The reduced wheel for segment 2 (FIG. 7b) shows perfect amphiphilicity between positions 028 and 046. The segment is then examined to determine how much longer the helical segment might be extended were assignments to be incorrect.

Position 027 ($i_N$) is a polar split assigned tentatively to the surface of the folded structure that lies within the inside arc of the helix projection. If this position is misassigned, then the next amphiphilic breaker occurs as position 025 ($i_N$–2), and no longer tentative helix is assigned in this direction.

In the other direction (FIG. 7c), position 047 ($i_C$) is a hydrophobic split assigned tentatively to the inside of the folded structure that lies within the surface arc of the helix projection. If this position is misassigned, then nothing contradicts amphiphilicity up to the APC S at position 050 ($i_N$+3). If position 050 is assumed to lie on the surface (remembering that absolute conservation is not extremely significant when the overall sequence divergence is only 050), and the amphiphilicity can be extended to the parse at position 053. However, most of the positions in this extension receive no assignments, and a helix wheel (FIG. 7c) constructed from position 53 backwards is not particularly convincing. Further, the conserved dipeptide HS is an indicator of an active site, and these are canonically assigned as coils. A coil assignment is also indicated by the parsing string SGGP in protein h (positions 50–53). The assignment is examined in light of more sequences in the section below.

Segment 3: Segment 3 starts at position 54 and ends at position 65. Surface and inside assignments are made for only 5 of the 12 positions that are assigned. These form an amphiphilic pattern on a helix wheel (FIG. 7d). However, the strongest characteristic of this segment is the large number (4, or 33%) of APC positions. This suggests an active site region, which is canonically assigned as a coil. Further, two positions (055 and 061) are APC G, parsing indicators that also indicate a coil. Finally, the GGG tripeptide seen in proteins a, d, and c indicates a coil. Thus, no assignment can be made from these sequences.

Segment 4: Segment 4 starts at position 067 and ends at position 124. This segment is clearly too long to form a single secondary structural unit in a protein of this size. Therefore, secondary parses are sought to subdivide the segment into subsegments before drawing helical wheels. Weaker parses are found at positions 070 (an isolated P), 081 (an isolated P), 092/093 (a GG dipeptide), and 111 (an APC G). The strongest of these parses is the APC G at position 111, and a tentative division is therefore made at this point. The segment preceding it is still rather long. For the purpose of drawing helix wheels, the distributed parse at position 092/093 is also used.

In the first half of this segment (designated segment 4ab), a helix wheel covering positions 67 through 92 displays no particular 3.6 position periodicity (FIG. 7e). A reduced helix wheel containing residues 69–79 does display amphiphilicity, however (FIG. 7e), and this section is tentatively assigned as an alpha helix. However, very few of the positions in this tentative helix have any strong surface assignments, and the designation is weak. Positions 82–86 display 2 residue periodicity, and are tentatively assigned as a beta strand.

In the second half of this segment (designated segment 4cd), a potential 3.6 position pattern of amphiphilicity might be seen in positions 103–113 (FIG. 7f). However, no reliable assignment can be made for this segment.

Segment 5: Segment 5 starts at position 124 and ends at position 131. No helical amphiphilicity can be seen in this segment (FIG. 7g). However, a 2 position alternating pattern of periodicity can be seen from position 125 to position 131, and this segment is assigned as a beta strand.

Segment 6: Segment 6 starts at position 131 and ends at position 140. No helical amphiphilicity can be seen in this segment (FIG. 7h). No 2 position alternating pattern of periodicity can be seen. However, given the large number of splits, this segment is tentatively assigned as a beta strand.

Adding More Sequences to the Alignment. So far, the secondary structure assignment has been built from a small alignment (Table 16) that contains only pathogenesis related proteins from plants. This increases the probability (but does not guarantee) that the proteins share similar functions. However, a search of the standard protein sequence data base discovers two other families of proteins that are clearly homologous to the PR proteins: sperm-coating glycoprotein (or testis-specific protein TPX-1) and a venom allergen from hornet. These can be added to the alignment (Table 17)

The secondary structure assignments can now be reviewed in light of a larger alignment that includes these additional sequences. This review is presented here for showing how the assignments made by the method of the present invention are influenced by the number of proteins in an alignment. Several questions can be addressed. With the additional sequences, does the parsing scheme hold up? Do the additional sequences reinforce the helical and other secondary structural assignments? Can stronger surface assignments be made? Do additional sequences contradict some active site assignments? Can the additional sequences be used to assign disulfide linkages?

In this discussion, only three subgroups will be considered. The first includes the PR1 proteins, the second the TPX proteins, and the third the venom allergens. The MPI values are understood to be those corresponding to those three groups. Special note should be made of how additional sequences allow more reliable algorithms to be used to assign surface and interior positions, and how assignments from less reliable algorithms become discounted in the presence of these stronger algorithms. For example, a polar split was used as an indicator of a surface position when using the small alignment. This was necessary, as the more reliable algorithms could not make enough assignments with few sequences. Below, polar split is no longer an automatic indicator of a surface position.

Step 3: Revising the Parses

Segment 1 has no counterpart in these additional sequences, and therefore cannot be reanalyzed. The significant alignment starts after the first parse (GVGP, 020–023).

A new parse is introduced into Segment 2 by a deletion of positions 041–044. The deletion is needed to align Cys 045 and His 049 in the new sequences, and appears to be reliable. This new parse confirms the weak parse made from the NS dipeptide in the small alignment truncates the helix assigned to segment 2 right before the end of amphiphilicity observed in the helix wheel.

The parse at position 053–054 is reinforced by insertion at this position.

A part of one protein contains a deletion at positions 61–63. This deletion could be removed by a rearrangement of the alignment, and this is done in the revised larger alignment.

The parse at positions 065–067 is reinforced by an insertion in the venom allergens at this position, and the parse is extended to position 069. The parse at position 069 can be moved two positions to the left by a minor rearrangement of the alignment. This leaves intact the assignment of a helix starting at position 068.

A new parse is introduced at positions 089–097 by scattered deletions. This reinforces the weak secondary parse suggested by the GG dipeptide at positions 092 and 093 in the small alignment. Further, it suggests that segment 4b should be assigned a standard secondary structure. A CM1 G at position 097 becomes a stronger parse, suggests that the secondary structural unit that follows begins at position 097.

A new parse is introduced by a single amino acid insertion between positions 117 and 118, right after a APC C, and a deletion at position 120. This further divides the long Segment 4, several residues after the end of amphiphilicity in the helix tentatively assigned for positions 97–111.

The parse at position 124 is shifted 2 positions to the left. This extends segment 5 to the left by 2 amino acids.

The parse at positions 131 and 132 is strongly reinforced. The APC P is found across the entire alignment.

Steps 4–7: Re-examine the surface, inside, active site, and secondary structure assignments in light of the additional sequence data Segment 2a: Segment 2a was tentatively assigned as a helix. The helix assignment is confirmed by increasing strengths of both interior and surface assignments throughout the segment. The revised assignments are shown in Table 19a, and a helix wheel in FIG. 8a. The inside/surface split at position 033 is confirmed, but no covariation is found. The four amino acid deletion at positions 041–044 corresponds to one turn of the helix. Nevertheless, the helix definitely ends before the APC C at position 045. The APC D might be important as a helix breaking unit forming a hydrogen bonding interaction with the backbone atoms in proteins with this extra turn. Thus, the probability that this is an active site position is diminished. Thus, the helix is assigned from positions 023–041 (18 residues, 5 turns).

Segment 2b: Segment 2b was tentatively assigned as an active site coil. The additional sequences have changed the view of this segment. The revised assignments are shown in Table 19b, with the corresponding helix wheel in FIG. 8b. The APC D (position 44) and the APC S (position 50) are not conserved in the additional sequences; these positions therefore are no longer assigned to the active site. The parse truncates this segment before position 45. There is clearly no longer any helical amphiphilicity in this segment. the additional sequences in the alignment, the segment looks like a beta strand. Strengthening of surface assignments allows a clear alternating pattern indicative of a beta strand to appear. A distributed parse at positions 51–52 is evident. This is assigned as a beta strand from positions 45–50, followed by a coil.

Segment 3: Segment 3 was tentatively assigned as an active site coil. A beta strand is possible for positions 55–60. There is too much conservation for a coil in this segment. The revised assignments are shown in Table 19c. Possible extension of this strand to position 54 and to position 61. The distributed parse at positions 63 and 64 remain even if the alignment is rearranged to shift the gap to the right. If the gap is not shifted, the parse starts at position 62.

Segments 4a and 4b: Segments 4a and 4b were tentatively assigned as a helix and uncertain, respectively. With the additional sequences, amphiphilicity is observed on a helix wheel from positions 068–079. The revised assignments are shown in Table 19d, and a helix wheel in FIG. 7b. This corresponds to a helix 12 residues in length. Amphiphilicity is broken by a surface position at position 080, on the inside arc of the helix wheel.

Extension of the helix in the direction of the amino terminus is not possible, because of the deletion parse at position 065–067. In the other direction, amphiphilicity is not broken at position $i_C+1$ through $i_C+4$. Amphiphilicity is next broken at position 085, and then at position 087. Thus, a second tentative helix is assigned for positions 068–084 (17 residues). This segment is soon followed by a deletion parse (positions 089), so at best, the helix could extend only by one more turn (positions 068–088, 21 residues)

Deciding which assignment is correct involves inspection of the functional subgroups separately. It is conceivable for the length of a helix to be different in different families of proteins; indeed, this appears in this case with these proteins. Thus, we examine amphiphilic splits and positions at the border between the surface and inside arcs of the helix wheel.

The Amphiphilic split at position 077 lies in the border region. It is inside in the PR and TPX proteins, and surface in the venom allergens. Position 080 is surface in the PR and TPX proteins, and inside in the venom allergens. These two positions create the following situation. Amphiphilicity is retained in the PR and TPX proteins up until position 79. The helix in these proteins stops here. However, in the venom allergens, amphiphilicity continues until the parse. Thus, it is conceivable that in PR and TPX proteins, the helix is shorter than in venom allergens. The core structure (one one used to build a tertiary structural model) is always the shorter of the two. Nevertheless, in building the tertiary structural model, space must be left for a helix extension.

Segments 4c and 4d: Segments 4c and 4d were tentatively assigned helix and uncertain, respectively. The revised assignments are shown in Table 19e, and a helix wheel in FIG. 8e. With the additional sequences, the parsing has changed. Instead of starting this segment at position 93, one must start at position 97. A shift in the alignment to move the gap 2 amino acids to the left is clearly justified, Comments: The first part of this segment is clearly in the active site. It is a general rule that it is difficult to assign secondary structure in the vicinity of an active site, as the evolutionary constraints on sequence divergence imposed by functional demands of the active site tend to dominate those that reflect secondary structure. An interesting segment. There is a remarkable stretch of amphiphilicity from position 92 to position 120. If this is a helix, it is 29 residues long, or 8 turns. This compares to the helix in segment 2a of only 5 turns. The Amphiphilicity is broken at position 118. The issue could be resolved by disulfide linkages. The disulfide linkages suggest that positions 90 and 96 are joined. Thus, the helix cannot start before position 97. The 97–120 stretch is only 6.67 turns, and is more plausible in length.

Thus, we build a revised helical wheel. The question is whether the amphiphilic splits at position 108 and 114 covary. Judging by the amphiphilic splits, the PR proteins are more exposed at the top of the helix than the TPX proteins, and more buried at the bottom of the helix than the venom allergen, and that the TPX helix is more buried overall.

Next, we must worry about whether the helix should include the APC residues. Normally, this question is decided following a search for evidence that residues preceding the APC residues map onto a helix conformably with residues that follow. In this case, there is no evidence for this. Second, if we knew the catalytic function of the protein, we would build a model for the active site, and try to assign catalytic roles to the APC residues, to try to orient them in space relative to the presumed substrate. However, we have no idea what catalytic role any of these proteins perform. Thus, we must resort to the third test; do the APC residues themselves fall with 3.6 residue periodicity on a helical wheel? Of course, with 4 APC positions in a row (positions 98–101), this is not possible prima facie. Thus, the default is taken, that these residues do not form part of a helix this long, that they form an active site coil, and the helix begins at position 99. Now, where does the helix end? Treat parse at 118 as definitive, as it is reinforced by a Pro split at this position in the TPX proteins. The helix therefore extends from position 99–117, a total of 19 amino acids, or 5.3 turns.

Segment 5. The revised assignments for this segment are shown in Table 19f. The addition of a the additional sequences has prompted the alignment to be rearranged so that the deletion is moved to the left by two amino acids. The short inside segment (positions 123–126) is followed by alternating assignments up until position 131 (FIG. 8f). This leads to a prediction that this segment forms a beta stand in positions 123–131.

Segment 6. The revised assignments for this segment are shown in Table 19g. The segment has no obvious helical amphiphilicity. The consecutive surface positions (positions 137–139) and a parse at position 140 indicate a coil (or a last turn of a surface helix) following position 137. The large number of splits supports the canonical assignment of a beta strand for positions 131–136.

Step 8. As summary of the secondary structure prediction for pathogenesis related protein and its family is given in Table 20, and diagrammed in FIG. 9. PR proteins from plants have 6 cysteine residues that appear to be involved in the formation of 3 disulfide bonds. While the pattern of disulfide bond formation is not known, an analysis of the pattern of variation suggests that cysteine 90 is linked with cysteine 96. Further, the most plausible connectivity of the other cysteines is between 45 and 117, and 112 and 127. The simplest folded structure that is consistent with these assignments is a central beta strand flanked on both sides by helices.

TABLE 1

A Comparison of the Secondary Structure Prediction and Crystallographic Reality in the Catalytic Domain of Protein Kinase[§]

| | Prediction | | Reality | |
|---|---|---|---|---|
| Alignment Position* | Predicted Secondary Structural Unit* | Predicted Extent of Secondary Structural Unit* | Actual Secondary Structural Unit in Crystal[†] | Actual Extent of Secondary Structural Unit[†] |
| 001–011 | coil | 41–51 | beta 1 | 43–48 |
| 012–022 | beta 2 | 52–62 | beta 2 | 57–63 |
| 023–041 | coil | 63–67 | coil | 64–66 |
| 042–048 | beta 3 | 68–74 | beta 3 | 67–75 |
| 049–060 | coil | 75–84 | alpha B | 76–82 |
| 061–074 | alpha C | 85–98 | alpha C | 84–97 |
| 075–083 | coil | 99–101 | coil | 98–105 |
| 084–093 | beta 4 | 102–111 | beta 4 | 106–111 |
| 094–102 | coil | 112–115 | coil | 112–114 |
| 103–111 | beta 5 | 116–123 | beta 5 | 115–120 |
| 112–114 | coil | 124–126 | coil | 121–127 |
| 115–124 | alpha D | 127–136 | alpha D | 128–135 |
| 126–130 | coil | 137–139 | coil | 136–139 |
| 131–152 | alpha E | 140–161 | alpha E | 140–159 |
| 153–156 | beta 6 | 162–165 | beta 6 | 161–164 |
| 157–162 | active site | 166–171 | coil | 165–170 |
| 163–166 | beta 7 | 172–175 | beta 7 | 171–175 |
| 167–176 | coil | 176–178 | coil | 176–177 |
| 177–186 | beta 8 | 179–188 | beta 8 + 9 | 178–191 |
| 187–200 | coil | 189–198 | coil | 192–198 |
| 201–212 | *beta* | 199–210 | *coil* | 199–210 |
| 213–225 | coil | 211–218 | coil | 211–217 |
| 226–241 | *beta* | 219–233 | *alphaF* | 218–233 |
| 242–261 | coil | 234–242 | coil | 234–243 |
| 262–274 | alpha G | 243–254 | alpha G | 244–252 |
| 275–285 | coil | 255–260 | coil | 253–262 |
| 286–301 | alpha H | 261–276 | alpha H | 263–272 |
| 302–306 | coil | 277–281 | coil | 273–281 |
| 307–312 | *beta* | 282–287 | *coil* | 282–287 |
| 313–318 | *coil* | 288–293 | *alpha I* | 288–293 |
| 319–325 | coil | 294–300 | coil | 294–300 |

[§]Bold entries indicate correct predictions.
Italicized entries indicate predictions that are possibly incorrect; see text for discussion.
The underlined entry (alignment positions 226–241) is the single serious error made in the secondary structure prediction.
Numbers in columns 3 and 5 refer to the positions in the sequence of the catalytic subunit of recombinant mouse cAMP-dependent protein kinase, the protein whose crystal structure was solved, as given in Knighton et al. (1991) op. cit.
Alignment position numbers (left column) do not correspond to these numbers due to insertions and deletions.
*From Benner & Gerloff (1991) op. cit.
[†]From Knighton et al. (1991) op. cit.

§ Bold entries indicate correct predictions. Italicized entries indicate predictions that are possibly incorrect; see text for discussion. The underlined entry (alignment positions 226–241) is the single serious error made in the secondary structure prediction. Numbers in columns 3 and 5 refer to the the positions in the sequence of the catalytic subunit of recombinant mouse cAMP-dependent protein kinase, the protein whose crystal structure was solved, as given in Knighton et al. (1991) op. cit. Alignment position numbers (left column) do not correspond to these numbers due to insertions and deletions.

TABLE 2

The One-letter Code for Amino Acids

| A | Ala | M | Met |
|---|---|---|---|
| C | Cys | N | Asn |
| D | Asp | P | Pro |

TABLE 2-continued

The One-letter Code for Amino Acids

| | | | |
|---|---|---|---|
| E | Glu | Q | Gln |
| F | Phe | R | Arg |
| G | Gly | S | Ser |
| H | His | T | Thr |
| I | Ile | V | Val |
| K | Lys | W | Trp |
| L | Leu | Y | Tyr |

TABLE 3

Alignment of Alcohol Dehygrogenases

```
001  SSSSSSSG AASS -----
002  TTTTTTTT TTNT ----T
003  AAAAAAAK AATT --AMI
004  -------- --V- -----
005  GGGGGGGG GGGG SSASP
006  KKKKKKKK KKQQ IIIVD
007  VVVVVVVV VVII PPPPK
008  IIIIIIII IIII EEKEQ
009  KKKKKKKK KKKR TTTVL
010  CCCCCCCC CCCC QQQQA
011  KKKKKKKK KRRK KKKWA
012  AAAAAAAA AAAA GAGAV
013  AAAAAAAA AAAA VIVQF
014  VVVVVVVI VVVV IIIVH
015  LLLLLLLA ATAA FFFVT
016  WWWWWWWW WWWW YYYEH
017  EEEEEEEE EEEE EEEKG
018  ENLVLLPA AAAA SSNAG
019  KKKKKHHG GGGG HNKGP
020  KKKKKKKK KKKK GGGTE
021  PPPPPPPP PPPP KKKPN
022  FFFFFFFL LLLL LLLPV
023  SSSSSTTC SSVV EEHVK
024  IIIIIIII IIII YHYYF
025  EEEEEEEE EEEE KKKKE
026  EEEDEDDE EEEE DDDQE
027  VVVVVIIV VVVV IIIVV
028  EEEEEEEE EEEE PPPPP
029  VVVVVVVV VVVV VVVVV
030  AAAAAAAA AAAA PPPPA
031  PPPPPPPP PPPP KKKEE
```

TABLE 3-continued

Alignment of Alcohol Dehygrogenases

```
032  PPPPPPPP PPPP PPPPP
033  KKKKKKKK QQQQ KKKGG
034  AAAAAAAA AAAK APPPQ
035  HHHYHHHH MMGH NNNDD
036  EEEEEEEE EEEE EEEEE
037  VVVVVVVV VVVV LLIIV
038  RRRRRRRR RRRR LLLLL
039  IIIIIIII VILI IIIVV
040  KKKKKKKQ KKKK NNNKV
041  MMMMMMMI IIII VVMIN
042  VVVVVVVI LLLL KKKRK
043  AAAAAAAA FYFF YYYYY
044  TTVVATTT TTTT SSSST
045  GGGGGGGS SASS GGGGG
046  IIIIIVVL LLLL VVVVV
047  CCCCCCCC CCCC CCCCC
048  RRGRRRRH HHHH HHHHH
049  SSTTSTSS TTTT TTTTT
050  DDDDDDDD DDDD DDDDD
051  DDDDEDDA VVVV LLLLL
052  HHHHHHHS YYYY HHHHH
053  VVVVVVAV FFFF AAAAA
054  VVVVVVVI WWWW WWWML
055  SSSSSSSD EEEE HHHKQ
056  GGGGGGGS AAAA GGGGG
057  TTTNNTSK KKKK DDDDD
058  -------- ---- WWWWW
059  -------F GGGG PPPPP
060  LLMLLLLE QQQQ LLLLL
061  VVVVVVFG TTTT PPPPP
062  TTTTTTTL PPPP VTVSA
063  PPPPPPPA VVLL KKKKK
064  LLLLLLLF FFFF LLLMM
065  PPPPPPPP PPPP PPPPP
066  VVVVVAAV RRRR LLLLL
067  IIIIIVVI IIII VVVII
068  AALLLLLV FLFF GGGGG
069  GGGGGGGG GGGG GGGGG
070  HHHHHHHH HHHH HHHHH
```

TABLE 3-continued

Alignment of Alcohol Dehygrogenases

```
071 EEEEEEEE EEEE EEEE
072 AAAAAGGA AAAA GGGGG
073 AAAAAAAA GGGG AAAAA
074 GGGGGGGG GGGG GGGGG
075 IIIIIIII IIII VVVVV
076 VVVVVVVV IVVV VVVVV
077 EEEEEEEE EEEE VVVVV
078 SSSSSSSS SSSS GGKAK
079 IIVVVVII VVVV MMLKV
080 GGGGGGGG GGGG GGGGG
081 EEEEEEEP EEEE EESEA
082 GGGGGGGG GGGG NNNLG
083 VVVVVVVV VVVV VVVVV
084 TTTTTTTT TTTT KKKKT
085 TTTTTCCN DDHD GGGDR
086 -------- ---- ---E-
087 -------- ---- ---D-
088 VVVVVVVV VVLL WWWFL
089 RRKKKKKK AAKQ KKKKK
090 PPPPPPPP PPPP IIVII
091 GGGGGGGG GGGG GGGGG
092 DDDDDDDD DDDD DDDDD
093 KKKKKKKK HHHH YYLRR
094 VVVVVVVV VVAV AAAAV
095 IIIIIIII LLLL GGGGG
096 PPPPPPPP PPPP IIIIV
097 LLLLLLLL VVVI KKKKK
098 FFAFFFFY FFFF WWWWW
099 TIITTSSA TTTT LLLLM
100 PPPPPPPP GGGG NNNNN
101 -------- ---- GGGGS
102 QQQQQQQL EEEE SSSSS
103 CCCCCCCC CCCC CCCCC
104 GGGGGGGR KKGG MMMLG
105 KKKKKEKK EEED AATSN
106 CCCCCCCC CCCC CCCCC
107 RSRRRRRK AAPR EEEE
108 VVIVIIIF HHHH YYFMY
```

TABLE 3-continued

Alignment of Alcohol Dehygrogenases

```
109 CCCCCCCC CCCC CCCCC
110 KKKKKKKL KKKQ EEMM
111 HHNNNHHS SSSS LLSQK
112 PPPPPPPP AEEE GGGAA
113 EEEEEEEL EEEE NNHDE
114 GGSSSSST SSSS EEEE
115 NNNNNNNN NNNN SSSPT
116 FLYYYFLL MMMM NNNLI
117 CCCCCCCC CCCC CCCCC
118 ------C- ---- -----
119 LLLLLSQG DDDD PPPPP
120 KKKKKRTK LLLL HHDHH
121 NNNNNSKI LLLL AAAAI
122 DSDDDDNS RRRR SDDDQ
123 LLVLLLLN IIII LLLLL
124 SSSGGLTL NNNN SSSSS
125 MMNNNMQK TVTT GGGGG
126 PPPPPPPS DDDE -----
127 RRQRRRKP RRRR -----
128 GGGGGGGA GGGG -----
129 -------S ---- -----
130 -------D ---- -----
131 -------Q ---- -----
132 -------Q VVVG -----
133 TTTTTTAL MMMM -----
134 MMLLLLLM IILI -----
135 QQQQQRLE AGNH -----
136 DDDDDDED DDDD -----
137 GGGGGGGK GGNG -----
138 TTTTTTTT KKKE -----
139 SSSRRSSS SSSS -----
140 RRRRRRRR RRRR -----
141 FFFFFFFF FFFF -----
142 TTTTTSST STSS -----
143 CCCCCCCC IIII -----
144 RRRRSKRK NSKN -----
145 GGRGGGGG GGGG -----
146 KKKKKKKK KQQK -----
147 PPPPPPQP PPPP -----
```

TABLE 3-continued
Alignment of Alcohol Dehygrogenases

```
148 IIIIIIIV IIVI -----
149 HHHHHHHY YFHY -----
150 HHHHHHNH HHHH -----
151 FFFFFFFF FFFF YYYYY
152 LLLLVILF VVVL TTTTT
153 GGGGGSSG GGGG HHHVV
154 TTITVTTT TTTT DDDDD
155 SSSSSSSS SSSS GGGGG
156 TTTTTTTT TTTT SSSTT
157 FFFFFFFF FFFF FFFFF
158 SSSSSSSS SSSS QQQQQ
159 QQQQQQQQ EEEE QEQQH
160 YYYYYYYY YYYY YYFYY
161 TTTTTTTT TTTT AAATC
162 VVVVVVVV VVVV TTTII
163 VVVVVVVV MIVV AAAGA
164 DDDDDDDS HHHH DDDKN
165 EEEEEDDD VVAS AAAAA
166 IINNNIII GGGG VVIAT
167 SSAAAAAN CCCQ QQQLH
168 VVVVVVVL VLVV AAAAA
169 AAAAAAAA AAAA AAAST
170 KKKKKKKK KKKK HHKKI
171 IIIIIIII IIII IIIII
172 DDDDDDDD NNNN PPQPP
173 AAAAAGAD PPPP QQQDE
174 AAAAAAAD QEDD GGGNS
175 SSSSSSAA AAAA TTTVV
176 PPPPPPPN PPPP DDDPP
177 LLLLLLLL LLLL LLLLL
178 EEEEEDDE DDDD AAADE
179 KKKKKKKR KKKK QEEAV
180 VVVVVVVV VVVV VVVAA
181 CCCCCCCC CCCC AAAAA
182 LLLLLLLL VIII PPPPP
183 IIIIIILI LLLV IIIII
184 GGGGGGGG SSSS LLLLM
185 CCCCCCCC CCCC CCCCC
186 GGGGGGGG GGGG AAAAA
187 FFFFFFFF IIIL GGGGG
188 SSSSSSSS SSCS IIVII
189 TTTTTTTT TTTT TTTTT
190 GGGGGGGG GGGG VVVVC
191 YYYYYYYY LLLL YYYYY
192 GGGGGGGG GGGG KKKKR
193 SSSSSSSA AAAA AAAGA
194 AAAAAAAA STTT LLLLL
195 VVVVVVVI ILIL KKKKK
196 KKNNKKQN NNNN SSEEE
197 VVVVVVVN VVVV -----
198 AAAAAAAA AAAA AAASS
199 KKKKKKKK KKKK NNDGK
200 VVVVVVVV PPPP LLLAV
201 TTTTTTTT PAKK MRKRG
202 QQPPPPPP KKPK AAAPP
203 GGGGGGGG GGGG GGGGG
204 SSSSSSSS SSSQ HHDQE
205 TTTTTTTT TTSS WWWTW
206 CCCCCCCC VVVV VAVVI
207 AAAAAAAA AAAA AAAAC
208 VVVVVVVV VIII IIIII
209 FFFFFFFF FFFF SSSVP
210 GGGGGGGG GGGG GGGGG
211 LLLLLLLL LLLL AAAAA
212 -------- ---- AAAGG
213 GGGGGGGG GGGG GGGGG
214 GGGGGGGG AAAA GGGGG
215 VVVVVVVV VVVV LLLLL
216 GGGGGGGG GGGG GGGGG
217 LLLLLLLL LLLL SSSSH
218 SSSSSSSS AAAG LLLLL
219 VVAAVVVA AAAA AAAAA
220 IIIVVIVV AMAA VVVQV
221 MMMMMMII GEEE QQQQQ
222 GGGGGGGG GGGG YYYYY
223 CCCCCCCC AAAA AAAAA
224 KKKKKKKK RRRR KKTKK
```

TABLE 3-continued

Alignment of Alcohol Dehygrogenases

```
225 AAAAAAAA ILII AAAAA
226 AAAAAAAA AASA MMMMM
227 GGGGGGGG GGGG GGGGA
228 AAAAAAAA AAAA YYYLM
229 AAAAAAAS SSSS -----
230 AAAAAAAA AAAA YYYLM
231 AAAAAAAS SSSS -----
232 RRRRRKRR RRRR RRRRR
233 IIIIIIII IIII VVVTV
234 IIIIIIII IIII LLLIV
235 GGAAAAAG GGGG GGGAA
236 VVVVVVVI VVVV IIIII
237 DDDDDDDD DDDD DDDDD
238 IIIIIIII LILF GGAST
239 NNNNNNNN NNVN GGGGG
240 KKKKKKKS PPSS EPEDD
241 DDDDDDDE SASK GGEED
242 KKKKKKKS RKRR KKKKK
243 FFFFFFFF FYFF EEEKA
244 AAAAAAAV EEED EEKAE
245 KKKKKKKK RKKK RTKEK
246 EEEEEEEA KKKE SSKQS
247 VVLLLLLL FFFF ILLLF
248 GGGGGGGG GGGG GGGGG
249 AAAAAAAA CCVV GGGAA
250 TTTTTTTT TTNT EEEEE
251 EEEEEDED EEEE VVVVV
252 CCCCCCCC FFFC FFFFF
253 VVIIIIIL VVVV IIIIL
254 NNNNNNNN NNNN DDDDD
255 PPPPPPPP PPPP FFFFF
256 QQQQQQQR KKKK TTTSK
257 DDDDDDDD DDED KKKKK
258 YYYYYYYL HHHH EETSE
259 KKKKKSTH NDDD KKKAA
260 KKKKKKKK KKKK DDNDD
261 PPPPPPPP PPPP IIMVM
262 IIIIIIII VVVI VVVVI
263 QQQQQQQQ QQQQ GSSAE
264 EEEEEEEE EEQQ AADDA
265 VVVVVVVV VVVV VVIVV
266 LLLLLLLI LLII LVQKK
267 TTKKKQQI AIIA KKEAA
268 EEEEEEEE EEEE -----
269 MMMMMMML MLMM AAAAC
270 SSTTTTTT TTTT TTTTT
271 NNDDDDDK NNND DNKPN
272 GGGGGGGG GGGG GGGGG
273 GGGGGGGG GGGG GGGGG
274 -------- ---- ---L-
275 -------- ---- ---G-
276 VVVVVVVV VVVV AAPAA
277 DDDDDDDD DDDD HHHHH
278 FFFFFFFF RRRR GGGAG
279 SSSSSSSA SSAS VIVVT
280 FFFFFFFL VVVV IIIIL
281 EEEEEEED EEEE NNNLV
282 VVVVVVVC CCCC VVVLL
283 IIIIIIIA TTTT SSSAS
284 GGGGGGGG GGGG VVVVT
285 RRRRQRRG NNSS SSSAS
286 LLLLLLLS IVIV EEEEP
287 DDDDDDDE NNQQ AAAKK
288 TTTTTTTT AAAA AAAPS
289 MMMMMMMM MMMM IIIFY
290 VVMMMTTK IIII EESQE
291 TTAAASSA QSSQ AALQQ
292 AASSSAAA AAAA SSSAA
293 LLLLLLLL FFFF TTTTA
294 SSLLLLLD EEEE RREEG
295 CCCCCSSC CCCC YYYYF
296 CCCCCCCT VVVV VCVVA
297 QQHHHHHT HHHH RRRRR
298 EEEEEASA DDDD -----
299 AAAAAAAA GGGG AAPSP
300 YYCCCCCW WWWW NNCHG
301 GGGGGGGG GGGG GGGGS
```

TABLE 3-continued
Alignment of Alcohol Dehygrogenases

```
302 VVTTTVVS VVVV TTTST
303 SSSSSSSC AAAA TVVVM
304 VVVVVVVT VVVV VVVVV
305 IIIIIVIF VVVV VVVIV
306 VVVVVVVI VVVV VVVIV
307 GGGGGGGG GGGG GGGGS
308 VVVVVVVV VVVV MLLLM
309 PPPPPPPA PPPP PPPPP
310 PPPPPPPA HHSS AAAAA
311 DDDADNSG KKKK GGNNG
312 SSSSSAAS DDDD AAAAA
313 QQQQQQQK ADDD KKYFK
314 NNNNNNSG EQAA CCVLL
315 LLLLLLLL FFFF CSKKG
316 SSSSSSST KKKK SSSAA
317 MMMIIMVI TTTT DDEPD
318 NNNNNNNF HHHH VVVVI
319 PPPPPPPP PPPP FFFFF
320 MMMMMMME MMMM NNSTW
321 LLLLLLSE NNNN QHHTL
322 LLLLLLLL FFFF VVVVT
323 LLLLLLLI LLLL VVVVV
324 SSTTTLLI NSNN KKKRK
325 GGGGGGGG EEEE -----
326 RRRRRRRR RKRR -----
327 TTTTTTTT TTTT -----
328 WWWWWWWI LLLL -----
329 KKKKKKKN KKKK SSSMM
330 GGGGGGGG GGGG IIIIL
331 AAAAAAAT TTTT SSNNK
332 IIIVIIIF FFFF IIIII
333 FFFLYFFF FFYF KVVKC
334 GGGGGGGG GGGG GGGGG
335 GGGGGGGG NNNN SSSSS
336 FFFFFFFW YYYY YYYYH
337 KKKKKKKK KKKK VVVVV
338 SSSSSSSS PPPP GGGGG
339 KKKKKKKV RRRK NNNNN
```

TABLE 3-continued
Alignment of Alcohol Dehygrogenases

```
340 DDEEEDDD TTTT RRRRR
341 SSCGSSAS DDDD AAAQI
342 VVVIVVVI LLLI DDDDD
343 PPPPPPPP PPPP TTTGS
344 KKKKKKKK NNNG RRRVI
345 LLLLLLLL VVVV EEEEE
346 VVVVVVVV VVVV AAAAA
347 AAAAAAAT EEEE LLLLL
348 DDDDDDDD LMKK DDDDE
349 FFFFFFFY YYYY FFFFY
350 MMMMMMMK MMMM FFFFV
351 AAAAAAAN KKKN AASAS
352 KKKKKKKK KKGK RRRRR
353 KKKKKKKK EEEE -----
354 FFFFFFFF LLLL -----
355 AASSSPPN EEEE GGGGG
356 LLLLLLLL VLLL LLLLL
357 DDDDDEDD EEEE VVIIV
358 PPAAAPPA KKKK KKKKK
359 LLLLLLLL FFFF SSSAP
360 IIIIIIIV IIII PPPPY
361 TTTTTTTT TTTT IIIFY
362 HHHHNHHH HHHH KKKKK
363 VVVVIVVT SSTT VVIKV
364 LLLLLLLL VVVV VVVAQ
365 PPPPPPPP PPPP GGGPP
366 FFFFFFFF FFFF LLLLF
367 EEEEEED ASSS SSSQS
368 KKKKKKKK EEEE TSEDT
369 IIIIIIII IIII LLLLL
370 NNNNNNNS NNNN PPPPP
371 EEEEEEEE KTKK EEKQD
372 GGGGGAAA AAAA IIVIV
373 FFFFFFFF FFFF YYYFY
374 DDDDDDDD DDDD EEDER
375 LLLLLLLL LLYY KKLLL
376 LLLLLLLM MMMM MMMMM
377 RRHHRRRN ALLL EEEGH
378 SSSSSSAQ KKKK KKKQE
```

TABLE 3-continued

Alignment of Alcohol Dehygrogenases

```
379  GGGGGGGG  GGGG  GGGGN
380  EKKKKKKK  EEEE  QQKKK
381  --------  ----  IIIII
382  SSSSSSSS  GGSS  VALAA
383  IIIIIIII  ILII  GGGGG
384  RRRRRRRR  RRRR  RRRRR
385  TTTTTTTT  CCCC  YYYYI
386  IIIVVVVI  IIII  VVVVV
387  LLLLLLLL  IMII  VVVLL
388  TTMTTTTI  RRKT  DDDED
389  FFFFFFFF  MMMM  TTTIL
```

The alcohol dehydrogenases are divided into those from mammals (left column), plants (middle column), and fungi (right column). From left to right, the sequences (read vertically), are horse liver E, horse liver S, human class 1 alpha, human class 1 beta, human class 1 gamma, human class 2, moust, rat, maize 1, maize 2, pea, Arabadopsis, *Saccharmoyces cerevisiae* 1, *Saccharomyces cerevisiae* 2, *Saccharomyces cerevisiae* 3, Aspergillus, *Schizosaccharomyces pombe*.

TABLE 4

Examples of Parsing Elements Drawn Elements Drawn from an Alignment of Alcohol Dehydrogenase

(i) Gap parse, confirmed in the undeleted sequences

```
057  TTTNNTSK  KKKK  DDDDD
058  --------  ----  WWWWW
059  -------F  GGGG  PPPPP
060  LLMLLLLE  QQQQ  LLLLL
```

(ii) APC P parse

```
032  PPPPPPPP  PPPP  PPPPP
065  PPPPPPPP  PPPP  PPPPP
```

(iii) Two Examples of Distributed Parses

```
030  AAAAAAAA  AAAA  PPPPA
031  PPPPPPPP  PPPP  KKKEE
061  VVVVVVFG  TTTT  PPPPP
062  TTTTTTTL  PPPP  VTVSA
063  PPPPPPPA  VVLL  KKKKK
```

(iv) APC G parse

```
203  GGGGGGGG  GGGG  GGGGG
210  GGGGGGGG  GGGG  GGGGG
```

(v) Combination parse

```
176  PPPPPPPN  PPPP  DDDPP
365  PPPPPPPP  PPPP  GGGPP
```

(vi) Distributed combination parse

(vii) String parse

```
017  EEEEEEEE  EEEE  EEEKG
018  ENLVLLPA  AAAA  SSNAG
019  KKKKKHHG  GGGG  HNKGP
020  KKKKKKKK  KKKK  GGGTE
```

TABLE 5

Examples of Surface Algorithms Applied to Two Parsed Segments of an Alignment of Alcohol Dehydrogenase
Italicized assignments do not indicate surface position, but are presented simply for reference.

The alignment presented to reflect subgroups with MPI ≥ ca. 40%

| | |
|---|---|
| 365 PPPPPPPPPPPP GGGPP | *combination parse* |
| 366 FFFFFFFFFFFF LLLLF | |
| 367 EEEEEEDASSS SSSQS | Surface Algorithm 1, 2 variable subgroups |
| 368 KKKKKKKEEEE TSEDT | Surface Algorithm 1, 2 variable subgroups |
| 369 IIIIIIIIIII LLLLL | |

TABLE 5-continued

Examples of Surface Algorithms Applied to Two Parsed
Segments of an Alignment of Alcohol Dehydrogenase
Italicized assignments do not indicate surface position, but
are presented simply for reference.

| | | |
|---|---|---|
| 370 | NNNNNNNSNNNN PPPPP | polar single variable |
| 371 | EEEEEEEKTKK EEKQD | Surface Algorithm 1, 2 variable subgroups |
| 372 | GGGGGAAAAAAA IIVIV | |
| 373 | FFFFFFFFFFFF YYYFY | |
| 374 | DDDDDDDDDDDD EEDER | polar single variable |
| 375 | LLLLLLLLLLYY KKLLL | Surface Algorithm 1, 2 variable subgroups |
| 376 | LLLLLLLMMMMM MMMMM | |
| 377 | RRHHRRRNALLL EEEGH | Surface Algorithm 1, 2 variable subgroups |
| 378 | SSSSSSAQKKKK KKKQE | Surface Algorithm 1, 2 variable subgroups |
| 379 | GGGGGGGGGGGG GGGGN | |
| 380 | EKKKKKKKEEEE QQKKK | Surface Algorithm 1, 2 variable subgroups |
| 381 | ------------ IIIII | *gap parse* |
| 382 | SSSSSSSSGGSS VALAA | |
| 383 | IIIIIIIIILII GGGGG | |
| 384 | RRRRRRRRRRRR RRRRR | *APC R* |
| 385 | TTTTTTTTCCCC YYYYI | |
| 386 | IIIVVVVIIIII VVVVV | |
| 387 | LLLLLLLLIMII VVVLL | |
| 388 | TTMTTTTIRRKT DDDED | Surface Algorithm 1, 2 variable subgroups |
| 389 | FFFFFFFFMMMM TTTIL | |

The alignment presented to reflect subgroups with MPI ≧ ca. 50%

| | | |
|---|---|---|
| 365 | PPPPPPPP PPPP GGGPP | *combination parse* |
| 366 | FFFFFFFF FFFF LLLLF | |
| 367 | EEEEEED ASSS SSSQS | Surface Algorithm 1, 3 variable subgroups |
| 368 | KKKKKKKK EEEE TSEDT | polar single variable |
| 369 | IIIIIIII IIII LLLLL | |
| 370 | NNNNNNNS NNNN PPPPP | polar single variable |
| 371 | EEEEEEEE KTKK EEKQD | Surface Algorithm 1, 2 variable subgroups |
| 372 | GGGGGAAA AAAA IIVIV | |
| 373 | FFFFFFFF FFFF YYYFY | |
| 374 | DDDDDDDD DDDD EEDER | polar single variable |
| 375 | LLLLLLLL LLYY KKLLL | Surface Algorithm 1, 2 variable subgroups |
| 376 | LLLLLLLM MMMM MMMMM | |
| 377 | RRHHRRRN ALLL EEEGH | Surface Algorithm 1, 3 variable subgroups |
| 378 | SSSSSSAQ KKKK KKKQE | Surface Algorithm 1, 2 variable subgroups |

TABLE 5-continued

Examples of Surface Algorithms Applied to Two Parsed
Segments of an Alignment of Alcohol Dehydrogenase
Italicized assignments do not indicate surface position, but
are presented simply for reference.

```
379  GGGGGGGG GGGG GGGGN

380  EKKKKKKK EEEE QQKKK            Surface Algorithm 1, 2 variable
                                    subgroups 381  -------- ---- IIIII            gap parse

382  SSSSSSSS GGSS VALAA

383  IIIIIIII ILII GGGGG

384  RRRRRRRR RRRR RRRRR            APC R

385  TTTTTTTT CCCC YYYYI

386  IIVVVVVI IIII VVVVV

387  LLLLLLLL IMII VVVLL

388  TTMTTTTI RRKT DDDED            Surface Algorithm 1, 3 variable
                                    subgroups 389  FFFFFFFF MMMM TTTIL
```
The alignment presented to reflect subgroups with MPI ≧ ca. 60%

```
365  PPPPPPPP PPPP GGGP P            combination parse

366  FFFFFFFF FFFF LLLL F

367  EEEEEED ASSS SSSQ S            Surface Algorithm 1, 3 variable
                                    subgroups 368  KKKKKKKK EEEE TSED T            polar single variable

369  IIIIIIII IIII LLLL L

370  NNNNNNNS NNNN PPPP P            polar split

371  EEEEEEEE KTKK EEKQ D            Surface Algorithm 1, 2 variable
                                    subgroups

372  GGGGGAAA AAAA IIVI V

373  FFFFFFFF FFFF YYYF Y

374  DDDDDDDD DDDD EEDE R            polar single variable

375  LLLLLLLL LLYY KKLL L            Surface Algorithm 1, 2 variable
                                    subgroups

376  LLLLLLLM MMMM MMMM M

377  RRHHRRRN ALLL EEEG H            Surface Algorithm 1, 3 variable
                                    subgroups 378  SSSSSSAQ KKKK KKKQ E            Surface Algorithm 1, 2 variable
                                    subgroups

379  GGGGGGGG GGGG GGGG N

380  EKKKKKKK EEEE QQKK K            Surface Algorithm 1, 2 variable
                                    subgroups 381  -------- ---- IIII I            gap parse

382  SSSSSSSS GGSS VALA A

383  IIIIIIII ILII GGGG G

384  RRRRRRRR RRRR RRRR R            APC R

385  TTTTTTTT CCCC YYYY I

386  IIIVVVVI IIII VVVV V
```

TABLE 5-continued

Examples of Surface Algorithms Applied to Two Parsed Segments of an Alignment of Alcohol Dehydrogenase
Italicized assignments do not indicate surface position, but are presented simply for reference.

```
387 LLLLLLLL IMII VVVL L

388 TTMTTTTI RRKT DDDE D              Surface Algorithm 1, 3 variable
                                       subgroups

389 FFFFFFFF MMMM TTTI L
```

The alignment presented to reflect subgroups with MPI ≥ ca. 70%

```
365 PPPPPPPP PPPP GGG P P             combination parse

366 FFFFFFFF FFFF LLL L F

367 EEEEEED ASSS SSS Q S              Surface Algorithm 1, 2 variable
                                       subgroups 368 KKKKKKKK EEEE TSE D T             polar single variable

369 IIIIIIII IIII LLL L L

370 NNNNNNNS NNNN PPP P P             polar split

371 EEEEEEEE KTKK EEK Q D             Surface Algorithm 1, 2 variable
                                       subgroups

372 GGGGGAAA AAAA IIV I V

373 FFFFFFFF FFFF YYY F Y

374 DDDDDDDD DDDD EED E R             polar single variable

375 LLLLLLLL LLYY KKL L L             Surface Algorithm 1, 2 variable
                                       subgroups

376 LLLLLLLM MMMM MMM M M

377 RRHHRRRN ALLL EEE G H             Surface Algorithm 1, 2 variable
                                       subgroups

378 SSSSSSAQ KKKK KKK Q E

379 GGGGGGGG GGGG GGG G N

380 EKKKKKKK EEEE QQK K K             Surface Algorithm 1, 2 variable
                                       subgroups 381 -------- ---- III I I             gap parse

382 SSSSSSSS GGSS VAL A A

383 IIIIIIII ILII GGG G G

384 RRRRRRRR RRRR RRR R R             APC R

385 TTTTTTTT CCCC YYY Y I

386 IIIVVVVI IIII VVV V V

387 LLLLLLLL IMII VVV L L

388 TTMTTTTI RRKT DDD E D             Surface Algorithm 1, 2 variable
                                       subgroups

389 FFFFFFFF MMMM TTT I L
```

The alignment presented to reflect subgroups with MPI ≥ ca. 80%

```
365 PPPPPPP P PPPP GGG P P            combination parse

366 FFFFFFF F FFFF LLL L F

367 EEEEEEE D ASSS SSS Q S

368 KKKKKKK K EEEE TSE D T            polar single variable
```

TABLE 5-continued

Examples of Surface Algorithms Applied to Two Parsed
Segments of an Alignment of Alcohol Dehydrogenase
Italicized assignments do not indicate surface position, but
are presented simply for reference.

```
369  IIIIIII I IIII LLL L L

370  NNNNNNN S NNNN PPP P P           polar split

371  EEEEEEE E KTKK EEK Q D           Surface Algorithm 1, 2 variable
                                      subgroups

372  GGGGGAA A AAAA IIV I V

373  FFFFFFF F FFFF YYY F Y

374  DDDDDDD D DDDD EED E R           polar single variable

375  LLLLLLL L LLYY KKL L L           Surface Algorithm 1, 2 variable
                                      subgroups

376  LLLLLLL M MMMM MMM M M

377  RRHHRRR N ALLL EEE G H           Surface Algorithm 1, 2 variable
                                      subgroups

378  SSSSSSA Q KKKK KKK Q E

379  GGGGGGG G GGGG GGG G N

380  EKKKKKK K EEEE QQK K K           Surface Algorithm 1, 2 variable
                                      subgroups 381  ------- - ---- III I I           gap parse

382  SSSSSSS S GGSS VAL A A

383  IIIIIII I ILII GGG G G

384  RRRRRRR R RRRR RRR R R           APC R

385  TTTTTTT T CCCC YYY Y I

386  IIIVVVV I IIII VVV V V

387  LLLLLLL L IMII VVV L L

388  TTMTTTT I RRKT DDD E D           Surface Algorithm 1, 2 variable
                                      subgroups

389  FFFFFFF F MMMM TTT I L
```

The alignment presented to reflect subgroups with MPI ≥ ca. 85%

```
365  PPPPP PP P PP PP GG G P P        combination parse

366  FFFFF FF F FF FF LL L L F

367  EEEEE EE D AS SS SS S Q S

368  KKKKK KK K EE EE TS E D T

369  IIIII II I II II LL L L L

370  NNNNN NN S NN NN PP P P P        polar split

371  EEEEE EE E KT KK EE K Q D        polar single variable

372  GGGGG AA A AA AA II V I V

373  FFFFF FF F FF FF YY Y F Y

374  DDDDD DD D DD DD EE D E R        polar split

375  LLLLL LL L LL YY KK L L L

376  LLLLL LL M MM MM MM M M M
```

TABLE 5-continued

Examples of Surface Algorithms Applied to Two Parsed Segments of an Alignment of Alcohol Dehydrogenase
*Italicized assignments do not indicate surface position, but are presented simply for reference.*

```
377 RRHHR RR N AL LL EE E G H          Surface Algorithm 1, 2 variable
                                        subgroups

378 SSSSS SA Q KK KK KK K Q E

379 GGGGG GG G GG GG GG G G N

380 EKKKK KK K EE EE QQ K K K          polar single variable

381 ----- -- - -- -- II I I I          gap parse

382 SSSSS SS S GG SS VA L A A

383 IIIII II I IL II GG G G G

384 RRRRR RR R RR RR RR R R R          APC R

385 TTTTT TT T CC CC YY Y Y I

386 IIIVV VV I II II VV V V V

387 LLLLL LL L IM II VV V L L

388 TTMT

TABLE 5-continued

Examples of Surface Algorithms Applied to Two Parsed
Segments of an Alignment of Alcohol Dehydrogenase
Italicized assignments do not indicate surface position, but
are presented simply for reference.

```
387 LL LLL LL L I M I I VV V L L

388 TT MTT TT I R R K T DD D E D

389 FF FFF FF F M M M M TT T I L
```

TABLE 6

Predictions made by the "Evolutionarily Sophisticated" Surface
Algorithm for Alcohol Dehydrogenase

| MPI | Residues identified | % of surface | % detected correct |
|---|---|---|---|
| 90% | 8 | 4 | 100 |
| 85% | 31 | 16 | 97 |
| 80% | 45 | 24 | 96 |
| 70% | 70 | 40 | 96 |
| 60% | 91 | 46 | 95 |
| 50% | 95 | 48 | 94 |

TABLE 7

Examples of Interior Algorithms Applied to an Alignment of
Alcohol Dehydrogenase.
Iltalicized assignments do not indicate surface position, but are
presented simply for reference.

The alignment presented to reflect subgroups with MPI ≧ ca. 40%

```
365 PPPPPPPPPPPP GGGPP       combination parse

366 FFFFFFFFFFFF LLLLF       Interior algorithm 4, hydrophobic single variable

367 EEEEEEDASSS SSSQS

368 KKKKKKKEEEE TSEDT

369 IIIIIIIIIII LLLLL        Interior algorithm 3, hydrophobic split

370 NNNNNNNSNNNN PPPPP

371 EEEEEEEKTKK EEKQD

372 GGGGGAAAAAAA IIVIV

373 FFFFFFFFFFFF YYYFY       Interior algorithm 4, hydrophobic single variable

374 DDDDDDDDDDDD EEDER

375 LLLLLLLLLLYY KKLLL

376 LLLLLLLMMMMM MMMMM       Interior algorithm 4, hydrophobic single variable

377 RRHHRRRNALLL EEEGH

378 SSSSSSAQKKKK KKKQE

379 GGGGGGGGGGGG GGGGN

380 EKKKKKKKEEEE QQKKK

381 ------------ IIIII       gap parse
```

TABLE 7-continued

Examples of Interior Algorithms Applied to an Alignment of
Alcohol Dehydrogenase.
Iltalicized assignments do not indicate surface position, but are
presented simply for reference.

| | | |
|---|---|---|
| 382 | SSSSSSSSGGSS VALAA | |
| 383 | IIIIIIIIILII GGGGG | |
| 384 | RRRRRRRRRRRR RRRRR | *APC R* |
| 385 | TTTTTTTTCCCC YYYYI | |
| 386 | IIIVVVVIIIII VVVVV | Interior algorithm 4, hydrophobic single variable |
| 387 | LLLLLLLLIMII VVVLL | Interior algorithm 2, hydrophobic variable |
| 388 | TTMTTTTIRRKT DDDED | |
| 389 | FFFFFFFFMMMM TTTIL | |

The alignment presented to reflect subgroups with MPI ≥ ca. 50%

| | | |
|---|---|---|
| 365 | PPPPPPPP PPPP GGGPP | *combination parse* |
| 366 | FFFFFFFF FFFF LLLLF | Interior algorithm 4, hydrophobic single variable |
| 367 | EEEEEED ASSS SSSQS | |
| 368 | KKKKKKKK EEEE TSEDT | |
| 369 | IIIIIIII IIII LLLLL | Interior algorithm 3, hydrophobic split |
| 370 | NNNNNNNS NNNN PPPPP | |
| 371 | EEEEEEEE KTKK EEKQD | |
| 372 | GGGGGAAA AAAA IIVIV | |
| 373 | FFFFFFFF FFFF YYYFY | Interior algorithm 4, hydrophobic single variable |
| 374 | DDDDDDDD DDDD EEDER | |
| 375 | LLLLLLLL LLYY KKLLL | |
| 376 | LLLLLLLM MMMM MMMMM | Interior algorithm 4, hydrophobic single variable |
| 377 | RRHHRRRN ALLL EEEGH | |
| 378 | SSSSSSAQ KKKK KKKQE | |
| 379 | GGGGGGGG GGGG GGGGN | |
| 380 | EKKKKKKK EEEE QQKKK | |
| 381 | -------- ---- IIIII | *gap parse* |
| 382 | SSSSSSSS GGSS VALAA | |
| 383 | IIIIIIII ILII GGGGG | |
| 384 | RRRRRRRR RRRR RRRRR | *APC R* |
| 385 | TTTTTTTT CCCC YYYYI | |
| 386 | IIIVVVVI IIII VVVVV | Interior algorithm 4, hydrophobic single variable |
| 387 | LLLLLLLL IMII VVVLL | Interior algorithm 2, hydrophobic variable |
| 388 | TTMTTTTI RRKT DDDED | |
| 389 | FFFFFFFF MMMM TTTIL | |

The alignment presented to reflect subgroups with MPI ≥ ca. 60%

| | | |
|---|---|---|
| 365 | PPPPPPPP PPPP GGGP P | *combination parse* |
| 366 | FFFFFFFF FFFF LLLL F | Interior algorithm 3, hydrophobic splitN |

TABLE 7-continued

Examples of Interior Algorithms Applied to an Alignment of
Alcohol Dehydrogenase.
Iltalicized assignments do not indicate surface position, but are
presented simply for reference.

380

| | | |
|---|---|---|
| 367 EEEEEEED ASSS SSSQ S | | |
| 368 KKKKKKKK EEEE TSED T | | |
| 369 IIIIIIII IIII LLLL L | Interior algorithm 3, hydrophobic split |
| 370 NNNNNNNS NNNN PPPP P | | |
| 371 EEEEEEEE KTKK EEKQ D | | |
| 372 GGGGGAAA AAAA IIVI V | | |
| 373 FFFFFFFF FFFF YYYF Y | Interior algorithm 4, hydrophobic single variable |
| 374 DDDDDDDD DDDD EEDE R | | |
| 375 LLLLLLLL LLYY KKLL L | | |
| 376 LLLLLLLM MMMM MMMM M | Interior algorithm 4, hydrophobic single variable |
| 377 RRHHRRRN ALLL EEEG H | | |
| 378 SSSSSSAQ KKKK KKKQ E | | |
| 379 GGGGGGGG GGGG GGGG N | | |
| 380 EKKKKKKK EEEE QQKK K | | |
| 381 -------- ---- IIII I | *gap parse* |
| 382 SSSSSSSS GGSS VALA A | | |
| 383 IIIIIIII ILII GGGG G | | |
| 384 RRRRRRRR RRRR RRRR R | *APC R* |
| 385 TTTTTTTT CCCC YYYY I | Interior algorithm 3, hydrophobic split |
| 386 IIIVVVVI IIII VVVV V | Interior algorithm 4, hydrophobic single variable |
| 387 LLLLLLLL IMII VVVL L | Interior algorithm 2, hydrophobic variable |
| 388 TTMTTTTI RRKT DDDE D | | |
| 389 FFFFFFFF MMMM TTTI L | | |

The alignment presented to reflect subgroups with MPI ≥ ca. 70%

| | | |
|---|---|---|
| 365 PPPPPPPP PPPP GGG P P | *combination parse* |
| 366 FFFFFFFF FFFF LLL L F | Interior algorithm 3, hydrophobic split |
| 367 EEEEEEED ASSS SSS Q S | | |
| 368 KKKKKKKK EEEE TSE D T | | |
| 369 IIIIIIII IIII LLL L L | Interior algorithm 3, hydrophobic split |
| 370 NNNNNNNS NNNN PPP P P | | |
| 371 EEEEEEEE KTKK EEK Q D | | |
| 372 GGGGGAAA AAAA IIV I V | | |
| 373 FFFFFFFF FFFF YYY F Y | Interior algorithm 3, hydrophobic split |
| 374 DDDDDDDD DDDD EED E R | | |
| 375 LLLLLLLL LLYY KKL L L | | |
| 376 LLLLLLLM MMMM MMM M M | Interior algorithm 4, hydrophobic single variable |

TABLE 7-continued

Examples of Interior Algorithms Applied to an Alignment of
Alcohol Dehydrogenase.
Iltalicized assignments do not indicate surface position, but are
presented simply for reference.

```
377 RRHHRRRN ALLL EEE G H
378 SSSSSSAQ KKKK KKK Q E
379 GGGGGGGG GGGG GGG G N
380 EKKKKKKK EEEE QQK K K
381 -------- ---- III I I        gap parse
382 SSSSSSSS GGSS VAL A A
383 IIIIIIII ILII GGG G G
384 RRRRRRRR RRRR RRR R R        APC R
385 TTTTTTTT CCCC YYY Y I        Interior algorithm 3, hydrophobic split
386 IIIVVVVI IIII VVV V V        Interior algorithm 4, hydrophobic single variable
387 LLLLLLLL IMII VVV L L        Interior algorithm 2, hydrophobic variable
388 TTMTTTTI RRKT DDD E D
389 FFFFFFFF MMMM TTT I L        Interior algorithm 3, hydrophobic split
```

The alignment presented to reflect subgroups with MPI ≧ ca. 80%

```
365 PPPPPPP P PPPP GGG P P        combination parse
366 FFFFFFF F FFFF LLL L F        Interior algorithm 3, hydrophobic split
367 EEEEEEE D ASSS SSS Q S
368 KKKKKKK K EEEE TSE D T
369 IIIIIII I IIII LLL L L        Interior algorithm 3, hydrophobic split
370 NNNNNNN S NNNN PPP P P
371 EEEEEEE E KTKK EEK Q D
372 GGGGGAA A AAAA IIV I V
373 FFFFFFF F FFFF YYY F Y        Interior algorithm 3, hydrophobic split
374 DDDDDDD D DDDD EED E R
375 LLLLLLL L LLYY KKL L L
376 LLLLLLL M MMMM MMM M M        Interior algorithm 3, hydrophobic split
377 RRHHRRR N ALLL EEE G H
378 SSSSSSA Q KKKK KKK Q E
379 GGGGGGG G GGGG GGG G N
380 EKKKKKK K EEEE QQK K K
381 ------- - ---- III I I        gap parse
382 SSSSSSS S GGSS VAL A A
383 IIIIIII I ILII GGG G G
384 RRRRRRR R RRRR RRR R R        APC R
385 TTTTTTT T CCCC YYY Y I        Interior algorithm 3, hydrophobic split
386 IIIVVVV I IIII VVV V V        Interior algorithm 4, hydrophobic single variable
387 LLLLLLL L IMII VVV L L        Interior algorithm 2, hydrophobic variable
```

TABLE 7-continued

Examples of Interior Algorithms Applied to an Alignment of Alcohol Dehydrogenase.
Italicized assignments do not indicate surface position, but are presented simply for reference.

```
388  TTMTTTT I RRKT DDD E D
389  FFFFFFF F MMMM TTT I L        Interior algorithm 3, hydrophobic split
```

The alignment presented to reflect subgroups with MPI ≥ ca. 85%

```
365  PPPPP PP P PP PP GG G P P     combination parse
366  FFFFF FF F FF FF LL L L F     Interior algorithm 3, hydrophobic split
367  EEEEE EE D AS SS SS S Q S
368  KKKKK KK K EE EE TS E D T
369  IIIII II I II II LL L L L     Interior algorithm 3, hydrophobic split
370  NNNNN NN S NN NN PP P P P
371  EEEEE EE E KT KK EE K Q D
372  GGGGG AA A AA AA II V I V     Interior algorithm 3, hydrophobic split
373  FFFFF FF F FF FF YY Y F Y     Interior algorithm 3, hydrophobic split
374  DDDDD DD D DD DD EE D E R
375  LLLLL LL L LL YY KK L L L
376  LLLLL LL M MM MM MM M M M     Interior algorithm 3, hydrophobic split
377  RRHHR RR N AL LL EE E G H
378  SSSSS SA Q KK KK KK K Q E
379  GGGGG GG G GG GG GG G G N
380  EKKKK KK K EE EE QQ K K K
381  ----- -- - -- -- II I I I     gap parse
382  SSSSS SS S GG SS VA L A A
383  IIIII II I IL II GG G G G     Interior algorithm 3, hydrophobic split
384  RRRRR RR R RR RR RR R R R     APC R
385  TTTTT TT T CC CC YY Y Y I     Interior algorithm 3, hydrophobic split
386  IIIVV VV I II II VV V V V     Interior algorithm 4, hydrophobic single variable
387  LLLLL LL L IM II VV V L L     Interior algorithm 2, hydrophobic variable
388  TTMTT TT I RR KT DD D E D
389  FFFFF FF F MM MM TT T I L     Interior algorithm 3, hydrophobic split
```

The alignment presented to reflect subgroups with MPI ≥ ca. 90%

```
365  PP PPP PP P P P P GG G P P    combination parse
366  FF FFF FF F F F F LL L L F    Interior algorithm 3, hydrophobic split
367  EE EEE EE D A S S SS S Q S
368  KK KKK KK K E E E TS E D T
369  II III II I I I I LL L L L    Interior algorithm 3, hydrophobic split
370  NN NNN NN S N N N PP P P P
371  EE EEE EE E K T K K EE K Q D
372  GG GGG AA A A A A II V I V    Interior algorithm 3, hydrophobic split
```

TABLE 7-continued

Examples of Interior Algorithms Applied to an Alignment of
Alcohol Dehydrogenase.
Iltalicized assignments do not indicate surface position, but are
presented simply for reference.

```
373 FF FFF FF F F F F F YY Y F Y  Interior algorithm 3, hydrophobic split

374 DD DDD DD D D D D D EE D E R

375 LL LLL LL L L L Y Y KK L L L

376 LL LLL LL M M M M M MM M M M  Interior algorithm 3, hydrophobic split

377 RR HHR RR N A L L L EE E G H

378 SS SSS SA Q K K K K KK K Q E

379 GG GGG GG G G G G GG G G N

380 EK KKK KK K E E E E QQ K K K

381 -- --- -- - - - - - II I I I   gap parse

382 SS SSS SS S G G S S VA L A A

383 II III II I I L I I GG G G G  Interior algorithm 3, hydrophobic split

384 RR RRR RR R R R R R RR R R R   APC R

385 TT TTT TT T C C C C YY Y Y I  Interior algorithm 3, hydrophobic split

386 II IVV VV I I I I I VV V V V  Interior algorithm 4, hydrophobic single variable 387 LL LLL LL L I M I I VV V L L  Interior algorithm 3, hydrophobic split

388 TT MTT TT I R R K T DD D E D

389 FF FFF FF F M M M M TT T I L  Interior algorithm 3, hydrophobic split
```

TABLE 8

Alignment of the Sequences of Homologous Kinases

```
protein #  ->  5        10        15      20     25    30      35       40        45       50        55        60          65       70    75    80         85     90
                |         |         |       |      |     |       |        |         |        |         |         |           |        |     |     |          |      |
001  41    DDGEKQHSS TTT-STST EDEEFDA GGGG AEESM DNQDTMGS SSSSEEG EESEEEEESI TTSEEE TTA EEEEDSRL DNNK
002  42    QQDDNDDDD DDDDDDDD EENNSVK NVDD NNDRE DEDERGSQ EEEEQQQ SSSSSTTSEQ DDEDDD EEE KKNKKQDI QNRN
003  43    FFFFFFFFF FFFFFFFF YYYYMYY YWWW YYYYY YYLLFFLY VVVVVVV LLILILLLIL IIILLV FLL IIILLLIV LLLL
004  44    EDEEQQQQN NNNNSNSN QQEENND QREE KQTET QKVERTRQ MQQQCCC RRTQKKKKQM TMIVVL KRR TTITNKVH VQSV
005  45    RRRRIIIII FFFFFFFF LLPPSII ILFF RKKPK LLQFNIFV LLLLLLL LLLLLLLLLL MMMLLL KKK LMQLLLLF IFFL
006  46    IIKKLLMLI LLLLLLLI FYKKKEK VGVL LVIVE VILLVHVG SLLLLML EEEIVVVELM KKHGGG IVG LSLRHLKN GGGG
007  47    KKKKRRRRD MMMMMMMK EEEEEEA KKEE EEEAK RDGDTGSP TKKKQHH VVRKKEEKRE HHNEEE KKG RRALKRWE RKKK
008  48    TTTTTTTT VVVVVVVV EDIIARL TTTT KKKEK KKKELAIL RRRRRRR KKRRRRRKKE KKKQQR VVV EEPLLFEV TTTT
009  49    LLLLLLLL LLLLLLLL LILLLLI LLVV VIIIV LIILLLIL IIIILLL LLLLLLLLLL LLLIII LLL LLLLLLLI LLLL
010  50    GGGGGGGG GGGGGGGG GGGGGGG GGGG GGGGG GGGGGGGG GGGGGGG GGGGGGGGGG GGGGG GGG GGGGGGGG GGGG
011  51    TTTTTTTV KKKKKKKK KKRRGSR ETAA EEEVE REAHSPAS STTTASS QQTNAAAARS GGGRRR SSM QQQSSSER SAAE
012  52    GGGGGGGG GGGGGGGG GGGGGGG GGGG GGGGG GGGGGGGG GGGGGGG GGGGGGGGGG GGGGG GGG GGGGGGGG GGGG
013  53    SSSSSSSG SSSSSSSS AAVVKKS SSSS TTTAT KTNNESAG SSSSGGG CCCQQQQQNQ QQQNNN AAA SSSAAAAH AAAE
014  54    FFFFFFFF FFFFFFFF FFSSFFF FTMM YYYYY YFSYFEYF FFFFFFF FFFFFFFFFF YYYFFF FFF FFFFFFFF FFFF
015  55    GGGGGGGG GGGGGGGG SSSSGGS GSGG GGGGA SSGGSGGG GGGGGGG GGGGGGGGGG GGGGG GGG GGGGGGGG GGGG
016  56    RRRRRRRR KKKKKKKK VVVVAQR KCKK VVVTC ESTNECVS TTTTSSS EEDEEREEEV EEDEEE TTR MMMEEEKC QKKK
```

TABLE 8-continued

Alignment of the Sequences of Homologous Kinases

```
017  57  VVVVVVVV VVVVVVVV VVVVVV VVVV VVVVV VVVVVVVV VVVVVVV VVVVVVVVVV VVVVVV VVV VVVVVVVV VVVV
018  58  MMMMHHHHE MMMMMMML RRRRCFV KRKK YYYYY FYVSFFYY YFFFYYY WWWWWGWWFR YYYFFF YYY YYYYYYFY VVVV
019  59  LLLLLLLLL LLLLLLLL RRRRTRR LLLL KKKKL EKKKQDKS KRRRKKK MMLMWWMMYR EEESSS KKK EEEEEELH EEEK
020  60  VVVVIIVIV ASSSAAAA CCCCCLV AAAV AAGAG AAAVVSAG GGGGAAA GGGGGGGAGG GAGGGG GGG GGGGGGAG AAAA
021  61  KKKKRRRRQ DEEEEDEE VVIITVE YKKK LRRRC IKLLESEI KRRLTTT TTTTYTYTKK VVYRRR LIV NVITTQET TTTT
022  62  HHHHSSSSL RRRRRRRR KKHHEEH HHHH DHHDQ NDHHDHDR WWWYYY WWWWYTYYWW WWWLLL WWW AALAALCL AAAA
023  63  MKKKRRVNK KKKKKRKR VLKKKKR TARR LKKPH IIVKPPIV HHHHRHH NNNNNTNNRR KKKRRR IIV RKKVLKHL HFYF
024  64  EEAAHHHHS GGGGGGGG LCPPSKA TKYQ RLTHS TTPPVDYA GGGGGGG GGGGNGGKNG KRRAAA PPP DGSDDTND DDDH
025          --------E -------- ------- ---- P---- -G--E--- ------- ---------- ------ EDE IVFIIELN LLLL
026          --------- -------- ------- ---- G---- -K------ ------- ---------- ------ GGG IVPLLDLD SGIK
027          --------- -------- ------- ---- Q---- -I------ ------- ---------- ------ EEE KKPGASPG HKHK
028          --------- -------- ------- ---- ----- -T------ ------- ---------- ------ KNN GDNVDEE- SESR
029          --------- -------- ------- ---- ----- -K------ ------- ---------- ------ --- EEGGG-Q- QDDA
030          --------- -------- ------- ---- ----- -K------ ------- ---------- ------ --- ---SS--- ----
031          --------- -------- ------- ---- ----- -F------ ------- ---------- ------ --- -------- ----
032          --------- -------- ------- ---- ----- -A------ ------- ---------- ------ --- -------- ----
033          --------- -------- ------- ---- ----- -S------ ------- ---------- ------ --- -------- ----
034          --------- -------- ------- ---- ----- -H------ ------- ---------- ------ --- -------- ----
035          --------- -------- ------- ---- ----- -F------ ------- ---------- ------ --- -------- ----
036          --------- -------- ------- ---- ----- -W------ ------- ---------- ------ --- -------- ----
037          --------- -------- ------- ---- ----- -N------ ------- ---------- ------ --- -------- ----
038          --------- -------- ------- ---- ----- -Y------ ------- ---------- ------ --- -------- ----
039  65  TSTTNNNNE TTTTSTSS ATTTTTT TTTT GSTST TGDTKYDD ------- ---------- YYHDDD VVV APVGGEDK AAAG
040  66  GGEEGGGGS EDDDDEDE GGCCGGR GGNK QGGGG TSSNTPGN ------- TTSNSTHHSS SGDNNN KKK EEDEEPKK TVAY
041  67  NNQQRRRRK EEEEEEEE QHKQLKQ QDEE RRQHR ENKVLQTL ----VVV TTTTTTTTII LNCTTT III TTRISQMI MLMT
042  68  HHYYYYYFT LLLLLLLL EEEEKVP KLVI IVIFK KYIIKRLP DDDDPPP RKKKKKKKDD TTTLLP PPP RREKRRLH KKTT
043  69  YYYYYYYYF YYYYYYYY YYYYLWY VACC VVVVI CVVMYVYV VVVVVVV VVVVVVVVVT VVIVVV VVV VVCVVVVC VVVV
044  70  AAAAAAAAA AAAAAAAA AAAAAAA AAAV AAAAA VAAAAIAA AAAAAAA AAAAAAAAAA AAAAAA AAA AAAAAAAA AAAA
045  71  MMMMMMILM IVVVIIII AAVVAGI LIVI LMMLI VLKTVVVI VVVVIII IIVIVVVVV VVVVVV III VIIVVIVV VVVV
046  72  KKKKKKKKK KKKKKKKK KKKKKKK KKKK KKKKK KKKKKKKK KKKKKKK KKKKKKKKKK KKKKKK KKK KKKKKKKK KKKK
047  73  IIIIVVVTI IIIIIIII IIIIVFM IIII KKSE IKTEKAAH IVVVQQQ TTTTTSSTTM TTASSS EVE TTTTTSAS MMMM
048  74  LLLLLLLLL LLLLLLLL IIIIIFI IIVV IIIVI LIIVLGLV LLLLVVV LLLLLLLMLM LLLCCC LLL VVVLLLLL LLLL
049  75  DDDDKKKK KKKKKKKK NNDDKKE NPNN RRRRK KYPRL-CE KKKKNNN KKKKKKKKRK KKKRRR RRL NNNKKRKN KKKK
050  76  KKKKKKKKK KKKKKKKK TTVIKAT KIRR LLLVT PVVLV-KK VVVVKKK PPPPPQQPEE EEEEEE EEK EEEKRKER SSPE
051  77  QQQQEEQHR DDDDDDDD KKTTQYK KRAA EEEPS VTEEK-DD VSSACCC GGGGGGGGGG DDDTTT ANS SANGGGAI TTSN
052  78  KKKKIIQTH VVVVVVVV KKGGTSY V-TS SDSNE KSQLF-GR DQQQTTT TTTTTSSSTT TTALLL TTT AAASAAST AAAA
053  79  VVVVVVVII VVVVIVIII LLGGPAR L-KK EEEGF K-NDS-LI PPPPKKR MMMMMMMMMM MMMPPP SSG SSTTTSED RHHS
054  80  VVVVVVVVV IIIIVIVI SSGGKKE A-AA DSEGK K-NEG-NS TTTTNDT ---------- ---PPP PPA LMDDD-SI SALP
```

TABLE 8-continued

Alignment of the Sequences of Homologous Kinases

```
055  81  KKKKRRKKD QQQQQQQQ AASS--- K-FY EEEGD K-SAP-ED PAAARLL ---------- ---DDE KKE RRRQQ--G SDTS
056  82  LLLLLLMLT DDDDDDDD RRFF--- S-LL GGGGG I-T-K-KW EEEELRR ---------- ------ --- -------- ----
057  83  KKKKKKKR DDDDDDDD --SS--- D-HH ---G- -------G ----AAA ---------- ------ --- -------- ----
058          --------- -------- --AS--- --KK ---G- -------E ------- ---------- ------ --- -------- ----
059          --------- -------- --EE--- --EQ ---G- -------L ------- ---------- ------ --- -------- ----
060  84  QQQQQQQQQ DDDDDDDD DDLLDEG M-RR VVVLL KSIKIWQN QQQQSSS SMSSSSSSSS EAPLIL AAS EEEEEEAE EEEE
061  85  IIIIVVVVQ VVVVVVVV HHRRKKR QYDD PPPPD RPIFRYKG FAAARQQ PPPPVAPVTE VLLKKK NNS RRRKKFRV KKRL
062  86  EEEEEEEE EEEEDEDE QQEEEEE GAKK SSSIM EQNRNTKT QQQQRRR EEKEQGVEAD EKHAAA KKE IITISAQS QEER
063  87  HHHHHHHH CCCCCCCC KKAAMNV RSRR TTTSS IRQQRSLR AAAASSN AAASARPAAD EDEKKK EEE EENEEEDQ AAAD
064  88  TTTTTTTI TTTTTTTT LLTTVIC IITT AAATA KILILTQV FFFFFFF FFFFFLFFFF FFFFFF IIF FFFFFLFF LLLL
065  89  LLLLNNNR MMMMLMLM EELLMRE EGIV IIIVI IYVLLSAP RKKKWWW LLLLLPLLLI LLLLLL LLL LLLLLLQL MMML
066  90  NNNNDDDDS VVVVVVVI RRKKLDS RMRR RRRRR LNRMQHRM NNNNAAA QQEEEAAAQE KEAQQQ DDR NNSKKQRT SSSS
067  91  EEEEEEEE EEEEEEEE EEEEEEE EEEE EEEEE EEEEEEEE EEEEEEE EEEEEEEEEE EEEEEE EEE EEEEEEEE EEEE
068  92  KKKKRRRRK KKKKKKKK AAVVIIL IIAA IIIVV NLLLVALV VMMMLLL AAAAAAAAAA AAAAAA AAA AAAAAAAA AAAA
069  93  RRRRLLRRQ RRRRRRRR RRDDESR SLSS SSSAK LNSESRAV AQQQNNN QQQQNNNNAK AAARKR YYY SSSHHQEI KKKN
070  94  IIIMMMMI VVVVVVVV IIIIVIV YMLL LLLLY RLIVILLL VVVVVII VIVILLLVIV VIIIII VVI VVVLLLLI IIVV
071  95  LLLLLLLLM LLLLLLLL CCLLMML LMGG LLLLL GLVLQLHL LLLLAAA MMMMMMMMMM MMMLLL MMM MMMMMMLM MMLL
072  96  QQQQSSKSQ AAAAAAAA RRRQNNR RRQQ KKKRQ GYKHRRAK RRRRRRR KKKKKKKKKT KKKKKK AAA KKKSSSTK SSSK
073  97  AAAAIILIG LLLLLLLL LLKKQCR LLII EEERE TINKARRK KKKKLLL KKLKTQQTKK EEDQQQ SGS GEEKKNMD HHYQ
074  98  VVVVVVVVA LPPPGMGG LLVVLLV LLLL LVLLM NMVCLLVV TTTT--- LLLLLLLLFL IMLYYY VVE FFFFFFLF LLLV
075      --------- DGGGGDGE --SS--- ---- -N-E- -TK-K-SS ------- ---------- ------ --- -------- GGG-
076      --------- ---KR-R- ------- ---- -D-A- -------S ------- ---------- ------ --- -------- ----
077      --------- ---PG-G- ------- ---- -E-F- -------- ------- ---------- ------ --- -------- ----
078      --------- ---PP-P- ------- ---- -N--- -------- ------- ---------- ------ --- -------- ----
079      --------- ----G-G- ------- ---- ----- -------- ------- ---------- ------ --- -------- ----
080      --------- ----G-G- ------- ---- ----- -------- ------- ---------- ------ --- -------- ----
081  99  NNNETTESH KKK-RKRK KKGGNHR RRYY KNREQ IGPNGDSD RRRRRRH RRRKQQQQRQ KKHSSN DGE TNDNDKQS PQNN
082 100  FFFFHHHHS PPP-PPPP HHHHHHH HHHH DRHHH ISHSHHHF HHHHHHH HHHHHHHHHH HHHHHH NSH CCTHHHHH HHHH
083 101  PPPPPPPPD PPP-HPHP PSPHRPA PPPP DSPPP TSEPDPPS VVVVDDD EDDDDQPDNP PPKPPP PPV HHYPPEQP LEMP
084 102  FFFFFFFFF FFFFFFFF NNNNNKN HNHH NNNNN LRNYHAYG NNNNNNN KKKKKRRRN NNNNNN HYN HHHNHNHN HHHH
085 103  LLLLIILII LLLLLLLL IIIILLI IIII ICIVV LVIIIIIV IIIIIII LLLLLLLLLL LLLIII VVL VVVIIIIV VIIV
086 104  VVVVIIIIV TTTTTTTV VVIIIVI ILCC VVVVI AAIVVLII LLLLVVI VVVVVVVVV VVVVVV CSL VVVLLVVL VVVI
087 105  KKRRRRRRR QQQQQQQQ RRQQQQQ KRRR RRSRE VPTDEPTR LLPLRRR QPQQRRRKAQ QQRRRR RRK RRRKKRRS NNNN
088 106  LLLLMMMML LLLLLLLL LLLLLCL LLLL LLLLL VLFFLLLL FFFFVVV LLLLLLLLLL LLLLLL LLL LLLQLLFL LLLL
089 107  EEEEWWWY HHHHHHHH HHKKYVV YYFF YLQMI KCYYNLHL MMMMVVV YYYYYYYHY LILIII LLL LLLLLVFL LLLY
090 108  FFYYGGGR SSSSSSSS DDDDADE DDEE DDDDD DDGDDRD GGGGAAA AAAAAAAAG GGGGGG GGA GGGGGGGG GGGG
091 109  SSASTTTTT CCCCTCTC SSTTAAV VVMM IIVVI PAAASLVW YFFFAAA VVVVVVVVVV VVVVVV IIV VVVVVIVI AAAA
092 110  FFFFFFFFF FFFFFFFF IIYYIFF IWCC VLLCF VKYFWHLF MMMSSS VVVVVVVCC CCCCCC CCC VVCCCCCC CCCC
093 111  KKKKQQQQK QQQQQQQQ SSEEEEE KTTT HHMAM SRYFEVEE TTTTTTT SSSSTTTST TTTTTT LLM SSSLLFTL TTTS
```

TABLE 8-continued

Alignment of the Sequences of Homologous Kinases

```
094 112    DDDDDDDD TTTTTTTT EETTTET SDLM SAQTA -VNIHVTR KRRRRRR EEEERQQKQK RRHQQQ TTS KQRLLDER KHIQ 095 113    NNNNAAASS VMMMPVPM EENNPKQ KHSS DEDSY -RQEGSEP ----TTT ----E---EH EEEKKK --- GGGNNTGS GGGD

096        --------- -------- ------- ---- A--R- --H----- ----PPP ---------- ------ --- -------E ----

097        --------- -------- ------- ---- ---T- --I----- ----AEE ---------- ------ --- -------- ----

098        --------- -------- ------- ---- ---D- --N----- ----GDG ---------- ------ --- -------- ----

099        --------- -------- ------- ---- ---R- -------- ----SSS ---------- ------ --- -------- ----

100        --------- -------- ------- ---- ---E- -------- ----NNN ---------- ------ --- -------- ----

101 114    SSSSQQRQK DDDDDDD GGTTHAE DQNN HSSID RDNGGGDD DPPPSSS EEEEEEEEER PPAQQQ SSS QQQEEERG GGGG 102 115    NNNNQQNQY RRRRRRRR HFFFENR EHHH KRKN TQEAFVAS NGGGLLL PPPPPPPPPP PPPPPP TTQ PPPPPPPS PPPP 103 116    LLLLIIIVL LLLLLLLL HHFFIIV IMFF LLLVL PVIVLTIF LFVFGGG IIIIIIIII FFFIII VVM TTAQQILP IVTL 104 117    YYYYFFFFY YYYYYYYF YYFFVVY IYYY YYYTN AIIYYCYV AAAATTT YYYYYYYYY YYYYYY QQM LLYYSLL YLLL 105 118    MMMMMMMM FFFEFFEF LLLLLMM MLMM LLLLL LAIMLVL IIIIIII IIIIIIIII IIIIII LLL VVVILLMV IVVL 106 119    VVVVIIVVL VVVVVVVV IVVVFVV VALL VVIVV IVLCQVVI VIIIIII VVVVIIIIVV IIIVVV IVI VIVIIIVV IIII 107 120    MMMMIMMMM MMMMMMMM FFFFMLM ILFF FFFFL FLMMVLLL TTTTMMM TTTTTTTTQT TTTMMM TTT MMMLLMFL TTTV 108 121    EEEE-DDDE EEEEEEEE DDDDEEE EEEE EEEEE EPEEEPQE QQQQEEE EEEEEEEEEE EEEEEE QQQ EEEEEEEP EEEE 109 122    YYYY-YYYA YYYYYYYY LLLLYML YYYY FFFHF HYYYLKYR WWWWFFF YFFYYYYFYY FFFLLL LLL LLLLLHYY YYYY 110 123    VVVVLIIIC VVVVVVVV VVMMIVA AVVV LLLVL VYSMCYCP CCCCGGG MMMMMMMMM MMMVVV MMM MMMMMMMM CCCA 111 124    PAPPKEEEL NNNNTNTN TTKKEST GPSS DDSDP NPDDEQPE EEEEGGG SSCNAEEASK TSCQQQ PPP ATKEEERK RCCK 112 125    GGGGVGGGG GGGGGGGG GGKRGGG NDGG LMMQT NHCGNANP GGGGNNN KKHKKNNKKH YHNGGG FYL HRKGGAHH YYYY 113 126    GGGGGGGGG GGGGGGGG GGGGGGG -GGG ----- TEGGG-GV SSSSVVV GGGGGGGGGG GGGGGG GGG GGVGGGGG GGGG

114        --------- -------- ------- ---- ----- -------Q ------- ---------- ------ --- -------- ----

115 127    EEEEREEEE DDDDDDDD EEEEEEE EEQQ DDDDD DESSSDDD SSSSTTT SSSSSSSSSS NNNDDD CCC DDFDDDDD DDDS 116 128    MMMMLLLLL LLLLLLLL LLLLLLL LLLL LLLLL FFLLLLLL LLLLLLL LLLLLLLLLL LLLFFF LLL LLLLLLLL LLLL 117 129    FFFFFFFFW MMMMMMMI FFFFFFF FFLL KKKRE KRDDDYFF YYYYHHH LLLLLVVLL LLLLLL LLL KKKLLLNR VLLR 118 130    SSSSSSSST YYYYYYYF EEDDEED DHHH RKKTV QTKKRTTD KHHHQQQ DDDDDDDDDN DDETTS DDD SSSTSSRN DNNG 119 131    HHHHLLLLI HHHHHHHQ DDYRRR YYYY YYYYV LFIIFYYF HHHHVVV FFFFFFFFFF YFYFFF YHY YYYYYYFF YFFF 120 132    LLLLLLLLL IIIIIIII IILLIII IIII MMLLI YYLYLII LLLLIII LLLLLLLLLL LLLLLL VVV LLLLLLLI LLLL 121 133    RRRRRRRRR QQQQQQQQ VVTTVII VRII EDDDK QRSDESTT HHHHYYY KKKKKKKKR RRRRRR RRR RRRRRRRR HRRR 122 134    RRRRKKKKD QQQQQQQQ AAEEDDA QKQQ GRSKD TDVEEREE VVVVGDG GENDSTTSER ESRTTS EEN SSAKGASN RRRE 123 135    IIIISSSSR VVVVLVLF RRKKEEK RHHH IIIAK --YSQRKR QAAAAAA EGPGDPPDGH CATEEE HNN LLHAAAHE NKKS 124 136    GGGGKQQQG GGGGGGGG EEVVDDG DGGG PSPPS --KSGLKG EDDDATT TDEEESSEDE NGDGGG KRR RRRRRRGT KARR 125 137    RRRRDRRRS KRRRKKKK YYTTYFS KPSS KEPPI --REQNVA TTTTGRR GGGGGGGGK RRKAAP DGD PPPMKAPH HEDK

126        --------- -------- ----H-E ---- DTGPL --FILPY- KRRRHSS KQRGIISRT QESRRH NRK EERAQTDN TASV

127        --------- -------- ------- ---- QGQG- --VGS-Q- ----PPP YYDAKKKKYL ETL--- --- AMSTKSA- FMFM

128        --------- -------- ------- ---- PAY-- --QGR--- ----EEE ---------I ------ --- EEGFFTK- LLIP 129 138    FFFFFFFFF FFFFFFFF YYLLLLF MLIL LLMLF LLFILLGL FFFFLLL LLLLVLLQLG VLLLLL ILI PPPLLLLP LLLL 130 139    SSSSPPPPE KKKKKKKK SSSTTTT SSRK GDDPT TPNDDGNQ QDDDSSS RKRKLTNPHN NDPRRK GGS TSTTTSGT SEDT 131 140    EEEENNNND EEEEEEEE EEEEEEE EEEE APSAP DIEEERSE MMMMLLL LLLLLIVLFM AAPVMM SSS LLYLLLLV YLLM
```

TABLE 8-continued

Alignment of the Sequences of Homologous Kinases

```
132 141    PPPPPPPPS PPPPPPPP AAKKVRR QRHH DRSEA YKLPFPHD FVVVGGG PPPPPNNPEG VVIKKK QQK QSGVTSGK TREG
133 142    HHHHVVVVT QHHHHQHV DDEEDED EEQH ILLTD EGTQRQLL QQQQKKK QQQNKKKKDL VAITTE YDA EKRDDEQD DDDD
134 143    AAAAAAAAT AAAAAAAA AATTTCA AAAA VVVII IIILVIIA LLLLCCC LLLLLLLLLL LLLLLL LLL MMILLLLL LLLL
135 144    RRRRQKKKR VVVVAVAV SSRRMIT RARR KQKKK RKSAWAKR IIIILLL VVVVILLIIL LLVLLI LLL IIYVLLLI VLLI
136 145    FFFFIFFFF FFFFFFFF HHKKVKR RHKK KKSDA YKKFKATG DDDDKKK DDDDDDDDYD YYQQQK NNN QQQDDAAG GHSS
137 146    YYYYFYYYY YYYYYYYY CCIIFYV FYFF FFYLW YYIIIVVF IVVVYYY MMMMFMMFIM MMMMMM WWW MMVLIMVF FFFF
138 147    AAAAAAAAT AAAAAAAA IIMMVML FLAA MTLMM LIAALSFF AAAASSS AAAASAASAC AAAVVM CCS AAACCCAG SSSA
139 148    AAAAAAAAA AAAAAAAA QQRRRRQ QSRR MYYRL FWYNVRLW RRRRLLL AAAAAAAATI TTSGGE VMT AGIVLISL YSYW
140 149    QQQQEEEEC EEEEEEEE QQAAQQM QQGG QQQQM EEGAEQQQ QQQQDDD QQQQQQQQQQ QQQDDN QQQ EEDDDQQ QQQQ
141 150    IIIIVVVVV IIIIIIII IILLIIV IIII LLIFT LLVVVLLV TTTTVVI IIVVIIIIVV IIIAAA III IIIIIVVV VVVI
142 151    VVVVCCICV SAAAASAA LLLLCSL ILAA CVLLL LLLIALIL AAAAVVV AAAAAAAAAS SAAAAA AAA AAASCAAA AAAS
143 152    LLLLLLLLE IIIIIIIA EEEEDED SDSS KNQRR KRNHLSSE QQQQNNN SDEAEEEESK SSSAAA KKK DDDKKNAK NQKQ
144 153    TTTTAAAAA GGGGGGGG AAVVGGG AAAA GGGGG AAGGGAAA GGGGGGG GGGGGGGGGG AGGGGG GGG GGGGGGGA GGGG
145 154    FFFFLLLLF LLLLLLLL VVIIIVV VVLL IVILV LLLLLVVV MMMMLLL MMMMMMMMMM MMMMMM MMM MMMCCCMM MMMM
146 155    EEEEEEEEA FFFFFFFF LLCCLER EAIQ ANVDY DKDKQDER DDDDLLL AAAAAAAAET ESSEEE NSS AAAVVSVK DAAQ
147 156    YYYYYYYYY FFFFFFFF HHATFYY YHYY YFFFH YFHEFYHH YYYYFFF YYYYYFFFYY YYYYYY YYY YYYYYYYY FFFY
148 157    LLLLLLLLL LLLLLLLL CCLLMIL CCLL CCCLC CVLLIICC LLLLLLL VIMIIIIILL LLLLLL LLL LLLLLLLL LLLL
149 158    HHHHHHHHH HQQQHHHH HHHHHHH HHHH HHHHH HHYKHHHH HHHHHHH EEEEEEEEEE EEEEEE EEE NNAEEEAA AAAA
150 159    SSSSSSASS KSSSNKNT QQKKKKA RRAA SSSAR SSREHRSN AAAASSS RRRRREEQSR KSASSS DDE AAARKDGS SSSE
151 160    LLLLKKHKK RKKKQRQK MMLLMQL HFNN HRRNN MKQQKQVC KKKKQQQ MMMMKRQRKH KRRKKK RVK KNKMMMLK KKKM
152 161    DDDDDDNDG GGGGGGGG GGNNRGG KRNN RRRCF GGKNNGGG NNNNSSS NNNNNNNNQN NNHCCH RRR KKKHRHHK NNNK
153 162    LLLLIIIII IIIIIIII VVIIVII IFII IIVII IIIIYIIV IIIIIII YYYYYYYLY FYFCCC LLL FFFFFFFF CCCL
154 163    IIIIIIITI IIIIIIIL VVVVLVT VRVV LILVL MIIIVIYL IIIIVLL VIIIIIIIII IIIIII VVV VVVIIVVV VIIV
155 164    YYYYYYYYY YYYYYYYY HHHHHHH HHHH HHHHH HHHHHHHH HHHHHHH HHHHHHHHHH HHHHHH HHH HHHHHHHH HHHH
156 165    RRRRRRRRR RRRRRRRR RRRRLLR RRRR RRRRR RRRRLRRR RRRRLLL RRRRRRRRRR RRRRRR RRR RRRRRRRR RRRR
157 166    DDDDDDDDD DDDDDDDD DDDDDDD DDDD DDDDD DDDDDDDD DDDDDDD DDDDDDDDDD DDDDDD DDD DDDDDDDD DDDD
158 167    LLLLLLLLL LLLLLLLL LLLLLLL LLLL LLLLL VIIVLILI MLLLLLL LLLLLLLLLL LLLLLL LLL LLLLLLLL LLLL
159 168    KKKKKKKKK KKKKKKKK KKKKKKK KKKK KKKKK KKKKKKKK KKKKKKK RRRRRRRAA AAAAAA AAA AAAAAAAA AAAA
160 169    PPPPPPPPP LLLLLLLL PPPPPPP PLII PPPPP PPPPPTPD SSSSPPP AAASAAAAAA AAAAAA AAA AAAAACTA AAAA
161 170    EEEEEEEEE DDDDDDDD EEEEEEE EEEE QQQEN HTSTAEEE NNNNAAA AAAAAAAARR RRRRRR RRR RRRRRRRR RRRR
162 171    NNNNNNNNN NNNNNNNN NNNNNNN NNNN NNNNN NNNNNNNN NNNNNNN NNNNNNNNNN NNNNNN NNN NNNNNNNN NNNN
163 172    LLLLIIIIL VVVVVVVV LLIIIIL LIII LLLIL VFIVIVIII IIIIIII IIIIVIIIVC CCCCCC VVV CCCCCCCC VVII
164 173    LLLLLLLLI MMMMMMML LLLLLML LLMM LLLLL MLLLMFML FFFFLLL LLLLLLLLLL LLLLLL LLL MMMLLLLM LLLL
165 174    IIIILLLLL LLLLLLLL LLLLCCY LIII IIIVF IFICIIVI LLLLIII VVVVVVVIV VVVVVV VVV VVVVVVVL ILLV
166 175    DDDDDDDDD DDDDDDDD AADDVVY DKSS NDDTS DNNSTNGD HHHHSSS GGGGSSSSGG GGSTTT KKR AAASSTGD CTTA
167 176    QQHHKKRKH SSSSASAA SSDDNNH EVDS KKDSP HLSAFTNL EEEEEEE EEENEDDAES EDEEEE TSL HEDVEEQE ENHE
168 177    QQQQNNNNR EEEEEEED KKDNTKP HNSS DEKGD EEKNEPDS GGGGQQK NNRGSTTSNE NNHKKK PPL DDDKKSGK GGGG
169 178    GGGGGGGGG GGGGGGGG LLMMTTG LESG GGGGG NLGQGEGR LLLLDDD LLLLLLLLNN HKNNNN QN- FFLDQTLF KHRR
170        --------- -------- KK--GGT -Q-- ----- RG-G--NG ------- ---------- ------ --- ---YYG-- ----
```

TABLE 8-continued

Alignment of the Sequences of Homologous Kinases

| | | |
|---|---|---|
| 171 | | --------- -------- GG--HTD ---- ----- -------- ------- ---------- ------ --- ---TGS-- ---- |
| 172 | | --------- -------- AA----S ---- ----- -------- ------- ---------- ------ --- ---SST-- ---- |
| 173 | | --------- -------- ------- ---- ----- -------- ------- ---------- ------ --- ---PCD-- ---- |
| 174 | | --------- -------- ------- ---- ----- -------- ------- ---------- ------ --- ---RSR-- ---- |
| 175 | | --------- -------- ------- ---- ----- -------- ------- ---------- ------ --- ----RR-- ---- |
| 176 | | --------- -------- ------- ---- ----- -------- ------- ---------- ------ --- -----R-- ---- |
| 177 | 179 | YYYYHHHHY HHHHHHHH AANNLSK NQEE NNTTQ KRQTTDTE TTTTVVV VVAIMSSVVV LLIVVT HHA TTTIVTVT LVIK |
| 178 | 180 | IIIIIIIA IIIIIIIV VVIIVII VIII LLIVI LGIVLIVI VVVVCCC CCCCCCCCAV VVVLLL VVG VVVVVVVV VATM |
| 179 | 181 | QQQQKKKK KKKKKKKK KKKKKKI KKKK KKKKK RVKKKVYK KKKKKKK KKKKKKKKKK KKKKKK KKE KKKKKKKK KKKK |
| 180 | 182 | VVVVIIIL IIIIIIII LLLLLLI IIII LLLLV LLLLILLL IIIIIII VIIIIIIIIV VVIIII IID IIIIIIIV IIII |
| 181 | 183 | TTTTTTTV AAAATATA AATTIIT AAII GAAAA IVCCGGAI GGGGSSS AAAAAAAACA AAASSS TTH GGGGGGGA CGCS |
| 182 | 184 | DDDDDDDD DDDDDDDD DDDDDDD DDDD DDDDD DDDDDDDD DDDDDDD DDDDDDDDDD DDDDDD DDD DDDDDDDD DDDD |
| 183 | 185 | FFFFFFFF FFFFFFFF FFFFFFF FFFF FFFFF WFFFFFFF FFFFFFF FFFFFFFFFF FFFFFF FFF FFFFFFFF FFFF |
| 184 | 186 | GGGGGGGG GGGGGGG GGGGGGG GGGG GGGGG GGGGGGGG GGGGGGG GGGGGGGGGG GGGGGG GGG GGGGGGGG GGGG |
| 185 | 187 | FFFFFFFF MMMMMMMM LLFFLLL LMLL LLLLL LLVVMALS LLLLCCC LLLLLLLLLL LLLMMM LLL MMMLLLML LLLL |
| 186 | 188 | AAAAAAAA CCCCCCCC AASSAAA SASS AAAAA AASSAAAG AAAASSS AAAAAAAAAA SAASSS AAA TTTAAASA AAAS |
| 187 | 189 | KKKKKKKK KKKKKKKK IICCRRS NTNN RRRRR EEKGSCTA TTTTEQQ RRRRRRRRRR RRRRRR KRK RRRRRRRR RRRR |
| 188 | 190 | RRRRYYEYK EEEEEEEE EEQQRRA IVII ASAIA FAKNVFTL VVVVKKK LLLLVLLVVY LLFEEQ LLL DDDDDDDD DDDD |
| 189 | 191 | VVVVVVVI HNNNNHNN VVLLYLR MEYF FFFYI YQLLWVEL KKKKLLL IIIIIIIIV MMMEEE LLL IIIIIIIM IIIV |
| 190 | 192 | KKKKPPQPG MIIIVMVI EQDQNEK TPDD GGGSP HMIVPQPK STTTEQQ EEKEEEEEAL TRKAAE GDS YYYYYYYY MMKY |
| 191 | 193 | GGGGDDTDF MWWWFMFV GGPPPSK DNSY VVIYA PDNAVGYD RRRRDDD DDDDDDDDDD GDEDDD AIS EEEKKKSD RNNE |
| 192 | 194 | RRRRVVVG DDDDPDPG EDGGNAG GDRR PPPQP GYSSPSST WWWWLLL NNDNNNNNDD DDDGGG EDD TTTNNSTK DDDE |
| 193 | 195 | TTTTTTTK GGGGGGGD QQEEEGD NSKK LLIMH QKILRRSV SSSSLRR EEEEEEEEEQ TTTVIV EES DDDDDDDE SSSD |
| 194 | | --------L VVVVSVSK QQKKKSD FCQQ RRRAE ESAAGS-Y GGGGCGC YYYYYYYYYY YYYYYY KTN YYYYYYYY NNNS |
| 195 | | --------T TTTTTTTT AALLLLC LLLL ANVLI YM---S-- SAAAFRR TTNTTTTTCT TTTAAA EEE YYYYYYYY YYYY |
| 196 | | --------- TTTTTTTT WW----L ---- YYY-L -I---P-- QQQQQQP AAPAAAAPS AAAAAS YYY RRRRRRRS IIVV |
| 197 | | --------- -------- ------M ---- ----- -S---F-- QPPPTA- RRCRRRRKS HHHSST HHK KKKKKKVV SVVK |
| 198 | 196 | WWWWYYWYW RKKKRRRK FFRRKKK KEHH TTTTT NADKMYDT EEEEYPH QQQQEEEEQG AAAGGG EDA GGTGGGGT GGGS |
| 199 | 197 | TTTTTTTT TTTTTTTT GGEEVVT TVTT HHHPS VNTTEGFD QQQQPPH GGGGGGGGGG GGGLLM GGG KKKEEERG SNNQ |
| 200 | 198 | LLLLLLLF FTFFFFFF FFVVNLT SYFF EEEVN RRFNRIGF PPPPLII AASAAAAAST AAARRK GGG GGGGGGTA TAAG |
| 201 | 199 | CCCCCCCC CCCCCCCC AACCFFC CCCC IIVV VAVIEACD TSSSGGG KKKKKKKKRK KKKQQQ KKK LLLLLLMK YRRR |
| 202 | 200 | GGGGGGGG GGGGGGG GGGGGGG GGGG VVVVV AGGGGGG GGGGGGG FFFFFFFFFF FFFVVI VVM LLLLLLLL LLLI |
| 203 | 201 | TTTTTTTT TTTTTTTT TTTTTTT SSSS TTTTT STTCDTST SSPSTTT PPPPPPPPPP PPPPP PPP PPPPPPPP PPPP |
| 204 | 202 | PPPPPPPP PPPPPPPP PPPPPPP PLLL LLLLR RRSQCILR VVVVYYY IIIIIIIIVI IIIVV III VVVVVVIV LVVV |
| 205 | 203 | EEEEDDDE DDDDDDDD GGSSEEE NHYY WWWWW YGTSEDFV LLLLTTT KKKKKKKKKK KKKKKK KKK RRRRRRRK KKKK |
| 206 | 204 | YYYYYYYY YYYYYYYY YYYYFFY YYFF YYYYY FYYYTYY WWWWHHH WWWWWWWWWW WWWWWW WWW WWWWWWWW WWWW |
| 207 | 205 | LLLLIIIV IIIIIIII LLLLLVI ALAA RRRRR KRMMINMS MMMMRQQ TTTTTTTTA TTTTTT MML MMMMMMMM MMMM |
| 208 | 206 | AAAAAAAA AAAAAAAA SSAASAA AAAA AASAA GASAAASP AAAAAAA AAAAAAAAAP AAAAAA AAA ASPAASPA AAAA |

TABLE 8-continued

Alignment of the Sequences of Homologous Kinases

| | | | | | | | | | | | | |
|---|---|---|---|---|---|---|---|---|---|---|---|---|
| 209 | 207 | PPPPPPPP | PPPPPPPP | PPPPPPP | PPPP | PPPPP | PPPPPPPP | PAAAPPP | PPPPPPPPPP | PPPPPP | LLL | PPPPPPPL | PPPI |
| 210 | 208 | EEEEEEEE | EEEEEEEE | EEEEEEE | EEEE | EEEEE | EEEEEEEE | EEEEEEE | EEEEEEEEEE | EEEEEE | EEE | EEEEEEEE | EEEE |
| 211 | 209 | IIIIVVVI | IIIIIIII | VVIIVVV | VILL | VVVVL | LVRRVVCW | VVVVLIL | AAAAAAAAV | SGGAAA | SSC | SSSSSSSS | SSSS |
| 212 | 210 | IIIIVIVI | IIIIIIII | LLIIVIL | IVLL | LLLLL | LLILLLQI | IITILLL | AAAAIIIIIL | LLLLLL | III | LLLLLIL | IIIL |
| 213 | | --------- | -------- | --EQ--- | ---- | LLLLF | VM-K--RR | RRRR--- | ---------- | ------ | --- | -------- | ---- |
| 214 | | --------- | -------- | --CC--- | ---- | ----- | ---S--E- | MMMM--- | ---------- | ------ | --- | -------- | ---- |
| 215 | | --------- | -------- | --SS--- | ---- | ----- | ---L--V- | QQQQ--- | ---------- | ------ | --- | -------- | ---- |
| 216 | | --------- | -------- | --MM--- | ---- | ----- | ---N--K- | -------- | ---------- | ------ | --- | -------- | ---- |
| 217 | 211 | LLLLSSTSL | AAAAAAAL | RRNGNNV | SSKK | GGGQG | DKQDAASY | DDDDKKK | LLLLNNNNIN | AAANNN | LLR | KKRMIVLQ | FFFF |
| 218 | 212 | SSSSTTTTN | YYYYYYYY | KKHHYYR | GHAA | GSSSA | YCGRNGSH | NPPPGGG | YYFYFYYFYY | YYFYYY | HRN | DDDDDDYT | NDND |
| 219 | 213 | KKKKKKKK | QQQQQQQQ | DEPPDEK | KKNQ | KRATK | QGNAHDSR | NNNNEEE | GGGGGGGGGT | NNNGGG | RRR | GGGGGGRQ | SCCH |
| 220 | 214 | GGGGPPPPG | PPPPPPPP | PAGGQPP | LPPP | QHR-H | MAVTLPFY | PPPPGII | RRRRCTTSKR | KKTRRR | IRV | VVVIVLKK | LVVI |
| 221 | 215 | YYYYYYYYH | YYYYYYYY | YYYYIIY | YYYY | YYYYY | YQYYYYAH | FYYYVAA | FFFFFFFFFF | FFFYYY | YFF | FFYFFFFF | YYYY |
| 222 | 216 | NNNNNNNND | GGGDGDG | GGGGSGT | ARTT | SSSAT | DSSTDTTG | SSSSTTT | TTTTTTTTSS | SSSSSS | TTT | TSTTTTT | TTTT |
| 223 | 217 | KKKKKKKI | KKKKKKKK | KKKKDYN | GGGG | TTTTS | YTIVKTAR | FFFFPPP | IIIIIIIIIS | ITSSSS | HHS | TTSTNTTT | TVFT |
| 224 | | --------- | -------- | ------- | PAPP | ----- | -------- | ------- | ---------- | ------ | --- | -------- | ---- |
| 225 | 218 | AAAASSSSS | SSSSSSSS | PPEEKES | EPEE | GGPPA | SKKQPTPS | QQQQKKK | KKKKKKKKKK | KKKEEE | QQK | SYAQHQEK | LQEQ |
| 226 | 219 | VVVVIIVVA | VVVVVVVV | VVVVTTV | VAVV | VVVVI | LIGSAVNA | SSSSAAA | SSSSSSSSSS | SSSSSS | SSS | SSSSSSSS | SSSS |
| 227 | 220 | DDDDDDDD | DDDDDDDD | DDDDDDD | DDDD | DDDDD | DDDDDDDA | DDDDDDD | DDDDDDDDDD | DDDDDD | DDD | DDDDDDDD | DDDD |
| 228 | 221 | WWWWWWWY | WWWWWWWW | LIMMMMM | VVVI | IIIMI | MIVIIIVV | VVVVIII | VVVVVVVVVV | VVVVVV | VVV | MVVVVVVV | VVVV |
| 229 | 222 | WWWWWWWW | WWWWWWWW | WWWWWWW | WWWW | WWWWW | WWWWWWWW | YYYYYY | WWWWWWWWWW | WWWWWW | WWW | WWFWMWWW | WWWW |
| 230 | 223 | AAAASSSSS | AAASSAAA | AASSSSA | SSSS | SSSSS | SSSSSSAS | SAAASSS | SSSSSSSSSA | AAASSS | SSA | SSSSAASS | SSSS |
| 231 | 224 | LLLLFFLFL | YFFFFYFY | CCTTLIL | CCFF | IVIVV | LVLLLALL | YYYYFFF | FFFFFFFFFF | FFFFFF | YYF | FFFFFFFFF | FYYF |
| 232 | 225 | GGGGGGGG | GGGGGGGG | GGGGGGG | GGGG | GGGGG | GGGGGGGG | GGGGGGG | GGGGGGGGGG | GGGGGG | GGG | GGGGGGGG | GGGG |
| 233 | 226 | VVVVIIVVI | VVVVVVVV | VVVVVVV | VVVI | CCTCV | CVLLILII | IVVVIII | IIIIIIIIIV | VVVIII | VVV | VVVIVVVV | IIIV |
| 234 | 227 | LLLLLLLL | LLLLLLLL | IIIIIII | IIVV | IIIII | MIMSTVIL | VVVVTTT | LLLLLLLLLL | LLLLLL | TTT | VVVLLLVV | LLFL |
| 235 | 228 | IIIIIIIM | LLLLLLLL | LLMMTCA | LLLL | FFFFF | LLIIVILL | LLLLLLL | LQLLLLLLM | LLLLLL | VVI | LLLIVCLL | LLLL |
| 236 | 229 | YYYYYYYY | YYYYYYYY | YYYYYYY | YYFY | AAAAA | ALILFFIY | YYYYWWW | TTTTYTTMMW | WWWWWW | WWW | WWWWWWWW | WWWW |
| 237 | 230 | EEEEEEEE | EEEEEEEE | IITTMII | VSVV | EEEEE | SSEEEEND | EEEEQQQ | EEEEEEEEEE | EEEEEE | EEE | EEEEEEEE | EEEE |
| 238 | 231 | MMMMMMML | MMMMMMMM | LLLLLLL | MLLL | MMLML | MLLMATLM | LLLLMMM | LLLLIIIILI | IIITTA | LLL | IIMITIIL | IILI |
| 239 | 232 | AAAALLLLL | LLLLLLLL | LLLLLVL | LLVV | CIAFM | ILVAAACV | MMMMTTT | TVIVVVVFF | AAAFFF | MML | TAALLLFM | FFFV |
| 240 | 233 | AAAAAAAT | AAAAAAAV | VVAASSS | CSCC | NRTRL | FGTLAVCC | TTTTTTT | TTTTTTTTT | TTSSSS | TTT | STTTTTTT | TSST |
| 241 | | --------- | -------- | ------- | ---- | ----- | -------- | ------- | KKKKYHHYYC | YYYLLL | FFF | LLLLLLYR | LLLL |
| 242 | 234 | GGGGGGGG | GGGGGGG | GGGGGGG | RNGG | RRKRR | RRGGNHKG | GGGGKRR | GGGGGGGGGG | GGGGGG | GGG | AAAGGGGG | GGGG |
| 243 | 235 | YYYYYYYS | QQQQQQQQ | YYSSLLT | RKKK | KSKKI | KRERINRD | ESSSQEE | RRRRKRRRQK | MMMAAA | SAQ | EEAHQQKA | GLSG |
| 244 | 236 | PPPPTTTP | PAAAPPPP | PPPPSSM | LLVV | PPPPP | FFFYVANI | LLLLAVV | VVIVIIIIVM | SSASSV | KKR | QQQQQQQP | TNSN |
| 245 | 237 | PPPPPPPP | PPPPPPPP | PPPPPPP | PPPP | ILLLY | PPPPLSPP | PPPPPPP | PPPPPPPPPP | PPPPPP | PPP | PPPPPPPP | PPPP |
| 246 | 238 | FFFFFFFF | FFFFFFFF | FFFFFFF | FFFF | FFFFL | FMLYPLWF | YYYYYYY | YYYYYYYYYY | YYYYYY | YYH | YYYYYYWY | YYYY |
| 247 | 239 | FFFFYYYS | DEEEDDDD | WWWWLME | DGDD | SPHCP | FFGPDFK- | SSSSSSS | PPPPPPPPPG | PPPPPA | DDE | QQQPPAYP | PPPP |

TABLE 8-continued

Alignment of the Sequences of Homologous Kinases

```
248 240   AAAADDDNG GGGGGGGG DDHHGGD DGDD GGGGG HQGPNSR- HHHH--- GGGGGGGGGR GAGNNN GGN GGGAGAQD EGGG
249       --------- -------- ------- ---- DDDNQ GSH-GAA- IIII--- ---------- ------ --- -------- ----
250       --------- -------- ------- ---- SSSSN HLN--PC- ------- ---------- ------ --- -------- ----
251       --------- -------- ------- ---- EEEED D---R--- ------- ---------- ------ --- -------- ----
252       --------- -------- ------- ---- IIIAV N---G--- ------- ---------- ------ --- -------- ----
253       --------- -------- ------- ---- ----- Y---P--- ------- ---------- ------ --- -------- ----
254       --------- -------- ------- ---- ----- ----K--- ------- ---------- ------ --- -------- ----
255       --------- -------- ------- ---- ----- ----R--- ------- ---------- ------ --- -------- ----
256       --------- -------- ------- ---- ----- ----G--- ------- ---------- ------ --- -------- ----
257       --------- -------- ------- ---- ----- ----P--- ------- ---------- ------ --- -------- ----
258       --------- -------- ------- ---- ----- ----C--- ------- ---------- ------ --- -------- ----
259       --------- -------- ------- ---- ----- ----D--- ------- ---------- ------ --- -------- ----
260 241   DDDDSSTSP EEEEEEEE EERRDDD EQEE DDDDD DDEQSSE NGGGGGG MMMMRMMMML IVLLLL III LLLHLRLV PLPI
261 242   QQQQNNTND DDDDDDDD DDKKDNN SNNN QEQQQ QDTTSQQH NCCSEEE VVNNTTTSHK DDESSS PPP SSSSSNSN MVVP
262 243   PPPPTTPTP EEEEEEEE QQQQDDR ITSS IILLM LAPYWITD RRRRRPP NNKNNNNNSN RLLNNN AAA NNNNNNNT NNDP
263 244   IIIIMMMM  DDDDEDEE HHMMTNT PDSS FFFGE VDDDQTDE DDDDQQQ RRRRAPPPRT STSQQQ SRK EEELIFTF DSSE
264 245   QQQQKKKKK EEEEEEEE RKLLEER VVVI KKRKV RSGNKRGE QQQQHYH EEEEDEEEE QDNQQQ EED QQQDEEED QKKR
265 246   IIIITTTTT LLLLLLLL LLMMTTL LILL IIIIT ILIILITI IIIIIVV VVVVVVVVV VVVTTT III VVVVVVAI FFFL
266 247   YYYYYYYYY FFFFFFFF YYLLLLY FYHH FFFFF ALLFRIYI IIIILQQ LLLLMIIIIV YYYRRR SPP LLLLLLIT YYYF
267 248   EEEEEEEN  QQQQQQQA QQRRNAR KNEE RQRDR KEDSSRRK FFFFYYY DEEETQQREE EHGEEE SDD KRRNHADV NKKN
268 249   KKKKKKKNI SSSSASAA QQMMNNQ NKKK VVALA VLLQGQSG MMMMAAA QQQQANNANR LKLFFA ILL FFYYHHCY ALML
269 250   IIIIIIII  IIIIIIII IIIIVVI IIII LLLIL LCLLDAYQ VVVVVVV VVVVLLLLIV LLLVVI LLI VVVVVVIL IVIL
270 251   VVVVLLLLL MMMMMMMT KKMMLTL SRKK GGGGG GTQSLQVV GGGGVVV EEEESEEEEQ EDEEEE EEE MMIQRKTL KKKK
271 252   SSSSNNQNR EEEEEEED AASDSSR NHQK TTTLT TIRASVHF RRRRAAA RRQRQRRRRR KKNKKQ KKV DEDTSEQQ RDET
272 253   GGGGAAGAG HHHHQHQH GGGGGAG GGGG PPPPP EFIIDHNF GGGGYYY GGGGGGGGGG DGGGGG GGG GGGGGGGG GGGG
273       --------I -------- ------- ---- NNNPT EGVVAVPR YYYYDNN YYYYYYYYFI YYFGGV EEL GGGGGGGR YYFH
274 254   KKKKEEED  NNNNTNTN AANKNTK VAKK EENED LWNDPDSQ ALLLLLL RRHRRRRRRI RRRRRR RRK YLVRRRER RQRR
275 255   VVVVLLVLI VVVVVVVV YYYYWWY YYVV AEEDR YKEGRETT SSSSRRR MMMMMMMML MMMLLL LLL LLMLLLLL MMMM
276 256   RRRRRRKVE SAAATSTS DDQQYTS TDED IVVDD AEPPLFL- PPPPPPP PPPPPVVPPE KEDPPE PPE DDEEEQEL AALE
277 257   FFFFFFYFF YYYYYYYY FFFFFFY LLYY WWWWW YLSPSSL- DDDDSSH CCCCRRRRKK RRGCCP QQQ QKRPSQRQ QQSR
278 258   PPPPPPPPP PPPPPPPP PPGGDDS PPPP PPPPP LRPPSPS- LLLLLLW PPPPVPPPPP PPPPPP PPP PPPPPPPP PPPP
279 259   SSSSPPPPK KKKKKKKK SSSSEDG KSQS DGERE DKRRTHI- SSSSSAQ PQPQEDDETK EPQEEE PPE DDERNPRE AAED
280 260   HHHHFFYFK SSSSSSSS PPPPEEE FSHH IVVDV KCLLDPL- KKKKAG- EGGDNNNNNS GGGLLQ III NNNNMAY  HFHN
281       --------- -------- EEEETAP ---- VTEVS YAPPNEP- LIIIAAA --------H- ------ --- -------- ----
282       --------- -------- WWWWFFW ---- YLSSS NAKSGS-- YSSFVVV --------Y- ------ --- -------- ----
283       --------- -------- DDDDEDP ---- LLLLF ILDDSR-- KSSSFFF ---------- ------ --- -------- ----
284       --------- -------- TTDDAES ---- PQQPM DHRKSL-- NNNNETT ---------- ------ --- -------- ----
285       --------- -------- ------- ---- DDDRT LGI-LT-- ----DAA ---------- ------ --- -------- ----
```

TABLE 8-continued

Alignment of the Sequences of Homologous Kinases

| | | | | | | | | | | | | | | |
|---|---|---|---|---|---|---|---|---|---|---|---|---|---|---|
| 286 | 261 | FFFFFFFFI | LMMMLLLL | VVYYVIV | LILL | LGLMA | VDYFGMIV | CCCCPTT | CCCCCCCFC | CCCCCC | CCC | CCCCCCCC | AAAC |
| 287 | 262 | SSSSNNQHA | SSSSSSSS | TTSSSSS | SSSS | DEDES | SHSSQDSS | PPPPGGG | PPPPPPPPA | PPPPPP | TTS | PPPPPTPP | SPPS |
| 288 | 263 | SSSSEEPPK | KKKKRKRK | PPDDDDN | PSII | PEEEE | PYKSGIRS | KKKKQKK | EEAIDEEEDK | EPPDDE | IIL | EDDDDEPD | DKAE |
| 289 | 264 | DDDDDDDDN | EEEEEEEE | EETTEDL | GAEE | RDNSY | EWEDGDEE | AAAARTT | SSSSEEEENE | KESAAD | DDD | RMFDDKEP | ENEE |
| 290 | 265 | LLLLVVVAA | AAAAAAAA | AAVVAAA | AAVV | GAGGA | ACMALVLC | MMMMLLL | LLLLLLLLII | VVVVVV | VVI | VLLLILVL | IIMM |
| 291 | 266 | KKKKKKVQA | VVVVVVVK | KKKKKKK | AQII | IILAL | LFTQDENQ | KRRRGQQ | HHYHYYYYYY | YYYFFY | YYY | TFHWRYYY | YYYY |
| 292 | 267 | DDDDDDDDN | SAAAASAE | DNDDDDD | GDSS | DEDQD | DQDDRYSH | RRRRDNN | DEEEDQHNQD | EDRRRR | MMC | DEKNDSAE | ESDR |
| 293 | 268 | LLLLLLLLL | IIIIIIIA | LLLLFFF | LLLL | LLLLF | FVFFVLLL | LLLLVIN | LIALILLILV | LLLLLLL | IIT | LLLLLLIV | IIIL |
| 294 | 269 | LLLLLLLLI | CCCCCCCC | IIVVVII | ILLL | LLLLM | LLVVVVLI | VLLLIIV | MMMMMMMMLM | MMMMMM | MML | MMMMMLMM | MMMM |
| 295 | 270 | RRRRSSSKK | KKKKKKKK | NNSSSSD | KHST | DSSLC | DENSECNK | ASSTQQQ | CNEIKRMMLK | RRLEEQ | VVL | RRQTTLRL | QQKL |
| 296 | 271 | NNNNRRKKK | GGGGGGGG | KQRRNNR | RRKR | KAKEG | KQRLQKRW | DDDDRSS | QLQHMLLRQL | AQQQQR | KKS | MMRQRLGK | KATQ |
| 297 | 272 | LLLLLLLLL | LLLLFLFF | MMFFLLL | MMMM | LMMMM | LCCCMAIC | CCCCCCC | CCTCCCCCCC | CCCCCC | CCC | CCCCCCCC | CCCC |
| 298 | 273 | LLLLIIIIC | MIMMLMLL | LLLLILL | LLLI | LLLLL | LFCLLLFL | VLLLWWW | WWWWWWWWWW | WWWWWW | WWW | WWWWWWWW | WWWW |
| 299 | 274 | QQQQTTTTR | TTTTTTTT | TTVVVKT | IDVV | AVITT | REIQSTDS | KKKKREE | RKRKKKKKDS | QQNAAE | MMH | QQHAARQH | EADK |
| 300 | 275 | VVVVRRARD | KKKKKKKK | IIVVKKV | VVVV | YYYFM | YMKKPFRL | KFFFPAA | KKLKEEENAH | WWWYYY | IIL | FYHQQTRP | ELAQ |
| 301 | 276 | DDDDDDDDN | HHHHHHHQ | NNQQEDD | NNDD | DDDNN | DDNIEDNR | VQQQSRR | EDDDKRRRVG | NDSEED | DDD | NNREDDEK | KEDE |
| 302 | 277 | LLLLLLLLP | PPPPPPPP | PPPPQMP | PPPP | PPPPP | HPEPPGPP | KRRRAAA | PPPPPPPPPP | PAPPPP | ASA | PPSPPPPA | FPPP |
| 303 | 278 | TTTTSSTSS | GGGGAAGN | SAQQGKG | LSKL | IAAHQ | VQRERAKS | EEEEALL | EDEEEEEEE | STSGGR | DEA | NKSDHWQE | ETLD |
| 304 | 279 | KKKKQQREE | KKKKKKKK | KKKDASA | NTRR | NHKKK | DKERNLTD | EEEEQQQ | EEEEEDDEKE | DDDQQR | SCM | MMAQNEQM | THKK |
| 305 | 280 | RRRRRRRRR | RRRRRRRR | RRRRRRR | RRRR | RRRRR | RRRRRRRR | RRRRRRR | RRRRRRRRRR | RRRRRR | RRR | RRRRRRRR | RRRR |
| 306 | 281 | FFFFLLILL | LLLLLLLL | IIYCMLM | IIAA | IIIIW | LSSPPPIP | PPPPPPP | PPPPPPPPPP | PPPPPP | PPP | PPPPPPPP | PPPP |
| 307 | 282 | GGGGGGGGG | GGGGGGGG | TTTSSNT | STTT | SSSST | TSSTTSTS | LLLLSGG | TTTTTTTTTA | STRSSS | KRT | TSSTTSSS | PTTV |
| 308 | 283 | NNNNNNNNN | CCCCSCSC | AAAAACA | IILL | AAGAA | AAIYIALF | FFFFAAA | FFFFFFFFFF | FFFFFF | FFF | FFFFFFIF | FFFF |
| 309 | 284 | LLLLLLLLL | GGGGGGGG | AHEEATL | HPKK | RKKFV | REHADAPE | PPPPREE | EEEEDDDEER | AKRSSG | RRK | LLLHFRKS | SQKA |
| 310 | 285 | KKKKQQQQK | PPPPPPPS | EEEEQQQ | EEQN | RRMRQ | EDEAQEEE | QQQQLLL | YYYYYYYYFV | ESDTAA | EEQ | EEDRYRDE | QQQD |
| 311 | 286 | DDNNNNDNN | EEEEDEDS | AAAACCA | IFVV | AAAAC | ALLLILLI | IIIILLL | LILLLLLILL | IIIIIV | LLL | IIIIICVL | LIII |
| 312 | 287 | GGGGGGGGG | GGGGGGGG | LLLLLLL | MFVV | ALLLL | MLLTLLSR | LLLLLQQ | QQQQQRRQNM | HHHYYH | IVT | VIIQQYHV | VCVS |
| 313 | 288 | VVVVTTSSV | EEEEEEEE | KKAAAQR | QSEE | IQNQE | AKHEACTN | SAAAVRK | ASSSSSSSHD | QHFQQQ | IST | NSADHNAS | LSQK |
| 314 | 289 | NNSSEEREK | RRRRPRPE | ------- | ---- | ----- | ----T--- | STTTDDD | FFFFVVVVYQ | AANEED | EEV | LSYQKTRR | LFLD |
| 315 | 290 | DDDDDDDDD | DDDDTDTD | ------- | ---- | ----- | ----D--- | IIIILLL | LLLLLLLLFL | FLLLLL | FFF | LILLLLLI | LLIL |
| 316 | 291 | IIIIVVIVI | VIIIIVIV | ------- | ---- | ----- | -------- | ------- | ---------- | ------ | --- | -------- | ---- |
| 317 | 292 | KKKKKKKKQ | RKKKRRRR | ------- | ---- | ----- | -------- | ------- | ---------- | ------ | --- | -------- | ---- |
| 318 | 293 | NNTTNNANK | EEDEAEAL | ------- | ---- | ----- | -------- | ---E--- | ---------- | ------ | --- | -------- | ---- |
| 319 | 294 | HHHHHHHHH | HHHHHHHH | HHHHHHH | DHHH | HQHHS | HTHHELLH | EEEETKK | EEEEDEDDEA | EEEQQI | SSA | KKEQQHQS | EQEE |
| 320 | 295 | KKKKPPPPK | AAAAGAGP | PPPPPPP | DPHP | PNPSD | PPDPVPVP | LLLLSAA | DDDDDDDDSL | THNSSA | KRE | DEPLEAAA | REKK |
| 321 | 296 | WWWWWWWWW | FFFFFFFF | WWFFWWW | WFWW | YYYYY | YFLWCLSW | LLLLLFF | YYYYFFFFFV | MMLIII | MMF | DEQFIILI | LQQM |

TABLE 8-continued

Alignment of the Sequences of Homologous Kinases

| | | |
|---|---|---|
| 322 | 297 | FFFFFFFFF FFFFFFFS IVFFLLV FLMM FLFLF FFILWFNM QQQQKRR FFFFYFFYSA FFIRRR AAA LMCRRSAF LAIM |
| 323 | 298 | AAAAKKSNE RRRRRRRR SCQQNQV KMVN QRNHK LNMVVQCQ HRRAGG TTTTTTTTQ QQSKKK RRR HEPNHTQS GQSV |
| 324 | 299 | TTTTEEEEG RYYYWRNR HQQENKS VGRR EDDKE PEKKEQKG SSSSEAA SASAAAAATT EVSRRR DDD PPNFSDAT EEEK |
| 325 | 300 | TTTTVVVVF IIIIIIII RRYYLDM DCGG SFLDL ILTTMKND LLLLLLL TTATTTTSL SGNHHH PPP SGSFPLPF GDSR |

TABLE 9

| | 02 | 03 | 04 | 05 | 06 | 07 | 08 | 09 | 11 | 12 | 13 | 14 | 15 | 16 | 17 | 18 | 20 | 21 | 22 | 23 | 24 | 25 | 26 | 28 | 29 | 30 | 31 | 33 | 34 | 35 | 36 | 37 | 39 | 40 | 41 | 42 | 43 | 44 | 45 | 46 |
|---|---|---|---|---|---|---|---|---|---|---|---|---|---|---|---|---|---|---|---|---|---|---|---|---|---|---|---|---|---|---|---|---|---|---|---|---|---|---|---|---|
| 01 | 99 | 95 | 95 | 60 | 62 | 65 | 62 | 56 | 51 | 52 | 52 | 51 | 50 | 51 | 50 | 50 | 42 | 42 | 43 | 42 | 38 | 41 | 44 | 44 | 44 | 43 | 43 | 33 | 34 | 36 | 31 | 34 | 32 | 26 | 33 | 38 | 34 | 31 | 34 | 36 |
| 02 | | 95 | 95 | 60 | 62 | 65 | 62 | 56 | 51 | 52 | 52 | 51 | 50 | 51 | 50 | 51 | 42 | 41 | 43 | 42 | 38 | 41 | 44 | 44 | 44 | 42 | 43 | 33 | 34 | 36 | 31 | 33 | 32 | 26 | 33 | 37 | 34 | 31 | 34 | 36 |
| 03 | | | 99 | 60 | 62 | 65 | 62 | 56 | 51 | 52 | 53 | 51 | 50 | 51 | 50 | 51 | 42 | 41 | 43 | 42 | 39 | 41 | 46 | 44 | 45 | 44 | 44 | 33 | 33 | 37 | 31 | 33 | 32 | 26 | 34 | 38 | 34 | 31 | 34 | 36 |
| 04 | | | | 60 | 62 | 66 | 62 | 57 | 52 | 53 | 53 | 51 | 50 | 52 | 50 | 51 | 42 | 41 | 44 | 42 | 39 | 41 | 46 | 44 | 44 | 42 | 44 | 33 | 33 | 37 | 31 | 33 | 32 | 26 | 34 | 37 | 34 | 31 | 35 | 36 |
| 05 | | | | | 62 | 66 | 62 | 57 | 52 | 53 | 53 | 51 | 47 | 48 | 46 | 48 | 42 | 41 | 40 | 41 | 38 | 40 | 42 | 45 | 43 | 41 | 42 | 33 | 33 | 33 | 32 | 33 | 31 | 27 | 34 | 35 | 34 | 32 | 36 | 36 |
| 06 | | | | | | 96 | 62 | 57 | 48 | 49 | 49 | 48 | 50 | 50 | 48 | 50 | 38 | 37 | 40 | 40 | 38 | 41 | 43 | 42 | 43 | 38 | 43 | 33 | 32 | 32 | 31 | 33 | 31 | 28 | 34 | 36 | 34 | 32 | 36 | 36 |
| 07 | | | | | | | 79 | 52 | 50 | 51 | 51 | 50 | 52 | 53 | 46 | 52 | 39 | 40 | 40 | 41 | 39 | 40 | 45 | 46 | 42 | 44 | 42 | 34 | 34 | 33 | 34 | 34 | 32 | 27 | 35 | 36 | 35 | 32 | 36 | 36 |
| 08 | | | | | | | | 87 | 54 | 54 | 54 | 53 | 50 | 53 | 48 | 52 | 39 | 39 | 41 | 40 | 39 | 40 | 44 | 42 | 45 | 42 | 42 | 32 | 32 | 33 | 30 | 32 | 31 | 29 | 34 | 34 | 34 | 32 | 36 | 36 |
| 09 | | | | | | | | 91 | 53 | 54 | 54 | 51 | 46 | 51 | 46 | 48 | 40 | 39 | 38 | 38 | 37 | 39 | 41 | 46 | 42 | 44 | 42 | 34 | 32 | 32 | 30 | 34 | 33 | 29 | 36 | 35 | 35 | 27 | 34 | 37 |
| 11 | | | | | | | | 82 | 55 | 48 | 48 | 48 | 48 | 48 | 48 | 51 | 38 | 40 | 38 | 36 | 38 | 38 | 42 | 46 | 41 | 40 | 40 | 32 | 34 | 33 | 30 | 33 | 32 | 27 | 33 | 34 | 34 | 27 | 32 | 35 |
| 12 | | | | | | | | | | 91 | 48 | 48 | 48 | 48 | 48 | 48 | 38 | 40 | 38 | 36 | 38 | 38 | 41 | 46 | 42 | 42 | 45 | 32 | 29 | 31 | 29 | 32 | 31 | 26 | 32 | 34 | 34 | 28 | 32 | 35 |
| 13 | | | | | | | | | | 99 | 92 | 48 | 47 | 53 | 47 | 48 | 41 | 40 | 37 | 37 | 35 | 37 | 40 | 44 | 42 | 42 | 43 | 34 | 29 | 31 | 30 | 34 | 32 | 27 | 33 | 34 | 35 | 29 | 34 | 37 |
| 14 | | | | | | | | | | | 96 | 97 | 48 | 50 | 46 | 51 | 40 | 41 | 38 | 36 | 36 | 36 | 40 | 42 | 39 | 42 | 40 | 32 | 28 | 31 | 29 | 32 | 31 | 25 | 31 | 32 | 34 | 28 | 34 | 35 |
| 15 | | | | | | | | | | | | 83 | 89 | 99 | 83 | 84 | 41 | 40 | 36 | 38 | 35 | 37 | 41 | 45 | 40 | 43 | 41 | 34 | 29 | 31 | 29 | 32 | 32 | 27 | 34 | 34 | 35 | 29 | 32 | 37 |
| 16 | | | | | | | | | | | | | 91 | 83 | 89 | 82 | 40 | 39 | 37 | 36 | 35 | 36 | 40 | 42 | 41 | 42 | 40 | 36 | 31 | 34 | 32 | 35 | 35 | 31 | 34 | 36 | 37 | 34 | 37 | 38 |
| 17 | | | | | | | | | | | | | | 83 | 98 | 79 | 38 | 38 | 36 | 37 | 36 | 39 | 41 | 45 | 39 | 41 | 36 | 37 | 34 | 35 | 47 | 38 | 35 | 30 | 36 | 38 | 35 | 33 | 38 | 38 |
| 18 | | | | | | | | | | | | | | | 83 | 78 | 42 | 41 | 38 | 36 | 35 | 38 | 50 | 50 | 49 | 44 | 40 | 37 | 35 | 37 | 47 | 38 | 34 | 30 | 34 | 36 | 34 | 34 | 34 | 39 |
| 20 | | | | | | | | | | | | | | | | | | 93 | 48 | 47 | 45 | 44 | 50 | 50 | 48 | 44 | 36 | 40 | 40 | 40 | 36 | 37 | 38 | 31 | 34 | 35 | 35 | 27 | 33 | 37 |
| 21 | | | | | | | | | | | | | | | | | | 94 | 47 | 45 | 44 | 43 | 46 | 43 | 43 | 42 | 40 | 34 | 39 | 39 | 37 | 39 | 36 | 30 | 36 | 37 | 34 | 28 | 34 | 38 |
| 22 | | | | | | | | | | | | | | | | | | | 62 | 44 | 43 | 62 | 46 | 42 | 42 | 44 | 36 | 40 | 35 | 37 | 33 | 38 | 38 | 31 | 35 | 35 | 34 | 29 | 33 | 36 |
| 23 | | | | | | | | | | | | | | | | | | | | | | | | 46 | 44 | 41 | 89 | 34 | 40 | 40 | 36 | 39 | 33 | 33 | 36 | 37 | 35 | 32 | 34 | 42 |
| 24 | | | | | | | | | | | | | | | | | | | | | | | | 50 | 48 | 48 | 51 | 34 | 35 | 39 | 50 | 52 | 47 | 34 | 36 | 42 | 37 | 34 | 41 | 40 |
| 25 | | | | | | | | | | | | | | | | | | | | | | | | 50 | 43 | 52 | 48 | 34 | 40 | 37 | 52 | 44 | 48 | 31 | 35 | 35 | 35 | 33 | 43 | 38 |
| 26 | | | | | | | | | | | | | | | | | | | | | | | | 43 | 42 | 48 | 89 | 34 | 35 | 33 | 51 | 44 | 36 | 33 | 30 | 35 | 34 | 34 | 38 | 33 |
| 28 | | | | | | | | | | | | | | | | | | | | | | | | | 46 | 54 | | | 69 | 67 | 70 | | | 33 | 30 | 32 | 33 | 36 | 37 | 31 |
| 29 | | | | | | | | | | | | | | | | | | | | | | | | | | | | | | 70 | | | 36 | 34 | | 30 | 27 | 30 | 30 | 32 |
| 30 | | | | | | | | | | | | | | | | | | | | | | | | | | | | | | | | | | 31 | 30 | 27 | 33 | 32 | 30 | 32 |
| 31 | | | | | | | | | | | | | | | | | | | | | | | | | | | | | | | | | | 34 | 30 | 47 | 34 | 32 | 37 | 32 |
| 33 | | | | | | | | | | | | | | | | | | | | | | | | | | | | | | | | | | | | | 34 | | | 30 |
| 34 | | | | | | | | | | | | | | | | | | | | | | | | | | | | | | | | | | | | | | | | 37 |

| | 48 | 49 | 50 | 51 | 52 | 53 | 54 | 56 | 57 | 58 | 59 | 60 | 61 | 62 | 63 | 64 | 65 | 67 | 68 | 69 | 70 | 71 | 72 | 74 | 75 | 76 | 78 | 79 | 80 | 81 | 82 | 83 | 84 | 85 | 87 | 88 | 89 | 90 |
|---|---|---|---|---|---|---|---|---|---|---|---|---|---|---|---|---|---|---|---|---|---|---|---|---|---|---|---|---|---|---|---|---|---|---|---|---|---|---|
| 01 | 32 | 33 | 32 | 33 | 30 | 30 | 29 | 35 | 35 | 34 | 36 | 34 | 33 | 34 | 33 | 36 | 34 | 37 | 38 | 35 | 35 | 34 | 36 | 34 | 33 | 35 | 31 | 31 | 30 | 30 | 31 | 30 | 32 | 32 | 33 | 31 | 33 | 34 |
| 02 | 32 | 33 | 32 | 33 | 30 | 30 | 29 | 35 | 35 | 34 | 36 | 34 | 33 | 34 | 33 | 36 | 34 | 37 | 39 | 35 | 35 | 34 | 36 | 33 | 33 | 35 | 32 | 33 | 31 | 30 | 31 | 31 | 33 | 31 | 33 | 31 | 33 | 34 |
| 03 | 33 | 33 | 32 | 33 | 30 | 30 | 39 | 35 | 35 | 34 | 35 | 34 | 33 | 34 | 33 | 36 | 34 | 38 | 39 | 35 | 35 | 34 | 373 | 34 | 34 | 35 | 32 | 33 | 31 | 30 | 31 | 31 | 33 | 31 | 32 | 32 | 34 | 34 |
| 04 | 33 | 33 | 32 | 34 | 32 | 30 | 29 | 35 | 35 | 35 | 36 | 34 | 34 | 34 | 34 | 36 | 34 | 38 | 39 | 35 | 36 | 36 | 373 | 34 | 34 | 35 | 33 | 34 | 32 | 32 | 31 | 33 | 33 | 34 | 32 | 31 | 33 | 33 |
| 05 | 33 | 35 | 35 | 34 | 32 | 30 | 30 | 34 | 35 | 35 | 35 | 34 | 34 | 34 | 34 | 36 | 34 | 36 | 35 | 34 | 37 | 37 | 38 | 34 | 32 | 33 | 33 | 30 | 32 | 32 | 31 | 33 | 33 | 34 | 34 | 34 | 35 | 34 |

TABLE 9-continued

| | 48 | 49 | 50 | 51 | 52 | 53 | 54 | 56 | 57 | 58 | 59 | 60 | 61 | 62 | 63 | 64 | 65 | 67 | 68 | 69 | 70 | 71 | 72 | 74 | 75 | 76 | 78 | 79 | 80 | 81 | 82 | 83 | 84 | 85 | 87 | 88 | 89 | 90 |
|---|---|---|---|---|---|---|---|---|---|---|---|---|---|---|---|---|---|---|---|---|---|---|---|---|---|---|---|---|---|---|---|---|---|---|---|---|---|---|
| 06 | 34 | 35 | 35 | 35 | 32 | 30 | 31 | 34 | 35 | 35 | 35 | 34 | 34 | 34 | 34 | 36 | 34 | 34 | 37 | 34 | 34 | 38 | 39 | 33 | 32 | 33 | 34 | 31 | 32 | 32 | 31 | 33 | 33 | 33 | 34 | 34 | 35 | 33 |
| 07 | 34 | 36 | 35 | 35 | 33 | 30 | 30 | 35 | 36 | 37 | 36 | 35 | 35 | 35 | 36 | 36 | 34 | 37 | 36 | 36 | 36 | 38 | 37 | 34 | 34 | 36 | 36 | 36 | 36 | 31 | 30 | 32 | 34 | 34 | 33 | 33 | 34 | 35 |
| 08 | 34 | 35 | 35 | 35 | 31 | 30 | 31 | 35 | 35 | 37 | 36 | 34 | 34 | 34 | 34 | 36 | 34 | 37 | 37 | 36 | 36 | 37 | 38 | 33 | 34 | 36 | 35 | 36 | 37 | 31 | 31 | 33 | 34 | 35 | 33 | 34 | 34 | 33 |
| 09 | 33 | 33 | 33 | 33 | 31 | 32 | 31 | 36 | 37 | 38 | 38 | 36 | 36 | 36 | 36 | 37 | 35 | 36 | 36 | 36 | 34 | 35 | 35 | 33 | 31 | 32 | 33 | 32 | 32 | 30 | 30 | 39 | 32 | 32 | 34 | 36 | 35 | 32 |
| 11 | 33 | 33 | 33 | 33 | 30 | 30 | 30 | 36 | 35 | 35 | 37 | 35 | 35 | 36 | 36 | 34 | 35 | 37 | 37 | 36 | 36 | 36 | 36 | 33 | 33 | 32 | 33 | 31 | 31 | 30 | 30 | 30 | 34 | 33 | 34 | 34 | 35 | 33 |
| 12 | 33 | 33 | 33 | 33 | 29 | 30 | 29 | 35 | 36 | 36 | 36 | 36 | 36 | 36 | 36 | 35 | 36 | 38 | 37 | 37 | 36 | 36 | 36 | 33 | 32 | 33 | 33 | 32 | 31 | 30 | 30 | 30 | 35 | 33 | 31 | 32 | 32 | 33 |
| 13 | 32 | 31 | 31 | 31 | 28 | 29 | 30 | 34 | 35 | 35 | 36 | 34 | 34 | 35 | 35 | 35 | 33 | 38 | 39 | 36 | 35 | 34 | 35 | 32 | 32 | 31 | 31 | 32 | 30 | 28 | 28 | 28 | 33 | 30 | 31 | 31 | 33 | 32 |
| 14 | 33 | 31 | 31 | 31 | 29 | 28 | 29 | 33 | 34 | 34 | 34 | 33 | 35 | 35 | 35 | 34 | 36 | 37 | 36 | 37 | 35 | 33 | 34 | 32 | 32 | 33 | 32 | 32 | 31 | 27 | 27 | 30 | 31 | 30 | 30 | 32 | 30 | 32 |
| 15 | 32 | 31 | 31 | 31 | 29 | 29 | 29 | 35 | 34 | 34 | 34 | 34 | 33 | 33 | 34 | 33 | 33 | 34 | 34 | 34 | 34 | 34 | 34 | 32 | 31 | 31 | 33 | 31 | 30 | 29 | 29 | 30 | 31 | 30 | 31 | 31 | 34 | 31 |
| 16 | 33 | 33 | 33 | 33 | 30 | 30 | 29 | 34 | 34 | 34 | 36 | 34 | 34 | 34 | 34 | 34 | 35 | 34 | 34 | 34 | 35 | 35 | 34 | 31 | 31 | 31 | 33 | 33 | 32 | 30 | 28 | 31 | 31 | 33 | 31 | 31 | 33 | 32 |
| 17 | 32 | 31 | 31 | 31 | 30 | 30 | 30 | 32 | 33 | 34 | 34 | 33 | 33 | 33 | 33 | 33 | 33 | 33 | 34 | 33 | 33 | 33 | 34 | 30 | 30 | 30 | 31 | 31 | 30 | 29 | 28 | 27 | 31 | 30 | 31 | 31 | 32 | 32 |
| 18 | 32 | 33 | 33 | 33 | 30 | 29 | 30 | 32 | 34 | 34 | 34 | 33 | 33 | 34 | 33 | 32 | 31 | 32 | 33 | 32 | 33 | 33 | 34 | 31 | 31 | 30 | 32 | 33 | 31 | 30 | 30 | 28 | 30 | 30 | 31 | 31 | 32 | 32 |
| 19 | 32 | 34 | 34 | 34 | 30 | 30 | 29 | 32 | 32 | 30 | 32 | 32 | 32 | 30 | 30 | 34 | 30 | 31 | 32 | 32 | 33 | 32 | 34 | 31 | 30 | 31 | 31 | 31 | 31 | 30 | 30 | 31 | 33 | 33 | 31 | 31 | 32 | 34 |
| 20 | 33 | 34 | 34 | 34 | 30 | 30 | 30 | 36 | 32 | 31 | 31 | 32 | 30 | 30 | 30 | 35 | 31 | 32 | 30 | 31 | 32 | 31 | 32 | 30 | 30 | 30 | 30 | 30 | 30 | 30 | 30 | 31 | 30 | 30 | 32 | 32 | 31 | 32 |
| 21 | 33 | 34 | 34 | 34 | 33 | 30 | 30 | 32 | 32 | 33 | 32 | 32 | 32 | 32 | 31 | 34 | 34 | 33 | 32 | 33 | 33 | 34 | 34 | 31 | 31 | 31 | 31 | 30 | 30 | 30 | 29 | 31 | 32 | 33 | 31 | 31 | 30 | 34 |
| 22 | 33 | 34 | 34 | 34 | 30 | 30 | 30 | 30 | 30 | 31 | 31 | 31 | 31 | 30 | 30 | 33 | 33 | 32 | 34 | 32 | 33 | 32 | 34 | 30 | 30 | 32 | 32 | 32 | 31 | 30 | 29 | 30 | 39 | 30 | 31 | 31 | 35 | 34 |
| 23 | 34 | 33 | 33 | 33 | 32 | 32 | 32 | 32 | 33 | 30 | 31 | 31 | 38 | 38 | 37 | 32 | 33 | 36 | 34 | 34 | 35 | 35 | 36 | 32 | 32 | 31 | 32 | 34 | 31 | 30 | 30 | 33 | 32 | 31 | 31 | 35 | 36 | 37 |
| 24 | 33 | 34 | 34 | 34 | 31 | 30 | 32 | 39 | 38 | 38 | 38 | 37 | 37 | 38 | 37 | 33 | 35 | 37 | 34 | 35 | 34 | 35 | 35 | 34 | 34 | 36 | 35 | 35 | 31 | 34 | 32 | 33 | 39 | 34 | 36 | 34 | 37 | 37 |
| 25 | 34 | 34 | 34 | 34 | 31 | 30 | 32 | 34 | 38 | 38 | 38 | 34 | 34 | 36 | 38 | 36 | 36 | 36 | 36 | 36 | 37 | 36 | 37 | 33 | 34 | 36 | 36 | 35 | 34 | 33 | 31 | 31 | 37 | 34 | 36 | 36 | 37 | 36 |
| 26 | 34 | 36 | 36 | 36 | 31 | 30 | 31 | 34 | 37 | 38 | 37 | 37 | 37 | 37 | 37 | 38 | 35 | 37 | 39 | 37 | 37 | 36 | 36 | 33 | 33 | 33 | 35 | 35 | 34 | 33 | 32 | 33 | 34 | 34 | 36 | 34 | 36 | 34 |
| 27 | 34 | 34 | 34 | 34 | 32 | 31 | 32 | 30 | 35 | 36 | 37 | 36 | 36 | 36 | 35 | 36 | 34 | 35 | 37 | 35 | 35 | 35 | 35 | 32 | 32 | 33 | 35 | 34 | 33 | 31 | 31 | 31 | 39 | 32 | 34 | 35 | 37 | 34 |
| 28 | 29 | 28 | 28 | 28 | 26 | 26 | 28 | 29 | 30 | 32 | 33 | 32 | 31 | 30 | 32 | 30 | 30 | 29 | 30 | 30 | 30 | 30 | 30 | 28 | 28 | 20 | 29 | 28 | 28 | 28 | 26 | 26 | 32 | 29 | 29 | 29 | 31 | 30 |
| 29 | 29 | 29 | 29 | 29 | 30 | 28 | 28 | 29 | 31 | 31 | 33 | 34 | 33 | 32 | 33 | 30 | 33 | 33 | 33 | 32 | 32 | 31 | 32 | 29 | 29 | 27 | 30 | 29 | 29 | 27 | 28 | 28 | 32 | 29 | 30 | 30 | 33 | 32 |
| 30 | 27 | 26 | 26 | 19 | 26 | 26 | 28 | 28 | 28 | 28 | 29 | 28 | 29 | 29 | 28 | 28 | 28 | 28 | 28 | 28 | 28 | 28 | 28 | 28 | 27 | 27 | 28 | 25 | 27 | 27 | 24 | 25 | 26 | 28 | 26 | 26 | 27 | 26 |
| 31 | 28 | 26 | 26 | 26 | 26 | 26 | 28 | 29 | 28 | 29 | 29 | 28 | 27 | 29 | 27 | 27 | 26 | 26 | 28 | 26 | 26 | 25 | 28 | 25 | 26 | 25 | 25 | 25 | 24 | 24 | 23 | 25 | 25 | 25 | 27 | 26 | 27 | 34 |
| 32 | 34 | 35 | 35 | 35 | 33 | 34 | 35 | 34 | 34 | 34 | 34 | 34 | 35 | 34 | 34 | 37 | 34 | 32 | 32 | 32 | 33 | 34 | 33 | 29 | 30 | 31 | 29 | 31 | 29 | 26 | 28 | 31 | 31 | 30 | 32 | 30 | 33 | 34 |
| 33 | 36 | 36 | 36 | 36 | 33 | 33 | 32 | 30 | 30 | 31 | 36 | 35 | 35 | 35 | 35 | 35 | 34 | 30 | 30 | 32 | 32 | 36 | 35 | 35 | 35 | 31 | 35 | 32 | 32 | 32 | 24 | 26 | 36 | 36 | 36 | 36 | 36 | 36 |
| 34 | 34 | 34 | 34 | 34 | 28 | 30 | 32 | 30 | 34 | 34 | 33 | 32 | 29 | 32 | 30 | 32 | 29 | 33 | 33 | 32 | 34 | 35 | 32 | 35 | 35 | 29 | 34 | 33 | 31 | 32 | 29 | 31 | 36 | 34 | 32 | 34 | 34 | 34 |
| 35 | 29 | 29 | 29 | 29 | 28 | 28 | 28 | 30 | 31 | 31 | 31 | 30 | 30 | 29 | 28 | 30 | 34 | 32 | 30 | 30 | 32 | 29 | 32 | 30 | 31 | 29 | 30 | 29 | 28 | 25 | 26 | 24 | 30 | 29 | 28 | 30 | 27 | 31 |
| 36 | 31 | 31 | 31 | 31 | 28 | 26 | 26 | 33 | 30 | 31 | 30 | 33 | 32 | 34 | 34 | 34 | 34 | 30 | 30 | 32 | 34 | 34 | 36 | 31 | 35 | 31 | 32 | 31 | 32 | 30 | 28 | 31 | 34 | 35 | 36 | 36 | 36 | 37 |
| 37 | 34 | 34 | 34 | 34 | 30 | 30 | 32 | 32 | 33 | 34 | 33 | 33 | 32 | 33 | 35 | 35 | 32 | 30 | 30 | 30 | 32 | 32 | 32 | 32 | 33 | 29 | 30 | 30 | 30 | 32 | 24 | 26 | 35 | 34 | 35 | 35 | 33 | 34 |
| 38 | 32 | 31 | 31 | 31 | 33 | 32 | 35 | 34 | 34 | 34 | 29 | 30 | 29 | 29 | 30 | 31 | 34 | 30 | 30 | 30 | 30 | 30 | 32 | 30 | 30 | 26 | 28 | 28 | 26 | 29 | 23 | 25 | 32 | 32 | 30 | 30 | 29 | 27 |
| 39 | 28 | 27 | 27 | 29 | 27 | 26 | 32 | 30 | 31 | 29 | 34 | 34 | 34 | 32 | 34 | 34 | 34 | 32 | 32 | 33 | 34 | 33 | 33 | 33 | 35 | 31 | 29 | 31 | 32 | 32 | 26 | 31 | 30 | 30 | 30 | 26 | 27 | 29 |
| 40 | 29 | 26 | 26 | 26 | 30 | 32 | 30 | 36 | 34 | 31 | 31 | 28 | 35 | 34 | 35 | 35 | 36 | 32 | 32 | 34 | 36 | 34 | 35 | 36 | 30 | 29 | 31 | 32 | 33 | 32 | 28 | 26 | 34 | 33 | 35 | 36 | 33 | 26 |
| 41 | 36 | 34 | 34 | 34 | 33 | 34 | 35 | 30 | 30 | 34 | 34 | 35 | 34 | 37 | 34 | 35 | 34 | 33 | 33 | 32 | 34 | 34 | 36 | 34 | 35 | 31 | 35 | 32 | 34 | 29 | 26 | 31 | 36 | 36 | 36 | 35 | 37 | 34 |
| 42 | 36 | 34 | 34 | 34 | 32 | 34 | 34 | 32 | 32 | 30 | 34 | 32 | 34 | 33 | 32 | 33 | 32 | 32 | 30 | 30 | 33 | 29 | 32 | 33 | 32 | 29 | 34 | 29 | 33 | 30 | 25 | 26 | 32 | 32 | 32 | 26 | 33 | 26 |
| 43 | 34 | 33 | 33 | 33 | 30 | 28 | 28 | 30 | 29 | 29 | 33 | 33 | 34 | 33 | 33 | 34 | 34 | 33 | 33 | 33 | 34 | 33 | 34 | 34 | 32 | 31 | 29 | 31 | 29 | 29 | 29 | 31 | 34 | 34 | 32 | 32 | 32 | 33 |
| 44 | 33 | 32 | 32 | 32 | 27 | 28 | 28 | 32 | 30 | 31 | 30 | 32 | 33 | 32 | 32 | 32 | 31 | 29 | 30 | 29 | 29 | 29 | 31 | 31 | 31 | 29 | 29 | 26 | 29 | 29 | 29 | 26 | 30 | 30 | 32 | 26 | 32 | 29 |
| 45 | 31 | 30 | 30 | 30 | 27 | 27 | 28 | 30 | 32 | 32 | 30 | 32 | 32 | 32 | 31 | 32 | 31 | 32 | 33 | 33 | 32 | 32 | 33 | 30 | 30 | 32 | 29 | 30 | 29 | 29 | 29 | 31 | 32 | 32 | 32 | 32 | 32 | 33 |
| 46 | 31 | 30 | 30 | 30 | 31 | 33 | 33 | 33 | 33 | 33 | 34 | 34 | 36 | 36 | 34 | 34 | 31 | 34 | 33 | 34 | 34 | 34 | 34 | 32 | 32 | 31 | 30 | 30 | 32 | 29 | 29 | 31 | 32 | 32 | 32 | 32 | 32 | 33 |

| | 48 | 49 | 50 | 51 | 52 | 53 | 54 | 56 | 57 | 58 | 59 | 60 | 61 | 62 | 63 | 64 | 65 | 67 | 68 | 69 | 70 | 71 | 72 | 74 | 75 | 76 | 78 | 79 | 80 | 81 | 82 | 83 | 84 | 85 | 87 | 88 | 89 | 90 |
|---|---|---|---|---|---|---|---|---|---|---|---|---|---|---|---|---|---|---|---|---|---|---|---|---|---|---|---|---|---|---|---|---|---|---|---|---|---|---|
| 48 | | 83 | 82 | 83 | 35 | 35 | 34 | 43 | 44 | 44 | 44 | 42 | 41 | 42 | 42 | 44 | 42 | 39 | 39 | 40 | 39 | 40 | 40 | 37 | 38 | 36 | 37 | 37 | 35 | 36 | 35 | 34 | 37 | 38 | 40 | 40 | 39 | 38 |
| 49 | 83 | | 99 | 98 | 36 | 35 | 34 | 42 | 42 | 42 | 43 | 42 | 41 | 41 | 41 | 43 | 40 | 40 | 41 | 41 | 40 | 40 | 40 | 38 | 38 | 36 | 36 | 36 | 36 | 36 | 36 | 35 | 37 | 38 | 39 | 38 | 40 | 38 |
| 50 | 82 | 99 | | 97 | 36 | 35 | 34 | 42 | 43 | 43 | 43 | 42 | 40 | 40 | 41 | 43 | 41 | 40 | 41 | 41 | 40 | 40 | 40 | 38 | 38 | 36 | 35 | 36 | 37 | 36 | 36 | 35 | 37 | 38 | 39 | 39 | 40 | 38 |
| 51 | 83 | 98 | 97 | | 35 | 35 | 34 | 42 | 42 | 43 | 43 | 42 | 40 | 40 | 41 | 43 | 40 | 40 | 40 | 41 | 40 | 40 | 40 | 38 | 38 | 36 | 33 | 34 | 33 | 31 | 31 | 34 | 37 | 38 | 38 | 39 | 39 | 38 |
| 52 | 35 | 36 | 36 | 35 | | 81 | 79 | 42 | 43 | 37 | 37 | 38 | 37 | 38 | 39 | 35 | 34 | 32 | 33 | 33 | 35 | 35 | 37 | 30 | 30 | 32 | 31 | 34 | 31 | 31 | 31 | 34 | 32 | 32 | 34 | 32 | 32 | 32 |
| 53 | 35 | 35 | 35 | 35 | 81 | | 93 | 42 | 36 | 38 | 38 | 39 | 38 | 38 | 40 | 35 | 33 | 33 | 34 | 35 | 35 | 35 | 37 | 30 | 30 | 32 | 33 | 33 | 30 | 34 | 31 | 33 | 31 | 32 | 33 | 32 | 31 | 32 |
| 54 | 34 | 34 | 34 | 34 | 79 | 93 | | 37 | 37 | 37 | 38 | 38 | 38 | 38 | 40 | 35 | 34 | 33 | 34 | 33 | 35 | 35 | 37 | 30 | 30 | 32 | 33 | 34 | 34 | 31 | 31 | 33 | 32 | 32 | 34 | 32 | 31 | 32 |
| 56 | 43 | 42 | 42 | 42 | 42 | 42 | 37 | | 91 | 83 | 87 | 73 | 69 | 74 | 75 | 66 | 57 | 58 | 60 | 56 | 53 | 53 | 52 | 46 | 49 | 46 | 48 | 47 | 46 | 50 | 50 | 48 | 46 | 46 | 47 | 48 | 46 | 47 |
| 57 | 44 | 42 | 43 | 42 | 43 | 36 | 37 | 91 | | 83 | 90 | 73 | 73 | 75 | 77 | 66 | 58 | 58 | 59 | 57 | 53 | 53 | 52 | 46 | 48 | 46 | 47 | 46 | 45 | 51 | 50 | 47 | 45 | 46 | 46 | 48 | 47 | 47 |
| 58 | 44 | 42 | 43 | 43 | 37 | 38 | 37 | 83 | 83 | | 83 | 74 | 70 | 70 | 80 | 65 | 57 | 58 | 58 | 56 | 53 | 53 | 51 | 45 | 48 | 45 | 46 | 47 | 43 | 48 | 47 | 47 | 46 | 46 | 46 | 47 | 48 | 49 |
| 59 | 44 | 43 | 43 | 43 | 37 | 38 | 38 | 87 | 90 | 83 | | 73 | 74 | 75 | 86 | 62 | 57 | 58 | 59 | 57 | 53 | 53 | 50 | 46 | 49 | 46 | 47 | 47 | 44 | 50 | 48 | 47 | 46 | 48 | 50 | 48 | 48 | 45 |
| 60 | 42 | 42 | 42 | 42 | 38 | 39 | 38 | 73 | 73 | 74 | 73 | | 75 | 80 | 79 | 60 | 58 | 56 | 58 | 56 | 50 | 50 | 52 | 45 | 46 | 45 | 46 | 47 | 43 | 50 | 47 | 47 | 46 | 46 | 50 | 47 | 49 | 46 |
| 61 | 41 | 41 | 40 | 40 | 37 | 38 | 38 | 69 | 73 | 70 | 74 | 75 | | 77 | | | 57 | 57 | 59 | 57 | 52 | 51 | 51 | 45 | 46 | 45 | 47 | 46 | 44 | 48 | 47 | 47 | 48 | 48 | 50 | 49 | 48 | 47 |

TABLE 9-continued

| | | | | | | | | | | | | | | | | | | | | | | | | |
|---|---|---|---|---|---|---|---|---|---|---|---|---|---|---|---|---|---|---|---|---|---|---|---|---|
| 62 | 82 | 61 | 58 | 58 | 59 | 58 | 53 | 52 | 52 | 47 | 45 | 46 | 46 | 43 | 50 | 48 | 47 | 47 | 46 | 48 | 48 | 48 | 46 | 49 |
| 63 | | 61 | 56 | 57 | 58 | 57 | 50 | 50 | 50 | 46 | 45 | 47 | 46 | 44 | 50 | 49 | 45 | 47 | 44 | 49 | 49 | 50 | 50 | 48 |
| 64 | | | 57 | 58 | 58 | 56 | 56 | 55 | 45 | 49 | 48 | 46 | 45 | 45 | 47 | 48 | 47 | 46 | 48 | 48 | 49 | 48 | 48 | 48 |
| 65 | | | | 57 | 59 | 56 | 52 | 52 | 45 | 48 | 46 | 45 | 44 | 44 | 49 | 48 | 48 | 47 | 47 | 48 | 47 | 45 | 46 |
| 67 | | | | | 81 | 71 | 53 | 53 | 50 | 47 | 50 | 51 | 44 | 49 | 49 | 47 | 52 | 48 | 50 | 47 | 47 | 48 | 50 |
| 68 | | | | | | 72 | 53 | 53 | 49 | 50 | 50 | 48 | 49 | 46 | 49 | 48 | 48 | 47 | 48 | 47 | 48 | 48 |
| 69 | | | | | | | 53 | 53 | 48 | 49 | 50 | 49 | 46 | 50 | 49 | 50 | 52 | 48 | 48 | 46 | 49 | 49 |
| 70 | | | | | | | | 52 | 43 | 50 | 50 | 50 | 47 | 51 | 49 | 48 | 48 | 47 | 49 | 47 | 48 |
| 71 | | | | | | | | 98 | 43 | 50 | 50 | 48 | 47 | 49 | 46 | 49 | 50 | 48 | 46 | 46 | 48 |
| 72 | | | | | | | | | 45 | 44 | 50 | 43 | 46 | 45 | 48 | 48 | 44 | 44 | 45 | 44 | 48 |
| 73 | | | | | | | | | 43 | 43 | 44 | 47 | 46 | 45 | 49 | 47 | 45 | 45 | 44 | 46 | 48 |
| 74 | | | | | | | | | 85 | 44 | 42 | 47 | 46 | 45 | 50 | 42 | 44 | 45 | 44 | 45 | 43 |
| 75 | | | | | | | | | | 41 | 70 | 45 | 46 | 49 | 47 | 53 | 45 | 47 | 45 | 44 | 51 |
| 76 | | | | | | | | | | 84 | 71 | 57 | 56 | 56 | 52 | 49 | 50 | 46 | 50 | 52 |
| 78 | | | | | | | | | | | | 54 | 51 | 52 | 46 | 51 | 51 | 45 | 51 |
| 79 | | | | | | | | | | | | 78 | 61 | 51 | 47 | 50 | 47 | 46 | 52 |
| 80 | | | | | | | | | | | | | 62 | 50 | 46 | 51 | 48 | 45 | 50 |
| 81 | | | | | | | | | | | | | | 49 | 46 | 47 | 44 | 50 | 47 |
| 82 | | | | | | | | | | | | | | | 48 | 50 | 48 | 48 | 50 |
| 83 | | | | | | | | | | | | | | | | 51 | 46 | 67 | 47 |
| 84 | | | | | | | | | | | | | | | | | 69 | 76 | 54 |
| 85 | | | | | | | | | | | | | | | | | | | 56 |
| 87 | | | | | | | | | | | | | | | | | | | 57 |
| 88 | | | | | | | | | | | | | | | | | | | |
| 89 | | | | | | | | | | | | | | | | | | | |

TABLE 10

Positional Surface, Parsing, Inside, and Active Site Assignments for Protein Kinase

| | Number of Variable Subgroups | | | | | | | | |
|---|---|---|---|---|---|---|---|---|---|
| | ≥10 | 9 | 8 | 7 | 6 | 5 | 4 | 3 | 2 |
| 001 | 11.5.8 | 4.8 | | | 7.5 | 9.4; 8.4 | | | |
| 002 | | | 5.7 | 6.6; 4.6 | | | | | 9.2; 8.2; 7.2 |
| 003 | INSIDE | | | | | | | | |
| 004 | 11.6.6 | | 4.6 | 7.4 | | | 8.3 | | |
| 005 | | | | 4.2 | | 5.2 | | | |
| 006 | 13.6.4 | 4.4 | 8.3 | | | | | | |
| 007 | 10.5.9 | 4.8 | 6.7 | | | | 7.3 | | |
| 008 | | | | | 5.5; 4.6 | | 8.4; 7.4; 6.4 | | |
| 009 | INSIDE | | | | | | | | |
| 010 | secondary parse | | | | | | | | |
| 011 | 10.4.5 | | | | | | | | |
| 012 | secondary parse | | | | | | | | |
| 013 | | | | | | 4.2 | | | |
| 014 | INSIDE | | | | | | | | |
| 015 | | | | | | | | | |
| 016 | | | 4.6 | | | 5.4 | | 6.3 | 7.2 |
| 017 | INSIDE | | | | | | | | |
| 018 | | | | | 4.2 | | | | |
| 019 | | | | | 4.6 | | | 5.2 | |
| 020 | INSIDE | | | | | | | | |
| 021 | 10.5.6 | | | 6.4; 4.5 | 8.3; 7.3 | | | 9.2 | |
| 022 | inside | 4.2 | | | | | | | |
| 023 | 10.6.7 | | 4.6 | 7.6 | | 8.4 | | 9.2 | |
| 024 | | 5.7 | | 6.5; 4.6 | 7.4 | 8.3 | | | |
| 025 | PRIMARY PARSE | | | | | | | 5.2; 4.3 | |
| 026 | PRIMARY PARSE | | | | | | | 4.2 | |
| 027 | PRIMARY PARSE | | | | | | 6.2; 5.2 | 4.2 | |
| 028 | PRIMARY PARSE | | | | | | 6.4; 5.4 | 4.3 | 8.2; 7.2 |
| 029 | PRIMARY PARSE | | | | | | | 5.2 | 4.2; 6.2 |
| 030 | PRIMARY PARSE | | | | | | | | |
| 031 | PRIMARY PARSE | | | | | | | | |
| 032 | PRIMARY PARSE | | | | | | | | |
| 033 | PRIMARY PARSE | | | | | | | | |
| 034 | PRIMARY PARSE | | | | | | | | |
| 035 | PRIMARY PARSE | | | | | | | | |
| 036 | PRIMARY PARSE | | | | | | | | |
| 037 | PRIMARY PARSE | | | | | | | | |
| 038 | PRIMARY PARSE | | | | | | | | |
| 039 | | | | 5.2 | 4.4 | | | | |
| 040 | | 5.7 | 6 | 7.4; 4.5 | 8.4 | | 9.3 | | |
| 041 | 10.5.6 | | 6.5 | 4.6 | | | 7.3 | 9.2; 8.2 | |
| 042 | | 6.4; 5.5 | | 4.5 | | | | | |
| 043 | INSIDE | | | | | | | | |
| 044 | INSIDE | | | | | | | | |
| 045 | INSIDE | | | | | | | | |
| 046 | Active Site | | | | | | | | |
| 047 | | | | 4.3 | | | | | |
| 048 | INSIDE | | | | | | | | |
| 049 | | | | | | 4.5 | 5.4 | | |
| 050 | | | 4.6 | | 5.4 | | | | |
| 051 | | | 4.6 | | 5.3 | | 6.3 | 8.5; 7.2 | |
| 052 | | | 5.3; 4.3 | 6.2 | | | | | |
| 053 | | 4.6 | 5.2 | | | | 6.2 | | |
| 054 | | | 4.5 | 5.2 | | | 6.3 | | |
| 055 | 10.4.7 | | 5.5 | | 6.4 | | 7.3 | 8.2 | |
| 056 | PRIMARY PARSE | | | | | | | 4.2 | |
| 057 | PRIMARY PARSE | | | | | | | | |
| 058 | PRIMARY PARSE | | | | | | | | |
| 059 | PRIMARY PARSE | | | | | | | 4.2 | |
| 060 | | | | 4.5 | | 5.2 | | | |
| 061 | | | 5.4; 4.6 | | | 6.2 | | | |
| 062 | | | | 5.5; 4.5 | 6.4 | 7.4 | | | |
| 063 | | | | 4.6 | | 5.5 | 7.3; 6.4 | 8.2 | 9.2 |
| 064 | INSIDE | | | | | | | | |
| 065 | | 4.3 | | | 5.3 | | | | |
| 066 | | | 5.7 | | 4.6 | | 7.3; 6.3 | | 8.2 |
| 067 | Active Site | | | | | | | | |
| 068 | INSIDE | | | | | | | | |
| 069 | | | 4.6 | | 5.4 | | 6.3 | 7.2 | 8.2 |
| 070 | INSIDE | | | | | | | | |
| 071 | INSIDE | | | | | | | | |
| 072 | | | | | 4.6 | | | | 7.2; 6.2; 5.2 |
| 073 | | | 5.4; 4.5 | | 6.3 | | 7.2 | | |

TABLE 10-continued

Positional Surface, Parsing, Inside, and Active Site Assignments for Protein Kinase

| | | | | Number of Variable Subgroups | | | | | |
|---|---|---|---|---|---|---|---|---|---|
| | ≧10 | 9 | 8 | 7 | 6 | 5 | 4 | 3 | 2 |
| 074 | INSIDE | | | | | | | | |
| 075 | PRIMARY PARSE | | | | | | 4.3 | | 6.2; 5.2 |
| 076 | PRIMARY PARSE | | | | | | | | 6.2; 5.2; 4.2 |
| 077 | PRIMARY PARSE | | | | | | | | |
| 078 | PRIMARY PARSE | | | | | | | | |
| 079 | PRIMARY PARSE | | | | | | | | |
| 080 | PRIMARY PARSE | | | | | | | | |
| 081 | 12.6.12 | 4.9 | 8.7; 7.8 | | | | | 9.3 | |
| 082 | | | | | | 5.2; 4.2 | 6.2 | | |
| 083 | 11.5.6 | | 6.4; 4.7 | | | | | | |
| 084 | | | | | 4.6 | | 5.4 | 6.2 | |
| 085 | INSIDE | | | | | | | | |
| 086 | INSIDE | | | | | | | | |
| 087 | | | | 5.6; 4.6 | | 6.2 | 8.2; 7.2 | | |
| 088 | INSIDE | | | | | | | | |
| 089 | INSIDE | | | | | | | | |
| 090 | inside | | | | | | 4.2 | | |
| 091 | INSIDE | | | | | | | | |
| 092 | INSIDE | | | | | | | | |
| 093 | INSIDE | | | | | | | | |
| 094 | 10.5.7 | | | 6.5 | | | 7.3 | 8.2 | |
| 095 | | | | 4.7 | 5.5 | | 6.2 | | |
| 096 | PRIMARY PARSE | | | | | | | 4.2 | |
| 097 | PRIMARY PARSE | | | | | | | | |
| 098 | PRIMARY PARSE | | | | | | | 4.3 | |
| 099 | PRIMARY PARSE | | | | | | | | |
| 100 | PRIMARY PARSE | | | | | | | | |
| 101 | | | | 4.5 | | 5.2 | 6.2 | | 7.2 |
| 102 | | | | 4.5 | 5.4 | | 6.3 | 7.2 | |
| 103 | INSIDE | | | | | | | | |
| 104 | INSIDE | | | | | | | | |
| 105 | inside | | | | | | | | 9.2 |
| 106 | INSIDE | | | | | | | | |
| 107 | INSIDE | | | | | | | | |
| 108 | | | | | | | | | 4.2 |
| 109 | INSIDE | | | | | | | | |
| 110 | INSIDE | | | | | | | | |
| 111 | | | | 6.6; 5.7 | 7.3; 4.6 | | 8.2 | | |
| 112 | | | | 5.4 | 6.4 | 7.3; 4.3 | | 8.2 | |
| 113 | PRIMARY PARSE | | | | | | | | |
| 114 | PRIMARY PARSE | | | | | | | | |
| 115 | | | | | | | 4.4 | | 6.2; 5.2 |
| 116 | INSIDE | | | | | | | | |
| 117 | | | | | | 4.3 | | | |
| 118 | | | | 6.4; 5.4 | 4.6 | | | | |
| 119 | INSIDE | | | | | | | | |
| 120 | INSIDE | | | | | | | | |
| 121 | | | | | | 4.5 | | 5.3 | 6.2 |
| 122 | | 5.7 | 4.8 | 6.5 | | | 7.3 | 8.2 | 9.2 |
| 123 | | | 5.3; 4.5 | 6.3 | | 7.2 | | | 8.2 |
| 124 | | 4.7 | 6.6; 5.6 | | 7.5 | | | 8.3 | 9.2 |
| 125 | 10.5.8 | 6.8; 4.8 | | | 7.4 | 8.3 | | 9.2 | |
| 126 | 11.5.7 | | | 7.5 | | | 8.3 | | |
| 127 | | | | | 6.3; 5.3 | 4.2 | | 7.2 | |
| 128 | PRIMARY PARSE | | | | | | | | |
| 129 | PRIMARY PARSE | | | | | | | | |
| 130 | 12.5.7 | 7.6; 4.7; 6.7 | | 8.4 | | | 9.3 | | |
| 131 | INSIDE | | | | | | | | |
| 132 | | 5.5; 4.7 | | 6.3 | | | | | |
| 133 | 11.5.6 | | 6.4; 4.5 | 7.4 | 8.4 | | | | |
| 134 | INSIDE | | | | | | | | |
| 135 | 10.5.2 | 6.2 | | 4.2 | | | | | |
| 136 | | | 5.5 | 4.6 | | 6.2 | | | |
| 137 | INSIDE | | | | | | | | |
| 138 | INSIDE | | | | | | | | |
| 139 | | | | 4.4 | | | | | |
| 140 | | | | | | | 4.3 | | 5.2 |
| 141 | INSIDE | | | | | | | | |
| 142 | INSIDE | | | | | | | | |
| 143 | | | | 4.7 | 5.5 | | 6.3 | | |
| 144 | | | | | | | | | |
| 145 | INSIDE | | | | | | | | |
| 146 | | 4.8 | 5.6 | | | 6.4 | | 7.2 | |

TABLE 10-continued

Positional Surface, Parsing, Inside, and Active Site Assignments for Protein Kinase

| | Number of Variable Subgroups | | | | | | | | |
|---|---|---|---|---|---|---|---|---|---|
| | ≥10 | 9 | 8 | 7 | 6 | 5 | 4 | 3 | 2 |
| 147 | INSIDE | | | | | | | | |
| 148 | INSIDE | | | | | | | | |
| 149 | | | | | | | | 4.2 | |
| 150 | | | | 4.6 | 5.5 | 6.4 | 7.3 | | 8.2 |
| 151 | | | 5.7 | 7.7; 6.7; 4.6 | | 8.5 | | | 9.2 |
| 152 | | | | 4.7 | 5.5 | | 6.3 | | |
| 153 | INSIDE | | | | | | | | |
| 154 | INSIDE | | | | | | | | |
| 155 | INSIDE | | | | | | | | |
| 156 | | | | | | | | | |
| 157 | Active Site | | | | | | | | |
| 158 | INSIDE | | | | | | | | |
| 159 | | | | | | | | | |
| 160 | secondary parse | | | | | | | | |
| 161 | | | | | | | | 4.3 | |
| 162 | Active Site | | | | | | | | |
| 163 | INSIDE | | | | | | | | |
| 164 | INSIDE | | | | | | | | |
| 165 | INSIDE | | | | | | | | |
| 166 | | | | 4.5 | 5.2 | | | | |
| 167 | 11.6.8 | 7.6 | 4.6 | | 8.4 | | | | |
| 168 | 10.5.9 | | 4.7 | | 6.6 | | 7.4 | 8.3 | 9.2 |
| 169 | | | | 5.5; 4.5 | 6.4 | | | 7.2 | |
| 170 | PRIMARY PARSE | | | | | | | | |
| 171 | PRIMARY PARSE | | | | | | | | |
| 172 | PRIMARY PARSE | | | | | | | | |
| 173 | PRIMARY PARSE | | | | | | | | |
| 174 | PRIMARY PARSE | | | | | | | | |
| 175 | PRIMARY PARSE | | | | | | | | |
| 176 | PRIMARY PARSE | | | | | | | | |
| 177 | | | 4.3 | | | | | | |
| 178 | INSIDE | | | | | | | | |
| 179 | Inside | | | | | | | | 5.2; 4.2 |
| 180 | INSIDE | | | | | | | | |
| 181 | INSIDE | | | | | | | | |
| 182 | Active Site | | | | | | | | |
| 183 | INSIDE | | | | | | | | |
| 184 | secondary parse | | | | | | | | |
| 185 | INSIDE | | | | | | | | |
| 186 | INSIDE | | | | | | | | |
| 187 | | | | | | | 4.4 | | 7.2; 6.2; 5.2 |
| 188 | | | | | | 6.2; 5.2 | 4.3 | | 7.2 |
| 189 | | | | 4.2 | | | | | |
| 190 | 12.5.10 | 4.6 | | | | 8.4 | | 9.2 | |
| 191 | | 4.5 | 5.3 | 6.3 | | 7.2 | | | |
| 192 | | | | 5.7; 4.6 | | | 7.4; 6.4 | | 8.2 |
| 193 | | 4.7 | | | 5.4 | | 6.2 | 7.2 | |
| 194 | | | | | 4.5 | | 5.3 | 7.2; 6.2 | |
| 195 | PRIMARY PARSE | | | | | 4.3 | 6.3; 5.3 | 7.2 | |
| 196 | PRIMARY PARSE | | | | | | | | |
| 197 | | | | 4.4 | 5.2 | | | | |
| 198 | | | | 4.4 | 6.3; 5.3 | | 7.2 | 8.2 | |
| 199 | | | | | 4.3 | | | | |
| 200 | | | 4.4 | | 5.2 | | | | |
| 201 | | | | 4.3 | | | 5.2 | | |
| 202 | INSIDE | | | | | | | | |
| 203 | secondary parse | | | | | | | | |
| 204 | secondary parse | | | | | | | | |
| 205 | | | | | | | | 4.2 | |
| 206 | INSIDE | | | | | | | | |
| 207 | INSIDE | | | | | | | | |
| 208 | INSIDE | | | | | | | | |
| 209 | secondary parse | | | | | | | | |
| 210 | Active Site | | | | | | | | |
| 211 | INSIDE | | | | | | | | |
| 212 | INSIDE | | | | | | | | |
| 213 | PRIMARY PARSE | | | | | | | | 4.2 |
| 214 | PRIMARY PARSE | | | | | | | | |
| 215 | PRIMARY PARSE | | | | | | | | |
| 216 | PRIMARY PARSE | | | | | | | | |
| 217 | | | | 5.4 | 6.3; 4.5 | | | | |
| 218 | | | 4.6 | 5.3 | 6.3 | | | 7.2 | |
| 219 | | | 4.7 | | | 5.4 | 6.3 | | 9.2; 8.2; 7.2 |

TABLE 10-continued

Positional Surface, Parsing, Inside, and Active Site Assignments for Protein Kinase

| | | | | Number of Variable Subgroups | | | | | |
|---|---|---|---|---|---|---|---|---|---|
| | ≥10 | 9 | 8 | 7 | 6 | 5 | 4 | 3 | 2 |
| 220 | 10.5.4 | 4.4 | 6.4 | | | | | | |
| 221 | INSIDE | | | | | | | | |
| 222 | | | | | | | | | 9.2 |
| 223 | | | | 4.3 | 5.2 | | | | |
| 224 | PRIMARY PARSE | | | | | | | | |
| 225 | | | | 4.7 | 5.3 | | | | |
| 226 | inside | | | | | | | | |
| 227 | CM1D | | | | | | | | |
| 228 | INSIDE | | | | | | | | |
| 229 | INSIDE | | | | | | | | |
| 230 | INSIDE | | | | | | | | |
| 231 | INSIDE | | | | | | | | |
| 232 | secondary parse | | | | | | | | |
| 233 | INSIDE | | | | | | | | |
| 234 | INSIDE | | | | | | | | |
| 235 | INSIDE | | | | | | | | |
| 236 | INSIDE | | | | | | | | |
| 237 | | | | | | | | | |
| 238 | INSIDE | | | | | | | | |
| 239 | INSIDE | | | | | | | | |
| 240 | INSIDE | | | | | | | | |
| 241 | PRIMARY PARSE | | | | | | | | 4.2 |
| 242 | | | | | | | 4.3 | | 6.2; 5.2 |
| 243 | | 4.7 | 6.5; 5.5 | | | | 7.3 | | |
| 244 | | | 5.2 | 4.2 | | | | | |
| 245 | secondary parse | | | | | | | | |
| 246 | INSIDE | | | | | | | | |
| 247 | | | | 5.2; 4.2 | | | | | |
| 248 | | | | | 4.5 | 5.3 | 6.2 | | |
| 249 | PRIMARY PARSE | | | | | | | | |
| 250 | PRIMARY PARSE | | | | | | | | |
| 251 | PRIMARY PARSE | | | | | | | | |
| 252 | PRIMARY PARSE | | | | | | | | |
| 253 | PRIMARY PARSE | | | | | | | | |
| 254 | PRIMARY PARSE | | | | | | | | |
| 255 | PRIMARY PARSE | | | | | | | | |
| 256 | PRIMARY PARSE | | | | | | | | |
| 257 | PRIMARY PARSE | | | | | | | | |
| 258 | PRIMARY PARSE | | | | | | | | |
| 259 | PRIMARY PARSE | | | | | | | | |
| 260 | | | | | 6.2; 5.4; 4.5 | | | 7.2 | |
| 261 | | | 5.7 | 4.6 | 6.5 | | 7.3 | | |
| 262 | | | | 4.5 | 6.3; 5.3 | | 7.2 | | |
| 263 | | | 5.5 | 4.6 | 6.4 | | 7.2 | | |
| 264 | 10.5.8 | 4.7 | 6.6 | | | 7.3 | 8.2 | | |
| 265 | INSIDE | | | | | | | | |
| 266 | INSIDE | | | | | | | | |
| 267 | | 5.8 | 6.7; 4.8 | | 7.5 | | 8.4 | | |
| 268 | 10.6.3 | | | 4.2 | | 7.2 | | | |
| 269 | INSIDE | | | | | | | | |
| 270 | | | | 5.3 | | 6.3; 4.3 | | 7.2 | |
| 271 | 11.5.11 | | 7.8; 4.7 | | | 8.5 | | | 9.2 |
| 272 | | | | | | | | | |
| 273 | | | | 4.4 | 5.2 | | | | |
| 274 | 10.5.8 | 4.8 | 6.6 | | 7.5 | | | | |
| 275 | | | | | | 4.2 | | | |
| 276 | 12.5.7 | 6.5 | 4.7 | | | 7.4 | 8.3 | | |
| 277 | | | 6.3; 5.3 | | 4.3 | | | | |
| 278 | secondary parse | | | | | | | | |
| 279 | 11.5.8 | 4.7 | 6.6 | | | | | | |
| 280 | | | | 5.2 | 4.5 | | | | |
| 281 | PRIMARY PARSE | | | | | 4.2 | | | |
| 282 | PRIMARY PARSE | | | | | | | | |
| 283 | PRIMARY PARSE | | | | | | | 4.3 | 5.2 |
| 284 | PRIMARY PARSE | | | | | 4.4 | | 5.2 | |
| 285 | PRIMARY PARSE | | | | | | | 4.2 | |
| 286 | INSIDE | | | | | | | | |
| 287 | | | | | 4.2 | 5.2 | | 6.2 | |
| 288 | 11.5.10 | 6.9 | 7.8; 4.7 | | | 8.5 | | | |
| 289 | | 5.9 | 4.8 | 6.7 | | | 7.4 | | 8.2 |
| 290 | INSIDE | | | | | | | | |
| 291 | | 6.4; 5.4 | | 7.3; 4.3 | | | | | |
| 292 | 10.5.9 | 6.9 | 7.7 | 4.6 | 8.4 | | 9.2 | | |

TABLE 10-continued

Positional Surface, Parsing, Inside, and Active Site Assignments for Protein Kinase

| | Number of Variable Subgroups | | | | | | | | |
|---|---|---|---|---|---|---|---|---|---|
| | ≧10 | 9 | 8 | 7 | 6 | 5 | 4 | 3 | 2 |
| 293 | INSIDE | | | | | | | | |
| 294 | INSIDE | | | | | | | | |
| 295 | 11.5.7 | 6.7; 4.6 | | 8.5; 7.5 | | | 9.2 | | |
| 296 | 12.5.11 | 4.9 | 7.6 | | 8.5 | | | 9.2 | |
| 297 | INSIDE | | | | | | | | |
| 298 | INSIDE | | | | | | | | |
| 299 | 11.5.7 | 4.6 | | 6.5 | | | | 7.3 | 8.2 |
| 300 | | | 5.4; 4.5 | | 7.4; 6.4 | | | | |
| 301 | 10.5.8 | 6.7; 4.8 | | 7.5 | | | | 8.3 | |
| 302 | | | 4.2 | | | | | | |
| 303 | 14.5.9 | | | 8.5 | | 9.2 | | | |
| 304 | 10.5.7 | 6.7 | 4.6 | | | | 8.3; 7.3 | | |
| 305 | Active site | | | | | | | | |
| 306 | secondary parse | | | | | | | | |
| 307 | | | 5.3; 4.3 | | 6.2 | | | | |
| 308 | INSIDE | | | | | | | | |
| 309 | 10.5.7 | 4.7 | 6.5 | | | 7.3 | | | |
| 310 | 10.5.7 | | 4.8 | 6.5 | | | 7.2 | | |
| 311 | | | | | 7.3; 6.3; 5.2 | | | | |
| 312 | INSIDE | | | | | | | | |
| 313 | 11.5.4 | | | 7.2 | | 8.2 | | | |
| 314 | 10.6.6 | | | | 7.4; 4.5 | | | 8.2 | |
| 315 | PRIMARY PARSE | | | | | | | | |
| 316 | PRIMARY PARSE | | | | | | | | |
| 317 | PRIMARY PARSE | | | | | | | | |
| 318 | PRIMARY PARSE | | | | | | 7.4; 6.4 | 9.3; 8.3; 5.3 | 4.2 |
| 319 | | | 5.4 | 4.5 | 6.4 | | | 7.2 | |
| 320 | 12.5.8 | 4.7 | | 7.2 | | | 8.2 | | |
| 321 | INSIDE | | | | | | | | |
| 322 | | 5.2 | | 4.3 | | | | | |
| 323 | 11.5.7 | | | | 7.4 | | 8.3 | | |
| 324 | 11.5.9 | 6.7 | | 4.7 | 7.4 | 9.3 | 8.2 | | |
| 325 | | | 5.3 | | 6.2; 4.5 | | | | |

TABLE 11

Secondary Structure Predictions for the Protein Kinase Family.

| unit | maximum positions | minimum positions | positions cAMP-PK | secondary struct. | max length | min length | cAMP PK | comments |
|---|---|---|---|---|---|---|---|---|
| 1 | 001–012 | 001–011 | 001–011 | coil | 12 | 11 | 11 | not active site (?, chem. modification) |
| 2 | 012–023 | 014–021 | 012–022 | beta | 12 | 8 | 11 | bend positions 15–16 |
| 3 | 023–042 | 025–041 | 023–041 | coil | 20 | 0 | 5 | not active site |
| 4 | 041–049 | 042–048 | 042–048 | beta | 9 | 7 | 7 | active site, bend 46 |
| 5 | 049–063 | 050–059 | 049–060 | coil | 15 | 1 | 10 | not active site |
| 6 | 060–075 | 064–073 | 061–074 | alpha | 16 | 10 | 14 | active site 67 |
| 7 | 074–083 | 075–083 | 075–083 | coil | 10 | 3 | 3 | not active site |
| 8 | 083–095 | 084–092 | 084–093 | beta | 13 | 9 | 10 | bend position 87 |
| 9 | 093–103 | 096–100 | 094–102 | coil | 11 | 0 | 8 | not active site |
| 10 | 101–111 | 103–107 | 103–111 | beta | 11 | 5 | 9 | bend position 108 |
| 11 | 108–115 | 112–114 | 112–114 | coil | 8 | 1 | 2 | active site 113 & 116 |
| 12 | 115–125 | 115–122 | 115–124 | alpha | 11 | 8 | 11 | confirmed in subfamilies |
| 13 | 123–132 | 126–128 | 126–130 | coil | 10 | 0 | 2 | not active site |
| 14 | 129–160 | 133–151 | 131–152 | alpha | 32 | 19 | 22 | surface helix |
| 15 | 152–160 | omitted | 153–156 | beta | 9 | 0 | 4 | weak assignment |
| 16 | 152–162 | 161–162 | 157–162 | active site | 11 | 2 | 6 | active site coil |
| 17 | 163–168 | 163–165 | 163–166 | beta | 6 | 3 | 4 | |
| 18 | 166–177 | 169–176 | 167–176 | coil | 12 | 0 | 3 | not active site |
| 19 | 177–187 | 178–184 | 177–186 | beta | 11 | 8 | 10 | active site bend 182 |
| 20 | 185–191 | omitted | omitted | alpha | 7 | 0 | 0 | divergent conformation |
| 21 | 185–204 | 192–197 | 187–200 | coil | 20 | 2 | 10 | active site coil |
| 22 | 198–217 | 205–208 | 201–212 | active site | 20 | 4 | 12 | parse at 203–204 & 208–209 |
| 23 | 209–225 | 218–224 | 213–225 | coil | 16 | 5 | 8 | not active site |
| 24 | 225–243 | 226–240 | 226–241 | alpha | 19 | 15 | 16 | entirely internal |
| 25 | 241–261 | 244–259 | 242–261 | coil | 20 | 4 | 8 | not active site |
| 26 | 260–275 | 263–272 | 262–274 | alpha | 16 | 10 | 13 | realign alignment |
| 27 | 273–288 | 276–284 | 275–285 | coil | 16 | 0 | 6 | not active site |
| 28 | 284–301 | 288–300 | 286–301 | alpha | 18 | 13 | 16 | |
| 29 | 301–313 | 302–306 | 302–306 | coil | 13 | 5 | 5 | active site (?) coil |

TABLE 11-continued

Secondary Structure Predictions for the Protein Kinase Family.

| unit | maximum positions | minimum positions | positions cAMP-PK | secondary struct. | max length | min length | cAMP PK | comments |
|---|---|---|---|---|---|---|---|---|
| 30 | 307–313 | omitted | 307–312 | beta | 7 | 0 | 6 | weak assignment |
| 31 | 313–318 | 314–318 | 313–318 | coil | 6 | 1 | 6 | not active site |
| 32 | 319–325+ | 319–325 | 319–325 | coil | 7+ | 7 | 7+ | possible short helix |

TABLE 12

Orientation of the Helix Between Positions 115 and 122 in Protein Kinase

| functional subgroup | MPI | outside-inside border | inside-outside border | |
|---|---|---|---|---|
| 1 | 50% | 115–119 | 117–121 | |
| 2 | 80% | 119–123 | 118–122 | largely buried? MPI = 80% |
| 3 | 45% | 119–116 | 121–118 | note shift in 2 proteins |
| 4 | 50% | 115–119 | 121–118 | |
| 5 | 45% | 115–119 | 120–117 | |
| 6 | 30% | 115–119 | 117 | 117 hydrophobic & philic |
| 7 | 35% | 115–119 | 121–118 | |
| 8 | 60% | 115–119 | 117–121 | |
| 9 | 50% | 115–119 | 117–121 | |
| 10 | 65% | 115–119 | 117–121 | |
| 11 | 50% | 115–119 | 117 | 117 hydrophobic & philic |
| 12 | 55% | 115–119 | 117 | 117 hydrophobic & philic |

TABLE 13

Number of Conserved Subgroups by Position Number in Clusters of Subgroups with Different Minimum Pairwise Identities (MPI) in Segments 19 and 20 of Protein Kinase

| position number | MPI | | | | | | |
|---|---|---|---|---|---|---|---|
| | 90 | 85 | 80 | 70 | 60 | 50 | 40% |
| 177 | 12 | 4 | 4 | 1 | 0 | 0 | 0 |
| 178 | 12 | 6 | 5 | 4 | 2 | 1 | 0 |
| 179 | 12 | 6 | 6 | 6 | 3 | 5 | 1 |
| 180 | 11 | 5 | 5 | 4 | 1 | 3 | 1 |
| 181 | 12 | 5 | 5 | 4 | 3 | 1 | 0 |
| 182 | 12 | 6 | 6 | 6 | 5 | 6 | 4 |
| 183 | 12 | 6 | 6 | 6 | 5 | 6 | 4 |
| 184 | 12 | 6 | 6 | 6 | 5 | 6 | 4 |
| 185 | 12 | 6 | 6 | 6 | 5 | 3 | 1 |
| 186 | 12 | 6 | 6 | 5 | 5 | 2 | 1 |
| 187 | 12 | 5 | 5 | 6 | 4 | 4 | 1 |
| 188 | 12 | 5 | 5 | 3 | 3 | 2 | 0 |
| 189 | 10 | 5 | 5 | 6 | 4 | 1 | 0 |
| 190 | 9 | 5 | 1 | 3 | 1 | 1 | 0 |
| 191 | 10 | 5 | 4 | 3 | 2 | 0 | 0 |
| 192 | 11 | 4 | 4 | 5 | 0 | 1 | 0 |
| 193 | 11 | 6 | 4 | 5 | 3 | 0 | 0 |
| 194 | 9 | 4 | 3 | 6 | 2 | 3 | 0 |

TABLE 14

Summary of Chemical Modification Data of Protein Kinases Pertaining to Assignments to the Active Site

| Position | Relevant Protection | Conservation | Assigned Role |
|---|---|---|---|
| K 007 | MgATP + peptide | not conserved | binds peptide |
| K 046 | MgATP | conserved | gamma P |
| K 050 | MgATP + peptide | not conserved | binds peptide |
| E 067 | MgATP | conserved | Mg ligand |
| E 089 | not protected | not conserved | no role |
| G 113 | peptide | not conserved | binds peptide |
| M 116 | peptide | not conserved | binds peptide |
| D 157 | not labeled | conserved | Mg ligand |
| N 162 | no information | conserved | binds ribose |
| E 161 | MgATP + peptide | not conserved | AS vicinity |
| D 182 | MgATP | conserved | general base |
| T 199 | peptide | not conserved | binds peptide |
| C 201 | peptide | not conserved | binds peptide |
| E 210 | not labeled | conserved | structural |
| D 227 | not labeled | almost conserved | structural |
| E 237 | MgATP + peptide | not conserved | AS no role |
| D 260 | not protected | not conserved | no role |
| R 305 | no information | conserved | uncertain |

TABLE 15

Covariation at Positions 87 and 108 in Functional Subgroups 7 and 11 Protein Kinase

| | Funct Subgroup | |
|---|---|---|
| | 7 | 11 |
| | oooo+++ | +++++++o |
| 87 | LLPLRRR | RRRKKRRS |
| 108 | QQQQEEE | EEEEEEEP |
| | oooo--- | -------o | o indicates an uncharged residue

+ indicates a residue bearing a positive charge

− indicates a residue bearing a negative charge

TABLE 16

Small Alignment for Pathogenesis Related Proteins from Plants

```
            0    0    1    1    2    2    3    3    4    4    5    5    6    6    7    7
            1    5    0    5    0    5    0    5    0    5    0    5    0    5    0    4
a - QNSPQDYLAVHNDARAQVGVGPMSWDANLASRAQNYANSRAGDCNLIHSGA__GENLAKGGGDF__TGRAAVQ d - QNSPQDYLAVHNDARAQVGVGPMSWDANLASRAQNYANSRAGDCNLIHSGA__GENLAKGGGDF__TGRAAVQ c - QNSPQDYLAVHNDARAQVGVGPMSWDANLASRAQNYANSRAGDCNLIHSGA__GENLAKGGGDF__TGRAAVQ g - QNSQQDYLDAHNTARADVGVEPLTWDDQVAAYAQNYASQLAADCNLVHSHGQYGENLAWGSGDF_LTAAKAVE e - AQNSQQDYLDAHNTARADVGVEPLTWDDQVAAYAQNYASQLAADCNLVHSHGQYGENLAEGSGDF_MTAAKAVE f - AQNSQQDYLDAHNTARADVGVEPLTWDNGVAAYAQNYVSQLAADCNLVHSHGQYGENLAQGSGDF_MTAAKAVE b -    PQETLVVHNKARAMVGVGPMVWNETLATYAQSYAHERARDCAMKHSLGPFGENLAAGWGT__MSGPVATE h - SENSPQDYLTPQNSARAAVGVGPVTWSTKLQQFAEKYAAQRAGDCRLQHSGGPYGENIFWGSAGFDWKAVDAVR
     .....*..* ..* * *.*..*.  .. .*..*. ..*... ....***.. *.......... *..

7    8    8    9    9    0    0    1    1    2    2    3    3    4
            5    0    5    0    5    0    5    0    5    0    5    0    5    0
a - LWVSERPSYNYATNQCVGGKKCRHYTQVVWRNSVRLGCGRARCNNGWWF_ISCNYDPVGNWLGQRPY d - LWVSERPSYNYATNQCVGGKKCRHYTQVVWRNSVRLGCGRARCNNGWWF_ISCNYDPVGNWIGQRPY c - LWVSERPDYNYATNQCVGGKMCGHYTQVVWRNSVRLGCGRARCNNGWWF_ISCNYDPVGNWVGERPY g - MWVNEKQYYAHDSNTCAQGQVCGHYTQVVWRNSVRVGCARVQCNNGGYI_VSCNYDPPGNVIGKSPY e - MWVDEKQYYDHDSNTCAQGQVCGHYTQVVWRNSVRVGCARVQCNNGGYV_VSCNYDPPGNYRGESPY f - MWVDEKQYYDHDSNTCAQGQVCGHYTQVVWRNSVRVGCARVKCNNGGYV_VSCNYDPPGNVIGQSPY b - YWMTEKENYDYDSNTCGGDGVCGHYTQIVWRDSVRLGCASVRCKNDEYIWVICSYDPPGNYIGQRPY h - SWVDEKQWYNYATNSCAAGKVCGHYTQVVWRATTSIGCARVVCRDNRGVFIICNYEPRGNIAGMKPY
     *..*...*.....*.*.....*.**.*......**....*......... *.*.*.** .*..**
```

TABLE 17

Large Alignment for Pathogenesis Related Proteins and their Homologues

```
            2    3    3    4    4    5         5    6    6    7    7    8    8
            5    0    5    0    5    0         5    0    5    0    5    0    5
a - --MSWDANLASRAQNYANSRAGDCNLIHSGA_____GENLAKGGGDF___TG_RAAVQLWVSERPSYNYA b - --LTWDDQVAAYAQNYASQLAADCNLVHSHG_____QYGENLAEGSGDF__MTA_AKAVEMWVDEKQYYDHD c - --LTWDNGVAAYAQNYVSQLAADCNLVHSHG_____QYGENLAQGSGDF__MTA_AKAVEMWVDEKQYYDHD d - --LTWDDQVAAYAQNYASQLAADCNLVHSHG_____QYGENLAWGSGDF__LTA_AKAVEMWVNEKQYYAHD e - --MTWDNRLAAYAQNYANQRIGDCGMIHSHG_____PYGENLAAA___FPQLNA_AGAVKMWVDEKRFYDYN f - LRVEWDHDAYVNAQKWANR____CIYNHSPLQHRTTTLKCGENLFMANYP____ASWSSVIQDWYDESLDFVFG h - LKMEWSIQATTNAQKWANK____CILEHSSKDDRKINIRCGENLYMSTDP____TLWSTVIQSWYNENEDFVYG g - LKMEWSREVTTNAQRWANK____CTLQHSDPEDRKTSTRCGENLYMSSDP____TSWSSAIQSWYDEILDFVYG i - NVLVWNDELAKIAQTWANQ____CDFNHDDCRN_TAKYQVGQNIAISSTTATQFDRPSKLIKQWEDEVTEFNYK j - NVLVWNDELAKIAQTWANQ____CSFGHDQCRN_TEKYQVGQNVAIASTTGNSYATMSKLIEMWEMEVKDFNPK
     . *...... ** .........* .#*.  ..   . *.*.. .   . . .... * .*  ....

1    1    1    1    1    1    1    1    1
                      9    9    0    0    1    1    2    2    3    3    4
                      0    5    0    5    0    5    0    5    0    5    0
```

TABLE 17-continued

Large Alignment for Pathogenesis Related Proteins and their Homologues

```
a - TNQCVGGKKC__RHYTQVVWRNSVRLGCGRARC_NNGW__WFISCNYDPVGNWIGQR-- b - SNTCAQGQVC__GHYTQVVWRNSVRVGCARVQC_NNGG__YVVSCNYDPPGNYRGES-- c - SNTCAQGQVC__GHYTQVVWRNSVRVGCARVKC_NNGG__YVVSCNYDPPGNVIGQS-- d - SNTCAQGQVC__GHYTQVVWRNSVRVGCARVQC_NNGG__YIVSCNYDPPGNVIGKS-- e - SNSCV_GGVC__GHYTQVVWRNSVRLGCARVRS_NNGW__FFITCNYDPPGNFIGQR-- f - FGPKKVG__VKVGHYTQVVWNSTFLVACGVAECPDQ_PLKYFYVCHYCPGGNYVGRLYSPYTEGEPCDSCPGNC h - VGAK_PN__SAVGHYTQLVWYSSFKIGCGIAYCPNQDNLKYFYVCHYCPMGNNVMKKSTPYQQGTPCASCPNNC g - VGPKSPN__AVVGHYTQLVWYSTYQVGCGIAYCPNQDSLKYYYVCQYCPAGNNMNRKNTPYQQGTPCAGCPDDC i - VG_LQNSNFRKVGHYTQMVWGKTKEIGCGSIKYIEDNWYTHYLVCNYGPGGNDFNQ---- j - KGTMGDNNFSKVGHYTQMVWGKTKEIGCGSVKYIENNWHTHYLVCNYGPAGNYMDQ----
       ..   .   ...**    .  .*. . . .. .   .. .*.* *.**. ...   ..  . ..  ..
```

TABLE 18

Positional Assignments for the Pathogenesis Related Proteins without their Homologues

| | |
|---|---|
| 001 | PARSE; gap in proteins a,d,c,g, and b. |
| 002 | PARSE; gap in protein b; otherwise, polar split (Q/E); surface |
| 003 | PARSE; gap in protein b; otherwise, APC N; no assignment |
| 004 | PARSE; gap in protein b; otherwise, APC S; no assignment |
| 005 | Neutral split (PQPP); parse |
| 006 | APC Q; active site |
| 007 | Polar split (DDED), surface |
| 008 | Hydrophobic split (YYTY), inside |
| 009 | APCL; INSIDE |
| 010 | Amphiphilic split (ADVT); no assignment |
| 011 | Hydrophobic split (VAVP); inside |
| 012 | Neutral split; no assignment |
| 013 | APC N; active site |
| 014 | Polar split (DTKS); surface |
| 015 | APC A; inside |
| 016 | APC R; active site |
| 017 | APC A; inside |
| 018 | Amphiphilic split (QDMA); no assignment |
| 019 | APC V; INSIDE |
| 020 | APC G; parse, inside |
| 021 | APC V; INSIDE |
| 022 | Hydrophilic split (GEGG); surface |
| 023 | APC P; PARSE |
| 024 | Hydrophobic split (MLMV); inside |
| 025 | Hydrophobic split (STVT); inside |
| 026 | APC W; INSIDE |
| 027 | Polar split (DDNS); surface |
| 028 | Polar variable, one subgroup; surface |
| 029 | Polar variable, one subgroup; surface |
| 030 | Hydrophobic split (LVLL); inside |
| 031 | Neutral split (AAAQ); no assignment |
| 032 | Neutral split (SATQ); no assignment |
| 033 | Amphiphilic split (RYYF); no assignment |
| 034 | APC A; inside |
| 035 | Polar split (QQQE); surface |
| 036 | Polar split (NNSK); surface |
| 037 | APC Y; INSIDE |
| 038 | Hydrophobic single variable; inside |
| 039 | Polar split (NSHA); surface |
| 040 | Polar split (SQEQ); surface |
| 041 | Amphiphilic split (RLRR); no assignment |
| 042 | APC A; inside |
| 043 | Polar split (GARG); surface |
| 044 | APC D; active site |
| 045 | APC C; disulfide bridge |
| 046 | Polar split (NNAR); surface |
| 047 | Hydrophobic split (LLML); inside |
| 048 | Amphiphilic split (IVKQ); no assignment |
| 049 | APC H; active site |
| 050 | APC S; active site |
| 051 | Hydrophobic split (GHLG); inside |
| 052 | Neutral split (AGGG); no assignment |
| 053 | PARSE; gap in proteins a, d, and c. Confirmed by P b and h. |
| 054 | PARSE; gap in proteins a, d, and c. Otherwise inside. |
| 055 | APC G; parse, inside |
| 056 | APC E; active site |
| 057 | APC N; active site |
| 058 | Hydrophobic split (LLLI); inside |
| 059 | Hydrophobic split (AAAF); inside |
| 060 | Polar variable, one subgroup; surface |
| 061 | APC G; parse, inside |
| 062 | Hydrophobic split (GSWS); inside |
| 063 | Neutral split (GGGA); no assignment |
| 064 | Polar split (DDTG); surface |
| 065 | PARSE; gap in protein b; otherwise inside |
| 066 | PARSE; gap |
| 067 | PARSE; gap in proteins a, c, and d; otherwise inside |
| 068 | Polar split (TTSK); surface |
| 069 | Neutral split (GAGA); no assignment |
| 070 | Amphiphilic split (RAPV); no assignment; weak parse |
| 071 | Amphiphilic split (AKVD); no assignment |
| 072 | APC A; inside |
| 073 | Hydrophobic split (VVTV); inside |
| 074 | Polar split (QEER); surface |
| 075 | Hydrophobic split (LMYS); inside |
| 076 | APC W; INSIDE |
| 077 | Hydrophobic split (VVMV); inside |
| 078 | Polar variable, one subgroup; surface |
| 079 | APC E; active site |
| 080 | Polar split (RKKK); surface |
| 081 | Polar split (PQEQ); surface; weak parse |
| 082 | Amphiphilic variable, one subgroup; surface |
| 083 | APC Y; inside |
| 084 | Polar variable, one subgroup; surface |
| 085 | Hydrophobic split (YHYY); inside |
| 086 | Polar split (ADDA); surface |
| 087 | Neutral split (TSST); no assignment |
| 088 | APC E; active site |
| 089 | Polar split (QTTS); surface |
| 090 | APC C; disulfide bridge |
| 091 | Hydrophobic split (VAGA); inside |
| 092 | Neutral split (GQGA); no assignment; parse |
| 093 | Polar split (GGDG); surface; parse |
| 094 | Polar split (KQGK); surface |

TABLE 18-continued

Positional Assignments for the Pathogenesis Related Proteins without their Homologues

| | |
|---|---|
| 095 | Polar variable, one subgroup; surface |
| 096 | APC C; disulfide bridge |
| 097 | Polar variable, one subgroup; surface |
| 098 | APC H; active site |
| 099 | APC Y; inside |
| 100 | APC T; inside |
| 101 | APC Q; active site |
| 102 | Hydrophobic split (VVIV); inside |
| 103 | APC V; inside |
| 104 | APC W; inside |
| 105 | APC R; active site |
| 106 | Polar split (NNDA); surface |
| 107 | Neutral split (SSST); no assignment |
| 108 | Hydrophobic split (VVVT); inside |
| 109 | Polar split (RRRS); surface |
| 110 | Hydrophobic split (LVLI); inside |
| 111 | APC G; parse |
| 112 | APC C; disulfide bridge |
| 113 | Neutral split (GAAA); no assignment |
| 114 | Polar split (RRSR); surface |
| 115 | Hydrophobic split (AVVV); inside |
| 116 | Amphiphilic variable, one subgroup; surface |
| 117 | APC C; disulfide bridge |
| 118 | Polar split (NNKR); surface |
| 119 | Polar split (NNND); surface |
| 120 | Polar split (GGDN); surface |
| 121 | Amphiphilic split (WGER); no assignment |
| 122 | Hydrophobic split (WYYG); inside |
| 123 | Hydrophobic variable, one subgroup; inside |
| 124 | PARSE; gap in protein a, d, c, g, e, and f; otherwise inside |
| 125 | Hydrophobic split (IVVI); inside |
| 126 | Hydrophobic split (SSII); inside |
| 127 | APC C; disulfide bridge |
| 128 | Polar split (NNSN); surface |
| 129 | APC Y; INSIDE |
| 130 | Polar split (DDDE); surface |
| 131 | APC P; PARSE |
| 132 | Amphiphilic split (VPPR); no assignment; parse |
| 133 | APC G; parse; inside |
| 134 | APC N; active site |
| 135 | Hydrophobic variable, one subgroup; inside |
| 136 | SURFACE; CM1 Hb; inside |
| 137 | APC G; parse |
| 138 | SURFACE |
| 139 | Polar split (RSRK); surface |
| 140 | APC P; PARSE |
| 141 | APC Y; INSIDE |

TABLE 19a

Revised Positional Assignments for Segment 2a of the Pathogenesis Related Proteins and their Homologues

| | |
|---|---|
| 23 | Parse |
| 24 | Hydrophobic variable; inside |
| 25 | Amphiphilic single variable; no assignment |
| 26 | APC W; inside |
| 27 | Polar single variable |
| 28 | Surface, 2 variable subgroups |
| 29 | Surface, 2 variable subgroups |
| 30 | Hydrophobic variable; inside |
| 31 | Hydrophobic single variable; inside |
| 32 | Surface assignment, criterion ii |
| 33 | Amphiphilic single variable; no assignment |
| 34 | APC A. inside |
| 35 | CM1 Q (note maize sequence) |
| 36 | Polar single variable |
| 37 | Hydrophobic split (YWW); inside |
| 38 | Hydrophobic single variable; inside |
| 39 | Polar single variable |
| 40 | Surface, 2 variable subgroups |
| 41 | Parse |

TABLE 19b

Revised Positional Assignments for Segment 2b of the Pathogenesis Related Proteins and their Homologues

| | |
|---|---|
| 45 | APC C |
| 46 | Surface, 3 variable subgroups |
| 47 | Hydrophobic variable, 2 subgroups; inside |
| 48 | Surface, 2 variable subgroups |
| 49 | APC H |
| 50 | Polar split (SSD); no longer APC |
| 51 | Surface, 3 variable subgroups |
| 52 | Surface, 2 variable subgroups |
| 53 | Parse |

TABLE 19c

Revised Positional Assignments for Segment 3 of the Pathogenesis Related Proteins and their Homologues

| | |
|---|---|
| 55 | APC G; parse |
| 56 | Polar split (EEQ); no longer APC E |
| 57 | APC N |
| 58 | Hydrophobic single variable; inside |
| 59 | Hydrophobic single variable; inside |
| 60 | Amphiphilic single variable; surface in pathogenesis related proteins; inside in venom allergen and TPX |
| 61 | Hydrogen bonding variable; no longer APC G |
| 62 | Parse, but deletion could be rearranged; surface |
| 63 | Parse, but deletion could be rearranged; surface |
| 64 | Parse |

TABLE 19d

Revised Positional Assignments for Segments 4a and 4b of the Pathogenesis Related Proteins and their Homologues

| | |
|---|---|
| 067 | Parse |
| 068 | Surface, 2 variable subgroups (deletion is moved to the left) |
| 069 | Hydrophobic variable, 2 subgroups; weak parse |
| 070 | Polar single variable |
| 071 | Surface, 2 variable subgroups |
| 072 | Hydrophobic single variable; inside |
| 073 | Hydrophobic split; inside |
| 074 | Surface, 2 variable subgroups |
| 075 | Surface, 2 variable subgroups |
| 076 | APC W; inside |
| 077 | Amphiphilic split (VYE) |
| 078 | Surface, 3 variable subgroups |
| 079 | APC E |
| 080 | Surface, 2 variable subgroups |
| 081 | Surface, 3 variable subgroups |
| 082 | Surface, 2 variable subgroups |
| 083 | Hydrophobic split (YFF) inside |
| 084 | Amphiphilic single variable |
| 085 | Hydrophobic variable, 3 subgroups; inside. |
| 086 | Polar single variable |
| 087 | Surface, 2 variable subgroups |
| 088 | Polar split (NGG) |
| 089 | Parse. |

TABLE 19e

Revised Positional Assignments for Segments 4c and 4d of the Pathogenesis Related Proteins and their Homologues

| | |
|---|---|
| 95 | Surface; 2 variable subgroups |
| 96 | Hydrophobic split (CVV); inside |
| 97 | Polar split (RGG) |
| 98 | APC H; active site |
| 99 | APC Y; inside |
| 100 | APC T; inside |
| 101 | APC Q; active site |
| 102 | Hydrophobic single variable; inside |

TABLE 19e-continued

Revised Positional Assignments for Segments 4c and 4d of the Pathogenesis Related Proteins and their Homologues

| | |
|---|---|
| 103 | APC V; inside |
| 104 | APC W; inside |
| 105 | No longer APC R; polar single variable |
| 106 | Polar split (NSK) |
| 107 | Hydrogen bonding single variable |
| 108 | Amphiphilic variable |
| 109 | Polar single variable |
| 110 | Hydrophobic variable, two subgroups; inside |
| 111 | CM1 G; inside, parse |
| 112 | APC C |
| 113 | Neutral single variable |
| 114 | Amphiphilic single variable |
| 115 | Hydrophobic variable; inside |
| 116 | Surface, 2 variable subgroups |
| 117 | No longer APC C; hydrophobic single variable |
| 117' | Parse |
| 118 | Polar single variable |
| 119 | Polar single variable |
| 120 | Parse |

TABLE 19f

Revised Positional Assignments for Segment 5 of the Pathogenesis Related Proteins and their Homologues

| | |
|---|---|
| 122 | Parse |
| 123 | Hydrophobic single variable; inside |
| 124 | Hydrophobic variable, 2 subgroups; inside |
| 125 | Hydrophobic single variable; inside |
| 126 | Hydrophobic single variable; inside |
| 127 | APC C |
| 128 | Polar single variable |
| 129 | APC Y; inside |
| 130 | Polar split (DCG) |
| 131 | Parse; APC P |

TABLE 19g

Revised Positional Assignments for Segment 6 of the Pathogenesis Related Proteins and their Homologues

| | |
|---|---|
| 131 | Parse; APC P |
| 132 | Parse |
| 133 | APC G; parse |

TABLE 19g-continued

Revised Positional Assignments for Segment 6 of the Pathogenesis Related Proteins and their Homologues

| | |
|---|---|
| 134 | APC N |
| 135 | Surface, 3 variable subgroups |
| 136 | Surface, 3 variable subgroups; Also CM1 Hb; inside |
| 137 | Surface, 2 variable subgroups |
| 138 | Surface, 2 variable subgroups |
| 139 | Parse; surface, 2 variable subgroups |
| 140 | Parse |

TABLE 20

Predicted Secondary Structure for Pathogenesis Related Proteins and their Homologues

| Positions | Secondary Structure Prediction | Length |
|---|---|---|
| 1–4 | Coil | 4 |
| 5–20 | Helix | 16 |
| 21–22 | Coil | 2 |
| 23–41 | Helix | 19 |
| 42–44 | Coil | 3 |
| 45–50 | Beta | 6 |
| 51–54 | Coil | 4 |
| 55–60 | Beta (possibly extend 54–61) | 6 |
| 61–67 | Coil | 7 |
| 68–86 | Helix (possibly bent at position 81) | 19 |
| 87–97 | Coil (tied by disulfide loop) | 11 |
| 98 | Active site | 1 |
| 99–117 | Helix | 19 |
| 118–122 | Coil | 5 |
| 123–130 | Beta | 8 |
| 131 | Parse | 1 |
| 132–136 | Beta | 4 |
| 137–140 | Coil | 4 |

SEQUENCE LISTING (1) GENERAL INFORMATION:

(iii) NUMBER OF SEQUENCES: 114

(2) INFORMATION FOR SEQ ID NO:1:

(i) SEQUENCE CHARACTERISTICS:
      (A) LENGTH: 260

(B) TYPE: amino acid (D) TOPOLOGY: linear (ii) MOLECULE TYPE:
      (A) DESCRIPTION: protein (vi) ORIGINAL SOURCE:

(A) ORGANISM: bovine alpha (ix) FEATURE: Protein kinase; Table 8 Column 1

(x) PUBLICATION INFORMATION:
     (A) AUTHORS:

Hanks, S. K.
         Quinn, A. M.
         Hunter, T.
     (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:1:

Asp Gln Phe Glu Arg Ile Lys Thr Leu Gly Thr Gly Ser Phe Gly
                005                 010                 015

Arg Val Met Leu Val Lys His Met Glu Thr Gly Asn His Tyr Ala
                020                 025                 030

Met Lys Ile Leu Asp Lys Gln Lys Val Val Lys Leu Lys Gln Ile
                035                 040                 045

Glu His Thr Leu Asn Glu Lys Arg Ile Leu Gln Ala Val Asn Phe
                050                 055                 060

Pro Phe Leu Val Lys Leu Glu Phe Ser Phe Lys Asp Asn Ser Asn
                065                 070                 075

Leu Tyr Met Val Met Glu Tyr Val Pro Gly Gly Glu Met Phe Ser
                080                 085                 090

His Leu Arg Arg Ile Gly Arg Phe Ser Glu Pro His Ala Arg Phe
                095                 100                 105

Tyr Ala Ala Gln Ile Val Leu Thr Phe Glu Tyr Leu His Ser Leu
                110                 115                 120

Asp Leu Ile Tyr Arg Asp Leu Lys Pro Glu Asn Leu Leu Ile Asp
                125                 130                 135

Gln Gln Gly Tyr Ile Gln Val Thr Asp Phe Gly Phe Ala Lys Arg
                140                 145                 150

Val Lys Gly Arg Thr Trp Thr Leu Cys Gly Thr Pro Glu Tyr Leu
                155                 160                 165

Ala Pro Glu Ile Ile Leu Ser Lys Gly Tyr Asn Lys Ala Val Asp
                170                 175                 180

Trp Trp Ala Leu Gly Val Leu Ile Tyr Glu Met Ala Ala Gly Tyr
                185                 190                 195

Pro Pro Phe Phe Ala Asp Gln Pro Ile Gln Ile Tyr Glu Lys Ile
                200                 205                 210

Val Ser Gly Lys Val Arg Phe Pro Ser His Phe Ser Ser Asp Leu
                215                 220                 225

Lys Asp Leu Leu Arg Asn Leu Leu Gln Val Asp Leu Thr Lys Arg
                230                 235                 240

Phe Gly Asn Leu Lys Asp Gly Val Asn Asp Ile Lys Asn His Lys
                245                 250                 255

Trp Phe Ala Thr Thr
                260

(2) INFORMATION FOR SEQ ID NO:2:

```
    (i) SEQUENCE CHARACTERISTICS:
        (A) LENGTH: 260

(B) TYPE: amino acid (D) TOPOLOGY: linear (ii) MOLECULE TYPE:
        (A) DESCRIPTION: protein (vi) ORIGINAL SOURCE:
        (A) ORGANISM: mouse alpha (ix) FEATURE: Protein kinase; literature sequence, Table 8 Column 2

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:2:

Asp Gln Phe Asp Arg Ile Lys Thr Leu Gly Thr Gly Ser Phe Gly
                005                 010                 015

Arg Val Met Leu Val Lys His Lys Glu Ser Gly Asn His Tyr Ala
                020                 025                 030

Met Lys Ile Leu Asp Lys Gln Lys Val Val Lys Leu Lys Gln Ile
                035                 040                 045

Glu His Thr Leu Asn Glu Lys Arg Ile Leu Gln Ala Val Asn Phe
                050                 055                 060

Pro Phe Leu Val Lys Leu Glu Phe Ser Phe Lys Asp Asn Ser Asn
                065                 070                 075

Leu Tyr Met Val Met Glu Tyr Val Ala Gly Gly Glu Met Phe Ser
                080                 085                 090

His Leu Arg Arg Ile Gly Arg Phe Ser Glu Pro His Ala Arg Phe
                095                 100                 105

Tyr Ala Ala Gln Ile Val Leu Thr Phe Glu Tyr Leu His Ser Leu
                110                 115                 120

Asp Leu Ile Tyr Arg Asp Leu Lys Pro Glu Asn Leu Leu Ile Asp
                125                 130                 135

Gln Gln Gly Tyr Ile Gln Val Thr Asp Phe Gly Phe Ala Lys Arg
                140                 145                 150

Val Lys Gly Arg Thr Trp Thr Leu Cys Gly Thr Pro Glu Tyr Leu
                155                 160                 165

Ala Pro Glu Ile Ile Leu Ser Lys Gly Tyr Asn Lys Ala Val Asp
                170                 175                 180

Trp Trp Ala Leu Gly Val Leu Ile Tyr Glu Met Ala Ala Gly Tyr
                185                 190                 195

Pro Pro Phe Phe Ala Asp Gln Pro Ile Gln Ile Tyr Glu Lys Ile
                200                 205                 210
```

-continued

```
Val Ser Gly Lys Val Arg Phe Pro Ser His Phe Ser Ser Asp Leu
            215                 220                 225

Lys Asp Leu Leu Arg Asn Leu Leu Gln Val Asp Leu Thr Lys Arg
            230                 235                 240

Phe Gly Asn Leu Lys Asp Gly Val Asn Asp Ile Lys Asn His Lys
            245                 250                 255

Trp Phe Ala Thr Thr
            260
```

(2) INFORMATION FOR SEQ ID NO:3:

(i) SEQUENCE CHARACTERISTICS:
        (A) LENGTH: 260

(B) TYPE: amino acid (D) TOPOLOGY: linear (ii) MOLECULE TYPE:
        (A) DESCRIPTION: protein (vi) ORIGINAL SOURCE:
        (A) ORGANISM: bovine beta (ix) FEATURE: Protein kinase; Table 8 Column 3

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:3:

```
Gly Asp Phe Glu Arg Lys Lys Thr Leu Gly Thr Gly Ser Phe Gly
            005                 010                 015

Arg Val Met Leu Val Lys His Lys Ala Thr Glu Gln Tyr Tyr Ala
            020                 025                 030

Met Lys Ile Leu Asp Lys Gln Lys Val Val Lys Leu Lys Gln Ile
            035                 040                 045

Glu His Thr Leu Asn Glu Lys Arg Ile Leu Gln Ala Val Asn Phe
            050                 055                 060

Pro Phe Leu Val Arg Leu Glu Tyr Ala Phe Lys Asp Asn Ser Asn
            065                 070                 075

Leu Tyr Met Val Met Glu Tyr Val Pro Gly Gly Glu Met Phe Ser
            080                 085                 090

His Leu Arg Arg Ile Gly Arg Phe Ser Glu Pro His Ala Arg Phe
            095                 100                 105

Tyr Ala Ala Gln Ile Val Leu Thr Phe Glu Tyr Leu His Ser Leu
            110                 115                 120

Asp Leu Ile Tyr Arg Asp Leu Lys Pro Glu Asn Leu Leu Ile Asp
            125                 130                 135

His Gln Gly Tyr Ile Gln Val Thr Asp Phe Gly Phe Ala Lys Arg
```

```
                        140                 145                 150
Val Lys Gly Arg Thr Trp Thr Leu Cys Gly Thr Pro Glu Tyr Leu
                155                 160                 165
Ala Pro Glu Ile Ile Leu Ser Lys Gly Tyr Asn Lys Ala Val Asp
                170                 175                 180
Trp Trp Ala Leu Gly Val Leu Ile Tyr Glu Met Ala Ala Gly Tyr
                185                 190                 195
Pro Pro Phe Phe Ala Asp Gln Pro Ile Gln Ile Tyr Glu Lys Ile
                200                 205                 210
Val Ser Gly Lys Val Arg Phe Pro Ser His Phe Ser Ser Asp Leu
                215                 220                 225
Lys Asp Leu Leu Arg Asn Leu Leu Gln Val Asp Leu Thr Lys Arg
                230                 235                 240
Phe Gly Asn Leu Lys Asn Gly Val Ser Asp Ile Lys Thr His Lys
                245                 250                 255
Trp Phe Ala Thr Thr
                260

(2) INFORMATION FOR SEQ ID NO:4:

(i) SEQUENCE CHARACTERISTICS:
        (A) LENGTH: 260

(B) TYPE: amino acid (D) TOPOLOGY: linear (ii) MOLECULE TYPE:
        (A) DESCRIPTION: protein (vi) ORIGINAL SOURCE:
        (A) ORGANISM: mouse beta (ix) FEATURE: Protein kinase; Table 8 Column 4

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:4:

Glu Asp Phe Glu Arg Lys Lys Thr Leu Gly Thr Gly Ser Phe Gly
                005                 010                 015
Arg Val Met Leu Val Lys His Lys Ala Thr Glu Gln Tyr Tyr Ala
                020                 025                 030
Met Lys Ile Leu Asp Lys Gln Lys Val Val Lys Leu Lys Gln Ile
                035                 040                 045
Glu His Thr Leu Asn Glu Lys Arg Ile Leu Gln Ala Val Glu Phe
                050                 055                 060
Pro Phe Leu Val Arg Leu Glu Tyr Ser Phe Lys Asp Asn Ser Asn
                065                 070                 075
```

```
Leu Tyr Met Val Met Glu Tyr Val Pro Gly Gly Glu Met Phe Ser
                080             085             090

His Leu Arg Arg Ile Gly Arg Phe Ser Glu Pro His Ala Arg Phe
                095             100             105

Tyr Ala Ala Gln Ile Val Leu Thr Phe Glu Tyr Leu His Ser Leu
                110             115             120

Asp Leu Ile Tyr Arg Asp Leu Lys Pro Glu Asn Leu Leu Ile Asp
                125             130             135

His Gln Gly Tyr Ile Gln Val Thr Asp Phe Gly Phe Ala Lys Arg
                140             145             150

Val Lys Gly Arg Thr Trp Thr Leu Cys Gly Thr Pro Glu Tyr Leu
                155             160             165

Ala Pro Glu Ile Ile Leu Ser Lys Gly Tyr Asn Lys Ala Val Asp
                170             175             180

Trp Trp Ala Leu Gly Val Leu Ile Tyr Glu Met Ala Ala Gly Tyr
                185             190             195

Pro Pro Phe Phe Ala Asp Gln Pro Ile Gln Ile Tyr Glu Lys Ile
                200             205             210

Val Ser Gly Lys Val Arg Phe Pro Ser His Phe Ser Ser Asp Leu
                215             220             225

Lys Asp Leu Leu Arg Asn Leu Leu Gln Val Asp Leu Thr Lys Arg
                230             235             240

Phe Gly Asn Leu Lys Asn Gly Val Ser Asp Ile Lys Thr His Lys
                245             250             255

Trp Phe Ala Thr Thr
                260
```

(2) INFORMATION FOR SEQ ID NO:5:

(i) SEQUENCE CHARACTERISTICS:
        (A) LENGTH: 258

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 5

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:5:

```
Lys Asn Phe Gln Ile Leu Arg Thr Leu Gly Thr Gly Ser Phe Gly
            005                 010                 015

Arg Val His Leu Ile Arg Ser Arg His Asn Gly Arg Tyr Tyr Ala
            020                 025                 030

Met Lys Val Leu Lys Lys Glu Ile Val Val Arg Leu Lys Gln Val
            035                 040                 045

Glu His Thr Asn Asp Glu Arg Leu Met Leu Ser Ile Val Thr His
            050                 055                 060

Pro Phe Ile Ile Arg Met Trp Gly Thr Phe Gln Asp Ala Gln Gln
            065                 070                 075

Ile Phe Met Ile Ile Leu Lys Val Gly Arg Leu Phe Ser Leu Leu
            080                 085                 090

Arg Lys Ser Lys Asp Phe Pro Asn Pro Val Ala Gln Ile Phe Ala
            095                 100                 105

Ala Glu Val Cys Leu Ala Leu Glu Tyr Leu His Ser Lys Asp Ile
            110                 115                 120

Ile Tyr Arg Asp Leu Lys Pro Glu Asn Ile Leu Leu Asp Lys Asn
            125                 130                 135

Gly His Ile Lys Ile Thr Asp Phe Gly Phe Ala Lys Tyr Val Pro
            140                 145                 150

Asp Val Thr Tyr Thr Leu Cys Gly Thr Pro Asp Tyr Ile Ala Pro
            155                 160                 165

Glu Val Val Ser Thr Lys Pro Tyr Asn Lys Ser Ile Asp Trp Trp
            170                 175                 180

Ser Phe Gly Ile Leu Ile Tyr Glu Met Leu Ala Gly Tyr Thr Pro
            185                 190                 195

Phe Tyr Asp Ser Asn Thr Met Lys Thr Tyr Glu Lys Ile Leu Asn
            200                 205                 210

Ala Glu Leu Arg Phe Pro Pro Phe Phe Asn Glu Asp Val Lys Asp
            215                 220                 225

Leu Leu Ser Arg Leu Ile Thr Arg Asp Leu Ser Gln Arg Leu Gly
            230                 235                 240

Asn Leu Gln Asn Gly Thr Glu Asp Val Lys Asn His Pro Trp Phe
            245                 250                 255

Lys Glu Val (2) INFORMATION FOR SEQ ID NO:6:

(i) SEQUENCE CHARACTERISTICS:
        (A) LENGTH: 260

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 6

(x) PUBLICATION INFORMATION:
        (A) AUTHORS:

Hanks, S. K.
                Quinn, A. M.
                Hunter, T.
```

(B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:6:

```
Gln Asp Phe Gln Ile Leu Arg Thr Leu Gly Thr Gly Ser Phe Gly
                005                 010                 015

Arg Val His Leu Ile Arg Ser Arg His Asn Gly Arg Tyr Tyr Ala
                020                 025                 030

Met Lys Val Leu Lys Lys Glu Ile Val Val Arg Leu Lys Gln Val
                035                 040                 045

Glu His Thr Asn Asp Glu Arg Leu Met Leu Ser Ile Val Thr His
                050                 055                 060

Pro Phe Ile Ile Arg Met Trp Gly Thr Phe Gln Asp Ala Gln Gln
                065                 070                 075

Ile Phe Met Ile Met Asp Tyr Ile Glu Gly Gly Glu Leu Phe Ser
                080                 085                 090

Leu Leu Arg Lys Ser Gln Arg Phe Pro Asn Pro Val Ala Lys Phe
                095                 100                 105

Tyr Ala Ala Glu Val Cys Leu Ala Leu Glu Tyr Leu His Ser Lys
                110                 115                 120

Asp Ile Ile Tyr Arg Asp Leu Lys Pro Glu Asn Ile Leu Leu Asp
                125                 130                 135

Lys Asn Gly His Ile Lys Ile Thr Asp Phe Gly Phe Ala Lys Tyr
                140                 145                 150

Val Pro Asp Val Thr Tyr Thr Leu Cys Gly Thr Pro Asp Tyr Ile
                155                 160                 165

Ala Pro Glu Val Val Ser Thr Lys Pro Tyr Asn Lys Ser Ile Asp
                170                 175                 180

Trp Trp Ser Phe Gly Ile Leu Ile Tyr Glu Met Leu Ala Gly Tyr
                185                 190                 195

Thr Pro Phe Tyr Asp Ser Asn Thr Met Lys Thr Tyr Glu Lys Ile
                200                 205                 210

Leu Asn Ala Glu Leu Arg Phe Pro Pro Phe Asn Glu Asp Val
                215                 220                 225

Lys Asp Leu Leu Ser Arg Leu Ile Thr Arg Asp Leu Ser Gln Arg
                230                 235                 240

Leu Gly Asn Leu Gln Asn Gly Thr Glu Asp Val Lys Asn His Pro
                245                 250                 255

Trp Phe Lys Glu Val
                260
```

(2) INFORMATION FOR SEQ ID NO:7:

(i) SEQUENCE CHARACTERISTICS:
      (A) LENGTH: 260

(B) TYPE: amino acid (D) TOPOLOGY: linear (ii) MOLECULE TYPE:
      (A) DESCRIPTION: protein (vi) ORIGINAL SOURCE:
    (A) ORGANISM: Saccharomyces cerevisiae (ix) FEATURE: Protein kinase; Table 8 Column 7

(x) PUBLICATION INFORMATION:
    (A) AUTHORS:
        Hanks, S. K.
        Quinn, A. M.
        Hunter, T.
    (B) TITLE: The protein kinase family
    (C) JOURNAL: Science
    (D) VOLUME: 241
    (F) PAGES: 42-52
    (G) DATE: 1988

(xi) SEQUENCE DESCRIPTION: SEQ ID NO:7:

His Asp Phe Gln Ile Met Arg Thr Leu Gly Thr Gly Ser Phe Gly
              005                 010                 015

Arg Val His Leu Val Arg Ser Val His Asn Gly Arg Tyr Tyr Ala
              020                 025                 030

Ile Lys Val Leu Lys Lys Gln Gln Val Val Lys Met Lys Gln Val
              035                 040                 045

Glu His Thr Asn Asp Glu Arg Arg Met Leu Lys Leu Val Glu His
              050                 055                 060

Pro Phe Leu Ile Arg Met Trp Gly Thr Phe Gln Asp Ala Arg Asn
              065                 070                 075

Ile Phe Met Val Met Asp Tyr Ile Glu Gly Gly Glu Leu Phe Ser
              080                 085                 090

Leu Leu Arg Lys Ser Gln Arg Phe Pro Asn Pro Val Ala Lys Phe
              095                 100                 105

Tyr Ala Ala Glu Val Ile Leu Ala Leu Glu Tyr Leu His Ala His
              110                 115                 120

Asn Ile Ile Tyr Arg Asp Leu Lys Pro Glu Asn Ile Leu Leu Asp
              125                 130                 135

Arg Asn Gly His Ile Lys Ile Thr Asp Phe Gly Phe Ala Lys Glu
              140                 145                 150

Val Gln Thr Val Thr Trp Thr Leu Cys Gly Thr Pro Asp Tyr Ile
              155                 160                 165

Ala Pro Glu Val Ile Thr Thr Lys Pro Tyr Asn Lys Ser Val Asp
              170                 175                 180

Trp Trp Ser Leu Gly Val Leu Ile Tyr Glu Met Leu Ala Gly Tyr
              185                 190                 195

Thr Pro Phe Tyr Asp Thr Thr Pro Met Lys Thr Tyr Glu Lys Ile
              200                 205                 210

Leu Gln Gly Lys Val Val Tyr Pro Pro Tyr Phe Gln Pro Asp Val
              215                 220                 225

Val Asp Leu Leu Ser Lys Leu Ile Thr Ala Asp Leu Thr Arg Arg
              230                 235                 240

Ile Gly Asn Leu Gln Asp Gly Ser Arg Asp Ile Lys Ala His Pro
              245                 250                 255

Trp Phe Ser Glu Val
              260

(2) INFORMATION FOR SEQ ID NO:8:

(i) SEQUENCE CHARACTERISTICS:
        (A) LENGTH: 260

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 8

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:8:

```
Ser Asp Phe Gln Ile Leu Arg Thr Leu Gly Thr Gly Ser Phe Gly
                005                 010                 015

Arg Val His Leu Ile Arg Ser Asn His Asn Gly Arg Phe Tyr Ala
                020                 025                 030

Leu Lys Thr Leu Lys Lys His Thr Ile Val Lys Leu Lys Gln Val
                035                 040                 045

Glu His Thr Asn Asp Glu Arg Arg Met Leu Ser Ile Val Ser His
                050                 055                 060

Pro Phe Ile Ile Arg Met Trp Gly Thr Phe Gln Asp Ser Gln Gln
                065                 070                 075

Val Phe Met Val Met Asp Tyr Ile Glu Gly Gly Glu Leu Phe Ser
                080                 085                 090

Leu Leu Arg Lys Ser Gln Arg Phe Pro Asn Pro Val Ala Lys Phe
                095                 100                 105

Tyr Ala Ala Glu Val Cys Leu Ala Leu Glu Tyr Leu His Ser Lys
                110                 115                 120

Asp Ile Thr Tyr Arg Asp Leu Lys Pro Glu Asn Ile Leu Leu Asp
                125                 130                 135

Lys Asn Gly His Ile Lys Ile Thr Asp Phe Gly Phe Ala Lys Tyr
                140                 145                 150

Val Pro Asp Val Thr Tyr Thr Leu Cys Gly Thr Pro Asp Tyr Ile
                155                 160                 165

Ala Pro Glu Val Val Ser Thr Lys Pro Tyr Asn Lys Ser Val Asp
                170                 175                 180

Trp Trp Ser Phe Gly Val Leu Ile Tyr Glu Met Leu Ala Gly Tyr
                185                 190                 195
```

```
Thr Pro Phe Tyr Asn Ser Asn Thr Met Lys Thr Tyr Glu Asn Ile
            200                 205                 210

Leu Asn Ala Glu Leu Lys Phe Pro Pro Phe His Pro Asp Ala
            215                 220                 225

Gln Asp Leu Leu Lys Lys Leu Ile Thr Arg Asp Leu Ser Glu Arg
            230                 235                 240

Leu Gly Asn Leu Gln Asn Gly Ser Glu Asp Val Lys Asn His Pro
            245                 250                 255

Trp Phe Asn Glu Val
            260
```

(2) INFORMATION FOR SEQ ID NO:9:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: bovine (ix) FEATURE: Protein kinase; Table 8 Column 9

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:9:

```
Ser Asp Phe Asn Ile Ile Asp Thr Leu Gly Val Gly Gly Phe Gly
            005                 010                 015

Arg Val Glu Leu Val Gln Leu Lys Ser Glu Glu Ser Lys Thr Phe
            020                 025                 030

Ala Met Lys Ile Leu Lys Lys Arg His Ile Val Asp Thr Arg Gln
            035                 040                 045

Gln Glu His Ile Arg Ser Glu Lys Gln Ile Met Gln Gly Ala His
            050                 055                 060

Ser Asp Phe Ile Val Arg Leu Tyr Arg Thr Phe Lys Asp Ser Lys
            065                 070                 075

Tyr Leu Tyr Met Leu Met Glu Ala Cys Leu Gly Gly Glu Leu Trp
            080                 085                 090

Thr Ile Leu Arg Asp Arg Gly Ser Phe Glu Asp Ser Thr Thr Arg
            095                 100                 105

Phe Tyr Thr Ala Cys Val Val Glu Ala Phe Ala Tyr Leu His Ser
            110                 115                 120

Lys Gly Ile Ile Tyr Arg Asp Leu Lys Pro Glu Asn Leu Ile Leu
```

```
                    125                 130                 135
Asp His Arg Gly Tyr Ala Lys Leu Val Asp Phe Gly Phe Ala Lys
                140                 145                 150

Lys Ile Gly Phe Gly Lys Leu Thr Trp Thr Phe Cys Gly Thr Pro
                155                 160                 165

Glu Tyr Val Ala Pro Glu Ile Ile Leu Asn Lys Gly His Asp Ile
                170                 175                 180

Ser Ala Asp Tyr Trp Ser Leu Gly Ile Leu Met Tyr Glu Leu Leu
                185                 190                 195

Thr Gly Ser Pro Pro Phe Ser Gly Pro Asp Pro Met Lys Thr Tyr
                200                 205                 210

Asn Ile Ile Leu Arg Gly Ile Asp Ile Glu Phe Pro Lys Lys Ile
                215                 220                 225

Ala Lys Asn Ala Ala Asn Leu Ile Lys Lys Leu Cys Arg Asp Asn
                230                 235                 240

Pro Ser Glu Arg Leu Gly Asn Leu Lys Asn Gly Val Lys Asp Ile
                245                 250                 255

Gln Lys His Lys Trp Phe Glu Gly Phe
                260
```

(2) INFORMATION FOR SEQ ID NO:10:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: bovine (ix) FEATURE: Protein kinase; Table 8 Column 11

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:10:

```
Thr Asp Phe Asn Phe Leu Met Val Leu Gly Lys Gly Ser Phe Gly
                005                 010                 015

Lys Val Met Leu Ala Asp Arg Lys Gly Thr Glu Glu Leu Tyr Ala
                020                 025                 030

Ile Lys Ile Leu Lys Lys Asp Val Val Ile Gln Asp Asp Asp Val
                035                 040                 045

Glu Cys Thr Met Val Glu Lys Arg Val Leu Ala Leu Leu Asp Lys
                050                 055                 060
```

Pro Pro Phe Leu Thr Gln Leu His Ser Cys Phe Gln Thr Val Asp
              065                    070                    075

Arg Leu Tyr Phe Val Met Glu Tyr Val Asn Gly Gly Asp Leu Met
              080                    085                    090

Tyr His Ile Gln Gln Val Gly Lys Phe Lys Glu Pro Gln Ala Val
              095                    100                    105

Phe Tyr Ala Ala Glu Ile Ser Ile Gly Leu Phe Phe Leu His Lys
              110                    115                    120

Arg Gly Ile Ile Tyr Arg Asp Leu Lys Leu Asp Asn Val Met Leu
              125                    130                    135

Asp Ser Glu Gly His Ile Lys Ile Ala Asp Phe Gly Met Cys Lys
              140                    145                    150

Glu His Met Met Asp Gly Val Thr Thr Arg Thr Phe Cys Gly Thr
              155                    160                    165

Pro Asp Tyr Ile Ala Pro Glu Ile Ile Ala Tyr Gln Pro Tyr Gly
              170                    175                    180

Lys Ser Val Asp Trp Trp Ala Tyr Gly Val Leu Leu Tyr Glu Met
              185                    190                    195

Leu Ala Gly Gln Pro Pro Phe Asp Gly Glu Asp Glu Asp Glu Leu
              200                    205                    210

Phe Gln Ser Ile Met Glu His Asn Val Ser Tyr Pro Lys Ser Leu
              215                    220                    225

Ser Lys Glu Ala Val Ser Ile Cys Lys Gly Leu Met Thr Lys His
              230                    235                    240

Pro Gly Lys Arg Leu Gly Cys Gly Pro Glu Gly Glu Arg Asp Val
              245                    250                    255

Arg Glu His Ala Phe Phe Arg Arg Ile
              260

(2) INFORMATION FOR SEQ ID NO:11:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: rabbit (ix) FEATURE: Protein kinase; Table 8 Column 12

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:11:

| Thr | Asp | Phe | Asn | Phe | Leu | Met | Val | Leu | Gly | Lys | Gly | Ser | Phe | Gly |
|---|---|---|---|---|---|---|---|---|---|---|---|---|---|---|
| | | | | 005 | | | | | 010 | | | | | 015 |

| Lys | Val | Met | Leu | Ser | Glu | Arg | Lys | Gly | Thr | Asp | Glu | Leu | Tyr | Ala |
|---|---|---|---|---|---|---|---|---|---|---|---|---|---|---|
| | | | | 020 | | | | | 025 | | | | | 030 |

| Val | Lys | Ile | Leu | Lys | Lys | Asp | Val | Ile | Gln | Asp | Asp | Val |
|---|---|---|---|---|---|---|---|---|---|---|---|---|
| | | | | 035 | | | | | 040 | | | 045 |

Glu Cys Thr Met Val Glu Lys Arg Val Leu Ala Leu Pro Gly Lys
                  050                 055                 060

Pro Pro Phe Leu Thr Gln Leu His Ser Cys Phe Gln Thr Met Asp
                  065                 070                 075

Arg Leu Tyr Phe Val Met Glu Tyr Val Asn Gly Gly Asp Leu Met
                  080                 085                 090

Tyr His Ile Gln Gln Val Gly Arg Phe Lys Glu Pro His Ala Val
                  095                 100                 105

Phe Tyr Ala Ala Glu Ile Ala Ile Gly Leu Phe Phe Leu Gln Ser
                  110                 115                 120

Lys Gly Ile Ile Tyr Arg Asp Leu Lys Leu Asp Asn Val Met Leu
                  125                 130                 135

Asp Ser Glu Gly His Ile Lys Ile Ala Asp Phe Gly Met Cys Lys
                  140                 145                 150

Glu Asn Ile Trp Asp Gly Val Thr Thr Lys Thr Thr Cys Gly Thr
                  155                 160                 165

Pro Asp Tyr Ile Ala Pro Glu Ile Ile Ala Tyr Gln Pro Tyr Gly
                  170                 175                 180

Lys Ser Val Asp Trp Trp Ala Phe Gly Val Leu Leu Tyr Glu Met
                  185                 190                 195

Leu Ala Gly Gln Ala Pro Phe Glu Gly Glu Asp Glu Asp Glu Leu
                  200                 205                 210

Phe Gln Ser Ile Met Glu His Asn Val Ala Tyr Pro Lys Ser Met
                  215                 220                 225

Ser Lys Glu Ala Val Ala Ile Cys Lys Gly Leu Ile Thr Lys His
                  230                 235                 240

Pro Gly Lys Arg Leu Gly Cys Gly Pro Glu Gly Glu Arg Asp Ile
                  245                 250                 255

Lys Glu His Ala Phe Phe Arg Tyr Ile
                  260

(2) INFORMATION FOR SEQ ID NO:12:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: bovine (ix) FEATURE: Protein kinase; Table 8 Column 13

(x) PUBLICATION INFORMATION:
        (A) AUTHORS:

Hanks, S. K.
Quinn, A. M.
Hunter, T.

(B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:12:

```
Thr Asp Phe Asn Phe Leu Met Val Leu Gly Lys Gly Ser Phe Gly
            005                 010                 015

Lys Val Met Leu Ser Glu Arg Lys Gly Thr Asp Glu Leu Tyr Ala
            020                 025                 030

Val Lys Ile Leu Lys Lys Asp Val Val Ile Gln Asp Asp Asp Val
            035                 040                 045

Glu Cys Thr Met Val Glu Lys Arg Val Leu Ala Leu Pro Gly Lys
            050                 055                 060

Pro Pro Phe Leu Thr Gln Leu His Ser Cys Phe Gln Thr Met Asp
            065                 070                 075

Arg Leu Tyr Phe Val Met Glu Tyr Val Asn Gly Gly Asp Leu Met
            080                 085                 090

Tyr His Ile Gln Gln Val Gly Arg Phe Lys Glu Pro His Ala Val
            095                 100                 105

Phe Tyr Ala Ala Glu Ile Ala Ile Gly Leu Phe Phe Leu Gln Ser
            110                 115                 120

Lys Gly Ile Ile Tyr Arg Asp Leu Lys Leu Asp Asn Val Met Leu
            125                 130                 135

Asp Ser Glu Gly His Ile Lys Ile Ala Asp Phe Gly Met Cys Lys
            140                 145                 150

Glu Asn Ile Trp Asp Gly Val Thr Thr Lys Thr Phe Cys Gly Thr
            155                 160                 165

Pro Asp Tyr Ile Ala Pro Glu Ile Ile Ala Tyr Gln Pro Tyr Gly
            170                 175                 180

Lys Ser Val Asp Trp Trp Ala Phe Gly Val Leu Leu Tyr Glu Met
            185                 190                 195

Leu Ala Gly Gln Ala Pro Phe Glu Gly Glu Asp Glu Asp Glu Leu
            200                 205                 210

Phe Gln Ser Ile Met Glu His Asn Val Ala Tyr Pro Lys Ser Met
            215                 220                 225

Ser Lys Glu Ala Val Ala Ile Cys Lys Gly Leu Met Thr Lys His
            230                 235                 240

Pro Gly Lys Arg Leu Gly Cys Gly Pro Glu Gly Glu Arg Asp Ile
            245                 250                 255

Lys Asp His Ala Phe Phe Arg Tyr Ile
            260
```

(2) INFORMATION FOR SEQ ID NO:13:

(i) SEQUENCE CHARACTERISTICS:
        (A) LENGTH: 263

(B) TYPE: amino acid (D) TOPOLOGY: linear (ii) MOLECULE TYPE:
    (A) DESCRIPTION: protein (vi) ORIGINAL SOURCE:
    (A) ORGANISM: rabbit (ix) FEATURE: Protein kinase; Table 8 Column 14

(x) PUBLICATION INFORMATION:
    (A) AUTHORS:

Hanks, S. K.
        Quinn, A. M.
        Hunter, T.
    (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:13:

```
Asp Phe Asn Phe Leu Met Val Leu Gly Lys Gly Ser Phe Gly Lys
            005                 010                 015

Val Met Leu Ser Glu Arg Lys Gly Thr Asp Glu Leu Tyr Ala Val
            020                 025                 030

Lys Ile Leu Lys Lys Asp Val Val Ile Gln Asp Asp Val Glu
            035                 040                 045

Cys Thr Met Val Glu Lys Arg Val Leu Ala Leu Pro Gly Lys Pro
            050                 055                 060

Pro Phe Leu Thr Gln Leu His Ser Cys Phe Gln Thr Met Asp Arg
            065                 070                 075

Leu Tyr Glu Val Met Glu Tyr Val Asn Gly Gly Asp Leu Met Tyr
            080                 085                 090

His Ile Gln Gln Val Gly Arg Phe Lys Glu Pro His Ala Val Phe
            095                 100                 105

Tyr Ala Ala Glu Ile Ala Ile Gly Leu Phe Phe Leu Gln Ser Lys
            110                 115                 120

Gly Ile Ile Tyr Arg Asp Leu Lys Leu Asp Asn Val Met Leu Asp
            125                 130                 135

Ser Glu Gly His Ile Lys Ile Ala Asp Phe Gly Met Cys Lys Glu
            140                 145                 150

Asn Ile Trp Asp Gly Val Thr Thr Lys Thr Phe Cys Gly Thr Pro
            155                 160                 165

Asp Tyr Ile Ala Pro Glu Ile Ile Ala Tyr Gln Pro Tyr Asp Lys
            170                 175                 180

Ser Val Asp Trp Trp Ser Phe Gly Val Leu Leu Tyr Glu Met Leu
            185                 190                 195

Ala Gly Gln Ala Pro Phe Glu Gly Glu Asp Glu Asp Glu Leu Phe
            200                 205                 210

Gln Ser Ile Met Glu His Asn Val Ala Tyr Pro Lys Ser Met Ser
            215                 220                 225

Lys Glu Ala Val Ala Ile Cys Lys Gly Leu Met Thr Lys His Pro
            230                 235                 240

Gly Lys Arg Leu Gly Cys Gly Pro Glu Gly Glu Arg Asp Ile Lys
```

```
                     245                 250                 255

Glu His Ala Phe Phe Arg Tyr Ile
                260

(2) INFORMATION FOR SEQ ID NO:14:

(i) SEQUENCE CHARACTERISTICS:
        (A) LENGTH: 269

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 15

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:14:

Ser Asp Phe Ser Phe Leu Met Val Leu Gly Lys Gly Ser Phe Gly
                005                 010                 015

Lys Val Met Leu Ala Glu Arg Arg Gly Ser Asp Glu Leu Tyr Ala
                020                 025                 030

Ile Lys Ile Leu Lys Lys Asp Val Ile Val Gln Asp Asp Asp Val
                035                 040                 045

Asp Cys Thr Leu Val Glu Lys Arg Val Leu Ala Leu Gly Gly Arg
                050                 055                 060

Gly Pro Gly Gly Arg Pro His Phe Leu Thr Gln Leu His Ser Thr
                065                 070                 075

Phe Gln Thr Pro Asp Arg Leu Tyr Phe Val Met Glu Tyr Val Thr
                080                 085                 090

Gly Gly Asp Leu Met Tyr His Ile Gln Gln Leu Gly Lys Phe Lys
                095                 100                 105

Glu Pro His Ala Ala Phe Tyr Ala Ala Glu Ile Ala Ile Gly Leu
                110                 115                 120

Phe Phe Leu His Asn Gln Gly Ile Ile Tyr Arg Asp Leu Lys Leu
                125                 130                 135

Asp Asn Val Met Leu Asp Ala Glu Gly His Ile Lys Ile Thr Asp
                140                 145                 150

Phe Gly Met Cys Lys Glu Asn Val Phe Pro Gly Ser Thr Thr Arg
                155                 160                 165

Thr Phe Cys Gly Thr Pro Asp Tyr Ile Ala Pro Glu Ile Ile Ala
                170                 175                 180
```

```
Tyr Gln Pro Tyr Gly Lys Ser Val Asp Trp Trp Ser Phe Gly Val
                185                 190                 195

Leu Leu Tyr Glu Met Leu Ala Gly Gln Pro Pro Phe Asp Gly Glu
                200                 205                 210

Asp Glu Glu Glu Leu Phe Gln Ala Ile Met Glu Gln Thr Val Thr
                215                 220                 225

Tyr Pro Lys Ser Leu Ser Arg Glu Ala Val Ala Ile Cys Lys Gly
                230                 235                 240

Phe Leu Thr Lys His Pro Ala Lys Arg Leu Gly Ser Gly Pro Asp
                245                 250                 255

Gly Glu Pro Thr Ile Arg Ala His Gly Phe Phe Arg Trp Ile
                260                 265
```

(2) INFORMATION FOR SEQ ID NO:15:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: bovine (ix) FEATURE: Protein kinase; Table 8 Column 16

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:15:

```
Thr Asp Phe Asn Phe Leu Met Val Leu Gly Lys Gly Ser Phe Gly
                005                 010                 015

Lys Val Met Leu Ala Asp Arg Lys Gly Thr Glu Glu Leu Tyr Ala
                020                 025                 030

Ile Lys Ile Leu Lys Lys Asp Val Val Ile Gln Asp Asp Asp Val
                035                 040                 045

Glu Cys Thr Met Val Glu Lys Arg Val Leu Ala Leu Met Asp Lys
                050                 055                 060

Pro Pro Phe Leu Thr Gln Leu His Ser Cys Phe Gln Thr Val Asp
                065                 070                 075

Arg Leu Tyr Phe Val Met Glu Tyr Val Asn Gly Gly Asp Leu Met
                080                 085                 090

Tyr His Ile Gln Gln Val Gly Lys Phe Lys Glu Pro Gln Ala Val
                095                 100                 105
```

-continued

```
Phe Tyr Ala Ala Glu Ile Ser Ile Gly Leu Phe Phe Leu His Lys
            110                 115                 120

Arg Gly Ile Ile Tyr Arg Asp Leu Lys Leu Asp Asn Val Met Leu
            125                 130                 135

Asp Ser Glu Gly His Ile Lys Ile Ala Asp Phe Gly Met Cys Lys
            140                 145                 150

Glu His Met Met Asp Gly Val Thr Thr Arg Thr Phe Cys Gly Thr
            155                 160                 165

Pro Asp Tyr Ile Ala Pro Glu Ile Ile Ala Tyr Gln Pro Tyr Gly
            170                 175                 180

Lys Ser Val Asp Trp Trp Ala Tyr Gly Val Leu Leu Tyr Glu Met
            185                 190                 195

Leu Ala Gly Gln Pro Pro Phe Asp Gly Glu Asp Glu Asp Glu Leu
            200                 205                 210

Phe Gln Ser Ile Met Glu His Asn Val Ser Tyr Pro Lys Ser Leu
            215                 220                 225

Ser Lys Glu Ala Val Ser Ile Cys Lys Gly Leu Met Thr Lys His
            230                 235                 240

Pro Ala Lys Arg Leu Gly Cys Gly Pro Glu Gly Glu Arg Asp Val
            245                 250                 255

Arg Glu His Ala Phe Phe Arg Arg Ile
            260
```

(2) INFORMATION FOR SEQ ID NO:16:

(i) SEQUENCE CHARACTERISTICS:
      (A) LENGTH: 269

(B) TYPE: amino acid (D) TOPOLOGY: linear (ii) MOLECULE TYPE:
      (A) DESCRIPTION: protein (vi) ORIGINAL SOURCE:
      (A) ORGANISM: human (ix) FEATURE: Protein kinase; Table 8 Column 17

(x) PUBLICATION INFORMATION:
      (A) AUTHORS:

Hanks, S. K.
          Quinn, A. M.
          Hunter, T.
      (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:16:

```
Ser Asp Phe Ser Phe Leu Met Val Leu Gly Lys Gly Ser Phe Gly
            005                 010                 015

Lys Val Met Leu Ala Glu Arg Arg Gly Ser Asp Glu Leu Tyr Ala
            020                 025                 030

Ile Lys Ile Leu Lys Lys Asp Val Ile Val Gln Asp Asp Asp Val
```

```
                    035                 040                 045
    Asp Cys Thr Leu Val Glu Lys Arg Val Leu Ala Leu Gly Gly Arg
                        050                 055                 060

Gly Pro Gly Gly Arg Pro His Phe Leu Thr Gln Leu His Ser Thr
                        065                 070                 075

Phe Gln Thr Pro Asp Arg Leu Tyr Glu Val Met Glu Tyr Val Thr
                        080                 085                 090

Gly Gly Asp Leu Met Tyr His Ile Gln Gln Leu Gly Lys Phe Lys
                        095                 100                 105

Glu Pro His Ala Ala Phe Tyr Ala Ala Glu Ile Ala Ile Gly Leu
                        110                 115                 120

Phe Phe Leu His Asn Gln Gly Ile Ile Tyr Arg Asp Leu Lys Leu
                        125                 130                 135

Asp Asn Val Met Leu Asp Ala Glu Gly His Ile Lys Ile Thr Asp
                        140                 145                 150

Phe Gly Met Cys Lys Glu Asn Val Phe Pro Gly Ser Thr Thr Arg
                        155                 160                 165

Thr Phe Cys Gly Thr Pro Asp Tyr Ile Ala Pro Glu Ile Ile Ala
                        170                 175                 180

Tyr Gln Pro Tyr Asp Lys Ser Val Asp Trp Trp Ala Phe Gly Val
                        185                 190                 195

Leu Leu Tyr Glu Met Leu Ala Gly Gln Pro Pro Phe Asp Gly Glu
                        200                 205                 210

Asp Glu Glu Glu Leu Phe Gln Ala Ile Met Glu Gln Thr Val Thr
                        215                 220                 225

Tyr Pro Lys Ser Leu Ser Arg Glu Ala Val Ala Ile Cys Lys Gly
                        230                 235                 240

Phe Leu Thr Lys His Pro Gly Lys Arg Leu Gly Ser Gly Pro Asp
                        245                 250                 255

Gly Glu Pro Thr Ile Arg Ala His Gly Phe Phe Arg Asn Ile
                        260                 265

(2) INFORMATION FOR SEQ ID NO:17:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: Drosophila melanogaster (ix) FEATURE: Protein kinase; Table 8 Column 18

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241
```

(F) PAGES: 42-52

(G) DATE: 1988

(xi) SEQUENCE DESCRIPTION: SEQ ID NO:17:

| | | | | | | | | | | | | | | |
|---|---|---|---|---|---|---|---|---|---|---|---|---|---|---|
|Thr|Asp|Phe|Asn|Phe|Ile|Lys|Val|Leu|Gly|Lys|Gly|Ser|Phe|Gly|
| | | | |005| | | |010| | | | |015| |
|Lys|Val|Leu|Leu|Ala|Glu|Arg|Lys|Gly|Ser|Glu|Glu|Leu|Tyr|Ala|
| | | | |020| | | |025| | | | |030| |
|Ile|Lys|Ile|Leu|Lys|Lys|Asp|Val|Ile|Ile|Gln|Asp|Asp|Asp|Val|
| | | | |035| | | |040| | | | |045| |
|Glu|Cys|Thr|Met|Ile|Glu|Lys|Arg|Val|Leu|Ala|Leu|Gly|Glu|Lys|
| | | | |050| | | |055| | | | |060| |
|Pro|Pro|Phe|Leu|Val|Gln|Leu|His|Ser|Cys|Phe|Gln|Thr|Met|Asp|
| | | | |065| | | |070| | | | |075| |
|Arg|Leu|Phe|Phe|Val|Met|Glu|Tyr|Val|Asn|Gly|Gly|Asp|Leu|Ile|
| | | | |080| | | |085| | | | |090| |
|Phe|Gln|Ile|Gln|Gln|Phe|Gly|Lys|Phe|Lys|Glu|Pro|Val|Ala|Val|
| | | | |095| | | |100| | | | |105| |
|Phe|Tyr|Ala|Ala|Glu|Ile|Ala|Ala|Gly|Leu|Phe|Phe|Leu|His|Thr|
| | | | |110| | | |115| | | | |120| |
|Lys|Gly|Ile|Leu|Tyr|Arg|Asp|Leu|Lys|Leu|Asp|Asn|Val|Leu|Leu|
| | | | |125| | | |130| | | | |135| |
|Asp|Ala|Asp|Gly|His|Val|Lys|Ile|Ala|Asp|Phe|Gly|Met|Cys|Lys|
| | | | |140| | | |145| | | | |150| |
|Glu|Asn|Ile|Val|Gly|Asp|Lys|Thr|Thr|Lys|Thr|Phe|Cys|Gly|Thr|
| | | | |155| | | |160| | | | |165| |
|Pro|Asp|Tyr|Ile|Ala|Pro|Glu|Ile|Ile|Leu|Tyr|Gln|Pro|Tyr|Gly|
| | | | |170| | | |175| | | | |180| |
|Lys|Ser|Val|Asp|Trp|Trp|Ala|Tyr|Gly|Val|Leu|Leu|Tyr|Glu|Met|
| | | | |185| | | |190| | | | |195| |
|Leu|Val|Gly|Gln|Pro|Pro|Phe|Asp|Gly|Glu|Asp|Glu|Glu|Glu|Leu|
| | | | |200| | | |205| | | | |210| |
|Phe|Ala|Ala|Ile|Thr|Asp|His|Asn|Val|Ser|Tyr|Pro|Lys|Ser|Leu|
| | | | |215| | | |220| | | | |225| |
|Ser|Lys|Glu|Ala|Lys|Glu|Ala|Cys|Lys|Gly|Phe|Leu|Thr|Lys|Gln|
| | | | |230| | | |235| | | | |240| |
|Pro|Asn|Lys|Arg|Leu|Gly|Cys|Gly|Ser|Ser|Gly|Glu|Glu|Asp|Val|
| | | | |245| | | |250| | | | |255| |
|Arg|Leu|His|Pro|Phe|Ser|Arg|Arg|Ile| | | | | | |
| | | | |260| | | | | | | | | | |

(2) INFORMATION FOR SEQ ID NO:18:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: rat (ix) FEATURE: Protein kinase; Table 8 Column 20

(x) PUBLICATION INFORMATION:
    (A) AUTHORS:

Hanks, S. K.
        Quinn, A. M.
        Hunter, T.
    (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:18:

Glu Glu Tyr Gln Leu Phe Glu Glu Leu Gly Lys Gly Ala Phe Ser
             005                 010                 015

Val Val Arg Arg Cys Val Lys Val Leu Ala Gly Gln Glu Tyr Ala
             020                 025                 030

Ala Lys Ile Ile Asn Thr Lys Lys Leu Ser Ala Arg Asp His Gln
             035                 040                 045

Lys Leu Glu Arg Glu Ala Arg Ile Cys Arg Leu Leu Lys His Pro
             050                 055                 060

Asn Ile Val Arg Leu His Asp Ser Ile Ser Glu Glu Gly His His
             065                 070                 075

Tyr Leu Ile Phe Asp Leu Val Thr Gly Gly Glu Leu Phe Glu Asp
             080                 085                 090

Ile Val Ala Arg Glu Tyr Tyr Ser Glu Ala Asp Ala Ser His Cys
             095                 100                 105

Ile Gln Gln Ile Leu Glu Ala Val Leu His Cys His Gln Met Gly
             110                 115                 120

Val Val His Arg Asp Leu Lys Pro Glu Asn Leu Leu Leu Ala Ser
             125                 130                 135

Lys Leu Lys Gly Ala Ala Val Lys Leu Ala Asp Phe Gly Leu Ala
             140                 145                 150

Ile Glu Val Glu Gly Glu Gln Gln Ala Trp Phe Gly Phe Ala Gly
             155                 160                 165

Thr Pro Gly Tyr Leu Ser Pro Glu Val Leu Arg Lys Asp Pro Tyr
             170                 175                 180

Gly Lys Pro Val Asp Leu Trp Ala Cys Gly Val Ile Leu Tyr Ile
             185                 190                 195

Leu Leu Val Gly Tyr Pro Pro Phe Trp Asp Glu Asp Gln His Arg
             200                 205                 210

Leu Tyr Gln Gln Ile Lys Ala Gly Ala Tyr Asp Phe Pro Ser Pro
             215                 220                 225

Glu Trp Asp Thr Val Thr Pro Glu Ala Lys Asp Leu Ile Asn Lys
             230                 235                 240

Met Leu Thr Ile Asn Pro Ser Lys Arg Ile Thr Ala Ala Glu Ala
             245                 250                 255

Leu Lys His Pro Trp Ile Ser His Arg
             260

(2) INFORMATION FOR SEQ ID NO:19:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: rat (ix) FEATURE: Protein kinase; Table 8 Column 21

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:19:

Asp Glu Tyr Gln Leu Tyr Glu Asp Ile Gly Lys Gly Ala Phe Ser
                005                 010                 015

Val Val Arg Arg Cys Val Lys Leu Cys Thr Gly His Glu Tyr Ala
                020                 025                 030

Ala Lys Ile Ile Asn Thr Lys Lys Leu Ser Ala Arg Asp His Gln
                035                 040                 045

Lys Leu Glu Arg Glu Ala Arg Ile Cys Arg Leu Leu Lys His Ser
                050                 055                 060

Asn Ile Val Arg Leu His Asp Ser Ile Ser Glu Glu Gly Phe His
                065                 070                 075

Tyr Leu Val Phe Asp Leu Val Thr Gly Gly Glu Leu Phe Glu Asp
                080                 085                 090

Ile Val Ala Arg Glu Tyr Tyr Ser Glu Ala Asp Ala Ser His Cys
                095                 100                 105

Ile Gln Gln Ile Leu Glu Ala Val Leu His Cys His Gln Met Gly
                110                 115                 120

Val Val His Arg Asp Leu Lys Pro Glu Asn Leu Leu Leu Ala Ser
                125                 130                 135

Lys Leu Lys Gly Ala Ala Val Lys Leu Ala Asp Phe Gly Leu Ala
                140                 145                 150

Ile Glu Val Gln Gly Asp Gln Ala Trp Phe Gly Phe Ala Gly
                155                 160                 165

Thr Pro Gly Tyr Leu Ser Pro Glu Val Leu Arg Lys Glu Ala Tyr
                170                 175                 180

Gly Lys Pro Val Asp Ile Trp Ala Cys Gly Val Ile Leu Tyr Ile
                185                 190                 195

Leu Leu Val Gly Tyr Pro Pro Phe Trp Asp Glu Asp Gln His Lys
                200                 205                 210

Leu Tyr Gln Gln Ile Lys Ala Gly Ala Tyr Asp Phe Pro Ser Pro
                215                 220                 225

```
Glu Trp Asp Thr Val Thr Pro Glu Ala Lys Asn Leu Ile Asn Gln
                230                 235                 240

Met Leu Thr Ile Asn Pro Ala Lys Arg Ile Thr Ala His Glu Ala
                245                 250                 255

Leu Lys His Pro Trp Val Cys Gln Arg
                260
```

(2) INFORMATION FOR SEQ ID NO:20:

(i) SEQUENCE CHARACTERISTICS:
        (A) LENGTH: 268

(B) TYPE: amino acid (D) TOPOLOGY: linear (ii) MOLECULE TYPE:
        (A) DESCRIPTION: protein (vi) ORIGINAL SOURCE:
        (A) ORGANISM: rabbit (ix) FEATURE: Protein kinase; 822 Table 8 Column 22

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:20:

```
Glu Asn Tyr Glu Pro Lys Glu Ile Leu Gly Arg Gly Val Ser Ser
                005                 010                 015

Val Val Arg Arg Cys Ile His Lys Pro Thr Cys Lys Glu Tyr Ala
                020                 025                 030

Val Lys Ile Ile Asp Val Thr Gly Gly Gly Ser Phe Ser Ala Glu
                035                 040                 045

Leu Arg Glu Ala Thr Leu Lys Glu Val Asp Ile Leu Arg Lys Val
                050                 055                 060

Ser Gly His Pro Asn Ile Ile Gln Leu Lys Asp Thr Tyr Glu Thr
                065                 070                 075

Asn Thr Phe Phe Phe Leu Val Phe Asp Leu Met Lys Lys Gly Glu
                080                 085                 090

Leu Phe Asp Tyr Leu Thr Glu Lys Val Thr Leu Ser Glu Lys Glu
                095                 100                 105

Thr Arg Lys Ile Met Arg Ala Leu Leu Glu Val Ile Cys Ala Leu
                110                 115                 120

His Lys Leu Asn Ile Val His Arg Asp Leu Lys Pro Glu Asn Ile
                125                 130                 135

Leu Leu Asp Asp Asp Met Asn Ile Lys Leu Thr Asp Phe Gly Phe
                140                 145                 150

Ser Cys Gln Leu Asp Pro Gly Glu Lys Leu Arg Glu Val Cys Gly
```

-continued

```
                    155                 160                 165
Thr Pro Ser Tyr Leu Ala Pro Glu Ile Ile Glu Cys Ser Met Asn
                170                 175                 180

His Pro Gly Tyr Gly Lys Glu Val Asp Met Trp Ser Thr Gly Val
                185                 190                 195

Ile Met Tyr Thr Leu Leu Ala Gly Ser Pro Pro Phe Trp His Arg
                200                 205                 210

Lys Gln Met Leu Met Leu Arg Met Ile Met Ser Gly Asn Tyr Gln
                215                 220                 225

Phe Gly Ser Pro Glu Trp Asp Asp Tyr Ser Asp Thr Val Lys Asp
                230                 235                 240

Leu Val Ser Arg Phe Leu Val Val Gln Pro Gln Lys Arg Tyr Thr
                245                 250                 255

Ala Glu Glu Ala Leu Ala His Pro Phe Phe Gln Gln Tyr
                260                 265
```

(2) INFORMATION FOR SEQ ID NO:21:

(i) SEQUENCE CHARACTERISTICS:
        (A) LENGTH: 268

(B) TYPE: amino acid (D) TOPOLOGY: linear (ii) MOLECULE TYPE:
        (A) DESCRIPTION: protein (vi) ORIGINAL SOURCE:
        (A) ORGANISM: mouse (ix) FEATURE: Protein kinase; Table 8 Column 23

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:21:

```
Glu Asn Tyr Glu Pro Lys Glu Ile Leu Gly Arg Gly Val Ser Ser
                005                 010                 015

Val Val Arg Arg Cys Ile His Lys Pro Thr Cys Gln Glu Tyr Ala
                020                 025                 030

Val Lys Ile Ile Asp Ile Thr Gly Gly Gly Ser Phe Ser Ser Glu
                035                 040                 045

Leu Arg Glu Ala Thr Leu Lys Glu Val Asp Ile Leu Gln Lys Val
                050                 055                 060

Ser Gly His His Asn Ile Ile Gln Leu Lys Asp Thr Tyr Glu Thr
                065                 070                 075

Asn Thr Phe Phe Phe Leu Val Phe Asp Leu Met Lys Arg Gly Glu
                080                 085                 090
```

```
Leu Phe Asp Tyr Leu Thr Glu Lys Val Thr Leu Thr Glu Lys Glu
                095                 100                 105

Thr Arg Lys Ile Met Arg Ala Leu Leu Glu Val Ile Cys Thr Leu
                110                 115                 120

His Lys Leu Asn Ile Val His Arg Asp Leu Lys Pro Glu Asn Ile
                125                 130                 135

Leu Leu Asp Asp Asn Met Asn Ile Lys Leu Thr Asp Phe Gly Phe
                140                 145                 150

Ser Cys Gln Leu Gln Pro Gly Glu Lys Leu Arg Glu Val Cys Gly
                155                 160                 165

Thr Pro Ser Tyr Leu Ala Pro Glu Ile Ile Gln Cys Ser Met Gly
                170                 175                 180

His Pro Gly Tyr Gly Lys Glu Val Asp Met Trp Ser Thr Gly Val
                185                 190                 195

Ile Met Tyr Thr Leu Leu Ala Gly Ser Pro Pro Phe Trp His Arg
                200                 205                 210

Lys Gln Met Leu Met Leu Arg Met Ile Met Asp Gly Lys Tyr Gln
                215                 220                 225

Phe Gly Ser Pro Glu Trp Asp Asp Tyr Ser Asp Thr Val Lys Asp
                230                 235                 240

Leu Val Ser Arg Phe Leu Val Val Gln Pro Gln Asp Arg Cys Ser
                245                 250                 255

Ala Glu Glu Ala Leu Ala His Pro Phe Phe Gln Glu Tyr
                260                 265
```

(2) INFORMATION FOR SEQ ID NO:22:

(i) SEQUENCE CHARACTERISTICS:
        (A) LENGTH: 261

(B) TYPE: amino acid (D) TOPOLOGY: linear (ii) MOLECULE TYPE:
        (A) DESCRIPTION: protein (vi) ORIGINAL SOURCE:
        (A) ORGANISM: rabbit (ix) FEATURE: Protein kinase; Table 8 Column 24

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:22:

```
Phe Ser Met Asn Ser Lys Glu Ala Leu Gly Gly Gly Lys Phe Gly
                005                 010                 015
```

```
Ala Val Cys Thr Cys Thr Glu Lys Ser Thr Gly Leu Lys Leu Ala
            020                 025                 030

Ala Lys Val Ile Lys Lys Gln Thr Pro Lys Asp Lys Glu Met Val
            035                 040                 045

Met Leu Glu Ile Glu Val Met Asn Gln Leu Asn His Arg Asn Leu
            050                 055                 060

Ile Gln Leu Tyr Ala Ala Ile Glu Thr Pro His Glu Ile Val Leu
            065                 070                 075

Phe Met Glu Tyr Ile Glu Gly Gly Leu Phe Glu Arg Ile Val
            080                 085                 090

Asp Glu Asp Tyr His Leu Thr Glu Val Asp Thr Met Val Phe Val
            095                 100                 105

Arg Gln Ile Cys Asp Gly Ile Leu Phe Met His Lys Met Arg Val
            110                 115                 120

Leu His Leu Asp Leu Lys Pro Glu Asn Ile Leu Cys Val Asn Thr
            125                 130                 135

Thr Gly His Leu Val Lys Ile Ile Asp Phe Gly Leu Ala Arg Arg
            140                 145                 150

Tyr Asn Pro Asn Glu Lys Leu Lys Val Asn Phe Gly Thr Pro Glu
            155                 160                 165

Phe Leu Ser Pro Glu Val Val Asn Tyr Asp Gln Ile Ser Asp Lys
            170                 175                 180

Thr Asp Met Trp Ser Leu Gly Val Ile Thr Tyr Met Leu Leu Ser
            185                 190                 195

Gly Leu Ser Pro Phe Leu Gly Asp Asp Thr Glu Thr Leu Asn
            200                 205                 210

Asn Val Leu Ser Gly Asn Trp Tyr Phe Asp Glu Glu Thr Phe Glu
            215                 220                 225

Ala Val Ser Asp Glu Ala Lys Asp Phe Val Ser Asn Leu Ile Val
            230                 235                 240

Lys Glu Gln Gly Ala Arg Met Ser Ala Ala Gln Cys Leu Ala His
            245                 250                 255

Pro Trp Leu Asn Asn Leu
            260

(2) INFORMATION FOR SEQ ID NO:23:

(i) SEQUENCE CHARACTERISTICS:
        (A) LENGTH: 260

(B) TYPE: amino acid (D) TOPOLOGY: linear (ii) MOLECULE TYPE:
        (A) DESCRIPTION: protein (vi) ORIGINAL SOURCE:
        (A) ORGANISM: chicken (ix) FEATURE: Protein kinase; Table 8 Column 25

(x) PUBLICATION INFORMATION:
        (A) AUTHORS:

Hanks, S. K.
            Quinn, A. M.
            Hunter, T.
        (B) TITLE: The protein kinase family
```

(C) JOURNAL: Science (D) VOLUME: 241

(F) PAGES: 42-52

(G) DATE: 1988

(xi) SEQUENCE DESCRIPTION: SEQ ID NO:23:

```
Asp Val Tyr Asn Ile Glu Glu Arg Leu Gly Ser Gly Lys Phe Gly
             005                 010                 015

Gln Val Phe Arg Leu Val Glu Lys Lys Thr Gly Lys Val Trp Ala
             020                 025                 030

Gly Lys Phe Phe Lys Ala Tyr Ser Ala Lys Glu Lys Glu Asn Ile
             035                 040                 045

Arg Asp Glu Ile Ser Ile Met Asn Cys Leu His His Pro Lys Leu
             050                 055                 060

Val Gln Cys Val Asp Ala Phe Glu Glu Lys Ala Asn Ile Val Met
             065                 070                 075

Val Leu Glu Met Val Ser Gly Gly Glu Leu Phe Glu Arg Ile Ile
             080                 085                 090

Asp Glu Asp Phe Leu Thr Glu Arg Glu Cys Ile Lys Tyr Met Arg
             095                 100                 105

Gln Ile Ser Glu Gly Val Glu Tyr Ile His Lys Gln Gly Ile Val
             110                 115                 120

His Leu Asp Leu Lys Pro Glu Asn Ile Met Cys Val Asn Lys Thr
             125                 130                 135

Gly Thr Ser Ile Lys Leu Ile Asp Phe Gly Leu Ala Arg Arg Leu
             140                 145                 150

Glu Ser Ala Gly Ser Leu Lys Val Leu Phe Gly Thr Pro Glu Phe
             155                 160                 165

Val Ala Pro Glu Val Ile Asn Tyr Glu Pro Ile Gly Tyr Glu Thr
             170                 175                 180

Asp Met Trp Ser Ile Gly Val Ile Cys Tyr Ile Leu Val Ser Gly
             185                 190                 195

Leu Ser Pro Phe Met Gly Asp Asn Asp Asn Glu Thr Leu Ala Asn
             200                 205                 210

Val Thr Ser Ala Thr Trp Thr Phe Asp Glu Ala Phe Asp Glu
             215                 220                 225

Ile Ser Asp Asp Ala Lys Asp Phe Ile Ser Asn Leu Leu Lys Lys
             230                 235                 240

Asp Met Lys Ser Arg Leu Asn Cys Thr Gln Cys Leu Gln His Pro
             245                 250                 255

Trp Leu Gln Lys Asp
             260
```

(2) INFORMATION FOR SEQ ID NO:24:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
    (A) ORGANISM: human (ix) FEATURE: Protein kinase; Table 8 Column 26

(x) PUBLICATION INFORMATION:
    (A) AUTHORS:

Hanks, S. K.
        Quinn, A. M.
        Hunter, T.
    (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:24:

```
Ala Lys Tyr Asp Ile Lys Ala Leu Ile Gly Arg Gly Ser Phe Ser
            005                 010                 015

Arg Val Val Arg Val Glu His Arg Ala Thr Arg Gln Pro Tyr Ala
            020                 025                 030

Ile Lys Met Ile Glu Thr Lys Tyr Arg Glu Gly Arg Glu Val Cys
            035                 040                 045

Glu Ser Glu Leu Arg Val Leu Arg Arg Val Arg His Ala Asn Ile
            050                 055                 060

Ile Gln Leu Val Glu Val Phe Glu Thr Gln Glu Arg Val Tyr Met
            065                 070                 075

Val Met Glu Leu Ala Thr Gly Gly Glu Leu Phe Asp Arg Ile Ile
            080                 085                 090

Ala Lys Gly Ser Glu Phe Thr Glu Arg Asp Ala Thr Arg Val Leu
            095                 100                 105

Gln Met Val Leu Asp Gly Val Arg Tyr Leu His Ala Leu Gly Ile
            110                 115                 120

Thr His Arg Asp Leu Lys Pro Glu Asn Leu Leu Tyr Tyr His Pro
            125                 130                 135

Gly Thr Asp Ser Lys Ile Ile Ile Thr Asp Phe Gly Leu Ala Ser
            140                 145                 150

Ala Arg Lys Lys Gly Asp Asp Cys Leu Met Lys Thr Thr Cys Gly
            155                 160                 165

Thr Pro Glu Tyr Ile Ala Pro Glu Val Leu Val Arg Lys Pro Tyr
            170                 175                 180

Thr Asn Ser Val Asp Met Trp Ala Leu Gly Val Ile Ala Tyr Ile
            185                 190                 195

Leu Leu Ser Gly Thr Met Pro Phe Glu Asp Asp Asn Arg Thr Arg
            200                 205                 210

Leu Tyr Arg Gln Ile Leu Arg Gly Lys Tyr Ser Tyr Ser Gly Glu
            215                 220                 225

Pro Trp Pro Ser Val Ser Asn Leu Ala Lys Asp Phe Ile Asp Arg
            230                 235                 240

Leu Leu Thr Val Asp Pro Gly Ala Arg Met Thr Ala Leu Gln Ala
            245                 250                 255

Leu Arg His Pro Trp Val Val Ser Met
            260
```

(2) INFORMATION FOR SEQ ID NO:25:

(i) SEQUENCE CHARACTERISTICS:
        (A) LENGTH: 257

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 28

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:25:

```
Gly Asn Tyr Gln Ile Val Lys Thr Leu Gly Glu Gly Ser Phe Gly
                005                 010                 015

Lys Val Lys Leu Ala Tyr His Thr Thr Thr Gly Gln Lys Val Ala
                020                 025                 030

Leu Lys Ile Ile Asn Lys Lys Val Leu Ala Lys Ser Asp Met Gln
                035                 040                 045

Gly Arg Ile Glu Arg Glu Ile Ser Tyr Leu Arg Leu Leu Arg His
                050                 055                 060

Pro His Ile Ile Lys Leu Tyr Asp Val Ile Lys Ser Lys Asp Glu
                065                 070                 075

Ile Ile Met Val Ile Glu Tyr Ala Gly Asn Glu Leu Phe Asp Tyr
                080                 085                 090

Ile Val Gln Arg Asp Lys Met Ser Glu Gln Glu Ala Arg Arg Phe
                095                 100                 105

Phe Gln Gln Ile Ile Ser Ala Val Glu Tyr Cys His Arg His Lys
                110                 115                 120

Ile Val His Arg Asp Leu Lys Pro Glu Asn Leu Leu Leu Asp Glu
                125                 130                 135

His Leu Asn Val Lys Ile Ala Asp Phe Gly Leu Ser Asn Ile Met
                140                 145                 150

Thr Asp Gly Asn Phe Leu Lys Thr Ser Cys Gly Ser Pro Asn Tyr
                155                 160                 165

Ala Ala Pro Glu Val Ile Ser Gly Lys Leu Tyr Ala Gly Pro Glu
                170                 175                 180

Val Asp Val Trp Ser Cys Gly Val Ile Leu Tyr Val Met Leu Cys
                185                 190                 195

Arg Arg Leu Pro Phe Asp Asp Glu Ser Ile Pro Val Leu Phe Lys
                200                 205                 210
```

```
Asn Ile Ser Asn Gly Val Tyr Thr Leu Pro Lys Phe Leu Ser Pro
                215                 220                 225

Gly Ala Ala Gly Leu Ile Lys Arg Met Leu Ile Val Asn Pro Leu
                230                 235                 240

Asn Arg Ile Ser Ile His Glu Ile Met Gln Asp Asp Trp Phe Lys
                245                 250                 255

Val Asp
```

(2) INFORMATION FOR SEQ ID NO:26:

(i) SEQUENCE CHARACTERISTICS:
        (A) LENGTH: 252

(B) TYPE: amino acid (D) TOPOLOGY: linear (ii) MOLECULE TYPE:
        (A) DESCRIPTION: protein (vi) ORIGINAL SOURCE:
        (A) ORGANISM: Schizosaccharomyces pombe (ix) FEATURE: Protein kinase; Table 8 Column 29

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:26:

```
Gly Val Trp Arg Leu Gly Lys Thr Leu Gly Thr Gly Ser Thr Ser
                005                 010                 015

Cys Val Arg Leu Ala Lys His Ala Lys Thr Gly Asp Leu Ala Ala
                020                 025                 030

Ile Lys Ile Ile Pro Ile Arg Tyr Ala Ser Ile Gly Met Glu Ile
                035                 040                 045

Leu Met Met Arg Leu Leu Arg His Pro Asn Ile Leu Arg Leu Tyr
                050                 055                 060

Asp Val Trp Thr Asp His Gln His Met Tyr Leu Ala Leu Glu Tyr
                065                 070                 075

Val Pro Asp Gly Glu Leu Phe His Tyr Ile Arg Lys His Gly Pro
                080                 085                 090

Leu Ser Glu Arg Glu Ala Ala His Tyr Leu Ser Gln Ile Leu Asp
                095                 100                 105

Ala Val Ala His Cys His Arg Phe Arg Phe Arg His Arg Asp Leu
                110                 115                 120

Lys Leu Glu Asn Ile Leu Ile Lys Val Asn Glu Gln Gln Ile Lys
                125                 130                 135

Ile Ala Asp Phe Gly Met Ala Thr Val Glu Pro Asn Asp Ser Cys
```

140                 145                 150

Leu Glu Asn Tyr Cys Gly Ser Leu His Tyr Leu Ala Pro Glu Ile
                155                 160                 165

Val Ser His Lys Pro Tyr Arg Gly Ala Pro Ala Asp Val Trp Ser
                170                 175                 180

Cys Gly Val Ile Leu Tyr Ser Leu Leu Ser Asn Lys Leu Pro Phe
                185                 190                 195

Gly Gly Gln Asn Thr Asp Val Ile Tyr Asn Lys Ile Arg His Gly
                200                 205                 210

Ala Tyr Asp Leu Pro Ser Ser Ile Ser Ser Ala Ala Gln Asp Leu
                215                 220                 225

Leu His Arg Met Leu Asp Val Asn Pro Ser Thr Arg Ile Thr Ile
                230                 235                 240

Pro Glu Phe Phe Ser His Pro Phe Leu Met Gly Cys
                245                 250

(2) INFORMATION FOR SEQ ID NO:27:

(i) SEQUENCE CHARACTERISTICS:
        (A) LENGTH: 260

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 30

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:27:

Gly Asp Trp Glu Phe Val Glu Thr Val Gly Ala Gly Ser Met Gly
                005                 010                 015

Lys Val Lys Leu Ala Lys His Arg Tyr Thr Asn Glu Val Cys Ala
                020                 025                 030

Val Lys Ile Val Asn Arg Ala Thr Lys Ala Phe Leu His Lys Glu
                035                 040                 045

Arg Asp Lys Arg Thr Ile Arg Glu Ala Ser Leu Gly Gln Ile Leu
                050                 055                 060

Tyr His Pro His Ile Cys Arg Leu Phe Glu Met Cys Thr Leu Ser
                065                 070                 075

Asn His Phe Tyr Met Leu Phe Glu Tyr Val Ser Gly Gly Gln Leu
                080                 085                 090

```
Leu His Tyr Ile Ile Gln His Gly Ser Ile Arg Glu His Gln Ala
                095                 100                 105

Arg Lys Phe Ala Arg Gly Ile Ala Ser Ala Leu Ile Tyr Leu His
                110                 115                 120

Ala Asn Asn Ile Val His Arg Asp Leu Lys Ile Glu Asn Ile Met
                125                 130                 135

Ile Ser Asp Ser Ser Glu Ile Lys Ile Ile Asp Phe Gly Leu Ser
                140                 145                 150

Asn Ile Tyr Asp Ser Arg Lys Gln Leu His Thr Phe Cys Gly Ser
                155                 160                 165

Leu Tyr Phe Ala Ala Pro Glu Leu Leu Lys Ala Asn Pro Tyr Thr
                170                 175                 180

Gly Pro Glu Val Asp Val Trp Ser Phe Gly Val Val Leu Phe Val
                185                 190                 195

Leu Val Cys Gly Lys Val Pro Phe Asp Asp Glu Asn Ser Ser Val
                200                 205                 210

Leu His Glu Lys Ile Lys Gln Gly Lys Val Glu Tyr Pro Gln His
                215                 220                 225

Leu Ser Ile Glu Val Ile Ser Leu Leu Ser Lys Met Leu Val Val
                230                 235                 240

Asp Pro Lys Arg Arg Ala Thr Leu Lys Gln Val Val Glu His His
                245                 250                 255

Trp Met Val Arg Gly
                260

(2) INFORMATION FOR SEQ ID NO:28:

(i) SEQUENCE CHARACTERISTICS:
        (A) LENGTH: 260

(B) TYPE: amino acid (D) TOPOLOGY: linear (ii) MOLECULE TYPE:
         (A) DESCRIPTION: protein (vi) ORIGINAL SOURCE:
         (A) ORGANISM: Saccharomyces cerevisiae (ix) FEATURE: Protein kinase; Table 8 Column 31

(x) PUBLICATION INFORMATION:
         (A) AUTHORS:

Hanks, S. K.
             Quinn, A. M.
             Hunter, T.
         (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:28:

Gly Asp Trp Glu Phe Leu Glu Thr Val Gly Ala Gly Ser Met Gly
                005                 010                 015
```

```
Lys Val Lys Leu Val Lys His Arg Gln Thr Lys Glu Ile Cys Val
            020                 025                 030

Ile Lys Ile Val Asn Arg Ala Ser Lys Ala Tyr Leu His Lys Gln
            035                 040                 045

Arg Asp Lys Arg Thr Val Arg Glu Ala Ser Leu Gly Gln Ile Leu
            050                 055                 060

Tyr His Pro His Ile Cys Arg Leu Phe Glu Met Cys Thr Met Ser
            065                 070                 075

Asn His Phe Tyr Met Leu Phe Glu Tyr Val Ser Gly Gly Gln Leu
            080                 085                 090

Leu His Tyr Ile Ile Gln His Gly Ser Leu Lys Glu His His Ala
            095                 100                 105

Arg Lys Phe Ala Arg Gly Ile Ala Ser Ala Leu Gln Tyr Leu His
            110                 115                 120

Ala Asn Asn Ile Val His Arg Asp Leu Lys Ile Glu Asn Ile Met
            125                 130                 135

Ile Ser Ser Ser Gly Glu Ile Lys Ile Ile Asp Phe Gly Leu Ser
            140                 145                 150

Asn Ile Phe Asp Tyr Arg Lys Gln Leu His Thr Phe Cys Gly Ser
            155                 160                 165

Leu Tyr Phe Ala Ala Pro Glu Leu Leu Lys Ala Gln Pro Tyr Thr
            170                 175                 180

Gly Pro Glu Val Asp Ile Trp Ser Phe Gly Ile Val Leu Tyr Val
            185                 190                 195

Leu Val Cys Gly Lys Val Pro Phe Asp Asp Glu Asn Ser Ser Ile
            200                 205                 210

Leu His Glu Lys Ile Lys Lys Gly Lys Val Asp Tyr Pro Ser His
            215                 220                 225

Leu Ser Ile Glu Val Ile Ser Leu Leu Thr Arg Met Ile Val Val
            230                 235                 240

Asp Pro Leu Arg Arg Ala Thr Leu Lys Asn Val Val Glu His Pro
            245                 250                 255

Trp Met Asn Arg Gly
            260

(2) INFORMATION FOR SEQ ID NO:29:

(i) SEQUENCE CHARACTERISTICS:
        (A) LENGTH: 274

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 33

(x) PUBLICATION INFORMATION:
        (A) AUTHORS:

Hanks, S. K.
            Quinn, A. M.
            Hunter, T.
        (B) TITLE: The protein kinase family
```

(C) JOURNAL: Science (D) VOLUME: 241

(F) PAGES: 42-52

(G) DATE: 1988

(xi) SEQUENCE DESCRIPTION: SEQ ID NO:29:

```
Ala Asn Tyr Lys Arg Leu Glu Lys Val Gly Glu Gly Thr Tyr Gly
                005                 010                 015

Val Val Tyr Lys Ala Leu Asp Leu Arg Pro Gly Gln Gly Gln Arg
                020                 025                 030

Val Val Ala Leu Lys Lys Ile Arg Leu Glu Ser Glu Asp Glu Gly
                035                 040                 045

Val Pro Ser Thr Ala Ile Arg Glu Ile Ser Leu Leu Lys Glu Leu
                050                 055                 060

Lys Asp Asp Asn Ile Val Arg Leu Tyr Asp Ile Val His Ser Asp
                065                 070                 075

Ala His Lys Leu Tyr Leu Val Phe Glu Phe Leu Asp Leu Asp Leu
                080                 085                 090

Lys Arg Tyr Met Glu Gly Ile Pro Lys Asp Gln Pro Leu Gly Ala
                095                 100                 105

Asp Ile Val Lys Lys Phe Met Met Gln Leu Cys Lys Gly Ile Ala
                110                 115                 120

Tyr Cys His Ser His Arg Ile Leu His Arg Asp Leu Lys Pro Gln
                125                 130                 135

Asn Leu Leu Ile Asn Lys Asp Gly Asn Leu Lys Leu Gly Asp Phe
                140                 145                 150

Gly Leu Ala Arg Ala Phe Gly Val Pro Leu Arg Ala Tyr Thr His
                155                 160                 165

Glu Ile Val Thr Leu Trp Tyr Arg Ala Pro Glu Val Leu Leu Gly
                170                 175                 180

Gly Lys Gln Tyr Ser Thr Gly Val Asp Ile Trp Ser Ile Gly Cys
                185                 190                 195

Ile Phe Ala Glu Met Cys Asn Arg Lys Pro Ile Phe Ser Gly Asp
                200                 205                 210

Ser Glu Ile Asp Gln Ile Phe Lys Ile Phe Arg Val Leu Gly Thr
                215                 220                 225

Pro Asn Glu Ala Ile Trp Pro Asp Ile Val Tyr Leu Pro Asp Leu
                230                 235                 240

Asp Pro Arg Gly Ile Asp Leu Leu Asp Lys Leu Leu Ala Tyr Asp
                245                 250                 255

Pro Ile Asn Arg Ile Ser Ala Arg Arg Ala Ala Ile His Pro Tyr
                260                 265                 270

Phe Gln Glu Ser
```

(2) INFORMATION FOR SEQ ID NO:30:

(i) SEQUENCE CHARACTERISTICS:
        (A) LENGTH: 274

(B) TYPE: amino acid (D) TOPOLOGY: linear (ii) MOLECULE TYPE:
        (A) DESCRIPTION: protein (vi) ORIGINAL SOURCE:
    (A) ORGANISM: Schizoaccharomyces pombe (ix) FEATURE: Protein kinase; Table 8 Column 34

(x) PUBLICATION INFORMATION:
    (A) AUTHORS:

Hanks, S. K.
        Quinn, A. M.
        Hunter, T.
    (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:30:

```
Glu Asn Tyr Gln Lys Val Glu Lys Ile Gly Glu Gly Thr Tyr Gly
            005                 010                 015

Val Val Tyr Lys Ala Arg His Lys Leu Ser Gly Arg Ile Val Ala
            020                 025                 030

Met Lys Lys Ile Arg Leu Glu Asp Glu Ser Glu Gly Val Pro Ser
            035                 040                 045

Thr Ala Ile Arg Glu Ile Ser Leu Leu Lys Glu Val Asn Asp Glu
            050                 055                 060

Asn Asn Arg Ser Asn Cys Val Arg Leu Leu Asp Ile Leu His Ala
            065                 070                 075

Glu Ser Lys Leu Tyr Leu Val Phe Glu Phe Leu Asp Met Asp Leu
            080                 085                 090

Lys Lys Tyr Met Asp Arg Ile Ser Glu Thr Gly Ala Leu Asp Pro
            095                 100                 105

Arg Leu Val Gln Lys Phe Thr Tyr Gln Leu Val Asn Gly Val Asn
            110                 115                 120

Phe Cys His Ser Arg Arg Ile Ile His Arg Asp Leu Lys Pro Gln
            125                 130                 135

Asn Leu Leu Ile Asp Lys Glu Gly Asn Leu Lys Leu Ala Asp Phe
            140                 145                 150

Gly Leu Ala Arg Ser Phe Gly Val Pro Leu Arg Asn Tyr Thr His
            155                 160                 165

Glu Ile Val Thr Leu Trp Tyr Arg Ala Pro Glu Val Leu Leu Gly
            170                 175                 180

Ser Arg His Tyr Ser Thr Gly Val Asp Ile Trp Ser Val Gly Cys
            185                 190                 195

Ile Phe Ala Glu Met Ile Arg Arg Ser Pro Leu Phe Pro Gly Asp
            200                 205                 210

Ser Glu Ile Asp Glu Ile Phe Lys Ile Phe Gln Val Leu Gly Thr
            215                 220                 225

Pro Asn Glu Glu Val Trp Pro Gly Val Thr Leu Leu Gln Asp Gly
            230                 235                 240

Glu Glu Asp Ala Ile Glu Leu Leu Ser Ala Met Leu Val Tyr Asp
            245                 250                 255

Pro Ala His Arg Ile Ser Ala Lys Arg Ala Leu Gln Gln Asn Tyr
            260                 265                 270
```

Leu Arg Asp Phe (2) INFORMATION FOR SEQ ID NO:31:

(i) SEQUENCE CHARACTERISTICS:
        (A) LENGTH: 270

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 35

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:31:

```
Glu Asp Tyr Thr Lys Ile Glu Lys Ile Gly Glu Gly Thr Tyr Gly
                005                 010                 015

Val Val Tyr Lys Gly Arg His Lys Thr Thr Gly Gln Val Val Ala
                020                 025                 030

Met Lys Lys Ile Arg Leu Glu Ser Glu Glu Glu Gly Val Pro Ser
                035                 040                 045

Thr Ala Ile Arg Glu Ile Ser Leu Leu Lys Glu Leu Arg His Pro
                050                 055                 060

Asn Ile Val Ser Leu Gln Asp Val Leu Met Gln Asp Ser Arg Leu
                065                 070                 075

Tyr Leu Ile Phe Glu Phe Leu Ser Met Asp Leu Lys Lys Tyr Leu
                080                 085                 090

Asp Ser Ile Pro Pro Gly Gln Tyr Met Asp Ser Ser Leu Val Lys
                095                 100                 105

Ser Tyr Leu Tyr Gln Ile Leu Gln Gly Ile Val Phe Cys His Ser
                110                 115                 120

Arg Arg Val Leu His Arg Asp Leu Lys Pro Gln Asn Leu Leu Ile
                125                 130                 135

Asp Asp Lys Gly Thr Ile Lys Leu Ala Asp Phe Gly Leu Ala Arg
                140                 145                 150

Ala Phe Gly Ile Pro Ile Arg Val Tyr Thr His Glu Val Val Thr
                155                 160                 165

Leu Trp Tyr Arg Ser Pro Glu Val Leu Leu Gly Ser Ala Arg Tyr
                170                 175                 180

Ser Thr Pro Val Asp Ile Trp Ser Ile Gly Thr Ile Phe Ala Glu
```

```
                    185                 190                 195
Leu Ala Thr Lys Lys Pro Leu Phe His Gly Asp Ser Glu Ile Asp
                    200                 205                 210

Gln Leu Phe Arg Ile Phe Arg Ala Leu Gly Thr Pro Asn Asn Glu
                    215                 220                 225

Val Trp Pro Glu Val Glu Ser Leu Gln Asp Leu Asp Glu Asn Gly
                    230                 235                 240

Leu Asp Leu Leu Ser Lys Met Leu Ile Tyr Asp Pro Ala Lys Arg
                    245                 250                 255

Ile Ser Gly Lys Met Ala Leu Asn His Pro Tyr Phe Asn Asp Leu
                    260                 265                 270
```

(2) INFORMATION FOR SEQ ID NO:32:

(i) SEQUENCE CHARACTERISTICS:
        (A) LENGTH: 278

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 36

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:32:

```
Ser Arg Tyr Glu Pro Val Ala Glu Ile Gly Val Gly Ala Tyr Gly
                    005                 010                 015

Thr Val Tyr Lys Ala Arg Asp Pro His Ser Gly His Phe Val Ala
                    020                 025                 030

Leu Lys Ser Val Arg Val Pro Asn Gly Gly Gly Gly Gly Gly Gly
                    035                 040                 045

Leu Pro Ile Ser Thr Val Arg Glu Val Ala Leu Leu Arg Arg Leu
                    050                 055                 060

Glu Ala Phe Glu His Pro Asn Val Val Arg Leu Met Asp Val Cys
                    065                 070                 075

Ala Thr Ser Arg Thr Asp Arg Glu Ile Lys Val Thr Leu Val Phe
                    080                 085                 090

Glu His Val Asp Gln Asp Leu Arg Thr Tyr Leu Asp Lys Ala Pro
                    095                 100                 105

Pro Pro Gly Leu Pro Ala Glu Thr Ile Lys Asp Leu Met Arg Gln
                    110                 115                 120
```

Phe Leu Arg Gly Leu Asp Phe Leu His Ala Asn Cys Ile Val His
                125                 130                 135

Arg Asp Leu Lys Pro Glu Asn Ile Leu Val Thr Ser Gly Gly Thr
                140                 145                 150

Val Lys Leu Ala Asp Phe Gly Leu Ala Arg Ile Tyr Ser Tyr Gln
                155                 160                 165

Met Ala Leu Thr Pro Val Val Thr Leu Trp Tyr Arg Ala Pro
                170                 175                 180

Glu Val Leu Leu Gln Ser Thr Tyr Ala Thr Pro Val Asp Met Trp
                185                 190                 195

Ser Val Gly Cys Ile Phe Ala Glu Met Phe Arg Arg Lys Pro Leu
                200                 205                 210

Phe Cys Gly Asn Ser Glu Ala Asp Gln Leu Gly Lys Ile Phe Asp
                215                 220                 225

Leu Ile Gly Leu Pro Pro Glu Asp Asp Trp Pro Arg Asp Val Ser
                230                 235                 240

Leu Pro Arg Met Glu Glu Ser Gly Ala Gln Leu Leu Leu Glu Met
                245                 250                 255

Leu Thr Phe Asn Pro His Lys Arg Ile Ser Ala Phe Arg Ala Leu
                260                 265                 270

Gln His Ser Tyr Leu His Lys Asp
                275

(2) INFORMATION FOR SEQ ID NO:33:

(i) SEQUENCE CHARACTERISTICS:
        (A) LENGTH: 268

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 37

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:33:

Met Glu Tyr Thr Lys Glu Lys Val Gly Glu Gly Thr Tyr Ala
                005                 010                 015

Val Val Tyr Leu Gly Cys Gln His Ser Thr Gly Arg Lys Ile Ala
                020                 025                 030

```
Ile Lys Glu Ile Lys Thr Ser Glu Phe Lys Asp Gly Leu Asp Met
            035                 040                 045

Ser Ala Ile Arg Glu Val Lys Tyr Leu Gln Glu Met Gln His Pro
            050                 055                 060

Asn Val Ile Glu Leu Ile Asp Ile Phe Met Ala Tyr Asp Asn Leu
            065                 070                 075

Asn Leu Val Leu Glu Phe Leu Pro Thr Asp Leu Glu Val Val Ile
            080                 085                 090

Lys Asp Lys Ser Ile Leu Phe Thr Pro Ala Asp Ile Lys Ala Trp
            095                 100                 105

Met Leu Met Thr Leu Arg Gly Val Tyr His Cys His Arg Asn Phe
            110                 115                 120

Ile Leu His Arg Asp Leu Lys Pro Asn Asn Leu Leu Phe Ser Pro
            125                 130                 135

Asp Gly Gln Ile Lys Val Ala Asp Phe Gly Leu Ala Arg Ala Ile
            140                 145                 150

Pro Ala Pro His Glu Ile Leu Thr Ser Asn Val Val Thr Arg Trp
            155                 160                 165

Tyr Arg Ala Pro Glu Leu Leu Phe Gly Ala Lys His Tyr Thr Ser
            170                 175                 180

Ala Ile Asp Ile Trp Ser Val Gly Val Ile Phe Ala Glu Leu Met
            185                 190                 195

Leu Arg Ile Pro Tyr Leu Pro Gly Gln Asn Asp Val Asp Gln Met
            200                 205                 210

Glu Val Thr Phe Arg Ala Leu Gly Thr Pro Thr Asp Arg Asp Trp
            215                 220                 225

Pro Glu Val Ser Ser Phe Met Thr Ala Ser Glu Tyr Ala Leu Asp
            230                 235                 240

Phe Met Cys Gly Met Leu Thr Met Asn Pro Gln Lys Arg Trp Thr
            245                 250                 255

Ala Val Gln Cys Leu Glu Ser Asp Tyr Phe Lys Glu Leu
            260                 265
```

(2) INFORMATION FOR SEQ ID NO:34:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: Drosophila melanogaster (ix) FEATURE: Protein kinase; Table 8 Column 39

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:34:

Asp Asp Tyr Gln Leu Val Arg Lys Leu Gly Arg Gly Lys Tyr Ser
                005                 010                 015

Glu Val Phe Glu Ala Ile Asn Ile Thr Thr Thr Glu Lys Cys Val
                020                 025                 030

Val Lys Ile Leu Lys Pro Val Lys Lys Lys Ile Lys Arg Glu
                035                 040                 045

Ile Lys Ile Leu Glu Asn Leu Arg Gly Gly Thr Asn Ile Ile Thr
                050                 055                 060

Leu Leu Ala Val Val Lys Asp Pro Val Ser Arg Thr Pro Ala Leu
                065                 070                 075

Ile Phe Glu His Val Asn Asn Thr Asp Phe Lys Gln Leu Tyr Gln
                080                 085                 090

Thr Leu Thr Asp Tyr Glu Ile Arg Tyr Tyr Leu Phe Glu Leu Leu
                095                 100                 105

Lys Ala Leu Asp Tyr Cys His Ser Met Gly Ile Met His Arg Asp
                110                 115                 120

Val Lys Pro His Asn Val Met Ile Asp His Glu Asn Arg Lys Leu
                125                 130                 135

Arg Leu Ile Asp Trp Gly Leu Ala Glu Phe Tyr His Pro Gly Gln
                140                 145                 150

Glu Tyr Asn Val Arg Val Ala Ser Arg Tyr Phe Lys Gly Pro Glu
                155                 160                 165

Leu Leu Val Asp Tyr Gln Met Tyr Asp Tyr Ser Leu Asp Met Trp
                170                 175                 180

Ser Leu Gly Cys Met Leu Ala Ser Met Ile Phe Arg Lys Phe Pro
                185                 190                 195

Phe Phe His Gly His Asp Asn Tyr Asp Gln Leu Val Arg Ile Ala
                200                 205                 210

Lys Val Leu Gly Thr Glu Glu Leu Tyr Ala Tyr Leu Asp Lys Tyr
                215                 220                 225

Asn Ile Asp Leu Val Ser Pro Glu Ala Leu Asp Phe Leu Asp Lys
                230                 235                 240

Leu Leu Arg Tyr Asp His Val Asp Arg Leu Thr Ala Arg Glu Ala
                245                 250                 255

Met Ala His Pro Tyr Phe Leu Pro Ile
                260

(2) INFORMATION FOR SEQ ID NO:35:

(i) SEQUENCE CHARACTERISTICS:
        (A) LENGTH: 276

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 40

(x) PUBLICATION INFORMATION:
    (A) AUTHORS:

Hanks, S. K.
        Quinn, A. M.
        Hunter, T.
    (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:35:

Asn Glu Tyr Lys Leu Ile Asp Lys Ile Gly Glu Gly Thr Phe Ser
              005                 010                 015

Ser Val Tyr Lys Ala Lys Asp Ile Thr Gly Lys Ile Thr Lys Lys
              020                 025                 030

Phe Ala Ser His Phe Trp Asn Tyr Gly Ser Asn Tyr Val Ala Leu
              035                 040                 045

Lys Lys Ile Tyr Val Thr Ser Ser Pro Gln Arg Ile Tyr Asn Glu
              050                 055                 060

Leu Asn Leu Leu Tyr Ile Met Thr Gly Ser Ser Arg Val Ala Pro
              065                 070                 075

Leu Cys Asp Ala Lys Arg Val Arg Asp Gln Val Ile Ala Val Leu
              080                 085                 090

Pro Tyr Tyr Pro His Glu Glu Phe Arg Thr Phe Tyr Arg Asp Leu
              095                 100                 105

Pro Ile Lys Gly Ile Lys Lys Tyr Ile Trp Glu Leu Leu Arg Ala
              110                 115                 120

Leu Lys Phe Val His Ser Lys Gly Ile Ile His Arg Asp Ile Lys
              125                 130                 135

Pro Thr Asn Phe Leu Phe Asn Leu Glu Leu Gly Arg Gly Val Leu
              140                 145                 150

Val Asp Phe Gly Leu Ala Glu Ala Gln Met Asp Tyr Lys Ser Met
              155                 160                 165

Ile Ser Ala Asn Arg Ala Gly Thr Arg Gly Phe Arg Ala Pro Glu
              170                 175                 180

Val Leu Met Lys Cys Gly Ala Gln Ser Thr Lys Ile Asp Ile Trp
              185                 190                 195

Ser Val Gly Val Ile Leu Leu Ser Leu Leu Gly Arg Arg Phe Pro
              200                 205                 210

Met Phe Gln Ser Leu Asp Asp Ala Asp Ser Leu Leu Glu Leu Cys
              215                 220                 225

Thr Ile Phe Gly Trp Lys Glu Leu Arg Lys Cys Ala Ala Leu His
              230                 235                 240

Gly Asp His Tyr Trp Cys Phe Gln Val Leu Glu Gln Cys Phe Glu
              245                 250                 255

Met Asp Pro Gln Lys Arg Ser Ser Ala Glu Asp Leu Leu Lys Thr
              260                 265                 270

Pro Phe Phe Asn Glu Leu
              275

(2) INFORMATION FOR SEQ ID NO:36:

(i) SEQUENCE CHARACTERISTICS:
        (A) LENGTH: 270

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 41

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:36:

```
Gln Asp Leu Val Gln Leu Gly Lys Ile Gly Ala Gly Asn Ser Gly
            005                 010                 015

Thr Val Val Lys Ala Leu His Val Pro Asp Ser Lys Ile Val Ala
            020                 025                 030

Lys Lys Thr Ile Pro Val Glu Gln Asn Asn Ser Thr Ile Ile Asn
            035                 040                 045

Gln Leu Val Arg Glu Leu Ser Ile Val Lys Asn Val Lys Pro His
            050                 055                 060

Glu Asn Ile Ile Thr Phe Tyr Gly Ala Tyr Tyr Asn Gln His Ile
            065                 070                 075

Asn Asn Glu Ile Ile Ile Leu Met Glu Tyr Ser Asp Cys Gly Ser
            080                 085                 090

Leu Asp Lys Ile Leu Ser Val Tyr Lys Arg Phe Val Gln Phe Asn
            095                 100                 105

Glu Leu Thr Ile Ser Lys Ile Ala Tyr Gly Val Leu Asn Gly Leu
            110                 115                 120

Asp His Leu Tyr Arg Gln Lys Ile Ile His Arg Asp Ile Lys Pro
            125                 130                 135

Ser Asn Val Leu Ile Asn Ser Lys Gly Gln Ile Lys Leu Cys Asp
            140                 145                 150

Phe Gly Val Ser Lys Lys Leu Ile Asn Ser Ile Ala Asp Thr Phe
            155                 160                 165

Val Gly Thr Ser Thr Tyr Met Ser Pro Glu Arg Ile Gln Gly Asn
            170                 175                 180

Val Tyr Ser Ile Lys Gly Asp Val Trp Ser Leu Gly Leu Met Ile
            185                 190                 195

Ile Glu Leu Val Thr Gly Glu Phe Pro Leu Gly Gly His Asn Asp
            200                 205                 210
```

Thr Pro Asp Gly Ile Leu Asp Leu Leu Gln Arg Ile Val Asn Glu
                215                 220                 225

Pro Ser Pro Arg Leu Pro Lys Asp Arg Ile Tyr Ser Lys Glu Met
                230                 235                 240

Thr Asp Phe Val Asn Arg Cys Cys Ile Lys Asn Glu Arg Glu Arg
                245                 250                 255

Ser Ser Ile His Glu Leu Leu His His Asp Leu Ile Met Lys Tyr
                260                 265                 270

(2) INFORMATION FOR SEQ ID NO:37:

(i) SEQUENCE CHARACTERISTICS:
        (A) LENGTH: 267

(B) TYPE: amino acid (D) TOPOLOGY: linear (ii) MOLECULE TYPE:
        (A) DESCRIPTION: protein (vi) ORIGINAL SOURCE:
        (A) ORGANISM: mouse (ix) FEATURE: Protein kinase; Table 8 Column 42

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:37:

Asp Glu Leu Glu Phe Leu Asp Glu Leu Gly His Gly Asn Tyr Gly
                005                 010                 015

Asn Val Ser Lys Val Leu His Lys Pro Thr Asn Val Ile Met Ala
                020                 025                 030

Thr Lys Glu Val Arg Leu Glu Leu Asp Glu Ala Lys Phe Arg Gln
                035                 040                 045

Ile Leu Met Glu Leu Glu Val Leu His Lys Cys Asn Ser Pro Tyr
                050                 055                 060

Ile Val Asp Phe Tyr Gly Ala Phe Phe Ile Glu Gly Ala Val Tyr
                065                 070                 075

Met Cys Met Glu Tyr Met Asp Gly Gly Ser Leu Asp Lys Ile Tyr
                080                 085                 090

Asp Glu Ser Ser Glu Ile Gly Gly Ile Asp Glu Pro Gln Leu Ala
                095                 100                 105

Phe Ile Ala Asn Ala Val Ile His Gly Leu Lys Glu Leu Lys Glu
                110                 115                 120

Gln Asn Ile Ile His Arg Asp Val Lys Pro Thr Asn Ile Leu Cys
                125                 130                 135

```
Ser Ala Asn Gln Gly Thr Val Lys Leu Cys Asp Phe Gly Val Ser
                140                 145                 150
Gly Asn Leu Val Ala Ser Leu Ala Lys Thr Asn Ile Gly Cys Gln
                155                 160                 165
Ser Tyr Met Ala Pro Glu Arg Ile Lys Ser Leu Asn Asp Arg Ala
                170                 175                 180
Thr Tyr Thr Val Gln Ser Asp Ile Trp Ser Leu Gly Leu Ser Ile
                185                 190                 195
Leu Glu Met Ala Leu Gly Arg Tyr Pro Tyr Pro Pro Glu Thr Tyr
                200                 205                 210
Asp Asn Ile Phe Ser Gln Leu Ser Ala Ile Val Asp Gly Pro Pro
                215                 220                 225
Pro Arg Leu Pro Ser Asp Lys Phe Ser Ser Asp Ala Gln Asp Phe
                230                 235                 240
Val Ser Leu Cys Leu Gln Lys Ile Pro Glu Arg Arg Pro Thr Tyr
                245                 250                 255
Ala Ala Leu Thr Glu His Pro Trp Leu Val Lys Tyr
                260                 265

(2) INFORMATION FOR SEQ ID NO:38:

(i) SEQUENCE CHARACTERISTICS:
        (A) LENGTH: 269

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 43

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:38:

Thr Arg Phe Arg Asn Val Thr Leu Leu Gly Ser Gly Glu Phe Ser
                005                 010                 015
Glu Val Phe Gln Val Glu Asp Pro Val Glu Lys Thr Leu Lys Tyr
                020                 025                 030
Ala Val Lys Lys Leu Lys Val Lys Phe Ser Gly Pro Lys Glu Arg
                035                 040                 045
Asn Arg Leu Leu Gln Glu Val Ser Ile Gln Arg Ala Leu Lys Gly
                050                 055                 060
His Asp His Ile Val Glu Leu Met Asp Ser Trp Glu His Gly Gly
```

```
                    065                 070                 075
Phe Leu Tyr Met Gln Val Glu Leu Cys Glu Asn Gly Ser Leu Asp
                080                 085                 090
Arg Phe Leu Glu Glu Gln Gly Gln Leu Ser Arg Leu Asp Glu Phe
                095                 100                 105
Arg Val Trp Lys Ile Leu Val Glu Val Ala Leu Gly Leu Gln Phe
                110                 115                 120
Ile His His Lys Asn Tyr Val His Leu Asp Leu Lys Pro Ala Asn
                125                 130                 135
Val Met Ile Thr Phe Glu Gly Thr Leu Lys Ile Gly Asp Phe Gly
                140                 145                 150
Met Ala Ser Val Trp Pro Val Pro Arg Gly Met Glu Arg Glu Gly
                155                 160                 165
Asp Cys Glu Tyr Ile Ala Pro Glu Val Leu Ala Asn His Leu Tyr
                170                 175                 180
Asp Lys Pro Ala Asp Ile Trp Ser Leu Gly Ile Thr Val Phe Glu
                185                 190                 195
Ala Ala Ala Asn Ile Val Leu Pro Asp Asn Gly Gln Ser Trp Gln
                200                 205                 210
Lys Leu Arg Ser Gly Asp Leu Ser Asp Ala Pro Arg Leu Ser Ser
                215                 220                 225
Thr Asp Asn Gly Ser Ser Leu Gly Gln Gly Gly Leu Asp Arg Val
                230                 235                 240
Val Glu Trp Met Leu Ser Pro Glu Pro Arg Asn Arg Pro Thr Ile
                245                 250                 255
Asp Gln Ile Leu Ala Thr Asp Glu Val Cys Trp Val Glu Met
                260                 265
```

(2) INFORMATION FOR SEQ ID NO:39:

(i) SEQUENCE CHARACTERISTICS:
        (A) LENGTH: 266

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 44

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:39:

Met Gly Phe Thr Ile His Gly Ala Leu Thr Pro Gly Ser Glu Gly
                005                 010                 015

Cys Val Phe Asp Ser Ser His Pro Asp Tyr Pro Gln Arg Val Ile
                020                 025                 030

Val Lys Ala Gly Trp Tyr Thr Ser Thr Ser His Glu Ala Arg Leu
                035                 040                 045

Leu Arg Arg Leu Asp His Pro Ala Ile Leu Pro Leu Leu Asp Leu
                050                 055                 060

His Val Val Ser Gly Val Thr Cys Leu Val Leu Pro Lys Tyr Gln
                065                 070                 075

Ala Asp Leu Tyr Thr Tyr Leu Ser Arg Arg Leu Asn Pro Leu Gly
                080                 085                 090

Arg Pro Gln Ile Ala Ala Val Ser Arg Gln Leu Leu Ser Ala Val
                095                 100                 105

Asp Tyr Ile His Arg Gln Gly Ile Ile His Arg Asp Ile Lys Thr
                110                 115                 120

Glu Asn Ile Phe Ile Asn Thr Pro Glu Asp Ile Cys Leu Gly Asp
                125                 130                 135

Phe Gly Ala Ala Cys Phe Val Gln Gly Ser Arg Ser Ser Pro Phe
                140                 145                 150

Tyr Gly Ile Ala Gly Thr Ile Asp Thr Asn Ala Pro Glu Val Leu
                155                 160                 165

Ala Gly Asp Pro Tyr Thr Thr Thr Val Asp Ile Trp Ser Ala Gly
                170                 175                 180

Leu Val Ile Phe Glu Thr Ala Val His Asn Ala Ser Leu Phe Ser
                185                 190                 195

Ala Pro Arg Gly Pro Lys Arg Gly Pro Cys Ser Gln Ile Thr Arg
                200                 205                 210

Ile Ile Arg Gln Ala Gln Val His Val Asp Glu Phe Ser Pro His
                215                 220                 225

Pro Glu Ser Arg Leu Thr Met Asp Ile Asp Val Glu Tyr Leu Val
                230                 235                 240

Cys Lys Ala Leu Thr Phe Asp Gly Ala Leu Arg Pro Ser Ala Ala
                245                 250                 255

Glu Leu Leu Cys Leu Pro Leu Phe Gln Gln Lys
                260                 265

(2) INFORMATION FOR SEQ ID NO:40:

(i) SEQUENCE CHARACTERISTICS:
        (A) LENGTH: 266

(B) TYPE: amino acid (D) TOPOLOGY: linear (ii) MOLECULE TYPE:
        (A) DESCRIPTION: protein (vi) ORIGINAL SOURCE:
        (A) ORGANISM: mouse (ix) FEATURE: Protein kinase; Table 8 Column 45

(x) PUBLICATION INFORMATION:
        (A) AUTHORS:

Hanks, S. K.

Quinn, A. M.
                Hunter, T.
            (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:40:

Gly Ser Leu Arg Phe Val Ser Ile Ile Gly Ala Gly Ala Tyr Gly
                005                 010                 015

Val Val Tyr Lys Ala Glu Asp Ile Tyr Asp Gly Thr Leu Tyr Ala
                020                 025                 030

Val Lys Ala Leu Cys Lys Asp Gly Leu Asn Glu Lys Gln Lys Lys
                035                 040                 045

Leu Gln Ala Arg Glu Leu Ala Leu His Ala Arg Val Ser Ser His
                050                 055                 060

Pro Tyr Ile Ile Thr Leu His Arg Val Leu Glu Thr Glu Asp Ala
                065                 070                 075

Ile Tyr Val Val Leu Gln Tyr Cys Pro Asn Gly Asp Leu Phe Thr
                080                 085                 090

Tyr Ile Thr Glu Lys Lys Val Tyr Gln Gly Asn Ser His Leu Ile
                095                 100                 105

Lys Thr Val Phe Leu Gln Leu Ile Ser Ala Val Glu His Cys His
                110                 115                 120

Ser Val Gly Ile Tyr His Arg Asp Leu Lys Pro Glu Asn Ile Met
                125                 130                 135

Val Gly Asn Asp Gly Asn Thr Val Tyr Leu Ala Asp Phe Gly Leu
                140                 145                 150

Ala Thr Thr Glu Pro Tyr Ser Ser Asp Phe Gly Cys Gly Ser Leu
                155                 160                 165

Phe Tyr Met Ser Pro Glu Cys Gln Arg Glu Val Lys Ser Ser Ser
                170                 175                 180

Phe Ala Thr Ala Pro Asn Asp Val Trp Ala Leu Gly Ile Ile Leu
                185                 190                 195

Ile Asn Leu Cys Cys Lys Arg Asn Pro Trp Lys Arg Ala Cys Ser
                200                 205                 210

Gln Thr Asp Gly Thr Tyr Arg Ser Tyr Val His Asn Pro Ser Thr
                215                 220                 225

Leu Leu Ser Ile Leu Pro Ile Ser Arg Glu Leu Asn Ser Leu Leu
                230                 235                 240

Asn Arg Ile Phe Asp Arg Asn Pro Lys Thr Arg Ile Thr Leu Pro
                245                 250                 255

Glu Leu Ser Thr Leu Val Ser Asn Cys Lys Asn
                260                 265

(2) INFORMATION FOR SEQ ID NO:41:

(i) SEQUENCE CHARACTERISTICS:
        (A) LENGTH: 257

(B) TYPE: amino acid (D) TOPOLOGY: linear

```
    (ii) MOLECULE TYPE:
         (A) DESCRIPTION: protein (vi) ORIGINAL SOURCE:
         (A) ORGANISM: rat (ix) FEATURE: Protein kinase; Table 8 Column 46

(x) PUBLICATION INFORMATION:
         (A) AUTHORS:

Hanks, S. K.
              Quinn, A. M.
              Hunter, T.
         (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:41:

Ser Gln Tyr Gln Val Gly Pro Leu Leu Gly Ser Gly Gly Phe Gly
            005                 010                 015

Ser Val Tyr Ser Gly Ile Arg Val Ala Asp Asn Leu Pro Val Ala
            020                 025                 030

Ile Lys His Val Glu Lys Asp Arg Ile Ser Asp Trp Gly Glu Asn
            035                 040                 045

Gly Thr Arg Val Pro Met Glu Val Val Leu Leu Lys Lys Val Ser
            050                 055                 060

Ser Asp Phe Ser Gly Val Ile Arg Leu Leu Asp Trp Phe Glu Arg
            065                 070                 075

Pro Asp Ser Phe Val Leu Ile Leu Glu Arg Pro Glu Pro Val Gln
            080                 085                 090

Asp Leu Phe Asp Phe Ile Thr Glu Arg Gly Ala Leu Gln Glu Asp
            095                 100                 105

Leu Ala Arg Gly Phe Phe Trp Gln Val Leu Glu Ala Val Arg His
            110                 115                 120

Cys His Asn Cys Gly Val Leu His Arg Asp Ile Lys Asp Glu Asn
            125                 130                 135

Ile Leu Ile Asp Leu Ser Arg Gly Glu Ile Lys Leu Ile Asp Phe
            140                 145                 150

Gly Ser Gly Ala Leu Leu Lys Asp Thr Val Tyr Thr Asp Phe Asp
            155                 160                 165

Gly Thr Arg Val Tyr Ser Pro Pro Glu Trp Ile Arg Tyr His Arg
            170                 175                 180

Tyr His Gly Arg Ser Ala Ala Val Trp Ser Leu Gly Ile Leu Leu
            185                 190                 195

Tyr Asp Met Val Cys Gly Asp Ile Pro Phe Asp Glu His Asp Glu
            200                 205                 210

Glu Ile Ile Lys Gly Gln Val Phe Phe Arg Gln Thr Val Ser Ser
            215                 220                 225

Glu Cys Gln His Leu Ile Lys Trp Cys Leu Ser Leu Arg Pro Ser
            230                 235                 240

Asp Arg Pro Ser Phe Glu Glu Ile Arg Asn His Pro Trp Met Gln
            245                 250                 255
```

Gly Asp (2) INFORMATION FOR SEQ ID NO:42:

(i) SEQUENCE CHARACTERISTICS:
        (A) LENGTH: 267

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 48

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:42:

```
Ser Glu Val Met Leu Ser Thr Arg Ile Gly Ser Gly Ser Phe Gly
                005                 010                 015

Thr Val Tyr Lys Gly Lys Trp His Gly Asp Val Ala Val Lys Ile
                020                 025                 030

Leu Lys Val Val Asp Pro Thr Pro Glu Leu Gln Phe Gln Ala Phe
                035                 040                 045

Arg Asn Glu Val Ala Val Leu Arg Lys Thr Arg His Val Asn Ile
                050                 055                 060

Leu Leu Phe Met Gly Tyr Met Thr Lys Asp Asn Leu Ala Ile Val
                065                 070                 075

Thr Gln Trp Cys Glu Gly Ser Ser Leu Tyr Lys His Leu His Val
                080                 085                 090

Gln Glu Thr Lys Phe Gln Met Phe Gln Leu Ile Asp Ile Ala Arg
                095                 100                 105

Gln Thr Ala Gln Gly Met Asp Tyr Leu His Ala Lys Asn Ile Ile
                110                 115                 120

His Arg Asp Met Lys Ser Asn Asn Ile Phe Leu His Glu Gly Leu
                125                 130                 135

Thr Val Lys Ile Gly Asp Phe Gly Leu Ala Thr Val Lys Ser Arg
                140                 145                 150

Trp Ser Gly Ser Gln Gln Glu Gln Pro Thr Gly Ser Val Leu Trp
                155                 160                 165

Met Ala Pro Glu Val Ile Arg Met Gln Asp Asn Asn Pro Phe Ser
                170                 175                 180

Phe Gln Ser Asp Val Tyr Ser Tyr Gly Ile Val Leu Tyr Glu Leu
                185                 190                 195
```

Met Thr Gly Glu Leu Pro Tyr Ser His Ile Asn Asn Arg Asp Gln
            200                 205                 210

Ile Ile Phe Met Val Gly Arg Gly Tyr Ala Ser Pro Asp Leu Ser
            215                 220                 225

Lys Leu Tyr Lys Asn Cys Pro Lys Ala Met Lys Arg Leu Val Ala
            230                 235                 240

Asp Cys Val Lys Val Lys Glu Glu Arg Pro Leu Phe Pro Gln
            245                 250                 255

Ile Leu Ser Ser Ile Glu Leu Leu Gln His Ser Leu
            260                 265

(2) INFORMATION FOR SEQ ID NO:43:

(i) SEQUENCE CHARACTERISTICS:
        (A) LENGTH: 266

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 49

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:43:

Ser Glu Val Gln Leu Leu Lys Arg Ile Gly Thr Gly Ser Phe Gly
            005                 010                 015

Thr Val Phe Arg Gly Arg Trp His Gly Asp Val Ala Val Lys Val
            020                 025                 030

Leu Lys Val Ser Gln Pro Thr Ala Glu Gln Ala Gln Ala Phe Lys
            035                 040                 045

Asn Glu Met Gln Val Leu Arg Lys Thr Arg His Val Asn Ile Leu
            050                 055                 060

Leu Phe Met Gly Phe Met Thr Arg Pro Gly Phe Ala Ile Ile Thr
            065                 070                 075

Gln Trp Cys Glu Gly Ser Ser Leu Tyr His His Leu His Val Ala
            080                 085                 090

Asp Thr Arg Phe Asp Met Val Gln Leu Ile Asp Val Ala Arg Gln
            095                 100                 105

Thr Ala Gln Gly Met Asp Tyr Leu His Ala Lys Asn Ile Ile His
            110                 115                 120

5,958,784

229                                                                                           230

-continued

```
Arg Asp Leu Lys Ser Asn Asn Ile Phe Leu His Glu Gly Leu Thr
            125                 130                 135

Val Lys Ile Gly Asp Phe Gly Leu Ala Thr Val Lys Thr Arg Trp
            140                 145                 150

Ser Gly Ala Gln Pro Glu Gln Pro Ser Gly Ser Val Leu Trp Met
            155                 160                 165

Ala Ala Glu Val Ile Arg Met Gln Asp Pro Asn Pro Tyr Ser Phe
            170                 175                 180

Gln Ser Asp Val Tyr Ala Tyr Gly Val Leu Tyr Glu Leu Met
            185                 190                 195

Thr Gly Ser Leu Pro Tyr Ser His Ile Gly Cys Arg Asp Gln Ile
            200                 205                 210

Ile Phe Met Val Gly Arg Gly Tyr Leu Ser Pro Asp Leu Ser Lys
            215                 220                 225

Ile Ser Ser Asn Cys Pro Lys Ala Met Arg Arg Leu Leu Ser Asp
            230                 235                 240

Cys Leu Lys Phe Gln Arg Glu Glu Arg Pro Leu Phe Pro Gln Ile
            245                 250                 255

Leu Ala Thr Ile Glu Leu Leu Gln Arg Ser Leu
            260                 265
```

(2) INFORMATION FOR SEQ ID NO:44:

(i) SEQUENCE CHARACTERISTICS:
        (A) LENGTH: 266

(B) TYPE: amino acid (D) TOPOLOGY: linear (ii) MOLECULE TYPE:
        (A) DESCRIPTION: protein (vi) ORIGINAL SOURCE:
        (A) ORGANISM: Saccharomyces cerevisiae (ix) FEATURE: Protein kinase; Table 8 Column 50

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:44:

```
Ser Glu Val Gln Leu Leu Lys Arg Ile Gly Thr Gly Ser Phe Gly
            005                 010                 015

Thr Val Phe Arg Gly Arg Trp His Gly Asp Val Ala Val Lys Val
            020                 025                 030

Leu Lys Val Ser Gln Pro Thr Ala Glu Gln Ala Gln Ala Phe Lys
            035                 040                 045

Asn Glu Met Gln Val Leu Arg Lys Thr Arg His Val Asn Ile Leu
```

```
                       050                 055                 060
Pro Phe Met Gly Phe Met Thr Arg Pro Gly Val Ala Ile Ile Thr
                065                 070                 075
Gln Trp Cys Glu Gly Ser Ser Leu Tyr His His Leu His Val Ala
                080                 085                 090
Asp Thr Arg Phe Asp Met Val Gln Leu Ile Asp Val Ala Arg Gln
                095                 100                 105
Thr Ala Gln Gly Met Asp Tyr Leu His Ala Lys Asn Ile Ile His
                110                 115                 120
Arg Asp Leu Lys Ser Asn Asn Ile Phe Leu His Glu Gly Leu Thr
                125                 130                 135
Val Lys Ile Gly Asp Phe Gly Leu Ala Thr Val Lys Thr Arg Trp
                140                 145                 150
Ser Gly Ala Gln Pro Glu Gln Pro Ser Gly Pro Val Leu Trp Met
                155                 160                 165
Ala Ala Glu Val Thr Arg Met Gln Asp Pro Asn Pro Tyr Ser Phe
                170                 175                 180
Gln Ser Asp Val Tyr Ala Tyr Gly Val Val Leu Tyr Glu Leu Met
                185                 190                 195
Thr Gly Ser Leu Pro Tyr Ser His Ile Gly Cys Arg Asp Gln Ile
                200                 205                 210
Ile Phe Met Val Gly Arg Gly Tyr Leu Ser Pro Asp Leu Ser Lys
                215                 220                 225
Ile Ser Ser Asn Cys Pro Lys Ala Met Arg Arg Leu Leu Ser Asp
                230                 235                 240
Cys Leu Lys Phe Gln Arg Glu Glu Arg Pro Leu Phe Pro Gln Ile
                245                 250                 255
Leu Ala Thr Ile Glu Leu Leu Gln Arg Ser Leu
                260                 265
```

(2) INFORMATION FOR SEQ ID NO:45:

(i) SEQUENCE CHARACTERISTICS:
      (A) LENGTH: 267

(B) TYPE: amino acid (D) TOPOLOGY: linear (ii) MOLECULE TYPE:
      (A) DESCRIPTION: protein (vi) ORIGINAL SOURCE:
      (A) ORGANISM: Schizosaccharomyces pombe (ix) FEATURE: Protein kinase; Table 8 Column 51

(x) PUBLICATION INFORMATION:
      (A) AUTHORS:

Hanks, S. K.
          Quinn, A. M.
          Hunter, T.
      (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:45:

Ser Glu Val Gln Leu Leu Lys Arg Ile Gly Thr Gly Ser Phe Gly
                005                 010                 015

Thr Val Phe Arg Gly Leu Trp His Gly Asp Val Ala Val Lys Val
                020                 025                 030

Leu Lys Val Ala Gln Pro Thr Ala Glu Gln Ala Gln Ala Phe Lys
                035                 040                 045

Asn Glu Met Gln Val Leu Arg Lys Thr Arg His Val Asn Ile Leu
                050                 055                 060

Leu Phe Met Gly Phe Met Thr Arg Pro Gly Phe Ala Ile Ile Thr
                065                 070                 075

Gln Trp Cys Glu Gly Ser Ser Leu Tyr His His Leu His Val Ala
                080                 085                 090

Asp Thr Arg Phe Asp Met Val Gln Leu Ile Asp Val Ala Arg Gln
                095                 100                 105

Thr Ala Gln Gly Met Asp Tyr Leu His Ala Lys Asn Ile Ile His
                110                 115                 120

Arg Asp Leu Lys Ser Asn Asn Ile Phe Leu His Glu Gly Leu Thr
                125                 130                 135

Val Lys Ile Gly Asp Phe Gly Leu Ala Thr Val Lys Thr Arg Trp
                140                 145                 150

Ser Gly Ala Gln Pro Glu Gln Pro Ser Gly Ser Val Leu Trp Met
                155                 160                 165

Ala Ala Glu Val Ile Arg Met Gln Asp Pro Asn Pro Tyr Ser Phe
                170                 175                 180

Gln Ser Asp Val Tyr Ala Tyr Gly Val Val Leu Tyr Glu Leu Met
                185                 190                 195

Thr Gly Ser Leu Pro Tyr Ser His Ile Gly Ser Arg Asp Gln Ile
                200                 205                 210

Ile Phe Met Val Gly Arg Gly Tyr Leu Ser Pro Asp Leu Ser Lys
                215                 220                 225

Ile Phe Ser Asn Cys Pro Lys Ala Met Arg Arg Leu Leu Thr Asp
                230                 235                 240

Cys Leu Lys Phe Gln Arg Glu Glu Arg Pro Leu Phe Pro Gln Ile
                245                 250                 255

Leu Ala Thr Ile Glu Glu Leu Leu Gln Arg Ser Leu
                260                 265

(2) INFORMATION FOR SEQ ID NO:46:

(i) SEQUENCE CHARACTERISTICS:
        (A) LENGTH: 271

(B) TYPE: amino acid (D) TOPOLOGY: linear (ii) MOLECULE TYPE:
        (A) DESCRIPTION: protein (vi) ORIGINAL SOURCE:
        (A) ORGANISM: Schizosaccharomyces pombe (ix) FEATURE: Protein kinase; Table 8 Column 52

(x) PUBLICATION INFORMATION:

(A) AUTHORS:

Hanks, S. K.
  Quinn, A. M.
  Hunter, T.

(B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:46:

```
Glu Gln Val Cys Leu Leu Gln Arg Leu Gly Ala Gly Gly Phe Gly
            005                 010                 015

Ser Val Tyr Lys Ala Thr Tyr Arg Gly Val Pro Val Ala Ile Lys
            020                 025                 030

Gln Val Asn Lys Cys Thr Lys Asn Arg Leu Ala Ser Arg Arg Ser
            035                 040                 045

Phe Trp Ala Glu Leu Asn Val Ala Arg Leu Arg His Asp Asn Ile
            050                 055                 060

Val Arg Val Val Ala Ala Ser Thr Arg Thr Pro Ala Gly Ser Asn
            065                 070                 075

Ser Leu Gly Thr Ile Ile Met Glu Phe Gly Gly Asn Val Thr Leu
            080                 085                 090

His Gln Val Ile Tyr Gly Ala Ala Gly His Pro Glu Leu Ser Leu
            095                 100                 105

Gly Lys Cys Leu Lys Tyr Ser Leu Asp Val Val Asn Gly Leu Leu
            110                 115                 120

Phe Leu His Ser Gln Ser Ile Val His Leu Asp Leu Lys Pro Ala
            125                 130                 135

Asn Ile Leu Ile Ser Glu Gln Asp Val Cys Lys Ile Ser Asp Phe
            140                 145                 150

Gly Cys Ser Glu Lys Leu Glu Asp Leu Leu Cys Phe Gln Thr Tyr
            155                 160                 165

Pro Leu Gly Gly Thr Tyr Thr His Arg Ala Pro Glu Leu Leu Lys
            170                 175                 180

Gly Glu Gly Val Thr Pro Lys Ala Asp Ile Tyr Ser Phe Ala Ile
            185                 190                 195

Thr Leu Trp Gln Met Thr Thr Lys Gln Ala Pro Tyr Ser Gly Glu
            200                 205                 210

Arg Gln His Ile Leu Tyr Ala Val Val Ala Tyr Asp Leu Arg Pro
            215                 220                 225

Ser Leu Ser Ala Ala Val Phe Glu Asp Pro Gly Gln Arg Leu Gly
            230                 235                 240

Asp Val Ile Gln Arg Cys Trp Arg Pro Ser Ala Ala Gln Arg Pro
            245                 250                 255

Ser Ala Arg Leu Leu Leu Val Asp Leu Thr Ser Leu Lys Ala Glu
            260                 265                 270

Leu
```

(2) INFORMATION FOR SEQ ID NO:47:

(i) SEQUENCE CHARACTERISTICS:
    (A) LENGTH: 271

(B) TYPE: amino acid (D) TOPOLOGY: linear (ii) MOLECULE TYPE:
    (A) DESCRIPTION: protein (vi) ORIGINAL SOURCE:
    (A) ORGANISM: mouse (ix) FEATURE: Protein kinase; Table 8 Column 53

(x) PUBLICATION INFORMATION:
    (A) AUTHORS:

Hanks, S. K.
        Quinn, A. M.
        Hunter, T.
    (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:47:

```
Glu Gln Val Cys Leu Met His Arg Leu Gly Ser Gly Gly Phe Gly
                005                 010                 015

Ser Val Tyr Lys Ala Thr Tyr His Gly Val Pro Val Ala Ile Lys
                020                 025                 030

Gln Val Asn Lys Cys Thr Lys Asp Leu Arg Ala Ser Gln Arg Ser
                035                 040                 045

Phe Trp Ala Glu Leu Asn Ile Ala Arg Leu Arg His Asp Asn Ile
                050                 055                 060

Val Arg Val Val Ala Ala Ser Thr Arg Thr Pro Glu Asp Ser Asn
                065                 070                 075

Ser Leu Gly Thr Ile Ile Met Glu Phe Gly Gly Asn Val Thr Leu
                080                 085                 090

His Gln Val Ile Tyr Asp Ala Thr Arg Ser Pro Glu Leu Ser Leu
                095                 100                 105

Gly Lys Cys Leu Lys Tyr Ser Leu Asp Val Val Asn Gly Leu Leu
                110                 115                 120

Phe Leu His Ser Gln Ser Ile Leu His Leu Asp Leu Lys Pro Ala
                125                 130                 135

Asn Ile Leu Ile Ser Glu Gln Asp Val Cys Lys Ile Ser Asp Phe
                140                 145                 150

Gly Cys Ser Gln Lys Leu Gln Asp Leu Arg Gly Arg Gln Ala Pro
                155                 160                 165

His Ile Gly Gly Thr Tyr Thr His Gln Ala Pro Glu Ile Leu Lys
                170                 175                 180

Gly Glu Ile Ala Thr Pro Lys Ala Asp Ile Tyr Ser Phe Gly Ile
                185                 190                 195

Thr Leu Trp Gln Met Thr Thr Arg Glu Val Pro Tyr Ser Gly Glu
                200                 205                 210

Pro Gln Tyr Val Gln Tyr Ala Val Val Ala Tyr Asn Leu Arg Pro
                215                 220                 225

Ser Leu Ala Gly Ala Val Phe Thr Ala Thr Gly Lys Thr Leu Gln
```

230                     235                     240

Asn Ile Ile Gln Ser Cys Trp Glu Ala Arg Ala Leu Gln Arg Pro
                245                     250                     255

Gly Ala Glu Leu Leu Gln Arg Asp Leu Lys Ala Phe Arg Gly Ala
                260                     265                     270

Leu (2) INFORMATION FOR SEQ ID NO:48:

(i) SEQUENCE CHARACTERISTICS:
        (A) LENGTH: 269

(B) TYPE: amino acid (D) TOPOLOGY: linear (ii) MOLECULE TYPE:
        (A) DESCRIPTION: protein (vi) ORIGINAL SOURCE:
        (A) ORGANISM: Herpes simplex (ix) FEATURE: Protein kinase; Table 8 Column 54

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:48:

Gly Gln Val Cys Leu Leu His Arg Leu Gly Ser Gly Phe Gly
                005                     010                     015

Ser Val Tyr Lys Ala Thr Tyr His Gly Val Pro Val Ala Ile Lys
                020                     025                     030

Gln Val Asn Lys Cys Thr Arg Thr Leu Arg Ala Ser Gln Arg Asn
                035                     040                     045

Phe Trp Ala Glu Leu Asn Ile Ala Arg Leu His His Asp Asn Ile
                050                     055                     060

Ile Arg Val Val Ala Ala Ser Thr Arg Thr Pro Glu Gly Ser Asn
                065                     070                     075

Ser Leu Gly Thr Ile Ile Met Glu Phe Gly Gly Asn Val Thr Leu
                080                     085                     090

His Gln Val Ile Tyr Gly Ala Thr Arg Ser Pro Glu Leu Ser Leu
                095                     100                     105

Gly Lys Cys Leu Lys Tyr Ser Leu Asp Ile Val Asn Gly Leu Leu
                110                     115                     120

Phe Leu His Ser Gln Ser Ile Leu His Leu Asp Leu Lys Pro Ala
                125                     130                     135

Asn Ile Leu Ile Ser Glu Lys Asp Val Cys Lys Ile Ser Asp Phe
                140                     145                     150

```
Gly Cys Ser Gln Lys Leu Gln Asp Leu Arg Cys Arg Pro His His
            155                 160                 165

Ile Gly Gly Thr Tyr Thr His Gln Ala Pro Glu Leu Leu Lys Gly
            170                 175                 180

Glu Ile Ala Thr Pro Lys Ala Asp Ile Tyr Ser Phe Gly Ile Thr
            185                 190                 195

Leu Trp Gln Met Thr Thr Arg Glu Val Pro Tyr Ser Gly Glu Pro
            200                 205                 210

Gln His Val Gln Tyr Ala Val Val Ala Tyr Asn Leu Arg Pro His
            215                 220                 225

Trp Gln Ala Val Phe Thr Ala Thr Gly Lys Thr Leu Gln Asn Asn
            230                 235                 240

Val Gln Ser Cys Trp Glu Ala Arg Ala Leu Gln Arg Pro Gly Ala
            245                 250                 255

Glu Leu Leu Gln Lys Asp Leu Lys Ala Phe Arg Gly Ala Leu
            260                 265
```

(2) INFORMATION FOR SEQ ID NO:49:

(i) SEQUENCE CHARACTERISTICS:
        (A) LENGTH: 259

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 56

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:49:

```
Glu Ser Leu Arg Leu Glu Val Lys Leu Gly Gln Gly Cys Phe Gly
            005                 010                 015

Glu Val Trp Met Gly Thr Trp Asn Gly Thr Thr Arg Val Ala Ile
            020                 025                 030

Lys Thr Leu Lys Pro Gly Thr Met Ser Pro Glu Ala Phe Leu Gln
            035                 040                 045

Glu Ala Gln Val Met Lys Lys Leu Arg His Glu Lys Leu Val Gln
            050                 055                 060

Leu Tyr Ala Val Val Ser Glu Glu Pro Ile Tyr Ile Val Thr Glu
            065                 070                 075

Tyr Met Ser Lys Gly Ser Leu Leu Asp Phe Leu Lys Gly Glu Thr
```

```
                    080                 085                 090
Gly Lys Tyr Leu Arg Leu Pro Gln Leu Val Asp Met Ala Ala Gln
                    095                 100                 105
Ile Ala Ser Gly Met Ala Tyr Val Glu Arg Met Asn Tyr Val His
                    110                 115                 120
Arg Asp Leu Arg Ala Ala Asn Ile Leu Val Gly Glu Asn Leu Val
                    125                 130                 135
Cys Lys Val Ala Asp Phe Gly Leu Ala Arg Leu Ile Glu Asp Asn
                    140                 145                 150
Glu Tyr Thr Ala Arg Gln Gly Ala Lys Phe Pro Ile Lys Trp Thr
                    155                 160                 165
Ala Pro Glu Ala Ala Leu Tyr Gly Arg Phe Thr Ile Lys Ser Asp
                    170                 175                 180
Val Trp Ser Phe Gly Ile Leu Leu Thr Glu Leu Thr Thr Lys Gly
                    185                 190                 195
Arg Val Pro Tyr Pro Gly Met Val Asn Arg Glu Val Leu Asp Gln
                    200                 205                 210
Val Glu Arg Gly Tyr Arg Met Pro Cys Pro Pro Glu Cys Pro Glu
                    215                 220                 225
Ser Leu His Asp Leu Met Cys Gln Cys Trp Arg Lys Glu Pro Glu
                    230                 235                 240
Glu Arg Pro Thr Phe Glu Tyr Leu Gln Ala Phe Leu Glu Asp Tyr
                    245                 250                 255
Phe Thr Ser Thr (2) INFORMATION FOR SEQ ID NO:50:

(i) SEQUENCE CHARACTERISTICS:
        (A) LENGTH: 259

(B) TYPE: amino acid (D) TOPOLOGY: linear (ii) MOLECULE TYPE:
         (A) DESCRIPTION: protein (vi) ORIGINAL SOURCE:
         (A) ORGANISM: human (ix) FEATURE: Protein kinase; Table 8 Column 57

(x) PUBLICATION INFORMATION:
         (A) AUTHORS:

Hanks, S. K.
             Quinn, A. M.
             Hunter, T.
         (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:50:

Glu Ser Leu Arg Leu Glu Val Lys Leu Gly Gln Gly Cys Phe Gly
                    005                 010                 015
```

```
Glu Val Trp Met Gly Thr Trp Asn Gly Thr Thr Lys Val Ala Ile
            020                 025                 030

Lys Thr Leu Lys Pro Gly Thr Met Met Pro Glu Ala Phe Leu Gln
            035                 040                 045

Glu Ala Gln Ile Met Lys Lys Leu Arg His Asp Lys Leu Val Pro
            050                 055                 060

Leu Tyr Ala Val Val Ser Glu Glu Pro Ile Tyr Ile Val Thr Glu
            065                 070                 075

Phe Met Ser Lys Gly Ser Leu Leu Asp Phe Leu Lys Glu Gly Asp
            080                 085                 090

Gly Lys Tyr Leu Lys Leu Pro Gln Leu Val Asp Met Ala Ala Gln
            095                 100                 105

Ile Ala Asp Gly Met Ala Tyr Ile Glu Arg Met Asn Tyr Ile His
            110                 115                 120

Arg Asp Leu Arg Ala Ala Asn Ile Leu Val Gly Glu Asn Leu Val
            125                 130                 135

Cys Lys Ile Ala Asp Phe Gly Leu Ala Arg Leu Ile Glu Asp Asn
            140                 145                 150

Glu Tyr Thr Ala Arg Gln Gly Ala Lys Phe Pro Ile Lys Trp Thr
            155                 160                 165

Ala Pro Glu Ala Ala Leu Tyr Gly Arg Phe Thr Ile Lys Ser Asp
            170                 175                 180

Val Trp Ser Phe Gly Ile Leu Gln Thr Glu Leu Val Thr Lys Gly
            185                 190                 195

Arg Val Pro Tyr Pro Gly Met Val Asn Arg Glu Val Leu Glu Gln
            200                 205                 210

Val Glu Arg Gly Tyr Arg Met Pro Cys Pro Gln Gly Cys Pro Glu
            215                 220                 225

Ser Leu His Glu Leu Met Asn Leu Cys Trp Lys Lys Asp Pro Asp
            230                 235                 240

Glu Arg Pro Thr Phe Glu Tyr Ile Gln Ser Phe Leu Glu Asp Tyr
            245                 250                 255

Phe Thr Ala Thr (2) INFORMATION FOR SEQ ID NO:51:

(i) SEQUENCE CHARACTERISTICS:
        (A) LENGTH: 259

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 58

(x) PUBLICATION INFORMATION:
        (A) AUTHORS:

Hanks, S. K.
            Quinn, A. M.
            Hunter, T.
        (B) TITLE: The protein kinase family (C) JOURNAL: Science
```

(D) VOLUME: 241

(F) PAGES: 42-52

(G) DATE: 1988

(xi) SEQUENCE DESCRIPTION: SEQ ID NO:51:

Ser Ser Ile Thr Leu Glu Arg Arg Leu Gly Thr Gly Cys Phe Gly
            005                 010                 015

Asp Val Trp Leu Gly Thr Trp Asn Gly Ser Thr Lys Val Ala Val
            020                 025                 030

Lys Thr Leu Lys Pro Gly Thr Met Ser Pro Lys Ala Phe Leu Glu
            035                 040                 045

Glu Ala Gln Val Met Lys Leu Leu Arg His Asp Lys Leu Val Gln
            050                 055                 060

Leu Tyr Ala Val Val Ser Glu Glu Pro Ile Tyr Ile Val Thr Glu
            065                 070                 075

Phe Met Cys His Gly Ser Leu Leu Asp Phe Leu Lys Asn Pro Glu
            080                 085                 090

Gly Gln Asp Leu Arg Leu Pro Gln Leu Val Asp Met Ala Ala Gln
            095                 100                 105

Val Ala Glu Gly Met Ala Tyr Met Glu Arg Met Asn Tyr Ile His
            110                 115                 120

Arg Asp Leu Arg Ala Ala Asn Ile Leu Val Gly Glu Arg Leu Ala
            125                 130                 135

Cys Lys Ile Ala Asp Phe Gly Leu Ala Arg Leu Ile Lys Asp Asp
            140                 145                 150

Glu Tyr Asn Pro Cys Gln Gly Ser Lys Phe Pro Ile Lys Trp Thr
            155                 160                 165

Ala Pro Glu Ala Ala Leu Phe Gly Arg Phe Thr Ile Lys Ser Asp
            170                 175                 180

Val Trp Ser Phe Gly Ile Leu Leu Thr Glu Leu Ile Thr Lys Gly
            185                 190                 195

Arg Ile Pro Tyr Pro Gly Met Asn Lys Arg Glu Val Leu Glu Gln
            200                 205                 210

Val Glu Gln Gly Tyr His Met Pro Cys Pro Pro Gly Cys Pro Ala
            215                 220                 225

Ser Leu Tyr Glu Ala Met Glu Gln Thr Trp Arg Leu Asp Pro Glu
            230                 235                 240

Glu Arg Pro Thr Phe Glu Tyr Leu Gln Ser Phe Leu Glu Asp Tyr
            245                 250                 255

Phe Thr Ser Ala (2) INFORMATION FOR SEQ ID NO:52:

(i) SEQUENCE CHARACTERISTICS:
        (A) LENGTH: 259

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 59

(x) PUBLICATION INFORMATION:
    (A) AUTHORS:

Hanks, S. K.
        Quinn, A. M.
        Hunter, T.
    (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:52:

Glu Ser Leu Gln Leu Ile Lys Arg Leu Gly Asn Gly Gln Phe Gly
                005                 010                 015

Glu Val Trp Met Gly Thr Trp Asn Gly Asn Thr Lys Val Ala Ile
                020                 025                 030

Lys Thr Leu Lys Pro Gly Thr Met Ser Pro Glu Ser Phe Leu Glu
                035                 040                 045

Glu Ala Gln Ile Met Lys Lys Leu Lys His Asp Lys Leu Val Gln
                050                 055                 060

Leu Tyr Ala Val Val Ser Glu Glu Pro Ile Tyr Ile Val Thr Glu
                065                 070                 075

Tyr Met Asn Lys Gly Ser Leu Leu Asp Phe Leu Lys Asp Gly Glu
                080                 085                 090

Gly Arg Ala Leu Lys Leu Pro Asn Leu Val Asp Met Ala Ala Gln
                095                 100                 105

Val Ala Ala Gly Met Ala Tyr Ile Glu Arg Met Asn Tyr Ile His
                110                 115                 120

Arg Asp Leu Arg Ser Ala Asn Ile Leu Val Gly Asn Gly Leu Ile
                125                 130                 135

Cys Lys Ile Ala Asp Phe Gly Leu Ala Arg Leu Ile Glu Asp Asn
                140                 145                 150

Glu Tyr Thr Ala Arg Gln Gly Ala Lys Phe Pro Ile Lys Trp Thr
                155                 160                 165

Ala Pro Glu Ala Ala Leu Tyr Gly Arg Phe Thr Ile Lys Ser Asp
                170                 175                 180

Val Trp Ser Phe Gly Ile Leu Leu Thr Glu Leu Val Thr Lys Gly
                185                 190                 195

Arg Val Pro Tyr Pro Gly Met Asn Asn Arg Glu Val Leu Glu Gln
                200                 205                 210

Val Glu Arg Gly Tyr Arg Met Pro Cys Pro Gln Asp Cys Pro Ile
                215                 220                 225

Ser Leu His Glu Leu Met Ile His Cys Trp Lys Lys Asp Pro Glu
                230                 235                 240

Glu Arg Pro Thr Phe Glu Tyr Leu Gln Ser Phe Leu Glu Asp Tyr
                245                 250                 255

Phe Thr Ala Thr (2) INFORMATION FOR SEQ ID NO:53:

(i) SEQUENCE CHARACTERISTICS:

(A) LENGTH: 260

(B) TYPE: amino acid (D) TOPOLOGY: linear (ii) MOLECULE TYPE:
    (A) DESCRIPTION: protein (vi) ORIGINAL SOURCE:
    (A) ORGANISM: human (ix) FEATURE: Protein kinase; Table 8 Column 60

(x) PUBLICATION INFORMATION:
    (A) AUTHORS:

Hanks, S. K.
        Quinn, A. M.
        Hunter, T.
    (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:53:

Glu Ser Ile Lys Leu Val Lys Arg Leu Gly Ala Gly Gln Phe Gly
                005             010             015

Glu Val Trp Met Gly Tyr Tyr Asn Asn Ser Thr Lys Val Ala Val
                020             025             030

Lys Thr Leu Lys Pro Gly Thr Met Ser Val Gln Ala Phe Leu Glu
                035             040             045

Glu Ala Asn Leu Met Lys Thr Leu Gln His Asp Lys Leu Val Arg
                050             055             060

Leu Tyr Ala Val Val Thr Arg Glu Glu Pro Ile Tyr Ile Ile Thr
                065             070             075

Glu Tyr Met Ala Lys Gly Ser Leu Leu Asp Phe Leu Lys Ser Asp
                080             085             090

Glu Gly Gly Lys Val Leu Leu Pro Lys Leu Ile Asp Phe Ser Ala
                095             100             105

Gln Ile Ala Glu Gly Met Ala Tyr Ile Glu Arg Lys Asn Tyr Ile
                110             115             120

His Arg Asp Leu Arg Ala Ala Asn Val Leu Val Ser Glu Ser Leu
                125             130             135

Met Cys Lys Ile Ala Asp Phe Gly Leu Ala Arg Val Ile Glu Asp
                140             145             150

Asn Glu Tyr Thr Ala Arg Glu Gly Ala Lys Phe Pro Ile Lys Trp
                155             160             165

Thr Ala Pro Glu Ala Ile Asn Phe Gly Cys Phe Thr Ile Lys Ser
                170             175             180

Asp Val Trp Ser Phe Gly Ile Leu Leu Tyr Glu Ile Val Thr Tyr
                185             190             195

Gly Lys Ile Pro Tyr Pro Gly Arg Thr Asn Ala Asp Val Met Thr
                200             205             210

Ala Leu Ser Gln Gly Tyr Arg Met Pro Arg Val Glu Asn Cys Pro
                215             220             225

```
Asp Glu Leu Tyr Asp Ile Met Lys Met Cys Trp Lys Glu Lys Pro
            230                 235                 240

Glu Glu Arg Pro Thr Phe Asp Tyr Leu Gln Ser Val Leu Asp Asp
            245                 250                 255

Phe Tyr Thr Ala Thr
            260

(2) INFORMATION FOR SEQ ID NO:54:

(i) SEQUENCE CHARACTERISTICS:
        (A) LENGTH: 259

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 61

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:54:

Glu Thr Leu Lys Leu Val Glu Arg Leu Gly Ala Gly Gln Phe Gly
            005                 010                 015

Arg Cys Gly Trp Gly Thr Thr Thr Gly Thr Thr Lys Val Ala Val
            020                 025                 030

Lys Ser Leu Lys Gln Gly Ser Met Ser Ala Gly Arg Leu Pro Ala
            035                 040                 045

Glu Ala Asn Leu Met Lys Gln Leu Gln His Gln Arg Leu Val Arg
            050                 055                 060

Leu Tyr Ala Val Val Thr Gln Glu Pro Ile Tyr Ile Ile Thr Glu
            065                 070                 075

Tyr Met Glu Asn Gly Ser Leu Val Asp Phe Leu Lys Thr Pro Ser
            080                 085                 090

Gly Ile Lys Leu Thr Ile Asn Lys Leu Leu Asp Met Ala Ala Gln
            095                 100                 105

Ile Ala Glu Gly Met Ala Phe Ile Glu Glu Arg Asn Tyr Ile His
            110                 115                 120

Arg Asp Leu Arg Ala Ala Asn Ile Leu Val Ser Asp Thr Leu Ser
            125                 130                 135

Cys Lys Ile Ala Asp Phe Gly Leu Ala Arg Leu Ile Glu Asp Asn
            140                 145                 150
```

Glu Tyr Thr Ala Arg Glu Gly Ala Lys Phe Pro Ile Lys Trp Thr
                155                 160                 165

Ala Pro Glu Ala Ile Asn Tyr Gly Thr Phe Thr Ile Lys Ser Asp
                170                 175                 180

Val Trp Ser Phe Gly Ile Leu Leu Thr Glu Ile Val Thr His Gly
                185                 190                 195

Arg Ile Pro Tyr Pro Gly Met Thr Asn Pro Glu Val Ile Gln Asn
                200                 205                 210

Leu Glu Arg Gly Tyr Arg Met Val Arg Pro Asp Asn Cys Pro Glu
                215                 220                 225

Glu Leu Tyr Gln Leu Met Arg Leu Cys Trp Lys Glu Arg Pro Glu
                230                 235                 240

Asp Arg Pro Thr Phe Asp Tyr Leu Arg Ser Val Leu Glu Asp Phe
                245                 250                 255

Phe Thr Ala Thr (2) INFORMATION FOR SEQ ID NO:55:

(i) SEQUENCE CHARACTERISTICS:
        (A) LENGTH: 259

(B) TYPE: amino acid (D) TOPOLOGY: linear (ii) MOLECULE TYPE:
        (A) DESCRIPTION: protein (vi) ORIGINAL SOURCE:
        (A) ORGANISM: mouse (ix) FEATURE: Protein kinase; Table 8 Column 62

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:55:

Glu Thr Leu Lys Leu Val Glu Arg Leu Gly Ala Gly Gln Phe Gly
                005                 010                 015

Glu Val Trp Met Gly Tyr Tyr Asn Gly His Thr Lys Val Ala Val
                020                 025                 030

Lys Ser Leu Lys Gln Gly Ser Met Ser Pro Val Pro Phe Leu Ala
                035                 040                 045

Glu Ala Asn Leu Met Lys Gln Leu Gln His Pro Arg Leu Val Arg
                050                 055                 060

Leu Tyr Ala Val Val Thr Gln Glu Pro Ile Tyr Ile Ile Thr Glu
                065                 070                 075

Tyr Met Glu Asn Gly Ser Leu Val Asp Phe Leu Lys Thr Pro Ser
                080                 085                 090

```
Gly Ile Lys Leu Asn Val Asn Lys Leu Leu Asp Met Ala Ala Gln
                095                 100                 105

Ile Ala Glu Gly Met Ala Phe Ile Glu Glu Gln Asn Tyr Ile His
                110                 115                 120

Arg Asp Leu Arg Ala Ala Asn Ile Leu Val Ser Asp Thr Leu Ser
                125                 130                 135

Cys Lys Ile Ala Asp Phe Gly Leu Ala Arg Leu Ile Glu Asp Asn
                140                 145                 150

Glu Tyr Thr Ala Arg Glu Gly Ala Lys Phe Pro Ile Lys Trp Thr
                155                 160                 165

Ala Pro Glu Ala Ile Asn Tyr Gly Thr Phe Thr Ile Lys Ser Asp
                170                 175                 180

Val Trp Ser Phe Gly Ile Leu Leu Thr Glu Ile Val Thr His Gly
                185                 190                 195

Arg Ile Pro Tyr Pro Gly Met Thr Asn Pro Glu Val Ile Gln Asn
                200                 205                 210

Leu Glu Arg Gly Tyr Arg Met Val Arg Pro Asp Asn Cys Pro Glu
                215                 220                 225

Glu Leu Tyr His Leu Met Met Leu Cys Trp Lys Arg Pro Glu
                230                 235                 240

Asp Arg Pro Thr Phe Asp Tyr Leu Arg Ser Val Leu Asp Asp Phe
                245                 250                 255

Phe Thr Ala Thr (2) INFORMATION FOR SEQ ID NO:56:

(i) SEQUENCE CHARACTERISTICS:
        (A) LENGTH: 259

(B) TYPE: amino acid (D) TOPOLOGY: linear (ii) MOLECULE TYPE:
         (A) DESCRIPTION: protein (vi) ORIGINAL SOURCE:
         (A) ORGANISM: human (ix) FEATURE: Protein kinase; Table 8 Column 63

(x) PUBLICATION INFORMATION:
         (A) AUTHORS:

Hanks, S. K.
             Quinn, A. M.
             Hunter, T.
         (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:56:

Glu Ser Leu Lys Leu Glu Lys Lys Leu Gly Ala Gly Gln Phe Gly
                005                 010                 015

Glu Val Trp Met Ala Thr Tyr Asn Lys His Thr Lys Val Ala Val
```

```
                    020                 025                 030

Lys Thr Met Lys Pro Gly Ser Met Ser Val Glu Ala Phe Leu Ala
                035                 040                 045

Glu Ala Asn Val Met Lys Thr Leu Gln His Asp Lys Leu Val Lys
                050                 055                 060

Leu His Ala Val Val Thr Lys Glu Pro Ile Tyr Ile Ile Thr Glu
                065                 070                 075

Phe Met Ala Lys Gly Ser Leu Leu Asp Phe Leu Lys Ser Asp Glu
                080                 085                 090

Gly Ser Lys Gln Pro Leu Pro Lys Leu Ile Asp Phe Ser Ala Gln
                095                 100                 105

Ile Ala Glu Gly Met Ala Phe Ile Glu Gln Arg Asn Tyr Ile His
                110                 115                 120

Arg Asp Leu Arg Ala Ala Asn Ile Leu Val Ser Ala Ser Leu Val
                125                 130                 135

Cys Lys Ile Ala Asp Phe Gly Leu Ala Arg Val Ile Glu Asp Asn
                140                 145                 150

Glu Tyr Thr Ala Arg Glu Gly Ala Lys Phe Pro Ile Lys Trp Thr
                155                 160                 165

Ala Pro Glu Ala Ile Asn Phe Gly Ser Phe Thr Ile Lys Ser Asp
                170                 175                 180

Val Trp Ser Phe Gly Ile Leu Leu Met Glu Ile Val Thr Tyr Gly
                185                 190                 195

Arg Ile Pro Tyr Pro Gly Met Ser Asn Pro Glu Val Ile Arg Ala
                200                 205                 210

Leu Glu Arg Gly Tyr Arg Met Pro Arg Pro Glu Asn Cys Pro Glu
                215                 220                 225

Glu Leu Tyr Asn Ile Met Met Arg Cys Trp Lys Asn Arg Pro Glu
                230                 235                 240

Glu Arg Pro Thr Phe Glu Tyr Ile Gln Ser Val Leu Asp Asp Phe
                245                 250                 255

Tyr Thr Ala Thr (2) INFORMATION FOR SEQ ID NO:57:

(i) SEQUENCE CHARACTERISTICS:
        (A) LENGTH: 262

(B) TYPE: amino acid (D) TOPOLOGY: linear (ii) MOLECULE TYPE:
         (A) DESCRIPTION: protein (vi) ORIGINAL SOURCE:
         (A) ORGANISM: Drosophila melanogaster (ix) FEATURE: Protein kinase; Table 8 Column 64

(x) PUBLICATION INFORMATION:
        (A) AUTHORS:

Hanks, S. K.
            Quinn, A. M.
            Hunter, T.
        (B) TITLE: The protein kinase family (C) JOURNAL: Science
```

(D) VOLUME: 241

(F) PAGES: 42-52

(G) DATE: 1988

(xi) SEQUENCE DESCRIPTION: SEQ ID NO:57:

```
Ser Glu Ile Gln Leu Leu Arg Lys Leu Gly Arg Gly Asn Phe Gly
            005                 010                 015

Glu Val Phe Tyr Gly Lys Trp Arg Asn Ser Ile Asp Val Ala Val
            020                 025                 030

Lys Thr Leu Arg Glu Gly Thr Met Ser Thr Ala Ala Phe Leu Gln
            035                 040                 045

Glu Ala Ala Ile Met Lys Lys Phe Arg His Asn Arg Leu Val Ala
            050                 055                 060

Leu Tyr Ala Val Cys Ser Gln Glu Glu Pro Ile Tyr Ile Val Gln
            065                 070                 075

Glu Tyr Met Ser Lys Gly Ser Leu Leu Asp Phe Leu Arg Glu Gly
            080                 085                 090

Asp Gly Arg Tyr Leu His Phe Glu Asp Leu Ile Tyr Ile Ala Thr
            095                 100                 105

Gln Val Ala Ser Gly Met Glu Tyr Leu Glu Ser Lys Gln Leu Ile
            110                 115                 120

His Arg Asp Leu Ala Ala Arg Asn Val Leu Ile Gly Glu Asn Asn
            125                 130                 135

Val Ala Lys Ile Cys Asp Phe Gly Leu Ala Arg Val Ile Ala Asp
            140                 145                 150

Asp Glu Tyr Cys Pro Lys Gln Gly Ser Arg Phe Pro Val Lys Trp
            155                 160                 165

Thr Ala Pro Glu Ala Ile Ile Tyr Gly Lys Phe Ser Ile Lys Ser
            170                 175                 180

Asp Val Trp Ser Phe Gly Ile Leu Leu Met Glu Leu Phe Thr Tyr
            185                 190                 195

Gly Gln Val Pro Tyr Pro Gly Met His Ser Arg Glu Val Ile Glu
            200                 205                 210

Asn Ile Glu Arg Gly Phe Arg Met Pro Lys Pro Thr Asn His Tyr
            215                 220                 225

Phe Pro Asp Asn Ile Tyr Gln Leu Leu Leu Gln Cys Trp Asp Ala
            230                 235                 240

Val Pro Glu Lys Arg Pro Thr Phe Glu Phe Leu Asn His Tyr Phe
            245                 250                 255

Glu Ser Phe Ser Thr Thr Ser
            260
```

(2) INFORMATION FOR SEQ ID NO:58:

(i) SEQUENCE CHARACTERISTICS:
        (A) LENGTH: 261

(B) TYPE: amino acid (D) TOPOLOGY: linear (ii) MOLECULE TYPE:
        (A) DESCRIPTION: protein (vi) ORIGINAL SOURCE:
        (A) ORGANISM: Drosophila melanogaster (ix) FEATURE: Protein kinase; Table 8 Column 65

(x) PUBLICATION INFORMATION:
    (A) AUTHORS:
        Hanks, S. K.
        Quinn, A. M.
        Hunter, T.
    (B) TITLE: The protein kinase family
    (C) JOURNAL: Science
    (D) VOLUME: 241
    (F) PAGES: 42-52
    (G) DATE: 1988

(xi) SEQUENCE DESCRIPTION: SEQ ID NO:58:

Ile Gln Leu Met Leu Met Glu Glu Leu Gly Ser Gly Gln Phe Gly
                005                 010                 015
Val Val Arg Arg Gly Lys Trp Arg Gly Ser Ile Asp Thr Ala Val
                020                 025                 030
Lys Met Met Lys Glu Gly Thr Met Ser Glu Asp Asp Phe Ile Glu
                035                 040                 045
Glu Ala Lys Val Met Thr Lys Leu Gln His Pro Asn Leu Val Gln
                050                 055                 060
Leu Tyr Gly Val Cys Thr Lys His Arg Pro Ile Tyr Ile Val Thr
                065                 070                 075
Glu Tyr Met Lys His Gly Ser Leu Leu Asn Phe Leu Arg Arg His
                080                 085                 090
Glu Lys Thr Leu Ile Gly Asn Met Gly Leu Leu Leu Asp Met Cys
                095                 100                 105
Ile Gln Val Ser Lys Gly Met Thr Tyr Leu Glu Arg His Asn Tyr
                110                 115                 120
Ile His Arg Asp Leu Ala Ala Arg Asn Cys Leu Val Gly Ser Glu
                125                 130                 135
Asn Val Val Lys Val Ala Asp Phe Gly Leu Ala Arg Tyr Val Leu
                140                 145                 150
Asp Asp Gln Tyr Thr Ser Ser Gly Gly Thr Lys Phe Pro Ile Lys
                155                 160                 165
Trp Ala Pro Pro Glu Val Leu Asn Tyr Thr Arg Phe Ser Ser Lys
                170                 175                 180
Ser Asp Val Trp Ala Phe Gly Val Leu Met Trp Glu Ile Phe Thr
                185                 190                 195
Cys Gly Lys Met Pro Tyr Gly Arg Leu Lys Asn Thr Glu Val Val
                200                 205                 210
Glu Arg Val Gln Arg Gly Ile Ile Leu Glu Lys Pro Lys Ser Cys
                215                 220                 225
Ala Lys Glu Ile Tyr Asp Val Met Lys Leu Cys Trp Ser His Gly
                230                 235                 240
Pro Glu Glu Arg Pro Ala Phe Arg Val Leu Met Asp Gln Leu Ala
                245                 250                 255
Leu Val Ala Gln Thr Leu
                260

(2) INFORMATION FOR SEQ ID NO:59:

(i) SEQUENCE CHARACTERISTICS:
        (A) LENGTH: 261

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 67

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:59:

Thr Asp Ile Thr Met Lys His Lys Leu Gly Gly Gly Gln Tyr Gly
                005                 010                 015

Glu Val Tyr Glu Gly Val Trp Lys Lys Tyr Ser Leu Thr Val Ala
                020                 025                 030

Val Lys Thr Leu Lys Glu Asp Thr Met Glu Val Glu Glu Phe Leu
                035                 040                 045

Lys Glu Ala Ala Val Met Lys Glu Ile Lys His Pro Asn Leu Val
                050                 055                 060

Gln Leu Leu Gly Val Cys Thr Arg Glu Pro Pro Phe Tyr Ile Ile
                065                 070                 075

Thr Glu Phe Met Thr Tyr Gly Asn Leu Leu Asp Tyr Leu Arg Glu
                080                 085                 090

Cys Asn Arg Gln Glu Val Asn Ala Val Val Leu Leu Tyr Met Ala
                095                 100                 105

Thr Gln Ile Ser Ser Ala Met Glu Tyr Leu Glu Lys Lys Asn Phe
                110                 115                 120

Ile His Arg Asp Leu Ala Ala Arg Asn Cys Leu Val Gly Glu Asn
                125                 130                 135

His Leu Val Lys Val Ala Asp Phe Gly Leu Ser Arg Leu Met Thr
                140                 145                 150

Gly Asp Thr Tyr Thr Ala His Ala Gly Ala Lys Phe Pro Ile Lys
                155                 160                 165

Trp Thr Ala Pro Glu Ser Leu Ala Tyr Asn Lys Phe Ser Ile Lys
                170                 175                 180

Ser Asp Val Trp Ala Phe Gly Val Leu Leu Trp Glu Ile Ala Thr
                185                 190                 195

Tyr Gly Met Ser Pro Tyr Pro Gly Ile Asp Arg Ser Gln Val Tyr
                200                 205                 210

Glu Leu Leu Glu Lys Asp Tyr Arg Met Lys Arg Pro Glu Gly Cys

```
                      215                 220                 225
Pro Glu Lys Val Tyr Glu Leu Met Arg Ala Cys Trp Gln Trp Asn
                230                 235                 240

Pro Ser Asp Arg Pro Ser Phe Ala Glu Ile His Gln Ala Phe Glu
                245                 250                 255

Thr Met Phe Gln Glu Ser
                260
```

(2) INFORMATION FOR SEQ ID NO:60:

(i) SEQUENCE CHARACTERISTICS:
        (A) LENGTH: 261

(B) TYPE: amino acid (D) TOPOLOGY: linear (ii) MOLECULE TYPE:
        (A) DESCRIPTION: protein (vi) ORIGINAL SOURCE:
        (A) ORGANISM: Drosophila melanogaster (ix) FEATURE: Protein kinase; Table 8 Column 68

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:60:

```
Thr Asp Ile Met Met Lys His Lys Leu Gly Gly Gly Gln Tyr Gly
                005                 010                 015

Glu Val Tyr Glu Ala Val Trp Lys Arg Tyr Gly Asn Thr Val Ala
                020                 025                 030

Val Lys Thr Leu Lys Glu Asp Thr Met Ala Leu Lys Asp Phe Leu
                035                 040                 045

Glu Glu Ala Ala Ile Met Lys Glu Met Lys His Pro Asn Leu Val
                050                 055                 060

Gln Leu Ile Gly Val Cys Thr Arg Glu Pro Pro Phe Tyr Ile Ile
                065                 070                 075

Thr Glu Phe Met Ser His Gly Asn Leu Leu Asp Phe Leu Arg Ser
                080                 085                 090

Ala Gly Arg Glu Thr Leu Asp Ala Val Ala Leu Leu Tyr Met Ala
                095                 100                 105

Thr Gln Ile Ala Ser Gly Met Ser Tyr Leu Glu Ser Arg Asn Tyr
                110                 115                 120

Ile His Arg Asp Leu Ala Ala Arg Asn Cys Leu Val Gly Asp Asn
                125                 130                 135

Lys Leu Val Lys Val Ala Asp Phe Gly Leu Ala Arg Leu Met Arg
                140                 145                 150
```

```
Asp Asp Thr Tyr Thr Ala His Ala Gly Ala Lys Phe Pro Ile Lys
            155                 160                 165

Trp Thr Ala Pro Glu Gly Leu Ala Tyr Asn Lys Phe Ser Thr Lys
            170                 175                 180

Ser Asp Val Trp Ala Phe Gly Val Leu Leu Trp Glu Ile Ala Thr
            185                 190                 195

Tyr Gly Met Ser Pro Tyr Pro Ala Ile Asp Leu Thr Asp Val Tyr
            200                 205                 210

His Lys Leu Asp Lys Gly Tyr Arg Met Glu Arg Pro Pro Gly Cys
            215                 220                 225

Pro Pro Glu Val Tyr Asp Leu Met Arg Gln Cys Trp Gln Trp Asp
            230                 235                 240

Ala Thr Asp Arg Pro Thr Phe Lys Ser Ile His His Ala Leu Glu
            245                 250                 255

His Met Phe Gln Val Gly
            260

(2) INFORMATION FOR SEQ ID NO:61:

(i) SEQUENCE CHARACTERISTICS:
        (A) LENGTH: 261

(B) TYPE: amino acid (D) TOPOLOGY: linear (ii) MOLECULE TYPE:
        (A) DESCRIPTION: protein (vi) ORIGINAL SOURCE:
        (A) ORGANISM: Caenorhabditis elegans (ix) FEATURE: Protein kinase; Table 8 Column 69

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:61:

Ser Glu Ile Ile Met His Asn Lys Leu Gly Gly Gly Gln Tyr Gly
            005                 010                 015

Asp Val Tyr Glu Gly Tyr Trp Lys Arg His Asp Cys Thr Ile Ala
            020                 025                 030

Val Lys Ala Leu Lys Glu Asp Ala Met Pro Leu His Glu Phe Leu
            035                 040                 045

Ala Glu Ala Ala Ile Met Lys Asp Leu His His Lys Asn Leu Val
            050                 055                 060

Arg Leu Leu Gly Val Cys Thr His Glu Ala Pro Phe Tyr Ile Ile
            065                 070                 075
```

```
Thr Glu Phe Met Cys Asn Gly Asn Leu Glu Tyr Leu Arg Arg
            080                 085                 090

Thr Asp Lys Ser Leu Leu Pro Pro Ile Ile Leu Val Gln Met Ala
            095                 100                 105

Ser Gln Ile Ala Ser Gly Met Ser Tyr Leu Glu Ala Arg His Phe
            110                 115                 120

Ile His Arg Asp Leu Ala Ala Arg Asn Cys Leu Val Ser Glu His
            125                 130                 135

Asn Ile Val Lys Ile Ala Asp Phe Gly Leu Ala Arg Phe Met Lys
            140                 145                 150

Glu Asp Thr Tyr Thr Ala His Ala Gly Ala Lys Phe Pro Ile Lys
            155                 160                 165

Trp Thr Ala Pro Glu Gly Leu Ala Phe Asn Thr Phe Ser Ser Lys
            170                 175                 180

Ser Asp Val Trp Ala Phe Gly Val Leu Leu Trp Glu Ile Ala Thr
            185                 190                 195

Tyr Gly Met Ala Pro Tyr Pro Gly Val Glu Leu Ser Asn Val Tyr
            200                 205                 210

Gly Leu Leu Glu Asn Gly Phe Arg Met Asp Gly Pro Gln Gly Cys
            215                 220                 225

Pro Pro Ser Val Tyr Arg Leu Met Leu Gln Cys Trp Asn Trp Ser
            230                 235                 240

Pro Ser Asp Arg Pro Arg Phe Arg Asp Ile His Phe Asn Leu Glu
            245                 250                 255

Asn Leu Ile Ser Ser Asn
            260
```

(2) INFORMATION FOR SEQ ID NO:62:

(i) SEQUENCE CHARACTERISTICS:
        (A) LENGTH: 262

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 70

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:62:

Glu Asp Leu Val Leu Gly Glu Gln Ile Gly Arg Gly Asn Phe Gly

```
                              005                     010                     015

Glu Val Phe Ser Gly Arg Leu Arg Ala Asp Asn Thr Leu Val Ala
                020                     025                     030

Val Lys Ser Cys Arg Glu Thr Leu Pro Pro Asp Leu Lys Ala Lys
                035                     040                     045

Phe Leu Gln Glu Ala Arg Ile Leu Lys Gln Tyr Ser His Pro Asn
                050                     055                     060

Ile Val Arg Leu Ile Gly Val Cys Thr Gln Lys Gln Pro Ile Tyr
                065                     070                     075

Ile Val Met Glu Leu Val Gln Gly Gly Asp Phe Leu Thr Phe Leu
                080                     085                     090

Arg Thr Glu Gly Ala Arg Leu Arg Val Lys Thr Leu Leu Gln Met
                095                     100                     105

Val Gly Asp Ala Ala Ala Gly Met Glu Tyr Leu Glu Ser Lys Cys
                110                     115                     120

Cys Ile His Arg Asp Leu Ala Ala Arg Asn Cys Leu Val Thr Glu
                125                     130                     135

Lys Asn Val Leu Lys Ile Ser Asp Phe Gly Met Ser Arg Glu Glu
                140                     145                     150

Ala Asp Gly Val Tyr Ala Ala Ser Gly Leu Arg Gln Val Pro Val
                155                     160                     165

Lys Trp Thr Ala Pro Glu Ala Leu Asn Tyr Gly Arg Tyr Ser Ser
                170                     175                     180

Glu Ser Asp Val Trp Ser Phe Gly Ile Leu Leu Trp Glu Thr Phe
                185                     190                     195

Ser Leu Gly Ala Ser Pro Tyr Pro Asn Leu Ser Asn Gln Gln Thr
                200                     205                     210

Arg Glu Phe Val Glu Lys Gly Gly Arg Leu Pro Cys Pro Glu Leu
                215                     220                     225

Cys Pro Asp Ala Val Phe Arg Leu Met Glu Gln Cys Trp Ala Tyr
                230                     235                     240

Glu Pro Gly Gln Arg Pro Ser Phe Ser Thr Ile Tyr Gln Glu Leu
                245                     250                     255

Gln Ser Ile Arg Lys Arg His
                260

(2) INFORMATION FOR SEQ ID NO:63:

(i) SEQUENCE CHARACTERISTICS:
        (A) LENGTH: 262

(B) TYPE: amino acid (D) TOPOLOGY: linear (ii) MOLECULE TYPE:
         (A) DESCRIPTION: protein (vi) ORIGINAL SOURCE:
         (A) ORGANISM: cat (ix) FEATURE: Protein kinase; Table 8 Column 71

(x) PUBLICATION INFORMATION:
        (A) AUTHORS:

Hanks, S. K.
              Quinn, A. M.
              Hunter, T.
```

(B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:63:

```
Glu Asp Leu Val Leu Gly Glu Gln Ile Gly Arg Gly Asn Phe Gly
                005                 010                 015
Glu Val Phe Ser Gly Arg Leu Arg Ala Asp Asn Thr Leu Val Ala
                020                 025                 030
Val Lys Ser Cys Arg Glu Thr Leu Pro Pro Asp Ile Lys Ala Lys
                035                 040                 045
Phe Leu Gln Glu Ala Lys Ile Leu Lys Gln Tyr Ser His Pro Asn
                050                 055                 060
Ile Val Arg Leu Ile Gly Val Cys Thr Gln Lys Gln Pro Ile Tyr
                065                 070                 075
Ile Val Met Glu Leu Val Gln Gly Gly Asp Phe Leu Thr Phe Leu
                080                 085                 090
Arg Thr Glu Gly Ala Arg Leu Arg Met Lys Thr Leu Leu Gln Met
                095                 100                 105
Val Gly Asp Ala Ala Gly Met Glu Tyr Leu Glu Ser Lys Cys
                110                 115                 120
Cys Ile His Arg Asp Leu Ala Ala Arg Asn Cys Leu Val Thr Glu
                125                 130                 135
Lys Asn Val Leu Lys Ile Ser Asp Phe Gly Met Ser Arg Glu Glu
                140                 145                 150
Ala Asp Gly Ile Tyr Ala Ala Ser Gly Leu Arg Gln Val Pro Val
                155                 160                 165
Lys Trp Thr Ala Pro Glu Ala Leu Asn Tyr Gly Arg Tyr Ser Ser
                170                 175                 180
Glu Ser Asp Val Trp Ser Phe Gly Ile Leu Leu Trp Glu Thr Phe
                185                 190                 195
Ser Leu Gly Ala Ser Pro Tyr Pro Asn Leu Ser Asn Gln Gln Thr
                200                 205                 210
Arg Glu Phe Val Glu Lys Gly Gly Arg Leu Pro Cys Pro Glu Leu
                215                 220                 225
Cys Pro Asp Ala Val Phe Arg Leu Met Glu Gln Cys Trp Ala Tyr
                230                 235                 240
Glu Pro Gly Gln Arg Pro Ser Phe Ser Ala Ile Tyr Gln Glu Leu
                245                 250                 255
Gln Ser Ile Arg Lys Arg His
                260
```

(2) INFORMATION FOR SEQ ID NO:64:

(i) SEQUENCE CHARACTERISTICS:
        (A) LENGTH: 262

(B) TYPE: amino acid (D) TOPOLOGY: linear (ii) MOLECULE TYPE:
        (A) DESCRIPTION: protein (vi) ORIGINAL SOURCE:
        (A) ORGANISM: chicken (ix) FEATURE: Protein kinase; Table 8 Column 72

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:64:

Glu Asp Val Leu Leu Gly Glu Arg Ile Gly Arg Gly Asn Phe Gly
             005                 010                 015

Glu Val Phe Ser Gly Arg Leu Arg Ala Asp Asn Thr Pro Val Ala
             020                 025                 030

Val Lys Ser Cys Arg Glu Thr Leu Pro Pro Glu Leu Lys Ala Lys
             035                 040                 045

Phe Leu Gln Glu Ala Arg Ile Leu Lys Gln Tyr Asn His Pro Asn
             050                 055                 060

Ile Val Arg Leu Ile Gly Val Cys Thr Gln Lys Gln Pro Ile Tyr
             065                 070                 075

Ile Val Met Glu Leu Val Gln Gly Gly Asp Phe Leu Ser Phe Leu
             080                 085                 090

Arg Ser Glu Gly Pro His Leu Lys Met Lys Glu Leu Ile Lys Met
             095                 100                 105

Met Glu Asn Ala Ala Ala Gly Met Glu Tyr Leu Glu Ser Lys His
             110                 115                 120

Cys Ile His Arg Asp Leu Ala Ala Arg Asn Cys Leu Val Thr Glu
             125                 130                 135

Lys Asn Thr Leu Lys Ile Ser Asp Phe Gly Met Ser Arg Gln Glu
             140                 145                 150

Glu Asp Gly Val Tyr Ala Ser Thr Gly Met Lys Gln Ile Pro Val
             155                 160                 165

Lys Trp Thr Ala Pro Glu Ala Leu Asn Tyr Gly Arg Tyr Ser Ser
             170                 175                 180

Glu Ser Asp Val Trp Ser Phe Gly Ile Leu Leu Trp Glu Ala Phe
             185                 190                 195

Ser Leu Gly Ala Val Pro Tyr Ala Asn Leu Ser Asn Gln Gln Thr
             200                 205                 210

Arg Glu Ala Ile Glu Gln Gly Val Arg Leu Glu Pro Pro Glu Gln
             215                 220                 225

Cys Pro Glu Asp Val Tyr Arg Leu Met Gln Arg Cys Trp Glu Tyr
             230                 235                 240

Asp Pro Arg Arg Arg Pro Ser Phe Gly Ala Val His Gln Asp Leu
             245                 250                 255

Ile Ala Ile Arg Lys Arg His
             260

(2) INFORMATION FOR SEQ ID NO:65:

(i) SEQUENCE CHARACTERISTICS:
        (A) LENGTH: 265

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 74

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:65:

```
Thr Glu Phe Lys Lys Ile Lys Val Leu Gly Ser Gly Ala Phe Gly
             005                 010                 015

Thr Val Tyr Lys Gly Leu Trp Ile Pro Glu Gly Glu Lys Val Lys
             020                 025                 030

Ile Pro Val Ala Ile Lys Glu Leu Arg Glu Ala Thr Ser Pro Lys
             035                 040                 045

Ala Asn Lys Glu Ile Leu Asp Glu Ala Tyr Val Met Ala Ser Val
             050                 055                 060

Asp Asn Pro His Val Cys Arg Leu Leu Gly Ile Cys Leu Thr Ser
             065                 070                 075

Thr Val Gln Leu Ile Thr Gln Leu Met Pro Phe Gly Cys Leu Leu
             080                 085                 090

Asp Tyr Val Arg Glu His Lys Asp Asn Ile Gly Ser Gln Tyr Leu
             095                 100                 105

Leu Asn Trp Cys Val Gln Ile Ala Lys Gly Met Asn Tyr Leu Glu
             110                 115                 120

Asp Arg Arg Leu Val His Arg Asp Leu Ala Ala Arg Asn Val Leu
             125                 130                 135

Val Lys Thr Pro Gln His Val Lys Ile Thr Asp Phe Gly Leu Ala
             140                 145                 150

Lys Leu Leu Gly Ala Glu Glu Lys Glu Tyr His Glu Gly Gly Lys
             155                 160                 165

Val Pro Ile Lys Trp Met Ala Leu Glu Ser Ile Leu His Arg Ile
             170                 175                 180

Tyr Thr His Gln Ser Asp Val Trp Ser Tyr Gly Val Thr Val Trp
             185                 190                 195
```

-continued

```
Glu Leu Met Thr Phe Gly Ser Lys Pro Tyr Asp Gly Ile Pro Ala
                200                 205                 210

Ser Glu Ile Ser Ser Ile Leu Glu Lys Gly Glu Arg Leu Pro Gln
                215                 220                 225

Pro Pro Ile Cys Thr Ile Asp Val Tyr Met Ile Met Val Lys Cys
                230                 235                 240

Trp Met Ile Asp Ala Asp Ser Arg Pro Lys Phe Arg Glu Leu Ile
                245                 250                 255

Ile Glu Phe Ser Lys Met Ala Arg Asp Pro
                260                 265
```

(2) INFORMATION FOR SEQ ID NO:66:

(i) SEQUENCE CHARACTERISTICS:
        (A) LENGTH: 265

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 75

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:66:

```
Thr Glu Leu Arg Lys Val Lys Val Leu Gly Ser Gly Ala Phe Gly
                005                 010                 015

Thr Val Tyr Lys Gly Ile Trp Ile Pro Asp Gly Glu Asn Val Lys
                020                 025                 030

Ile Pro Val Ala Ile Lys Val Leu Arg Glu Asn Thr Ser Pro Lys
                035                 040                 045

Ala Asn Lys Glu Ile Leu Asp Glu Ala Tyr Val Met Ala Gly Val
                050                 055                 060

Gly Ser Pro Tyr Val Ser Arg Leu Leu Gly Ile Cys Leu Thr Ser
                065                 070                 075

Thr Val Gln Leu Val Thr Gln Leu Met Pro Tyr Gly Cys Leu Leu
                080                 085                 090

Asp His Val Arg Glu Asn Arg Gly Arg Leu Gly Ser Gln Asp Leu
                095                 100                 105

Leu Asn Trp Cys Met Gln Ile Ala Lys Gly Met Ser Tyr Leu Glu
                110                 115                 120

Asp Val Arg Leu Val His Arg Asp Leu Ala Ala Arg Asn Val Leu
```

```
                          125                 130                 135
Val Lys Ser Pro Asn His Val Lys Ile Thr Asp Phe Gly Leu Ala
                140                 145                 150
Arg Leu Leu Asp Ile Asp Glu Thr Glu Tyr His Asp Gly Gly Lys
                155                 160                 165
Val Pro Ile Lys Trp Met Ala Leu Glu Ser Ile Leu Arg Arg Arg
                170                 175                 180
Phe Thr His Gln Ser Asp Val Trp Ser Tyr Gly Val Thr Val Trp
                185                 190                 195
Glu Leu Met Thr Phe Gly Ala Lys Pro Tyr Asp Gly Ile Pro Ala
                200                 205                 210
Arg Glu Ile Pro Asp Leu Leu Glu Lys Gly Glu Arg Leu Pro Gln
                215                 220                 225
Pro Pro Ile Cys Thr Ile Asp Val Tyr Met Ile Met Val Lys Cys
                230                 235                 240
Trp Met Ile Asp Ser Glu Cys Arg Pro Arg Phe Arg Glu Leu Val
                245                 250                 255
Ser Glu Phe Ser Arg Met Ala Arg Asp Pro
                260                 265

(2) INFORMATION FOR SEQ ID NO:67:

(i) SEQUENCE CHARACTERISTICS:
        (A) LENGTH: 264

(B) TYPE: amino acid (D) TOPOLOGY: linear (ii) MOLECULE TYPE:
        (A) DESCRIPTION: protein (vi) ORIGINAL SOURCE:
        (A) ORGANISM: Drosophila melanogaster (ix) FEATURE: Protein kinase; Table 8 Column 76

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:67:

Ala Glu Leu Arg Lys Gly Gly Val Leu Gly Met Gly Ala Phe Gly
                005                 010                 015
Arg Val Tyr Lys Gly Val Trp Val Pro Glu Gly Glu Asn Val Lys
                020                 025                 030
Ile Pro Val Ala Ile Lys Glu Leu Leu Lys Ser Thr Gly Ala Glu
                035                 040                 045
Ser Ser Glu Glu Phe Leu Arg Glu Ala Tyr Ile Met Ala Ser Glu
                050                 055                 060
```

```
Glu His Val Asn Leu Leu Lys Leu Leu Ala Val Cys Met Ser Ser
                065                 070                 075

Gln Met Met Leu Ile Thr Gln Leu Met Pro Leu Gly Cys Leu Leu
                080                 085                 090

Asp Tyr Val Arg Asn Asn Arg Asp Lys Ile Ser Ser Lys Ala Leu
                095                 100                 105

Leu Asn Trp Ser Thr Gln Ile Ala Lys Gly Met Ser Tyr Leu Glu
                110                 115                 120

Glu Lys Arg Leu Val His Arg Asp Leu Ala Ala Arg Asn Val Leu
                125                 130                 135

Val Arg Leu Leu Ala Gly Glu Asp His Asp Phe Gly Leu Ala Lys
                140                 145                 150

Leu Leu Ser Ser Asp Ser Asn Glu Tyr Lys Ala Gly Gly Lys Met
                155                 160                 165

Pro Ile Lys Trp Leu Ala Leu Glu Cys Ile Arg Asn Arg Val Phe
                170                 175                 180

Thr Ser Lys Ser Asp Val Trp Ala Phe Gly Val Thr Ile Trp Glu
                185                 190                 195

Leu Leu Thr Phe Gly Gln Arg Pro His Glu Asn Ile Pro Ala Lys
                200                 205                 210

Asp Ile Pro Asp Leu Ile Glu Val Gly Leu Lys Leu Glu Gln Pro
                215                 220                 225

Glu Ile Cys Ser Leu Asp Ile Tyr Cys Thr Leu Leu Ser Cys Trp
                230                 235                 240

His Leu Asp Ala Ala Met Arg Pro Thr Phe Lys Gln Leu Thr Thr
                245                 250                 255

Val Phe Ala Glu Phe Ala Arg Asp Pro
                260

(2) INFORMATION FOR SEQ ID NO:68:

(i) SEQUENCE CHARACTERISTICS:
        (A) LENGTH: 269

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 78

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988
```

(xi) SEQUENCE DESCRIPTION: SEQ ID NO:68:

| Glu | Lys | Ile | Thr | Leu | Leu | Arg | Glu | Leu | Gly | Gln | Gly | Ser | Phe | Gly |
|-----|-----|-----|-----|-----|-----|-----|-----|-----|-----|-----|-----|-----|-----|-----|
|     |     |     |     | 005 |     |     |     |     | 010 |     |     |     |     | 015 |
| Met | Val | Tyr | Glu | Gly | Asn | Ala | Arg | Asp | Ile | Ile | Lys | Gly | Glu | Ala |
|     |     |     |     | 020 |     |     |     |     | 025 |     |     |     |     | 030 |
| Glu | Thr | Arg | Val | Ala | Val | Lys | Thr | Val | Asn | Glu | Ser | Ala | Ser | Leu |
|     |     |     |     | 035 |     |     |     |     | 040 |     |     |     |     | 045 |
| Arg | Glu | Arg | Ile | Glu | Phe | Leu | Asn | Glu | Ala | Ser | Val | Met | Lys | Gly |
|     |     |     |     | 050 |     |     |     |     | 055 |     |     |     |     | 060 |
| Phe | Thr | Cys | His | His | Val | Val | Arg | Leu | Leu | Gly | Val | Val | Ser | Lys |
|     |     |     |     | 065 |     |     |     |     | 070 |     |     |     |     | 075 |
| Gly | Gln | Pro | Thr | Leu | Val | Val | Met | Glu | Leu | Met | Ala | His | Gly | Asp |
|     |     |     |     | 080 |     |     |     |     | 085 |     |     |     |     | 090 |
| Leu | Lys | Ser | Tyr | Leu | Arg | Ser | Leu | Arg | Pro | Glu | Ala | Glu | Pro | Thr |
|     |     |     |     | 095 |     |     |     |     | 100 |     |     |     |     | 105 |
| Leu | Gln | Glu | Met | Ile | Gln | Met | Ala | Ala | Glu | Ile | Ala | Asp | Gly | Met |
|     |     |     |     | 110 |     |     |     |     | 115 |     |     |     |     | 120 |
| Ala | Tyr | Leu | Asn | Ala | Lys | Lys | Phe | Val | His | Arg | Asp | Leu | Ala | Ala |
|     |     |     |     | 125 |     |     |     |     | 130 |     |     |     |     | 135 |
| Arg | Asn | Cys | Met | Val | Ala | His | Asp | Phe | Thr | Val | Lys | Ile | Gly | Asp |
|     |     |     |     | 140 |     |     |     |     | 145 |     |     |     |     | 150 |
| Phe | Gly | Met | Thr | Arg | Asp | Ile | Tyr | Glu | Thr | Asp | Tyr | Tyr | Arg | Lys |
|     |     |     |     | 155 |     |     |     |     | 160 |     |     |     |     | 165 |
| Gly | Lys | Gly | Leu | Leu | Pro | Val | Arg | Trp | Met | Ala | Pro | Glu | Ser | Leu |
|     |     |     |     | 170 |     |     |     |     | 175 |     |     |     |     | 180 |
| Lys | Asp | Gly | Val | Phe | Thr | Thr | Ser | Ser | Asp | Met | Trp | Ser | Phe | Gly |
|     |     |     |     | 185 |     |     |     |     | 190 |     |     |     |     | 195 |
| Val | Val | Leu | Trp | Glu | Ile | Thr | Ser | Leu | Ala | Glu | Gln | Pro | Tyr | Gln |
|     |     |     |     | 200 |     |     |     |     | 205 |     |     |     |     | 210 |
| Gly | Leu | Ser | Asn | Glu | Gln | Val | Leu | Lys | Phe | Val | Met | Asp | Gly | Gly |
|     |     |     |     | 215 |     |     |     |     | 220 |     |     |     |     | 225 |
| Tyr | Leu | Asp | Gln | Pro | Asp | Asn | Cys | Pro | Glu | Arg | Val | Thr | Asp | Leu |
|     |     |     |     | 230 |     |     |     |     | 235 |     |     |     |     | 240 |
| Met | Arg | Met | Cys | Trp | Gln | Phe | Asn | Pro | Asn | Met | Arg | Pro | Thr | Phe |
|     |     |     |     | 245 |     |     |     |     | 250 |     |     |     |     | 255 |
| Leu | Glu | Ile | Val | Asn | Leu | Leu | Lys | Asp | Asp | Leu | His | Pro | Ser |     |
|     |     |     |     | 260 |     |     |     |     | 265 |     |     |     |     |     |

(2) INFORMATION FOR SEQ ID NO:69:

(i) SEQUENCE CHARACTERISTICS:
        (A) LENGTH: 269

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 79

(x) PUBLICATION INFORMATION:
        (A) AUTHORS:

Hanks, S. K.
Quinn, A. M.
Hunter, T.

(B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:69:

```
Glu Lys Ile Thr Met Ser Arg Glu Leu Gly Gln Gly Ser Phe Gly
            005                 010                 015

Met Val Tyr Glu Gly Val Ala Lys Gly Val Val Lys Asp Glu Pro
            020                 025                 030

Glu Thr Arg Val Ala Ile Lys Thr Val Asn Glu Ala Ala Ser Met
            035                 040                 045

Arg Glu Arg Ile Glu Phe Leu Asn Glu Ala Ser Val Met Lys Glu
            050                 055                 060

Phe Asn Cys His His Val Val Arg Leu Leu Gly Val Val Ser Gln
            065                 070                 075

Gly Gln Pro Thr Leu Val Ile Met Glu Leu Met Thr Arg Gly Asp
            080                 085                 090

Leu Lys Ser Tyr Leu Arg Ser Leu Arg Pro Glu Met Glu Pro Ser
            095                 100                 105

Leu Ser Lys Met Ile Gln Met Ala Gly Glu Ile Ala Asp Gly Met
            110                 115                 120

Ala Tyr Leu Asn Ala Asn Lys Phe Val His Arg Asp Leu Ala Ala
            125                 130                 135

Arg Asn Cys Met Val Ala Glu Asp Phe Thr Val Lys Ile Gly Asp
            140                 145                 150

Phe Gly Met Thr Arg Asp Ile Tyr Glu Thr Asp Tyr Tyr Arg Lys
            155                 160                 165

Gly Lys Gly Leu Leu Pro Val Arg Trp Met Ser Pro Glu Ser Leu
            170                 175                 180

Lys Asp Gly Val Phe Thr Thr Tyr Ser Asp Val Trp Ser Phe Gly
            185                 190                 195

Val Val Leu Trp Glu Ile Ala Thr Leu Ala Glu Gln Pro Tyr Gln
            200                 205                 210

Gly Leu Ser Asn Glu Gln Val Leu Arg Phe Val Met Glu Gly Gly
            215                 220                 225

Leu Leu Asp Lys Pro Asp Asn Cys Pro Asp Met Leu Phe Glu Leu
            230                 235                 240

Met Arg Met Cys Trp Gln Tyr Asn Pro Lys Met Arg Pro Ser Phe
            245                 250                 255

Leu Glu Ile Ile Ser Ser Ile Lys Glu Glu Met Glu Pro Gly
            260                 265
```

(2) INFORMATION FOR SEQ ID NO:70:

(i) SEQUENCE CHARACTERISTICS:
      (A) LENGTH: 269

(B) TYPE: amino acid (D) TOPOLOGY: linear (ii) MOLECULE TYPE:
             (A) DESCRIPTION: protein (vi) ORIGINAL SOURCE:
             (A) ORGANISM: Drosophila melanogaster (ix) FEATURE: Protein kinase; Table 8 Column 80

(x) PUBLICATION INFORMATION:
             (A) AUTHORS:

Hanks, S. K.
                 Quinn, A. M.
                 Hunter, T.
             (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:70:

Glu Asn Ile Ile Gln Leu Ala Pro Leu Gly Gln Gly Ser Phe Gly
            005                 010                 015

Met Val Tyr Glu Gly Ile Leu Lys Ser Phe Pro Pro Asn Gly Val
            020                 025                 030

Asp Arg Glu Cys Ala Ile Lys Thr Val Asn Glu Asn Ala Thr Asp
            035                 040                 045

Arg Glu Arg Thr Asn Phe Leu Ser Glu Ala Ser Val Met Lys Glu
            050                 055                 060

Phe Asp Thr Tyr His Val Val Arg Leu Leu Gly Val Cys Ser Arg
            065                 070                 075

Gly Gln Pro Ala Leu Val Val Met Glu Leu Met Lys Lys Val Phe
            080                 085                 090

Leu Lys Ser Tyr Leu Arg Ala His Arg Pro Arg Ser Gly Pro Thr
            095                 100                 105

Tyr Gly Arg Ile Tyr Gln Val Ala Ile Glu Ile Ala Asp Gly Met
            110                 115                 120

Ala Tyr Leu Ala Ala Lys Lys Phe Val His Arg Asp Leu Ala Ala
            125                 130                 135

Arg Asn Cys Met Val Ala Asp Asp Leu Thr Val Lys Ile Gly Asp
            140                 145                 150

Phe Gly Met Thr Arg Asp Ile Tyr Glu Thr Asp Tyr Tyr Arg Lys
            155                 160                 165

Thr Lys Gly Leu Leu Pro Val Arg Trp Met Pro Pro Glu Ser Leu
            170                 175                 180

Arg Asp Gly Val Tyr Ser Ser Ala Ser Asp Val Phe Ser Phe Gly
            185                 190                 195

Val Val Leu Trp Glu Met Ala Thr Leu Ala Ala Gln Pro Tyr Gln
            200                 205                 210

Gly Leu Ser Asn Glu Gln Val Leu Arg Tyr Val Ile Asp Gly Gly
            215                 220                 225

Val Met Glu Arg Pro Glu Asn Cys Pro Asp Phe Leu His Lys Leu
            230                 235                 240

Met Gln Arg Cys Trp His His Arg Ser Ser Ala Arg Pro Ser Phe

```
                        245                 250                 255

Leu Asp Ile Ile Ala Tyr Leu Glu Pro Gln Cys Pro Asn Ser
                260                 265

(2) INFORMATION FOR SEQ ID NO:71:

(i) SEQUENCE CHARACTERISTICS:
        (A) LENGTH: 275

(B) TYPE: amino acid (D) TOPOLOGY: linear (ii) MOLECULE TYPE:
         (A) DESCRIPTION: protein (vi) ORIGINAL SOURCE:
         (A) ORGANISM: human (ix) FEATURE: Protein kinase; Table 8 Column 81

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:71:

Glu Lys Leu Thr Leu Arg Leu Leu Gly Ser Gly Ala Phe Gly
                005                 010                 015

Glu Val Tyr Glu Gly Thr Ala Val Asp Ile Leu Gly Val Gly Ser
                020                 025                 030

Gly Glu Ile Lys Val Ala Val Lys Thr Leu Lys Lys Gly Ser Thr
                035                 040                 045

Asp Gln Glu Lys Ile Glu Phe Leu Lys Glu Ala His Leu Met Ser
                050                 055                 060

Lys Phe Asn His Pro Asn Ile Leu Lys Gln Leu Gly Val Cys Leu
                065                 070                 075

Leu Asn Glu Pro Gln Tyr Ile Ile Leu Glu Leu Met Glu Gly Gly
                080                 085                 090

Asp Leu Leu Thr Tyr Leu Arg Lys Ala Arg Met Ala Thr Phe Leu
                095                 100                 105

Thr Leu Val Asp Leu Val Asp Leu Cys Val Asp Ile Ser Lys Gly
                110                 115                 120

Cys Val Tyr Leu Glu Arg Met His Phe Ile His Arg Asp Leu Ala
                125                 130                 135

Ala Arg Asn Cys Leu Val Ser Val Lys Asp Tyr Thr Ser Pro Arg
                140                 145                 150

Ile Val Lys Ile Gly Asp Phe Gly Leu Ala Arg Asp Ile Tyr Lys
                155                 160                 165

Asn Asp Tyr Tyr Arg Lys Gly Glu Gly Leu Leu Pro Val Arg Trp
                170                 175                 180
```

```
Met Ala Pro Glu Ser Leu Met Asp Gly Ile Phe Thr Thr Gln Ser
                185                 190                 195

Asp Val Trp Ser Phe Gly Ile Leu Ile Trp Glu Ile Leu Thr Leu
                200                 205                 210

Gly His Gln Pro Tyr Pro Ala His Ser Asn Leu Asp Val Leu Asn
                215                 220                 225

Tyr Val Gln Thr Gly Gly Arg Leu Glu Pro Pro Arg Asn Cys Pro
                230                 235                 240

Asp Asp Leu Trp Asn Leu Met Thr Gln Cys Trp Ala Gln Glu Pro
                245                 250                 255

Asp Gln Arg Pro Thr Phe His Arg Ile Gln Asp Gln Leu Gln Leu
                260                 265                 270

Phe Arg Asn Phe Phe
                275

(2) INFORMATION FOR SEQ ID NO:72:

(i) SEQUENCE CHARACTERISTICS:
        (A) LENGTH: 276

(B) TYPE: amino acid (D) TOPOLOGY: linear (ii) MOLECULE TYPE:
        (A) DESCRIPTION: protein (vi) ORIGINAL SOURCE:
        (A) ORGANISM: chicken (ix) FEATURE: Protein kinase; Table 8 Column 82

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:72:

Asp Lys Leu Asn Leu His Lys Leu Leu Gly Ser Gly Ala Phe Gly
                005                 010                 015

Glu Val Tyr Glu Gly Thr Ala Leu Asp Ile Leu Ala Asp Gly Ser
                020                 025                 030

Gly Glu Ser Arg Val Ala Val Lys Thr Leu Lys Arg Gly Ala Thr
                035                 040                 045

Asp Gln Glu Lys Ser Glu Phe Leu Lys Glu Ala His Leu Met Ser
                050                 055                 060

Lys Phe Asp His Pro His Ile Leu Lys Leu Leu Gly Val Cys Leu
                065                 070                 075

Leu Asn Glu Pro Gln Tyr Leu Ile Leu Glu Leu Met Glu Gly Gly
                080                 085                 090
```

```
Asp Leu Leu Ser Tyr Leu Arg Gly Ala Arg Lys Gln Lys Phe Leu
            095                 100                 105

Thr Leu Thr Asp Leu Leu Asp Ile Cys Leu Asp Ile Cys Lys Gly
            110                 115                 120

Cys Val Tyr Leu Glu Lys Met Arg Phe Ile His Arg Asp Leu Ala
            125                 130                 135

Ala Arg Asn Cys Leu Val Ser Glu Lys Gln Tyr Gly Ser Cys Ser
            140                 145                 150

Arg Val Val Lys Ile Gly Asp Phe Gly Leu Ala Arg Asp Ile Tyr
            155                 160                 165

Lys Asn Asp Tyr Tyr Arg Lys Gly Glu Gly Leu Leu Pro Val Arg
            170                 175                 180

Trp Met Ala Pro Glu Ser Leu Ile Asp Gly Val Phe Thr Asn His
            185                 190                 195

Ser Asp Val Met Ala Phe Gly Val Leu Val Trp Glu Thr Leu Thr
            200                 205                 210

Leu Gly Gln Gln Pro Tyr Pro Gly Leu Ser Asn Ile Glu Val Leu
            215                 220                 225

His His Val Arg Ser Gly Gly Arg Leu Glu Ser Pro Asn Asn Cys
            230                 235                 240

Pro Asp Asp Ile Arg Asp Leu Met Thr Arg Cys Trp Ala Gln Asp
            245                 250                 255

Pro His Asn Arg Pro Thr Phe Phe Tyr Ile Gln His Lys Leu Gln
            260                 265                 270

Glu Ile Arg His Ser Pro
            275
```

(2) INFORMATION FOR SEQ ID NO:73:

(i) SEQUENCE CHARACTERISTICS:
        (A) LENGTH: 273

(B) TYPE: amino acid (D) TOPOLOGY: linear (ii) MOLECULE TYPE:
        (A) DESCRIPTION: protein (vi) ORIGINAL SOURCE:
        (A) ORGANISM: Drosophila melanogaster (ix) FEATURE: Protein kinase; Table 8 Column 83

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:73:

Ser Gln Leu Lys Leu Leu Arg Phe Leu Gly Ser Gly Ala Phe Gly

```
                       005                 010                 015
Glu Val Tyr Glu Gly Gln Leu Lys Thr Glu Asp Ser Glu Glu Pro
                020                 025                 030
Gln Arg Val Ala Ile Lys Ser Leu Arg Lys Gly Ala Ser Glu Phe
                035                 040                 045
Ala Glu Leu Leu Gln Glu Ala Gln Leu Met Ser Asn Phe Lys His
                050                 055                 060
Glu Asn Ile Val Arg Leu Val Gly Ile Cys Phe Asp Thr Glu Pro
                065                 070                 075
Ile Ser Leu Ile Met Glu His Met Glu Ala Gly Asp Leu Leu Ser
                080                 085                 090
Tyr Leu Arg Ala Ala Arg Ala Thr Ser Thr Leu Ser Leu Ser Glu
                095                 100                 105
Leu Leu Ala Met Cys Ile Asp Val Ala Asn Gly Cys Ser Tyr Leu
                110                 115                 120
Glu Asp Met His Phe Val His Arg Asp Leu Ala Cys Arg Asn Cys
                125                 130                 135
Leu Val Thr Glu Ser Thr Gly Ser Thr Asp Arg Arg Arg Thr Val
                140                 145                 150
Lys Ile Gly Asp Phe Gly Leu Ala Arg Asp Ile Tyr Lys Ser Asp
                155                 160                 165
Tyr Tyr Arg Lys Gly Glu Gly Leu Leu Pro Val Arg Trp Met Ser
                170                 175                 180
Pro Glu Ser Leu Val Asp Gly Leu Phe Thr Thr Gln Ser Asp Val
                185                 190                 195
Trp Ala Phe Gly Val Leu Cys Trp Glu Ile Leu Thr Leu Gly Gln
                200                 205                 210
Gln Pro Tyr Ala Ala Arg Asn Asn Phe Glu Val Leu Ala His Val
                215                 220                 225
Lys Glu Gly Gly Arg Leu Gln Gln Pro Pro Met Cys Thr Glu Lys
                230                 235                 240
Leu Tyr Ser Leu Leu Leu Cys Trp Arg Thr Asp Pro Trp Glu
                245                 250                 255
Arg Pro Ser Phe Arg Arg Cys Tyr Asn Thr Leu His Ala Ile Ser
                260                 265                 270
Thr Asp Leu (2) INFORMATION FOR SEQ ID NO:74:

(i) SEQUENCE CHARACTERISTICS:
        (A) LENGTH: 268

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 84

(x) PUBLICATION INFORMATION:
        (A) AUTHORS:

Hanks, S. K.
```

Quinn, A. M.
Hunter, T.
(B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:74:

Arg Asp Ile Val Leu Lys Trp Glu Leu Gly Glu Gly Ala Phe Gly
                005                 010                 015

Lys Val Phe Leu Ala Glu Cys His Asn Leu Leu Pro Glu Gln Asp
                020                 025                 030

Lys Met Leu Val Ala Val Lys Ala Leu Lys Glu Ala Ser Glu Ser
                035                 040                 045

Ala Arg Gln Asp Phe Gln Arg Glu Val Glu Leu Leu Thr Met Leu
                050                 055                 060

Gln His Gln His Ile Val Arg Phe Phe Gly Val Cys Thr Glu Gly
                065                 070                 075

Arg Pro Leu Leu Met Val Phe Glu Tyr Met Arg His Gly Asp Leu
                080                 085                 090

Asn Arg Phe Leu Arg Ser His Gly Pro Asp Ala Lys Leu Gly Leu
                095                 100                 105

Gly Gln Leu Leu Ala Val Ala Ser Gln Val Ala Ala Gly Met Val
                110                 115                 120

Tyr Leu Ala Gly Leu His Phe Val His Arg Asp Leu Ala Thr Arg
                125                 130                 135

Asn Cys Leu Val Gly Gln Gly Leu Val Val Lys Ile Gly Asp Phe
                140                 145                 150

Gly Met Ser Arg Asp Ile Tyr Ser Thr Asp Tyr Tyr Arg Val Gly
                155                 160                 165

Arg Thr Met Leu Pro Ile Arg Trp Met Pro Pro Glu Ser Ile Leu
                170                 175                 180

Tyr Arg Lys Phe Thr Thr Glu Ser Asp Val Trp Ser Phe Gly Val
                185                 190                 195

Val Leu Trp Glu Ile Phe Thr Tyr Gly Lys Gln Pro Trp Tyr Gln
                200                 205                 210

Leu Ser Asn Thr Glu Ala Ile Asp Cys Ile Thr Gln Gly Arg Glu
                215                 220                 225

Leu Glu Arg Pro Arg Ala Cys Pro Pro Glu Val Tyr Ala Ile Met
                230                 235                 240

Arg Gly Cys Trp Gln Arg Glu Pro Gln Gln Arg Pro Ser Ile Lys
                245                 250                 255

Asp Val His Ala Arg Leu Gln Ala Leu Ala Gln Ala Pro
                260                 265

(2) INFORMATION FOR SEQ ID NO:75:

(i) SEQUENCE CHARACTERISTICS:
(A) LENGTH: 266

(B) TYPE: amino acid (D) TOPOLOGY: linear

```
    (ii) MOLECULE TYPE:
         (A) DESCRIPTION: protein (vi) ORIGINAL SOURCE:
         (A) ORGANISM: human (ix) FEATURE: Protein kinase; Table 8 Column 85

(x) PUBLICATION INFORMATION:
         (A) AUTHORS:

Hanks, S. K.
             Quinn, A. M.
             Hunter, T.
         (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:75:

Leu Ile Val His Phe Asn Glu Val Ile Gly Arg Gly His Phe Gly
             005                 010                 015

Cys Val Tyr His Gly Thr Leu Leu Asp Asn Asp Gly Lys Lys Ile
             020                 025                 030

His Cys Ala Val Lys Ser Leu Asn Arg Ile Thr Asp Ile Gly Glu
             035                 040                 045

Val Ser Gln Phe Leu Thr Glu Gly Ile Ile Met Lys Asp Phe Ser
             050                 055                 060

His Pro Asn Val Leu Ser Leu Leu Gly Ile Cys Leu Arg Ser Glu
             065                 070                 075

Gly Ser Pro Leu Val Val Leu Pro Tyr Met Lys His Gly Asp Leu
             080                 085                 090

Arg Asn Phe Ile Arg Asn Glu Thr His Asn Pro Thr Val Lys Asp
             095                 100                 105

Leu Ile Gly Phe Gly Leu Gln Val Ala Lys Ala Met Lys Tyr Leu
             110                 115                 120

Ala Ser Lys Lys Phe Val His Arg Asp Leu Ala Ala Arg Asn Cys
             125                 130                 135

Met Leu Asp Glu Lys Phe Thr Val Lys Val Ala Asp Phe Gly Leu
             140                 145                 150

Ala Arg Asp Met Tyr Asp Lys Glu Tyr Tyr Ser Val Thr Gly Ala
             155                 160                 165

Lys Leu Pro Val Lys Trp Met Ala Leu Glu Ser Leu Gln Thr Gln
             170                 175                 180

Lys Phe Thr Thr Lys Ser Asp Val Trp Ser Phe Gly Val Val Leu
             185                 190                 195

Trp Glu Leu Met Thr Arg Gly Ala Pro Pro Tyr Pro Asp Val Asn
             200                 205                 210

Thr Phe Asp Ile Thr Val Tyr Leu Leu Gln Gly Arg Arg Leu Leu
             215                 220                 225

Gln Pro Glu Tyr Cys Pro Asp Pro Leu Tyr Glu Val Met Leu Lys
             230                 235                 240

Cys Trp His Pro Lys Ala Glu Met Arg Pro Ser Phe Ser Glu Leu
             245                 250                 255
```

Val Ser Arg Ile Ser Ala Ile Phe Ser Thr Phe
            260                 265

(2) INFORMATION FOR SEQ ID NO:76:

(i) SEQUENCE CHARACTERISTICS:
        (A) LENGTH: 270

(B) TYPE: amino acid (D) TOPOLOGY: linear (ii) MOLECULE TYPE:
        (A) DESCRIPTION: protein (vi) ORIGINAL SOURCE:
        (A) ORGANISM: mouse (ix) FEATURE: Protein kinase; Table 8 Column 87

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:76:

Asp Gln Leu Val Ile Gly Arg Thr Leu Gly Ser Gly Ala Phe Gly
            005                 010                 015

Gln Val Val Glu Ala Thr Ala His Asp Leu Ser His Ser Gln Ala
            020                 025                 030

Thr Met Lys Val Ala Val Lys Met Leu Lys Ser Thr Ala Arg Ser
            035                 040                 045

Ser Glu Lys Gln Ala Leu Met Ser Glu Leu Lys Ile Met Ser His
            050                 055                 060

Leu Gly Pro His Leu His Val Val Asn Leu Leu Gly Ala Cys Thr
            065                 070                 075

Lys Gly Gly Pro Ile Tyr Ile Ile Thr Glu Tyr Cys Arg Tyr Gly
            080                 085                 090

Asp Leu Val Asp Tyr Leu His Arg Asn Lys His Thr Phe Leu Leu
            095                 100                 105

Ser Tyr Thr Asp Leu Val Gly Phe Ser Tyr Gln Val Ala Asn Gly
            110                 115                 120

Met Asp Phe Leu Ala Ser Lys Asn Cys Val His Arg Asp Leu Ala
            125                 130                 135

Ala Arg Asn Val Leu Ile Cys Glu Gly Lys Leu Val Lys Ile Cys
            140                 145                 150

Asp Phe Gly Leu Ala Arg Asp Ile Met Arg Asp Ser Asn Tyr Ile
            155                 160                 165

Ser Gly Ser Thr Tyr Leu Pro Leu Lys Trp Met Ala Pro Glu Ser
            170                 175                 180

Ile Phe Asn Ser Leu Tyr Thr Thr Leu Ser Asp Val Trp Ser Phe 185                 190                 195

Gly Ile Leu Leu Trp Glu Ile Phe Thr Leu Gly Gly Thr Pro Tyr
                200                 205                 210

Pro Glu Pro Met Asn Asp Gln Phe Tyr Asn Ala Ile Lys Arg Gly
                215                 220                 225

Tyr Arg Met Ala Gln Pro Ala His Ala Ser Asp Glu Ile Tyr Glu
                230                 235                 240

Ile Met Gln Lys Cys Trp Glu Lys Phe Glu Thr Arg Pro Pro
                245                 250                 255

Phe Ser Gln Leu Val Leu Leu Leu Glu Arg Leu Leu Gly Glu Gly
                260                 265                 270

(2) INFORMATION FOR SEQ ID NO:77:

(i) SEQUENCE CHARACTERISTICS:
        (A) LENGTH: 270

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 88

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:77:

Asn Asn Leu Gln Phe Gly Lys Thr Leu Gly Ala Gly Ala Phe Gly
                005                 010                 015

Lys Val Val Glu Ala Thr Ala Phe Asp Leu Gly Lys Glu Asp Ala
                020                 025                 030

Val Leu Lys Val Ala Val Lys Met Leu Lys Ser Thr Ala His Ala
                035                 040                 045

Asp Glu Lys Glu Ala Leu Met Ser Glu Leu Lys Ile Met Ser His
                050                 055                 060

Leu Gly Gln His Glu His Ile Val Asn Leu Leu Gly Ala Cys Thr
                065                 070                 075

His Gly Gly Pro Val Leu Val Ile Thr Glu Tyr Cys Cys Tyr Gly
                080                 085                 090

Asp Leu Leu Asn Phe Leu Arg Arg Lys Ala Glu Ala Met Leu Leu
                095                 100                 105

Glu Leu Arg Asp Leu Leu His Phe Ser Gln Val Ala Gln Gly
                110                 115                 120

```
Met Ala Phe Leu Ala Ser Lys Asn Cys Ile His Arg Asp Leu Ala
            125                 130                 135

Ala Arg Asn Val Leu Leu Thr Asn Gly His Val Ala Lys Ile Gly
            140                 145                 150

Asp Phe Gly Leu Ala Arg Asp Ile Met Asn Asp Ser Asn Tyr Ile
            155                 160                 165

Val Gly Asn Ala Arg Leu Pro Val Lys Trp Met Ala Pro Glu Ser
            170                 175                 180

Ile Phe Asp Cys Val Tyr Thr Val Gln Ser Asp Val Trp Ser Tyr
            185                 190                 195

Gly Ile Leu Leu Trp Glu Ile Phe Ser Leu Gly Leu Asn Pro Tyr
            200                 205                 210

Pro Gly Leu Val Asn Ser Lys Phe Tyr Lys Leu Val Lys Asp Gly
            215                 220                 225

Tyr Gln Met Ala Gln Pro Ala Phe Ala Pro Lys Asn Ile Tyr Ser
            230                 235                 240

Ile Met Gln Ala Cys Trp Ala Leu Glu Pro Thr His Arg Pro Thr
            245                 250                 255

Phe Gln Gln Ile Cys Ser Phe Leu Gln Glu Gln Ala Gln Glu Asp
            260                 265                 270
```

(2) INFORMATION FOR SEQ ID NO:78:

(i) SEQUENCE CHARACTERISTICS:
        (A) LENGTH: 270

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 89

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52

(G) DATE: 1988

(xi) SEQUENCE DESCRIPTION: SEQ ID NO:78:

```
Asn Arg Leu Ser Phe Gly Lys Thr Leu Gly Ala Gly Ala Phe Gly
            005                 010                 015

Lys Val Val Glu Ala Thr Ala Tyr Asp Leu Ile His Ser Asp Ala
            020                 025                 030

Ala Met Thr Val Ala Val Lys Met Leu Lys Pro Ser Ala His Leu
            035                 040                 045
```

```
Thr Glu Arg Glu Ala Leu Met Ser Glu Leu Lys Val Leu Ser Tyr
              050                 055                 060

Leu Gly Asn His Met His Ile Val Asn Leu Leu Gly Ala Cys Thr
              065                 070                 075

Ile Gly Gly Pro Thr Leu Val Ile Thr Glu Tyr Cys Cys Tyr Gly
              080                 085                 090

Asp Leu Leu Asn Phe Leu Arg Arg Lys Arg Asp Ser Phe Ile Leu
              095                 100                 105

Asp Leu Glu Asp Leu Leu Ser Phe Ser Tyr Gln Val Ala Lys Gly
              110                 115                 120

Met Ala Phe Leu Ala Ser Lys Asn Cys Ile His Arg Asp Leu Ala
              125                 130                 135

Ala Arg Asn Ile Leu Leu Thr His Gly Arg Ile Thr Lys Ile Cys
              140                 145                 150

Asp Phe Gly Leu Ala Arg Asp Ile Lys Asn Asp Ser Asn Tyr Val
              155                 160                 165

Val Gly Asn Ala Arg Leu Pro Val Lys Trp Met Ala Pro Glu Ser
              170                 175                 180

Ile Phe Asn Cys Val Tyr Thr Phe Glu Ser Asp Val Trp Ser Tyr
              185                 190                 195

Gly Ile Phe Leu Trp Glu Leu Phe Ser Leu Gly Ser Ser Pro Tyr
              200                 205                 210

Pro Gly Pro Val Asp Ser Lys Phe Tyr Lys Met Ile Lys Glu Gly
              215                 220                 225

Phe Arg Met Leu Ser Pro Glu His Ala Pro Ala Glu Met Tyr Asp
              230                 235                 240

Ile Met Lys Thr Cys Trp Asp Ala Asp Pro Leu Lys Arg Pro Thr
              245                 250                 255

Phe Lys Gln Ile Val Gln Leu Ile Glu Lys Gln Ile Ser Glu Ser
              260                 265                 270

(2) INFORMATION FOR SEQ ID NO:79:

(i) SEQUENCE CHARACTERISTICS:
        (A) LENGTH: 269

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Protein kinase; Table 8 Column 90

(x) PUBLICATION INFORMATION:
        (A) AUTHORS:

Hanks, S. K.
            Quinn, A. M.
            Hunter, T.
        (B) TITLE: The protein kinase family (C) JOURNAL: Science (D) VOLUME: 241

(F) PAGES: 42-52
```

(G) DATE: 1988

(xi) SEQUENCE DESCRIPTION: SEQ ID NO:79:

Lys Asn Leu Val Leu Gly Lys Thr Leu Gly Glu Gly Glu Phe Gly
                005                 010                 015

Lys Val Val Lys Ala Thr Ala Phe His Leu Lys Lys Arg Ala Gly
                020                 025                 030

Tyr Thr Thr Val Ala Val Lys Met Leu Lys Glu Asn Ala Ser Pro
                035                 040                 045

Ser Glu Leu Arg Asp Leu Leu Ser Glu Phe Asn Val Leu Lys Gln
                050                 055                 060

Val Asn His Pro His Val Ile Asn Leu Tyr Gly Ala Cys Ser Gln
                065                 070                 075

Asp Gly Pro Leu Leu Leu Ile Val Glu Tyr Ala Lys Tyr Gly Ser
                080                 085                 090

Leu Arg Gly Phe Leu Arg Glu Ser Arg Lys Val Met Pro Leu Thr
                095                 100                 105

Met Gly Asp Leu Ile Ser Phe Ala Trp Gln Ile Ser Gln Gly Met
                110                 115                 120

Gln Tyr Leu Ala Glu Met Lys Leu Val His Arg Asp Leu Ala Ala
                125                 130                 135

Arg Asn Ile Leu Val Ala Glu Gly Arg Lys Met Lys Ile Ser Asp
                140                 145                 150

Phe Gly Leu Ser Arg Asp Val Tyr Glu Glu Asp Ser Tyr Val Lys
                155                 160                 165

Ser Gln Gly Arg Ile Pro Val Lys Trp Met Ala Ile Glu Ser Leu
                170                 175                 180

Phe Asp His Ile Tyr Thr Thr Gln Ser Asp Val Trp Ser Phe Gly
                185                 190                 195

Val Leu Leu Trp Glu Ile Val Thr Leu Gly Gly Asn Pro Tyr Pro
                200                 205                 210

Gly Ile Pro Pro Glu Arg Leu Phe Asn Leu Leu Lys Thr Gly His
                215                 220                 225

Arg Met Glu Arg Pro Asp Asn Cys Ser Glu Glu Met Tyr Arg Leu
                230                 235                 240

Met Leu Gln Cys Trp Lys Gln Glu Pro Asp Lys Arg Pro Val Phe
                245                 250                 255

Ala Asp Ile Ser Lys Asp Leu Glu Lys Met Met Val Lys Arg
                260                 265

(2) INFORMATION FOR SEQ ID NO:80:

(i) SEQUENCE CHARACTERISTICS:
        (A) LENGTH: 374

(B) TYPE: amino acid (D) TOPOLOGY: linear (ii) MOLECULE TYPE:
        (A) DESCRIPTION: protein (vi) ORIGINAL SOURCE:
        (A) ORGANISM: horse (ix) FEATURE: Alcohol dehydrogenase, Table 3 Column 1

(x) PUBLICATION INFORMATION:
    (A) AUTHORS:

Joernvall, H.
        Persson, M.
        Jeffery, J.

(B) TITLE: Alcohol dehydrogenases (C) JOURNAL: Proceedings of the National Academy of Sciences,
                 USA
    (D) VOLUME: 78

(F) PAGES: 4226-4230

(G) DATE: 1981

(xi) SEQUENCE DESCRIPTION: SEQ ID NO:80:

Ser Thr Ala Gly Lys Val Ile Lys Cys Lys Ala Ala Val Leu Trp
            005                 010                 015

Glu Glu Lys Lys Pro Phe Ser Ile Glu Glu Val Glu Val Ala Pro
            020                 025                 030

Pro Lys Ala His Glu Val Arg Ile Lys Met Val Ala Thr Gly Ile
            035                 040                 045

Cys Arg Ser Asp Asp His Val Val Ser Gly Thr Leu Val Thr Pro
            050                 055                 060

Leu Pro Val Ile Ala Gly His Glu Ala Ala Gly Ile Val Glu Ser
            065                 070                 075

Ile Gly Glu Gly Val Thr Thr Val Arg Pro Gly Asp Lys Val Ile
            080                 085                 090

Pro Leu Phe Thr Pro Gln Cys Gly Lys Cys Arg Val Cys Lys His
            095                 100                 105

Pro Glu Gly Asn Phe Cys Leu Lys Asn Asp Leu Ser Met Pro Arg
            110                 115                 120

Gly Thr Met Gln Asp Gly Thr Ser Arg Phe Thr Cys Arg Gly Lys
            125                 130                 135

Pro Ile His His Phe Leu Gly Thr Ser Thr Phe Ser Gln Tyr Thr
            140                 145                 150

Val Val Asp Glu Ile Ser Val Ala Lys Ile Asp Ala Ala Ser Pro
            155                 160                 165

Leu Glu Lys Val Cys Leu Ile Gly Cys Gly Phe Ser Thr Gly Tyr
            170                 175                 180

Gly Ser Ala Val Lys Val Ala Lys Val Thr Gln Gly Ser Thr Cys
            185                 190                 195

Ala Val Phe Gly Leu Gly Gly Val Gly Leu Ser Val Ile Met Gly
            200                 205                 210

Cys Lys Ala Ala Gly Ala Ala Ala Arg Ile Ile Gly Val Asp
            215                 220                 225

Ile Asn Lys Asp Lys Phe Ala Lys Glu Val Gly Ala Thr Glu Cys
            230                 235                 240

Val Asn Pro Gln Asp Tyr Lys Lys Pro Ile Gln Glu Val Leu Thr
            245                 250                 255

Glu Met Ser Asn Gly Gly Val Asp Phe Ser Phe Glu Val Ile Gly
            260                 265                 270

Arg Leu Asp Thr Met Val Thr Ala Leu Ser Cys Cys Gln Glu Ala
            275                 280                 285

Tyr Gly Val Ser Val Ile Val Gly Val Pro Pro Asp Ser Gln Asn
            290                 295                 300

Leu Ser Met Asn Pro Met Leu Leu Leu Ser Gly Arg Thr Trp Lys

```
                    305                 310                 315
Gly Ala Ile Phe Gly Gly Phe Lys Ser Lys Asp Ser Val Pro Lys
                320                 325                 330

Leu Val Ala Asp Phe Met Ala Lys Lys Phe Ala Leu Asp Pro Leu
                335                 340                 345

Ile Thr His Val Leu Pro Phe Glu Lys Ile Asn Glu Gly Phe Asp
                350                 355                 360

Leu Leu Arg Ser Gly Glu Ser Ile Arg Thr Ile Leu Thr Phe
                365                 370
```

(2) INFORMATION FOR SEQ ID NO:81:

(i) SEQUENCE CHARACTERISTICS:
        (A) LENGTH: 374

(B) TYPE: amino acid (D) TOPOLOGY: linear (ii) MOLECULE TYPE:
        (A) DESCRIPTION: protein (vi) ORIGINAL SOURCE:
        (A) ORGANISM: horse (ix) FEATURE: Alcohol dehydrogenase, Table 3 Column 2

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
              USA
        (D) VOLUME: 78

(F) PAGES: 4226-4230

(G) DATE: 1981

(xi) SEQUENCE DESCRIPTION: SEQ ID NO:81:

```
Ser Thr Ala Gly Lys Val Ile Lys Cys Lys Ala Ala Val Leu Trp
                005                 010                 015

Glu Asn Lys Lys Pro Phe Ser Ile Glu Glu Val Glu Val Ala Pro
                020                 025                 030

Pro Lys Ala His Glu Val Arg Ile Lys Met Val Ala Thr Gly Ile
                035                 040                 045

Cys Arg Ser Asp Asp His Val Val Ser Gly Thr Leu Val Thr Pro
                050                 055                 060

Leu Pro Val Ile Ala Gly His Glu Ala Ala Gly Ile Val Glu Ser
                065                 070                 075

Ile Gly Glu Gly Val Thr Thr Val Arg Pro Gly Asp Lys Val Ile
                080                 085                 090

Pro Leu Phe Ile Pro Gln Cys Gly Lys Cys Ser Val Cys Lys His
                095                 100                 105

Pro Glu Gly Asn Leu Cys Leu Lys Asn Ser Leu Ser Met Pro Arg
                110                 115                 120

Gly Thr Met Gln Asp Gly Thr Ser Arg Phe Thr Cys Arg Gly Lys
                125                 130                 135
```

```
Pro Ile His His Phe Leu Gly Thr Ser Thr Phe Ser Gln Tyr Thr
                140                 145                 150

Val Val Asp Glu Ile Ser Val Ala Lys Ile Asp Ala Ala Ser Pro
                155                 160                 165

Leu Glu Lys Val Cys Leu Ile Gly Cys Gly Phe Ser Thr Gly Tyr
                170                 175                 180

Gly Ser Ala Val Lys Val Ala Lys Val Thr Gln Gly Ser Thr Cys
                185                 190                 195

Ala Val Phe Gly Leu Gly Gly Val Gly Leu Ser Val Ile Met Gly
                200                 205                 210

Cys Lys Ala Ala Gly Ala Ala Ala Arg Ile Ile Gly Val Asp
                215                 220                 225

Ile Asn Lys Asp Lys Phe Ala Lys Glu Val Gly Ala Thr Glu Cys
                230                 235                 240

Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly
                260                 265                 270

Arg Leu Asp Thr Met Val Thr Ala Leu Ser Cys Cys Gln Glu Ala
                275                 280                 285

Tyr Gly Val Ser Val Ile Val Gly Val Pro Pro Asp Ser Gln Asn
                290                 295                 300

Leu Ser Met Asn Pro Met Leu Leu Leu Ser Gly Arg Thr Trp Lys
                305                 310                 315

Gly Ala Ile Phe Gly Gly Phe Lys Ser Lys Asp Ser Val Pro Lys
                320                 325                 330

Leu Val Ala Asp Phe Met Ala Lys Lys Phe Ala Leu Asp Pro Leu
                335                 340                 345

Ile Thr His Val Leu Pro Phe Glu Lys Ile Asn Glu Gly Phe Asp
                350                 355                 360

Leu Leu Arg Ser Gly Lys Ser Ile Arg Thr Ile Leu Thr Phe
                365                     370

(2) INFORMATION FOR SEQ ID NO:82:

(i) SEQUENCE CHARACTERISTICS:
        (A) LENGTH: 374

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Alcohol dehydrogenase, Table 3 Column 3

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
                USA
```

(D) VOLUME: 78

(F) PAGES: 4226-4230

(G) DATE: 1981

(xi) SEQUENCE DESCRIPTION: SEQ ID NO:82:

```
Ser Thr Ala Gly Lys Val Ile Lys Cys Lys Ala Ala Val Leu Trp
        005                 010                 015

Glu Leu Lys Lys Pro Phe Ser Ile Glu Glu Val Glu Val Ala Pro
        020                 025                 030

Pro Lys Ala His Glu Val Arg Ile Lys Met Val Ala Val Gly Ile
        035                 040                 045

Cys Gly Thr Asp Asp His Val Val Ser Gly Thr Met Val Thr Pro
        050                 055                 060

Leu Pro Val Ile Leu Gly His Glu Ala Ala Gly Ile Val Glu Ser
        065                 070                 075

Val Gly Glu Gly Val Thr Thr Val Lys Pro Gly Asp Lys Val Ile
        080                 085                 090

Pro Leu Ala Ile Pro Gln Cys Gly Lys Cys Arg Ile Cys Lys Asn
        095                 100                 105

Pro Glu Ser Asn Tyr Cys Leu Lys Asn Asp Val Ser Asn Pro Gln
        110                 115                 120

Gly Thr Leu Gln Asp Gly Thr Ser Arg Phe Thr Cys Arg Arg Lys
        125                 130                 135

Pro Ile His His Phe Leu Gly Ile Ser Thr Phe Ser Gln Tyr Thr
        140                 145                 150

Val Val Asp Glu Asn Ala Val Ala Lys Ile Asp Ala Ala Ser Pro
        155                 160                 165

Leu Glu Lys Val Cys Leu Ile Gly Cys Gly Phe Ser Thr Gly Tyr
        170                 175                 180

Gly Ser Ala Val Asn Val Ala Lys Val Thr Pro Gly Ser Thr Cys
        185                 190                 195

Ala Val Phe Gly Leu Gly Gly Val Gly Leu Ser Ala Ile Met Gly
        200                 205                 210

Cys Lys Ala Ala Gly Ala Ala Ala Arg Ile Ile Ala Val Asp
        215                 220                 225

Ile Asn Lys Asp Lys Phe Ala Lys Glu Leu Gly Ala Thr Glu Cys
        230                 235                 240

Ile Asn Pro Gln Asp Tyr Lys Lys Pro Ile Gln Glu Val Leu Lys
        245                 250                 255

Glu Met Thr Asp Gly Gly Val Asp Phe Ser Phe Glu Val Ile Gly
        260                 265                 270

Arg Leu Asp Thr Met Met Ala Ser Leu Leu Cys Cys His Glu Ala
        275                 280                 285

Cys Gly Thr Ser Val Ile Val Gly Val Pro Pro Asp Ser Gln Asn
        290                 295                 300

Leu Ser Met Asn Pro Met Leu Leu Leu Thr Gly Arg Thr Trp Lys
        305                 310                 315

Gly Ala Ile Phe Gly Gly Phe Lys Ser Lys Glu Cys Val Pro Lys
        320                 325                 330

Leu Val Ala Asp Phe Met Ala Lys Lys Phe Ser Leu Asp Ala Leu
        335                 340                 345

Ile Thr His Val Leu Pro Phe Glu Lys Ile Asn Glu Gly Phe Asp
        350                 355                 360
```

```
Leu Leu His Ser Gly Lys Ser Ile Arg Thr Ile Leu Met Phe
            365                 370
```

(2) INFORMATION FOR SEQ ID NO:83:

(i) SEQUENCE CHARACTERISTICS:
        (A) LENGTH: 374

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Alcohol dehydrogenase, Table 3 Column 4

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
            USA
        (D) VOLUME: 78

(F) PAGES: 4226-4230

(G) DATE: 1981

(xi) SEQUENCE DESCRIPTION: SEQ ID NO:83:

```
Ser Thr Ala Gly Lys Val Ile Lys Cys Lys Ala Ala Val Leu Trp
            005                 010                 015

Glu Val Lys Lys Pro Phe Ser Ile Glu Asp Val Glu Val Ala Pro
            020                 025                 030

Pro Lys Ala Tyr Glu Val Arg Ile Lys Met Val Ala Val Gly Ile
            035                 040                 045

Cys Arg Thr Asp Asp His Val Val Ser Gly Asn Leu Val Thr Pro
            050                 055                 060

Leu Pro Val Ile Leu Gly His Glu Ala Ala Gly Ile Val Glu Ser
            065                 070                 075

Val Gly Glu Gly Val Thr Thr Val Lys Pro Gly Asp Lys Val Ile
            080                 085                 090

Pro Leu Phe Thr Pro Gln Cys Gly Lys Cys Arg Val Cys Lys Asn
            095                 100                 105

Pro Glu Ser Asn Tyr Cys Leu Lys Asn Asp Leu Gly Asn Pro Arg
            110                 115                 120

Gly Thr Leu Gln Asp Gly Thr Arg Arg Phe Thr Cys Arg Gly Lys
            125                 130                 135

Pro Ile His His Phe Leu Gly Thr Ser Thr Phe Ser Gln Tyr Thr
            140                 145                 150

Val Val Asp Glu Asn Ala Val Ala Lys Ile Asp Ala Ala Ser Pro
            155                 160                 165

Leu Glu Lys Val Cys Leu Ile Gly Cys Gly Phe Ser Thr Gly Tyr
            170                 175                 180
```

```
Gly Ser Ala Val Asn Val Ala Lys Val Thr Pro Gly Ser Thr Cys
            185                 190                 195

Ala Val Phe Gly Leu Gly Val Gly Leu Ser Ala Val Met Gly
            200                 205                 210

Cys Lys Ala Ala Gly Ala Ala Ala Arg Ile Ile Ala Val Asp
            215                 220                 225

Ile Asn Lys Asp Lys Phe Ala Lys Glu Leu Gly Ala Thr Glu Cys
            230                 235                 240

Ile Asn Pro Gln Asp Tyr Lys Lys Pro Ile Gln Glu Val Leu Lys
            245                 250                 255

Glu Met Thr Asp Gly Gly Val Asp Phe Ser Phe Glu Val Ile Gly
            260                 265                 270

Arg Leu Asp Thr Met Met Ala Ser Leu Leu Cys Cys His Glu Ala
            275                 280                 285

Cys Gly Thr Ser Val Ile Val Gly Val Pro Pro Ala Ser Gln Asn
            290                 295                 300

Leu Ser Ile Asn Pro Met Leu Leu Thr Gly Arg Thr Trp Lys
            305                 310                 315

Gly Ala Val Leu Gly Phe Lys Ser Lys Glu Gly Ile Pro Lys
            320                 325                 330

Leu Val Ala Asp Phe Met Ala Lys Lys Phe Ser Leu Asp Ala Leu
            335                 340                 345

Ile Thr His Val Leu Pro Phe Glu Lys Ile Asn Glu Gly Phe Asp
            350                 355                 360

Leu Leu His Ser Gly Lys Ser Ile Arg Thr Val Leu Thr Phe
            365                 370
```

(2) INFORMATION FOR SEQ ID NO:84:

(i) SEQUENCE CHARACTERISTICS:
        (A) LENGTH: 374

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: Alcohol dehydrogenase, Table 3 Column 5

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
            USA
        (D) VOLUME: 78

(F) PAGES: 4226-4230

(G) DATE: 1981

(xi) SEQUENCE DESCRIPTION: SEQ ID NO:84:

Ser Thr Ala Gly Lys Val Ile Lys Cys Lys Ala Ala Val Leu Trp

-continued

|                                           005                                      010                                     015            |
| Glu Leu Lys Lys Pro Phe Ser Ile Glu Val Glu Val Ala Pro
                020                                      025                                     030            |
| Pro Lys Ala His Glu Val Arg Ile Lys Met Val Ala Ala Gly Ile
                035                                      040                                     045            |
| Cys Arg Ser Asp Glu His Val Val Ser Gly Asn Leu Val Thr Pro
                050                                      055                                     060            |
| Leu Pro Val Ile Leu Gly His Glu Ala Ala Gly Ile Val Glu Ser
                065                                      070                                     075            |
| Val Gly Glu Gly Val Thr Thr Val Lys Pro Gly Asp Lys Val Ile
                080                                      085                                     090            |
| Pro Leu Phe Thr Pro Gln Cys Gly Lys Cys Arg Ile Cys Lys Asn
                095                                      100                                     105            |
| Pro Glu Ser Asn Tyr Cys Leu Lys Asn Asp Leu Gly Asn Pro Arg
                110                                      115                                     120            |
| Gly Thr Leu Gln Asp Gly Thr Arg Arg Phe Thr Cys Ser Gly Lys
                125                                      130                                     135            |
| Pro Ile His His Phe Val Gly Val Ser Thr Phe Ser Gln Tyr Thr
                140                                      145                                     150            |
| Val Val Asp Glu Asn Ala Val Ala Lys Ile Asp Ala Ala Ser Pro
                155                                      160                                     165            |
| Leu Glu Lys Val Cys Leu Ile Gly Cys Gly Phe Ser Thr Gly Tyr
                170                                      175                                     180            |
| Gly Ser Ala Val Lys Val Ala Lys Val Thr Pro Gly Ser Thr Cys
                185                                      190                                     195            |
| Ala Val Phe Gly Leu Gly Gly Val Gly Leu Ser Val Val Met Gly
                200                                      205                                     210            |
| Cys Lys Ala Ala Gly Ala Ala Ala Arg Ile Ile Ala Val Asp
                215                                      220                                     225            |
| Ile Asn Lys Asp Lys Phe Ala Lys Glu Leu Gly Ala Thr Glu Cys
                230                                      235                                     240            |
| Ile Asn Pro Gln Asp Tyr Lys Lys Pro Ile Gln Glu Val Leu Lys
                245                                      250                                     255            |
| Glu Met Thr Asp Gly Gly Val Asp Phe Ser Phe Glu Val Ile Gly
                260                                      265                                     270            |
| Gln Leu Asp Thr Met Met Ala Ser Leu Leu Cys Cys His Glu Ala
                275                                      280                                     285            |
| Cys Gly Thr Ser Val Ile Val Gly Val Pro Pro Asp Ser Gln Asn
                290                                      295                                     300            |
| Leu Ser Ile Asn Pro Met Leu Leu Leu Thr Gly Arg Thr Trp Lys
                305                                      310                                     315            |
| Gly Ala Ile Tyr Gly Gly Phe Lys Ser Lys Glu Ser Val Pro Lys
                320                                      325                                     330            |
| Leu Val Ala Asp Phe Met Ala Lys Lys Phe Ser Leu Asp Ala Leu
                335                                      340                                     345            |
| Ile Thr Asn Ile Leu Pro Phe Glu Lys Ile Asn Glu Gly Phe Asp
                350                                      355                                     360            |
| Leu Leu Arg Ser Gly Lys Ser Ile Arg Thr Val Leu Thr Phe
                365                                      370                                                   |

(2) INFORMATION FOR SEQ ID NO:85:

(i) SEQUENCE CHARACTERISTICS:
        (A) LENGTH: 374

(B) TYPE: amino acid (D) TOPOLOGY: linear (ii) MOLECULE TYPE:
(A) DESCRIPTION: protein (vi) ORIGINAL SOURCE:
(A) ORGANISM: mouse (ix) FEATURE: Alcohol dehydrogenase, Table 3 Column 6

(x) PUBLICATION INFORMATION:
(A) AUTHORS:

Joernvall, H.
Persson, M.
Jeffery, J.
(B) TITLE: Alcohol dehydrogenases (C) JOURNAL: Proceedings of the National Academy of Sciences, USA
(D) VOLUME: 78

(F) PAGES: 4226-4230

(G) DATE: 1981

(xi) SEQUENCE DESCRIPTION: SEQ ID NO:85:

```
Ser Thr Ala Gly Lys Val Ile Lys Cys Lys Ala Ala Val Leu Trp
            005                 010                 015

Glu Leu His Lys Pro Phe Thr Ile Glu Asp Ile Glu Val Ala Pro
            020                 025                 030

Pro Lys Ala His Glu Val Arg Ile Lys Met Val Ala Thr Gly Val
            035                 040                 045

Cys Arg Thr Asp Asp His Val Val Ser Gly Thr Leu Val Thr Pro
            050                 055                 060

Leu Pro Ala Val Leu Gly His Glu Gly Ala Gly Ile Val Glu Ser
            065                 070                 075

Val Gly Glu Gly Val Thr Cys Val Lys Pro Gly Asp Lys Val Ile
            080                 085                 090

Pro Leu Phe Ser Pro Gln Cys Gly Glu Cys Arg Ile Cys Lys His
            095                 100                 105

Pro Glu Ser Asn Phe Cys Ser Arg Ser Asp Leu Leu Met Pro Arg
            110                 115                 120

Gly Thr Leu Arg Asp Gly Thr Ser Arg Phe Ser Cys Lys Gly Lys
            125                 130                 135

Pro Ile His His Phe Ile Ser Thr Ser Thr Phe Ser Gln Tyr Thr
            140                 145                 150

Val Val Asp Asp Ile Ala Val Ala Lys Ile Asp Gly Ala Ser Pro
            155                 160                 165

Leu Asp Lys Val Cys Leu Ile Gly Cys Gly Phe Ser Thr Gly Tyr
            170                 175                 180

Gly Ser Ala Val Lys Val Ala Lys Val Thr Pro Gly Ser Thr Cys
            185                 190                 195

Ala Val Phe Gly Leu Gly Gly Val Gly Leu Ser Val Ile Met Gly
            200                 205                 210

Cys Lys Ala Ala Gly Ala Ala Ala Lys Ile Ile Ala Val Asp
            215                 220                 225

Ile Asn Lys Asp Lys Phe Ala Lys Glu Leu Gly Ala Thr Asp Cys
```

```
                     230                 235                 240
Ile Asn Pro Gln Asp Tyr Ser Lys Pro Ile Gln Glu Val Leu Gln
                245                 250                 255

Glu Met Thr Asp Gly Gly Val Asp Phe Ser Phe Glu Val Ile Gly
                260                 265                 270

Arg Leu Asp Thr Met Thr Ser Ala Leu Leu Ser Cys His Ala Ala
                275                 280                 285

Cys Gly Val Ser Val Val Gly Val Pro Pro Asn Ala Gln Asn
                290                 295                 300

Leu Ser Met Asn Pro Met Leu Leu Leu Gly Arg Thr Trp Lys
                305                 310                 315

Gly Ala Ile Phe Gly Gly Phe Lys Ser Lys Asp Ser Val Pro Lys
                320                 325                 330

Leu Val Ala Asp Phe Met Ala Lys Lys Phe Pro Leu Glu Pro Leu
                335                 340                 345

Ile Thr His Val Leu Pro Phe Glu Lys Ile Asn Glu Ala Phe Asp
                350                 355                 360

Leu Leu Arg Ser Gly Lys Ser Ile Arg Thr Val Leu Thr Phe
                365                 370

(2) INFORMATION FOR SEQ ID NO:86:

(i) SEQUENCE CHARACTERISTICS:
        (A) LENGTH: 375

(B) TYPE: amino acid (D) TOPOLOGY: linear (ii) MOLECULE TYPE:
        (A) DESCRIPTION: protein (vi) ORIGINAL SOURCE:
        (A) ORGANISM: rat (ix) FEATURE: Alcohol dehydrogenase, Table 3 Column 7

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
                USA
        (D) VOLUME: 78

(F) PAGES: 4226-4230

(G) DATE: 1981

(xi) SEQUENCE DESCRIPTION: SEQ ID NO:86:

Ser Thr Ala Gly Lys Val Ile Lys Cys Lys Ala Ala Val Leu Trp
                005                 010                 015

Glu Pro His Lys Pro Phe Thr Ile Glu Asp Ile Glu Val Ala Pro
                020                 025                 030

Pro Lys Ala His Glu Val Arg Ile Lys Met Val Ala Thr Gly Val
                035                 040                 045

Cys Arg Ser Asp Asp His Ala Val Ser Gly Ser Leu Phe Thr Pro
                050                 055                 060
```

Leu Pro Ala Val Leu Gly His Glu Gly Ala Gly Ile Val Glu Ser
                065                 070                 075

Ile Gly Glu Gly Val Thr Cys Val Lys Pro Gly Asp Lys Val Ile
                080                 085                 090

Pro Leu Phe Ser Pro Gln Cys Gly Lys Cys Arg Ile Cys Lys His
                095                 100                 105

Pro Glu Ser Asn Leu Cys Cys Gln Thr Lys Asn Leu Thr Gln Pro
                110                 115                 120

Lys Gly Ala Leu Leu Glu Gly Thr Ser Arg Phe Ser Cys Arg Gly
                125                 130                 135

Lys Gln Ile His Asn Phe Leu Ser Thr Ser Thr Phe Ser Gln Tyr
                140                 145                 150

Thr Val Val Asp Asp Ile Ala Val Ala Lys Ile Asp Ala Ala Ala
                155                 160                 165

Pro Leu Asp Lys Val Cys Leu Leu Gly Cys Gly Phe Ser Thr Gly
                170                 175                 180

Tyr Gly Ser Ala Val Gln Val Ala Lys Val Thr Pro Gly Ser Thr
                185                 190                 195

Cys Ala Val Phe Gly Leu Gly Gly Val Gly Leu Ser Val Val Ile
                200                 205                 210

Gly Cys Lys Thr Ala Gly Ala Ala Ala Arg Ile Ile Ala Val
                215                 220                 225

Asp Ile Asn Lys Asp Lys Phe Ala Lys Glu Leu Gly Ala Thr Glu
                230                 235                 240

Cys Ile Asn Pro Gln Asp Tyr Thr Lys Pro Ile Gln Glu Val Leu
                245                 250                 255

Gln Glu Met Thr Asp Gly Gly Val Asp Phe Ser Phe Glu Val Ile
                260                 265                 270

Gly Arg Leu Asp Thr Met Thr Ser Ala Leu Leu Ser Cys His Ser
                275                 280                 285

Ala Cys Gly Val Ser Val Ile Val Gly Val Pro Pro Ser Ala Gln
                290                 295                 300

Ser Leu Ser Val Asn Pro Met Ser Leu Leu Leu Gly Arg Thr Trp
                305                 310                 315

Lys Gly Ala Ile Phe Gly Gly Phe Lys Ser Lys Asp Ala Val Pro
                320                 325                 330

Lys Leu Val Ala Asp Phe Met Ala Lys Lys Phe Pro Leu Asp Pro
                335                 340                 345

Leu Ile Thr His Val Leu Pro Phe Glu Lys Ile Asn Glu Ala Phe
                350                 355                 360

Asp Leu Leu Arg Ala Gly Lys Ser Ile Arg Thr Val Leu Thr Phe
                365                 370                 375

(2) INFORMATION FOR SEQ ID NO:87:

(i) SEQUENCE CHARACTERISTICS:
        (A) LENGTH: 379

(B) TYPE: amino acid (D) TOPOLOGY: linear (ii) MOLECULE TYPE:
        (A) DESCRIPTION: protein (vi) ORIGINAL SOURCE:

(A) ORGANISM: human (ix) FEATURE: Alcohol dehydrogenase, Table 3 Column 8

(x) PUBLICATION INFORMATION:
    (A) AUTHORS:
        Joernvall, H.
        Persson, M.
        Jeffery, J.
    (B) TITLE: Alcohol dehydrogenases
    (C) JOURNAL: Proceedings of the National Academy of Sciences, USA
    (D) VOLUME: 78
    (F) PAGES: 4226-4230
    (G) DATE: 1981

(xi) SEQUENCE DESCRIPTION: SEQ ID NO:87:

```
Gly Thr Lys Gly Lys Val Ile Lys Cys Lys Ala Ala Ile Ala Trp
            005                 010                 015

Glu Ala Gly Lys Pro Leu Cys Ile Glu Glu Val Glu Val Ala Pro
            020                 025                 030

Pro Lys Ala His Glu Val Arg Ile Gln Ile Ile Ala Thr Ser Leu
            035                 040                 045

Cys His Ser Asp Ala Ser Val Ile Asp Ser Lys Phe Glu Gly Leu
            050                 055                 060

Ala Phe Pro Val Ile Val Gly His Glu Ala Ala Gly Ile Val Glu
            065                 070                 075

Ser Ile Gly Pro Gly Val Thr Asn Val Lys Pro Gly Asp Lys Val
            080                 085                 090

Ile Pro Leu Tyr Ala Pro Leu Cys Arg Lys Cys Lys Phe Cys Leu
            095                 100                 105

Ser Pro Leu Thr Asn Leu Cys Gly Lys Ile Ser Asn Leu Lys Ser
            110                 115                 120

Pro Ala Ser Asp Gln Gln Leu Met Glu Asp Lys Thr Ser Arg Phe
            125                 130                 135

Thr Cys Lys Gly Lys Pro Val Tyr His Phe Phe Gly Thr Ser Thr
            140                 145                 150

Phe Ser Gln Tyr Thr Val Val Ser Asp Ile Asn Leu Ala Lys Ile
            155                 160                 165

Asp Asp Asp Ala Asn Leu Glu Arg Val Cys Leu Ile Gly Cys Gly
            170                 175                 180

Phe Ser Thr Gly Tyr Gly Ala Ala Ile Asn Asn Ala Lys Val Thr
            185                 190                 195

Pro Gly Ser Thr Cys Ala Val Phe Gly Leu Gly Gly Val Gly Leu
            200                 205                 210

Ser Ala Val Ile Gly Cys Lys Ala Ala Gly Ala Ser Ala Ser Arg
            215                 220                 225

Ile Ile Gly Ile Asp Ile Asn Ser Glu Lys Phe Val Lys Ala Leu
            230                 235                 240

Gly Ala Thr Asp Cys Leu Asn Pro Arg Asp Leu His Lys Pro Ile
            245                 250                 255

Gln Glu Val Ile Ile Glu Leu Thr Lys Gly Gly Val Asp Phe Ala
            260                 265                 270

Leu Asp Cys Ala Gly Gly Ser Glu Thr Met Lys Ala Ala Leu Asp
            275                 280                 285
```

```
Cys Thr Thr Ala Gly Trp Gly Ser Cys Thr Phe Ile Gly Val Ala
                290                 295                 300

Ala Gly Ser Lys Gly Leu Thr Ile Phe Pro Glu Glu Leu Ile Ile
                305                 310                 315

Gly Arg Thr Ile Asn Gly Thr Phe Phe Gly Gly Trp Lys Ser Val
                320                 325                 330

Asp Ser Ile Pro Lys Leu Val Thr Asp Tyr Lys Asn Lys Lys Phe
                335                 340                 345

Asn Leu Asp Ala Leu Val Thr His Thr Leu Pro Phe Asp Lys Ile
                350                 355                 360

Ser Glu Ala Phe Asp Leu Met Asn Gln Gly Lys Ser Ile Arg Thr
                365                 370                 375

Ile Leu Ile Phe (2) INFORMATION FOR SEQ ID NO:88:

(i) SEQUENCE CHARACTERISTICS:
        (A) LENGTH: 376

(B) TYPE: amino acid (D) TOPOLOGY: linear (ii) MOLECULE TYPE:
        (A) DESCRIPTION: protein (vi) ORIGINAL SOURCE:
        (A) ORGANISM: maize (ix) FEATURE: Alcohol dehydrogenase, Table 3 Column 10

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
                USA
        (D) VOLUME: 78

(F) PAGES: 4226-4230

(G) DATE: 1981

(xi) SEQUENCE DESCRIPTION: SEQ ID NO:88:

Ala Thr Ala Gly Lys Val Ile Lys Cys Lys Ala Ala Val Ala Trp
                005                 010                 015

Glu Ala Gly Lys Pro Leu Ser Ile Glu Glu Val Glu Val Ala Pro
                020                 025                 030

Pro Gln Ala Met Glu Val Arg Val Lys Ile Leu Phe Thr Ser Leu
                035                 040                 045

Cys His Thr Asp Val Tyr Phe Trp Glu Ala Lys Gly Gln Thr Pro
                050                 055                 060

Val Phe Pro Arg Ile Phe Gly His Glu Ala Gly Ile Ile Glu
                065                 070                 075

Ser Val Gly Glu Gly Val Thr Asp Val Ala Pro Gly Asp His Val
                080                 085                 090

Leu Pro Val Phe Thr Gly Glu Cys Lys Glu Cys Ala His Cys Lys
```

```
                095                 100                 105
Ser Ala Glu Ser Asn Met Cys Asp Leu Leu Arg Ile Asn Thr Asp
                110                 115                 120
Arg Gly Val Met Ile Ala Asp Gly Lys Ser Arg Phe Ser Ile Asn
                125                 130                 135
Gly Lys Pro Ile Tyr His Phe Val Gly Thr Ser Thr Phe Ser Glu
                140                 145                 150
Tyr Thr Val Met His Val Gly Cys Val Ala Lys Ile Asn Pro Gln
                155                 160                 165
Ala Pro Leu Asp Lys Val Cys Val Leu Ser Cys Gly Ile Ser Thr
                170                 175                 180
Gly Leu Gly Ala Ser Ile Asn Val Ala Lys Pro Pro Lys Gly Ser
                185                 190                 195
Thr Val Ala Val Phe Gly Leu Gly Ala Val Gly Leu Ala Ala Ala
                200                 205                 210
Gly Gly Ala Arg Ile Ala Gly Ala Ser Ala Ser Arg Ile Ile Gly
                215                 220                 225
Val Asp Leu Asn Pro Ser Arg Phe Glu Arg Lys Phe Gly Cys Thr
                230                 235                 240
Glu Phe Val Asn Pro Lys Asp His Asn Lys Pro Val Gln Glu Val
                245                 250                 255
Leu Ala Glu Met Thr Asn Gly Gly Val Asp Arg Ser Val Glu Cys
                260                 265                 270
Thr Gly Asn Ile Asn Ala Met Ile Gln Ala Phe Glu Cys Val His
                275                 280                 285
Asp Gly Trp Gly Val Ala Val Val Val Gly Val Pro His Lys Asp
                290                 295                 300
Ala Glu Phe Lys Thr His Pro Met Asn Phe Leu Asn Glu Arg Thr
                305                 310                 315
Leu Lys Gly Thr Phe Phe Gly Asn Tyr Lys Pro Arg Thr Asp Leu
                320                 325                 330
Pro Asn Val Val Glu Leu Tyr Met Lys Lys Glu Leu Glu Val Glu
                335                 340                 345
Lys Phe Ile Thr His Ser Val Pro Phe Ala Glu Ile Asn Lys Ala
                350                 355                 360
Phe Asp Leu Met Ala Lys Gly Glu Gly Ile Arg Cys Ile Ile Arg
                365                 370                 375
Met
```

(2) INFORMATION FOR SEQ ID NO:89:

(i) SEQUENCE CHARACTERISTICS:
        (A) LENGTH: 376

(B) TYPE: amino acid (D) TOPOLOGY: linear (ii) MOLECULE TYPE:
        (A) DESCRIPTION: protein (vi) ORIGINAL SOURCE:
        (A) ORGANISM: maize (ix) FEATURE: Alcohol dehydrogenase, Table 3 Column 11

(x) PUBLICATION INFORMATION:

(A) AUTHORS:

Joernvall, H.
    Persson, M.
    Jeffery, J.

(B) TITLE: Alcohol dehydrogenases (C) JOURNAL: Proceedings of the National Academy of Sciences, USA (D) VOLUME: 78

(F) PAGES: 4226-4230

(G) DATE: 1981

(xi) SEQUENCE DESCRIPTION: SEQ ID NO:89:

```
Ala Thr Ala Gly Lys Val Ile Lys Cys Arg Ala Ala Val Thr Trp
            005                 010                 015
Glu Ala Gly Lys Pro Leu Ser Ile Glu Glu Val Glu Val Ala Pro
            020                 025                 030
Pro Gln Ala Met Glu Val Arg Ile Lys Ile Leu Tyr Thr Ala Leu
            035                 040                 045
Cys His Thr Asp Val Tyr Phe Trp Glu Ala Lys Gly Gln Thr Pro
            050                 055                 060
Val Phe Pro Arg Ile Leu Gly His Glu Ala Gly Gly Ile Val Glu
            065                 070                 075
Ser Val Gly Glu Gly Val Thr Asp Val Ala Pro Gly Asp His Val
            080                 085                 090
Leu Pro Val Phe Thr Gly Glu Cys Lys Glu Cys Ala His Cys Lys
            095                 100                 105
Ser Glu Glu Ser Asn Met Cys Asp Leu Leu Arg Ile Asn Val Asp
            110                 115                 120
Arg Gly Val Met Ile Gly Asp Gly Lys Ser Arg Phe Thr Ile Ser
            125                 130                 135
Gly Gln Pro Ile Phe His Phe Val Gly Thr Ser Thr Phe Ser Glu
            140                 145                 150
Tyr Thr Val Ile His Val Gly Cys Leu Ala Lys Ile Asn Pro Glu
            155                 160                 165
Ala Pro Leu Asp Lys Val Cys Ile Leu Ser Cys Gly Ile Ser Thr
            170                 175                 180
Gly Leu Gly Ala Thr Leu Asn Val Ala Lys Pro Ala Lys Gly Ser
            185                 190                 195
Thr Val Ala Ile Phe Gly Leu Gly Ala Val Gly Leu Ala Ala Met
            200                 205                 210
Glu Gly Ala Arg Leu Ala Gly Ala Ser Ala Ser Arg Ile Ile Gly
            215                 220                 225
Val Asp Ile Asn Pro Ala Lys Tyr Glu Lys Lys Phe Gly Cys Thr
            230                 235                 240
Glu Phe Val Asn Pro Lys Asp His Asp Lys Pro Val Gln Glu Val
            245                 250                 255
Leu Ile Glu Leu Thr Asn Gly Gly Val Asp Arg Ser Val Glu Cys
            260                 265                 270
Thr Gly Asn Val Asn Ala Met Ile Ser Ala Phe Glu Cys Val His
            275                 280                 285
Asp Gly Trp Gly Val Ala Val Val Val Gly Val Pro His Lys Asp
            290                 295                 300
Asp Gln Phe Lys Thr His Pro Met Asn Phe Leu Ser Glu Lys Thr
            305                 310                 315
```

```
Leu Lys Gly Thr Phe Phe Gly Asn Tyr Lys Pro Arg Thr Asp Leu
                320                 325                 330

Pro Asn Val Val Glu Met Tyr Met Lys Lys Glu Leu Glu Leu Glu
                335                 340                 345

Lys Phe Ile Thr His Ser Val Pro Phe Ser Glu Ile Asn Thr Ala
                350                 355                 360

Phe Asp Leu Met Leu Lys Gly Glu Gly Leu Arg Cys Ile Met Arg
                365                 370                 375

Met
```

(2) INFORMATION FOR SEQ ID NO:90:

(i) SEQUENCE CHARACTERISTICS:
        (A) LENGTH: 377

(B) TYPE: amino acid (D) TOPOLOGY: linear (ii) MOLECULE TYPE:
        (A) DESCRIPTION: protein (vi) ORIGINAL SOURCE:
        (A) ORGANISM: pea (ix) FEATURE: Alcohol dehydrogenase, Table 3 Column 12

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
            USA
        (D) VOLUME: 78

(F) PAGES: 4226-4230

(G) DATE: 1981

(xi) SEQUENCE DESCRIPTION: SEQ ID NO:90:

```
Ser Asn Thr Val Gly Gln Ile Ile Lys Cys Arg Ala Ala Val Ala
                005                 010                 015

Trp Glu Ala Gly Lys Pro Leu Val Ile Glu Glu Val Glu Val Ala
                020                 025                 030

Pro Pro Gln Ala Gly Glu Val Arg Leu Lys Ile Leu Phe Thr Ser
                035                 040                 045

Leu Cys His Thr Asp Val Tyr Phe Trp Glu Ala Lys Gly Gln Thr
                050                 055                 060

Pro Leu Phe Pro Arg Ile Phe Gly His Glu Ala Gly Gly Ile Val
                065                 070                 075

Glu Ser Val Gly Glu Gly Val Thr His Leu Lys Pro Gly Asp His
                080                 085                 090

Ala Leu Pro Val Phe Thr Gly Glu Cys Gly Glu Cys Pro His Cys
                095                 100                 105

Lys Ser Glu Glu Ser Asn Met Cys Asp Leu Leu Arg Ile Asn Thr
                110                 115                 120

Asp Arg Gly Val Met Leu Asn Asp Asn Lys Ser Arg Phe Ser Ile
```

```
                      125                 130                 135
Lys Gly Gln Pro Val His His Phe Val Gly Thr Ser Thr Phe Ser
                140                 145                 150

Glu Tyr Thr Val Val His Ala Gly Cys Val Ala Lys Ile Asn Pro
                155                 160                 165

Asp Ala Pro Leu Asp Lys Val Cys Ile Leu Ser Cys Gly Ile Cys
                170                 175                 180

Thr Gly Leu Gly Ala Thr Ile Asn Val Ala Lys Pro Lys Pro Gly
                185                 190                 195

Ser Ser Val Ala Ile Phe Gly Leu Gly Ala Val Gly Leu Ala Ala
                200                 205                 210

Ala Glu Gly Ala Arg Ile Ser Gly Ala Ser Ala Ser Arg Ile Ile
                215                 220                 225

Gly Val Asp Leu Val Ser Ser Arg Phe Glu Lys Lys Phe Gly Val
                230                 235                 240

Asn Glu Phe Val Asn Pro Lys Glu His Asp Lys Pro Val Gln Gln
                245                 250                 255

Val Ile Ala Glu Met Thr Asn Gly Gly Val Asp Arg Ala Val Glu
                260                 265                 270

Cys Thr Gly Ser Ile Gln Ala Met Ile Ser Ala Phe Glu Cys Val
                275                 280                 285

His Asp Gly Trp Gly Val Ala Val Val Gly Val Pro Ser Lys
                290                 295                 300

Asp Asp Ala Phe Lys Thr His Pro Met Asn Phe Leu Asn Glu Arg
                305                 310                 315

Thr Leu Lys Gly Thr Phe Tyr Gly Asn Tyr Lys Pro Arg Thr Asp
                320                 325                 330

Leu Pro Asn Val Val Glu Lys Tyr Met Lys Gly Glu Leu Glu Leu
                335                 340                 345

Glu Lys Phe Ile Thr His Thr Val Pro Phe Ser Glu Ile Asn Lys
                350                 355                 360

Ala Phe Asp Tyr Met Leu Lys Gly Glu Ser Ile Arg Cys Ile Ile
                365                 370                 375

Lys Met (2) INFORMATION FOR SEQ ID NO:91:

(i) SEQUENCE CHARACTERISTICS:
        (A) LENGTH: 376

(B) TYPE: amino acid (D) TOPOLOGY: linear (ii) MOLECULE TYPE:
         (A) DESCRIPTION: protein (vi) ORIGINAL SOURCE:
         (A) ORGANISM: Arabidopsis (ix) FEATURE: Alcohol dehydrogenase, Table 3 Column 13

(x) PUBLICATION INFORMATION:
        (A) AUTHORS:

Joernvall, H.
            Persson, M.
            Jeffery, J.
        (B) TITLE: Alcohol dehydrogenases
```

(C) JOURNAL: Proceedings of the National Academy of Sciences, USA
(D) VOLUME: 78

(F) PAGES: 4226-4230

(G) DATE: 1981

(xi) SEQUENCE DESCRIPTION: SEQ ID NO:91:

```
Ser Thr Thr Gly Gln Ile Ile Arg Cys Lys Ala Ala Val Ala Trp
            005                 010                 015

Glu Ala Gly Lys Pro Leu Val Ile Glu Glu Val Ala Pro
            020                 025                 030

Pro Gln Lys His Glu Val Arg Ile Lys Ile Leu Phe Thr Ser Leu
            035                 040                 045

Cys His Thr Asp Val Tyr Phe Trp Glu Ala Lys Gly Gln Thr Pro
            050                 055                 060

Leu Phe Pro Arg Ile Phe Gly His Glu Ala Gly Ile Val Glu
            065                 070                 075

Ser Val Gly Glu Gly Val Thr Asp Leu Gln Pro Gly Asp His Val
            080                 085                 090

Leu Pro Ile Phe Thr Gly Glu Cys Gly Asp Cys Arg His Cys Gln
            095                 100                 105

Ser Glu Glu Ser Asn Met Cys Asp Leu Leu Arg Ile Asn Thr Glu
            110                 115                 120

Arg Gly Gly Met Ile His Asp Gly Glu Ser Arg Phe Ser Ile Asn
            125                 130                 135

Gly Lys Pro Ile Tyr His Phe Leu Gly Thr Ser Thr Phe Ser Glu
            140                 145                 150

Tyr Thr Val Val His Ser Gly Gln Val Ala Lys Ile Asn Pro Asp
            155                 160                 165

Ala Pro Leu Asp Lys Val Cys Ile Val Ser Cys Gly Leu Ser Thr
            170                 175                 180

Gly Leu Gly Ala Thr Leu Asn Val Ala Lys Pro Lys Lys Gly Gln
            185                 190                 195

Ser Val Ala Ile Phe Gly Leu Gly Ala Val Gly Leu Gly Ala Ala
            200                 205                 210

Glu Gly Ala Arg Ile Ala Gly Ala Ser Ala Ser Arg Ile Ile Gly
            215                 220                 225

Val Asp Phe Asn Ser Lys Arg Phe Asp Lys Glu Phe Gly Val Thr
            230                 235                 240

Glu Cys Val Asn Pro Lys Asp His Asp Lys Pro Ile Gln Gln Val
            245                 250                 255

Ile Ala Glu Met Thr Asp Gly Gly Val Asp Arg Ser Val Glu Cys
            260                 265                 270

Thr Gly Ser Val Gln Ala Met Ile Gln Ala Phe Glu Cys Val His
            275                 280                 285

Asp Gly Trp Gly Val Ala Val Val Gly Val Pro Ser Lys Asp
            290                 295                 300

Asp Ala Phe Lys Thr His Pro Met Asn Phe Leu Asn Glu Arg Thr
            305                 310                 315

Leu Lys Gly Thr Phe Phe Gly Asn Tyr Lys Pro Lys Thr Asp Ile
            320                 325                 330

Pro Gly Val Val Glu Lys Tyr Met Asn Lys Glu Leu Glu Leu Glu
            335                 340                 345
```

```
Lys Phe Ile Thr His Thr Val Pro Phe Ser Glu Ile Asn Lys Ala
                350             355             360

Phe Asp Tyr Met Leu Lys Gly Glu Ser Ile Arg Cys Ile Ile Thr
                365             370             375

Met
```

(2) INFORMATION FOR SEQ ID NO:92:

(i) SEQUENCE CHARACTERISTICS:
        (A) LENGTH: 344

(B) TYPE: amino acid (D) TOPOLOGY: linear (ii) MOLECULE TYPE:
        (A) DESCRIPTION: protein (vi) ORIGINAL SOURCE:
        (A) ORGANISM: Scizosaccharomyces pombe (ix) FEATURE: Alcohol dehydrogenase, Table 3 Column 15

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
            USA
        (D) VOLUME: 78

(F) PAGES: 4226-4230

(G) DATE: 1981

(xi) SEQUENCE DESCRIPTION: SEQ ID NO:92:

```
Ser Ile Pro Glu Thr Gln Lys Gly Val Ile Phe Tyr Glu Ser His
                005             010             015

Gly Lys Leu Glu Tyr Lys Asp Ile Pro Val Pro Lys Pro Lys Ala
                020             025             030

Asn Glu Leu Leu Ile Asn Val Lys Tyr Ser Gly Val Cys His Thr
                035             040             045

Asp Leu His Ala Trp His Gly Asp Trp Pro Leu Pro Val Lys Leu
                050             055             060

Pro Leu Val Gly Gly His Glu Gly Ala Gly Val Val Val Gly Met
                065             070             075

Gly Glu Asn Val Lys Gly Trp Lys Ile Gly Asp Tyr Ala Gly Ile
                080             085             090

Lys Trp Leu Asn Gly Ser Cys Met Ala Cys Glu Tyr Cys Glu Leu
                095             100             105

Gly Asn Glu Ser Asn Cys Pro His Ala Ser Leu Ser Gly Tyr Thr
                110             115             120

His Asp Gly Ser Phe Gln Gln Tyr Ala Thr Ala Asp Ala Val Gln
                125             130             135

Ala Ala His Ile Pro Gln Gly Thr Asp Leu Ala Gln Val Ala Pro
                140             145             150

Ile Leu Cys Ala Gly Ile Thr Val Tyr Lys Ala Leu Lys Ser Ala
```

```
                    155                 160                 165
Asn Leu Met Ala Gly His Trp Val Ala Ile Ser Gly Ala Ala Gly
                170                 175                 180

Gly Leu Gly Ser Leu Ala Val Gln Tyr Ala Lys Ala Met Gly Tyr
                185                 190                 195

Tyr Arg Val Leu Gly Ile Asp Gly Gly Glu Gly Lys Glu Glu Arg
                200                 205                 210

Ser Ile Gly Gly Glu Val Phe Ile Asp Phe Thr Lys Glu Lys Asp
                215                 220                 225

Ile Val Gly Ala Val Leu Lys Ala Thr Asp Gly Gly Ala His Gly
                230                 235                 240

Val Ile Asn Val Ser Val Ser Glu Ala Ala Ile Glu Ala Ser Thr
                245                 250                 255

Arg Tyr Val Arg Ala Asn Gly Thr Thr Val Val Gly Met Pro
                260                 265                 270

Ala Gly Ala Lys Cys Cys Ser Asp Val Phe Asn Gln Val Val Lys
                275                 280                 285

Ser Ile Ser Ile Lys Gly Ser Tyr Val Gly Asn Arg Ala Asp Thr
                290                 295                 300

Arg Glu Ala Leu Asp Phe Phe Ala Arg Gly Leu Val Lys Ser Pro
                305                 310                 315

Ile Lys Val Val Gly Leu Ser Thr Leu Pro Glu Ile Tyr Glu Lys
                320                 325                 330

Met Glu Lys Gly Gln Ile Val Gly Arg Tyr Val Val Asp Thr
                335                 340
```

(2) INFORMATION FOR SEQ ID NO:93:

(i) SEQUENCE CHARACTERISTICS:
        (A) LENGTH: 344

(B) TYPE: amino acid (D) TOPOLOGY: linear (ii) MOLECULE TYPE:
        (A) DESCRIPTION: protein (vi) ORIGINAL SOURCE:
        (A) ORGANISM: Aspergillus (ix) FEATURE: Alcohol dehydrogenase, Table 3 Column 16

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
            USA
        (D) VOLUME: 78

(F) PAGES: 4226-4230

(G) DATE: 1981

(xi) SEQUENCE DESCRIPTION: SEQ ID NO:93:

```
Ser Ile Pro Glu Thr Gln Lys Ala Ile Ile Phe Tyr Glu Ser Asn
                005                 010                 015
```

```
Gly Lys Leu Glu His Lys Asp Ile Pro Val Pro Lys Pro Lys Pro
                020             025             030

Asn Glu Leu Leu Ile Asn Val Lys Tyr Ser Gly Val Cys His Thr
                035             040             045

Asp Leu His Ala Trp His Gly Asp Trp Pro Leu Pro Thr Lys Leu
                050             055             060

Pro Leu Val Gly Gly His Glu Gly Ala Gly Val Val Val Gly Met
                065             070             075

Gly Glu Asn Val Lys Gly Trp Lys Ile Gly Asp Tyr Ala Gly Ile
                080             085             090

Lys Trp Leu Asn Gly Ser Cys Met Ala Cys Glu Tyr Cys Glu Leu
                095             100             105

Gly Asn Glu Ser Asn Cys Pro His Ala Asp Leu Ser Gly Tyr Thr
                110             115             120

His Asp Gly Ser Phe Gln Glu Tyr Ala Thr Ala Asp Ala Val Gln
                125             130             135

Ala Ala His Ile Pro Gln Gly Thr Asp Leu Ala Glu Val Ala Pro
                140             145             150

Ile Leu Cys Ala Gly Ile Thr Val Tyr Lys Ala Leu Lys Ser Ala
                155             160             165

Asn Leu Arg Ala Gly His Trp Ala Ala Ile Ser Gly Ala Ala Gly
                170             175             180

Gly Leu Gly Ser Leu Ala Val Gln Tyr Ala Lys Ala Met Gly Tyr
                185             190             195

Tyr Arg Val Leu Gly Ile Asp Gly Gly Pro Gly Lys Glu Glu Thr
                200             205             210

Ser Leu Gly Gly Glu Val Phe Ile Asp Phe Thr Lys Glu Lys Asp
                215             220             225

Ile Val Ser Ala Val Val Lys Ala Thr Asn Gly Gly Ala His Gly
                230             235             240

Ile Ile Asn Val Ser Val Ser Glu Ala Ala Ile Glu Ala Ser Thr
                245             250             255

Arg Tyr Cys Arg Ala Asn Gly Thr Val Val Val Val Gly Leu Pro
                260             265             270

Ala Gly Ala Lys Cys Ser Ser Asp Val Phe Asn His Val Val Lys
                275             280             285

Ser Ile Ser Ile Val Gly Ser Tyr Val Gly Asn Arg Ala Asp Thr
                290             295             300

Arg Glu Ala Leu Asp Phe Phe Ala Arg Gly Leu Val Lys Ser Pro
                305             310             315

Ile Lys Val Val Gly Leu Ser Ser Leu Pro Glu Ile Tyr Glu Lys
                320             325             330

Met Glu Lys Gly Gln Ile Ala Gly Arg Tyr Val Val Asp Thr
                335             340
```

(2) INFORMATION FOR SEQ ID NO:94:

(i) SEQUENCE CHARACTERISTICS:
        (A) LENGTH: 345

(B) TYPE: amino acid (D) TOPOLOGY: linear (ii) MOLECULE TYPE:
        (A) DESCRIPTION: protein (vi) ORIGINAL SOURCE:
    (A) ORGANISM: Sacharomyces cerivisiae (ix) FEATURE: Alcohol dehydrogenase, Table 3 Column 17

(x) PUBLICATION INFORMATION:
    (A) AUTHORS:

Joernvall, H.
        Persson, M.
        Jeffery, J.
    (B) TITLE: Alcohol dehydrogenases (C) JOURNAL: Proceedings of the National Academy of Sciences,
                USA
    (D) VOLUME: 78

(F) PAGES: 4226-4230

(G) DATE: 1981

(xi) SEQUENCE DESCRIPTION: SEQ ID NO:94:

Ala Ala Ile Pro Lys Thr Gln Lys Gly Val Ile Phe Tyr Glu Asn
            005                 010                 015

Lys Gly Lys Leu His Tyr Lys Asp Ile Pro Val Pro Lys Pro Lys
            020                 025                 030

Pro Asn Glu Ile Leu Ile Asn Met Lys Tyr Ser Gly Val Cys His
            035                 040                 045

Thr Asp Leu His Ala Trp His Gly Asp Trp Pro Leu Pro Val Lys
            050                 055                 060

Leu Pro Leu Val Gly Gly His Glu Gly Ala Gly Val Val Val Lys
            065                 070                 075

Leu Gly Ser Asn Val Lys Gly Trp Lys Val Gly Asp Leu Ala Gly
            080                 085                 090

Ile Lys Trp Leu Asn Gly Ser Cys Met Thr Cys Glu Phe Cys Glu
            095                 100                 105

Ser Gly His Glu Ser Asn Cys Pro Asp Ala Asp Leu Ser Gly Tyr
            110                 115                 120

Thr His Asp Gly Ser Phe Gln Gln Phe Ala Thr Ala Asp Ala Ile
            125                 130                 135

Gln Ala Ala Lys Ile Gln Gln Gly Thr Asp Leu Ala Glu Val Ala
            140                 145                 150

Pro Ile Leu Cys Ala Gly Val Thr Val Tyr Lys Ala Leu Lys Glu
            155                 160                 165

Ala Asp Leu Lys Ala Gly Asp Trp Val Ala Ile Ser Gly Ala Ala
            170                 175                 180

Gly Gly Leu Gly Ser Leu Ala Val Gln Tyr Ala Thr Ala Met Gly
            185                 190                 195

Tyr Tyr Arg Val Leu Gly Ile Asp Ala Gly Glu Glu Lys Glu Lys
            200                 205                 210

Lys Lys Leu Gly Gly Glu Val Phe Ile Asp Phe Thr Lys Thr Lys
            215                 220                 225

Asn Met Val Ser Asp Ile Gln Glu Ala Thr Lys Gly Gly Pro His
            230                 235                 240

Gly Val Ile Asn Val Ser Val Ser Glu Ala Ala Ile Ser Leu Ser
            245                 250                 255

Thr Glu Tyr Val Arg Pro Cys Gly Thr Val Val Val Gly Leu
            260                 265                 270

```
Pro Ala Asn Ala Tyr Val Lys Ser Glu Val Phe Ser His Val Val
                275                 280                 285

Lys Ser Ile Asn Ile Val Gly Ser Tyr Val Gly Asn Arg Ala Asp
                290                 295                 300

Thr Arg Glu Ala Leu Asp Phe Phe Ser Arg Gly Leu Ile Lys Ser
                305                 310                 315

Pro Ile Lys Ile Val Gly Leu Ser Glu Leu Pro Lys Val Tyr Asp
                320                 325                 330

Leu Met Glu Lys Gly Lys Ile Leu Gly Arg Tyr Val Val Asp Thr
                335                 340                 345

(2) INFORMATION FOR SEQ ID NO:95:

(i) SEQUENCE CHARACTERISTICS:
        (A) LENGTH: 349

(B) TYPE: amino acid (D) TOPOLOGY: linear (ii) MOLECULE TYPE:
        (A) DESCRIPTION: protein (vi) ORIGINAL SOURCE:
        (A) ORGANISM: Sacharomyces cerivisiae (ix) FEATURE: Alcohol dehydrogenase, Table 3 Column 18

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
                    USA
        (D) VOLUME: 78

(F) PAGES: 4226-4230

(G) DATE: 1981

(xi) SEQUENCE DESCRIPTION: SEQ ID NO:95:

Met Ser Val Pro Glu Val Gln Trp Ala Gln Val Val Glu Lys Ala
                005                 010                 015

Gly Thr Pro Pro Val Tyr Lys Gln Val Pro Val Pro Glu Pro Gly
                020                 025                 030

Pro Asp Glu Ile Leu Val Lys Ile Arg Tyr Ser Gly Val Cys His
                035                 040                 045

Thr Asp Leu His Ala Met Lys Gly Asp Trp Pro Leu Pro Ser Lys
                050                 055                 060

Met Pro Leu Ile Gly Gly His Glu Gly Ala Gly Val Val Val Ala
                065                 070                 075

Lys Gly Glu Leu Val Lys Asp Glu Asp Phe Lys Ile Gly Asp Arg
                080                 085                 090

Ala Gly Ile Lys Trp Leu Asn Gly Ser Cys Leu Ser Cys Glu Met
                095                 100                 105

Cys Met Gln Ala Asp Glu Pro Leu Cys Pro His Ala Asp Leu Ser
                110                 115                 120
```

-continued

```
Gly Tyr Thr Val Asp Gly Thr Phe Gln Gln Tyr Thr Ile Gly Lys
            125                 130                 135

Ala Ala Leu Ala Ser Lys Ile Pro Asp Asn Val Pro Leu Asp Ala
            140                 145                 150

Ala Ala Pro Ile Leu Cys Ala Gly Ile Thr Val Tyr Lys Gly Leu
            155                 160                 165

Lys Glu Ser Gly Ala Arg Pro Gly Gln Thr Val Ala Ile Val Gly
            170                 175                 180

Ala Gly Gly Gly Leu Gly Ser Leu Ala Gln Gln Tyr Ala Lys Ala
            185                 190                 195

Met Gly Leu Leu Arg Thr Ile Ala Ile Asp Ser Gly Asp Glu Lys
            200                 205                 210

Lys Ala Glu Gln Leu Gly Ala Glu Val Phe Ile Asp Phe Ser Lys
            215                 220                 225

Ser Ala Asp Val Val Ala Asp Val Lys Ala Ala Thr Pro Gly Gly
            230                 235                 240

Leu Gly Ala His Ala Val Ile Leu Leu Ala Val Ala Glu Lys Pro
            245                 250                 255

Phe Gln Gln Ala Thr Glu Tyr Val Arg Ser His Gly Ser Val Val
            260                 265                 270

Ile Ile Gly Leu Pro Ala Asn Ala Phe Leu Lys Ala Pro Val Phe
            275                 280                 285

Thr Thr Val Val Arg Met Ile Asn Ile Lys Gly Ser Tyr Val Gly
            290                 295                 300

Asn Arg Gln Asp Gly Val Glu Ala Leu Asp Phe Phe Ala Arg Gly
            305                 310                 315

Leu Ile Lys Ala Pro Phe Lys Lys Ala Pro Leu Gln Asp Leu Pro
            320                 325                 330

Gln Ile Phe Glu Leu Met Gly Gln Gly Lys Ile Ala Gly Arg Tyr
            335                 340                 345

Val Leu Glu Ile
```

(2) INFORMATION FOR SEQ ID NO:96:

(i) SEQUENCE CHARACTERISTICS:
        (A) LENGTH: 346

(B) TYPE: amino acid (D) TOPOLOGY: linear (ii) MOLECULE TYPE:
        (A) DESCRIPTION: protein (vi) ORIGINAL SOURCE:
        (A) ORGANISM: Sacharomyces cerivisiae (ix) FEATURE: Alcohol dehydrogenase, Table 3 Column 19

(x) PUBLICATION INFORMATION:
        (A) AUTHORS:

Joernvall, H.
            Persson, M.
            Jeffery, J.
        (B) TITLE: Alcohol dehydrogenases (C) JOURNAL: Proceedings of the National Academy of Sciences,
            USA
        (D) VOLUME: 78

(F) PAGES: 4226-4230

(G) DATE: 1981

(xi) SEQUENCE DESCRIPTION: SEQ ID NO:96:

Thr Ile Pro Asp Lys Gln Leu Ala Ala Val Phe His Thr His Gly
              005                 010                 015

Gly Pro Glu Asn Val Lys Phe Glu Glu Val Pro Val Ala Glu Pro
              020                 025                 030

Gly Gln Asp Glu Val Leu Val Val Asn Lys Tyr Thr Gly Val Cys
              035                 040                 045

His Thr Asp Leu His Ala Leu Gln Gly Asp Trp Pro Leu Pro Ala
              050                 055                 060

Lys Met Pro Leu Ile Gly Gly His Glu Gly Ala Gly Val Val Val
              065                 070                 075

Lys Val Gly Ala Gly Val Thr Arg Leu Lys Ile Gly Asp Arg Val
              080                 085                 090

Gly Val Lys Trp Met Asn Ser Ser Cys Gly Asn Cys Glu Tyr Cys
              095                 100                 105

Met Lys Ala Glu Glu Thr Ile Cys Pro His Ile Gln Leu Ser Gly
              110                 115                 120

Tyr Thr Val Asp Gly Thr Phe Gln His Tyr Cys Ile Ala Asn Ala
              125                 130                 135

Thr His Ala Thr Ile Ile Pro Glu Ser Val Pro Leu Glu Val Ala
              140                 145                 150

Ala Pro Ile Met Cys Ala Gly Ile Thr Cys Tyr Arg Ala Leu Lys
              155                 160                 165

Glu Ser Lys Val Gly Pro Gly Glu Trp Ile Cys Ile Pro Gly Ala
              170                 175                 180

Gly Gly Gly Leu Gly His Leu Ala Val Gln Tyr Ala Lys Ala Met
              185                 190                 195

Ala Met Met Arg Val Val Ala Ile Asp Thr Gly Asp Asp Lys Ala
              200                 205                 210

Glu Lys Ser Phe Gly Ala Glu Val Phe Leu Asp Phe Lys Lys Glu
              215                 220                 225

Ala Asp Met Ile Glu Ala Val Lys Ala Cys Thr Asn Gly Gly Ala
              230                 235                 240

His Gly Thr Leu Val Leu Ser Thr Ser Pro Lys Ser Tyr Glu Gln
              245                 250                 255

Ala Ala Gly Phe Ala Arg Pro Gly Ser Thr Met Val Val Val Ser
              260                 265                 270

Met Pro Ala Gly Ala Lys Leu Gly Ala Asp Ile Phe Trp Leu Thr
              275                 280                 285

Val Lys Met Leu Lys Ile Cys Gly Ser His Val Gly Asn Arg Ile
              290                 295                 300

Asp Ser Ile Glu Ala Leu Glu Tyr Val Ser Arg Gly Leu Val Lys
              305                 310                 315

Pro Tyr Tyr Lys Val Gln Pro Phe Ser Thr Leu Pro Asp Val Tyr
              320                 325                 330

Arg Leu Met His Glu Asn Lys Ile Ala Gly Arg Ile Val Leu Asp
              335                 340                 345

Leu (2) INFORMATION FOR SEQ ID NO:97:

(i) SEQUENCE CHARACTERISTICS:
    (A) LENGTH: 135

(B) TYPE: amino acid (D) TOPOLOGY: linear (ii) MOLECULE TYPE:
     (A) DESCRIPTION: protein (vi) ORIGINAL SOURCE:
     (A) ORGANISM: tobacco (ix) FEATURE: Pathogenesis related protein, Table 16 Row 1

(x) PUBLICATION INFORMATION:
    (A) AUTHORS:

Cutt, J. R.
        Dixon, D. C.
        Carr, J. P.
        Klessig, D. F.
    (B) TITLE: Isolation and nucleotide sequence of cDNA clones
               for the pathogenesis related proteins of
               Nicotiniana tabacum induced by TMV infection.
    (C) JOURNAL: Nucleic Acids Research (D) VOLUME: 16

(F) PAGES: 9861-

(G) DATE: 1988

(xi) SEQUENCE DESCRIPTION: SEQ ID NO:97:

Gln Asn Ser Pro Gln Asp Tyr Leu Ala Val His Asn Asp Ala Arg
                005             010             015

Ala Gln Val Gly Val Gly Pro Met Ser Trp Asp Ala Asn Leu Ala
                020             025             030

Ser Arg Ala Gln Asn Tyr Ala Asn Ser Arg Ala Gly Asp Cys Asn
                035             040             045

Leu Ile His Ser Gly Ala Gly Glu Asn Leu Ala Lys Gly Gly Gly
                050             055             060

Asp Phe Thr Gly Arg Ala Ala Val Gln Leu Trp Val Ser Glu Arg
                065             070             075

Pro Ser Tyr Asn Tyr Ala Thr Asn Gln Cys Val Gly Gly Lys Lys
                080             085             090

Cys Arg His Tyr Thr Gln Val Val Trp Arg Asn Ser Val Arg Leu
                095             100             105

Gly Cys Gly Arg Ala Arg Cys Asn Asn Gly Trp Trp Phe Ile Ser
                110             115             120

Cys Asn Tyr Asp Pro Val Gly Asn Trp Leu Gly Gln Arg Pro Tyr
                125             130             135

(2) INFORMATION FOR SEQ ID NO:98:

(i) SEQUENCE CHARACTERISTICS:
        (A) LENGTH: 135

(B) TYPE: amino acid (D) TOPOLOGY: linear (ii) MOLECULE TYPE:
         (A) DESCRIPTION: protein (vi) ORIGINAL SOURCE:
    (A) ORGANISM: Lycopersicon esculentum (ix) FEATURE: Pathogenesis related protein, Table 16 Row 2

(x) PUBLICATION INFORMATION:
    (A) AUTHORS:

Cutt, J. R.
        Dixon, D. C.
        Carr, J. P.
        Klessig, D. F.
    (B) TITLE: Isolation and nucleotide sequence of cDNA clones
              for the pathogenesis related proteins of
              Nicotiniana tabacum induced by TMV infection.
    (C) JOURNAL: Nucleic Acids Research (D) VOLUME: 16

(F) PAGES: 9861

(G) DATE: 1988

(xi) SEQUENCE DESCRIPTION: SEQ ID NO:98:

Gln Asn Ser Pro Gln Asp Tyr Leu Ala Val His Asn Asp Ala Arg
                005             010             015

Ala Gln Val Gly Val Gly Pro Met Ser Trp Asp Ala Asn Leu Ala
                020             025             030

Ser Arg Ala Gln Asn Tyr Ala Asn Ser Arg Ala Gly Asp Cys Asn
                035             040             045

Leu Ile His Ser Gly Ala Gly Glu Asn Leu Ala Lys Gly Gly Gly
                050             055             060

Asp Phe Thr Gly Arg Ala Ala Val Gln Leu Trp Val Ser Glu Arg
                065             070             075

Pro Ser Tyr Asn Tyr Ala Thr Asn Gln Cys Val Gly Gly Lys Lys
                080             085             090

Cys Arg His Tyr Thr Gln Val Val Trp Arg Asn Ser Val Arg Leu
                095             100             105

Gly Cys Gly Arg Ala Arg Cys Asn Asn Gly Trp Trp Phe Ile Ser
                110             115             120

Cys Asn Tyr Asp Pro Val Gly Asn Trp Ile Gly Gln Arg Pro Tyr
                125             130             135

(2) INFORMATION FOR SEQ ID NO:99:

(i) SEQUENCE CHARACTERISTICS:
        (A) LENGTH: 135

(B) TYPE: amino acid (D) TOPOLOGY: linear (ii) MOLECULE TYPE:
        (A) DESCRIPTION: protein (vi) ORIGINAL SOURCE:
        (A) ORGANISM: Lycopersicon esculentum (ix) FEATURE: Pathogenesis related protein; Table 16 Row 3

(x) PUBLICATION INFORMATION:
        (A) AUTHORS:

Cutt, J. R.
Dixon, D. C.
Carr, J. P.
Klessig, D. F.
(B) TITLE: Isolation and nucleotide sequence of cDNA clones for the pathogenesis related proteins of Nicotiniana tabacum induced by TMV infection.
(C) JOURNAL: Nucleic Acids Research (D) VOLUME: 16

(F) PAGES: 9861

(G) DATE: 1988

(xi) SEQUENCE DESCRIPTION: SEQ ID NO:99:

```
Gln Asn Ser Pro Gln Asp Tyr Leu Ala Val His Asn Asp Ala Arg
            005             010              015

Ala Gln Val Gly Val Gly Pro Met Ser Trp Asp Ala Asn Leu Ala
            020             025              030

Ser Arg Ala Gln Asn Tyr Ala Asn Ser Arg Ala Gly Asp Cys Asn
            035             040              045

Leu Ile His Ser Gly Ala Gly Glu Asn Leu Ala Lys Gly Gly Gly
            050             055              060

Asp Phe Thr Gly Arg Ala Ala Val Gln Leu Trp Val Ser Glu Arg
            065             070              075

Pro Asp Tyr Asn Tyr Ala Thr Asn Gln Cys Val Gly Gly Lys Met
            080             085              090

Cys Gly His Tyr Thr Gln Val Val Trp Arg Asn Ser Val Arg Leu
            095             100              105

Gly Cys Gly Arg Ala Arg Cys Asn Asn Gly Trp Trp Phe Ile Ser
            110             115              120

Cys Asn Tyr Asp Pro Val Gly Asn Trp Val Gly Glu Arg Pro Tyr
            125             130              135
```

(2) INFORMATION FOR SEQ ID NO:100:

(i) SEQUENCE CHARACTERISTICS:
       (A) LENGTH: 138

(B) TYPE: amino acid (D) TOPOLOGY: linear (ii) MOLECULE TYPE:
       (A) DESCRIPTION: protein (vi) ORIGINAL SOURCE:
       (A) ORGANISM: tobacco (ix) FEATURE: Pathogenesis related protein; Table 16 Row 4

(x) PUBLICATION INFORMATION:
       (A) AUTHORS:

Cutt, J. R.
           Dixon, D. C.
           Carr, J. P.
           Klessig, D. F.
       (B) TITLE: Isolation and nucleotide sequence of cDNA clones for the pathogenesis related proteins of Nicotiniana tabacum induced by TMV infection.
       (C) JOURNAL: Nucleic Acids Research (D) VOLUME: 16

(F) PAGES: 9861

(G) DATE: 1988

(xi) SEQUENCE DESCRIPTION: SEQ ID NO:100:

Gln Asn Ser Gln Gln Asp Tyr Leu Asp Ala His Asn Thr Ala Arg
              005                 010                 015

Ala Asp Val Gly Val Glu Pro Leu Thr Trp Asp Gln Val Ala
              020                 025                 030

Ala Tyr Ala Gln Asn Tyr Ala Ser Gln Leu Ala Ala Asp Cys Asn
              035                 040                 045

Leu Val His Ser His Gly Gln Tyr Gly Glu Asn Leu Ala Trp Gly
              050                 055                 060

Ser Gly Asp Phe Leu Thr Ala Ala Lys Ala Val Glu Met Trp Val
              065                 070                 075

Asn Glu Lys Gln Tyr Tyr Ala His Asp Ser Asn Thr Cys Ala Gln
              080                 085                 090

Gly Gln Val Cys Gly His Tyr Thr Gln Val Val Trp Arg Asn Ser
              095                 100                 105

Val Arg Val Gly Cys Ala Arg Val Gln Cys Asn Asn Gly Gly Tyr
              110                 115                 120

Ile Val Ser Cys Asn Tyr Asp Pro Pro Gly Asn Val Ile Gly Lys
              125                 130                 135

Ser Pro Tyr
        140

(2) INFORMATION FOR SEQ ID NO:101:

(i) SEQUENCE CHARACTERISTICS:
       (A) LENGTH: 139

(B) TYPE: amino acid (D) TOPOLOGY: linear (ii) MOLECULE TYPE:
        (A) DESCRIPTION: protein (vi) ORIGINAL SOURCE:
        (A) ORGANISM: tobacco (ix) FEATURE: Pathogenesis related protein; Table 16 Row 5

(x) PUBLICATION INFORMATION:
       (A) AUTHORS:

Cutt, J. R.
           Dixon, D. C.
           Carr, J. P.
           Klessig, D. F.
       (B) TITLE: Isolation and nucleotide sequence of cDNA clones
                  for the pathogenesis related proteins of
                  Nicotiniana tabacum induced by TMV infection.
       (C) JOURNAL: Nucleic Acids Research (D) VOLUME: 16

(F) PAGES: 9861

(G) DATE: 1988

(xi) SEQUENCE DESCRIPTION: SEQ ID NO:101:

Ala Gln Asn Ser Gln Gln Asp Tyr Leu Asp Ala His Asn Thr Ala

```
                    005                 010                 015
Arg Ala Asp Val Gly Val Glu Pro Leu Thr Trp Asp Asp Gln Val
                    020                 025                 030
Ala Ala Tyr Ala Gln Asn Tyr Ala Ser Gln Leu Ala Ala Asp Cys
                    035                 040                 045
Asn Leu Val His Ser His Gly Gln Tyr Gly Glu Asn Leu Ala Glu
                    050                 055                 060
Gly Ser Gly Asp Phe Met Thr Ala Ala Lys Ala Val Glu Met Trp
                    065                 070                 075
Val Asp Glu Lys Gln Tyr Tyr Asp His Asp Ser Asn Thr Cys Ala
                    080                 085                 090
Gln Gly Gln Val Cys Gly His Tyr Thr Gln Val Val Trp Arg Asn
                    095                 100                 105
Ser Val Arg Val Gly Cys Ala Arg Val Gln Cys Asn Asn Gly Gly
                    110                 115                 120
Tyr Val Val Ser Cys Asn Tyr Asp Pro Pro Gly Asn Tyr Arg Gly
                    125                 130                 135
Glu Ser Pro Tyr
                    140                 145                 150
```

(2) INFORMATION FOR SEQ ID NO:102:

(i) SEQUENCE CHARACTERISTICS:
        (A) LENGTH: 139

(B) TYPE: amino acid (D) TOPOLOGY: linear (ii) MOLECULE TYPE:
       (A) DESCRIPTION: protein (vi) ORIGINAL SOURCE:
       (A) ORGANISM: tobacco (ix) FEATURE: Pathogenesis related protein; Table 16 Row 6

(x) PUBLICATION INFORMATION:
       (A) AUTHORS:

Cutt, J. R.
           Dixon, D. C.
           Carr, J. P.
           Klessig, D. F.
       (B) TITLE: Isolation and nucleotide sequence of cDNA clones
           for the pathogenesis related proteins of
           Nicotiniana tabacum induced by TMV infection.
       (C) JOURNAL: Nucleic Acids Research (D) VOLUME: 16

(F) PAGES: 9861

(G) DATE: 1988

(xi) SEQUENCE DESCRIPTION: SEQ ID NO:102:

```
Ala Gln Asn Ser Gln Gln Asp Tyr Leu Asp Ala His Asn Thr Ala
                    005                 010                 015
Arg Ala Asp Val Gly Val Glu Pro Leu Thr Trp Asp Asn Gly Val
                    020                 025                 030
Ala Ala Tyr Ala Gln Asn Tyr Val Ser Gln Leu Ala Ala Asp Cys
                    035                 040                 045
```

```
Asn Leu Val His Ser His Gly Gln Tyr Gly Glu Asn Leu Ala Gln
            050                 055                 060

Gly Ser Gly Asp Phe Met Thr Ala Ala Lys Ala Val Glu Met Trp
            065                 070                 075

Val Asp Glu Lys Gln Tyr Tyr Asp His Asp Ser Asn Thr Cys Ala
            080                 085                 090

Gln Gly Gln Val Cys Gly His Tyr Thr Gln Val Val Trp Arg Asn
            095                 100                 105

Ser Val Arg Val Gly Cys Ala Arg Val Lys Cys Asn Asn Gly Gly
            110                 115                 120

Tyr Val Val Ser Cys Asn Tyr Asp Pro Pro Gly Asn Val Ile Gly
            125                 130                 135

Gln Ser Pro Tyr
            140                 145                 150

(2) INFORMATION FOR SEQ ID NO:103:

(i) SEQUENCE CHARACTERISTICS:
        (A) LENGTH: 135

(B) TYPE: amino acid (D) TOPOLOGY: linear (ii) MOLECULE TYPE:
        (A) DESCRIPTION: protein (vi) ORIGINAL SOURCE:
        (A) ORGANISM: Arabidopsis thaliana (ix) FEATURE: Pathogenesis related protein; Table 16 Row 7

(x) PUBLICATION INFORMATION:
        (A) AUTHORS:

Cutt, J. R.
            Dixon, D. C.
            Carr, J. P.
            Klessig, D. F.
        (B) TITLE: Isolation and nucleotide sequence of cDNA clones
                for the pathogenesis related proteins of
                Nicotiniana tabacum induced by TMV infection.
        (C) JOURNAL: Nucleic Acids Research (D) VOLUME: 16

(F) PAGES: 9861

(G) DATE: 1988

(xi) SEQUENCE DESCRIPTION: SEQ ID NO:103:

Pro Gln Glu Thr Leu Val Val His Asn Lys Ala Arg Ala Met Val
            005                 010                 015

Gly Val Gly Pro Met Val Trp Asn Glu Thr Leu Ala Thr Tyr Ala
            020                 025                 030

Gln Ser Tyr Ala His Glu Arg Ala Arg Asp Cys Ala Met Lys His
            035                 040                 045

Ser Leu Gly Pro Phe Gly Glu Asn Leu Ala Ala Gly Trp Gly Thr
            050                 055                 060

Met Ser Gly Pro Val Ala Thr Glu Tyr Trp Met Thr Glu Lys Glu
            065                 070                 075

Asn Tyr Asp Tyr Asp Ser Asn Thr Cys Gly Gly Asp Gly Val Cys
            080                 085                 090
```

```
Gly His Tyr Thr Gln Ile Val Trp Arg Asp Ser Val Arg Leu Gly
                095                 100                 105

Cys Ala Ser Val Arg Cys Lys Asn Asp Glu Tyr Ile Trp Val Ile
                110                 115                 120

Cys Ser Tyr Asp Pro Pro Gly Asn Tyr Ile Gly Gln Arg Pro Tyr
                125                 130                 135
```

(2) INFORMATION FOR SEQ ID NO:104:

(i) SEQUENCE CHARACTERISTICS:
        (A) LENGTH: 141

(B) TYPE: amino acid (D) TOPOLOGY: linear (ii) MOLECULE TYPE:
        (A) DESCRIPTION: protein (vi) ORIGINAL SOURCE:
        (A) ORGANISM: maize (ix) FEATURE: Pathogenesis related protein; Table 16 Row 8

(x) PUBLICATION INFORMATION:
        (A) AUTHORS:

Cutt, J. R.
            Dixon, D. C.
            Carr, J. P.
            Klessig, D. F.
        (B) TITLE: Isolation and nucleotide sequence of cDNA clones
            for the pathogenesis related proteins of
            Nicotiniana tabacum induced by TMV infection.
        (C) JOURNAL: Nucleic Acids Research (D) VOLUME: 16

(F) PAGES: 9861

(G) DATE: 1988

(xi) SEQUENCE DESCRIPTION: SEQ ID NO:104:

```
Ser Glu Asn Ser Pro Gln Asp Tyr Leu Thr Pro Gln Asn Ser Ala
                005                 010                 015

Arg Ala Ala Val Gly Val Gly Pro Val Thr Trp Ser Thr Lys Leu
                020                 025                 030

Gln Gln Phe Ala Glu Lys Tyr Ala Ala Gln Arg Ala Gly Asp Cys
                035                 040                 045

Arg Leu Gln His Ser Gly Gly Pro Tyr Gly Glu Asn Ile Phe Trp
                050                 055                 060

Gly Ser Ala Gly Phe Asp Trp Lys Ala Val Asp Ala Val Arg Ser
                065                 070                 075

Trp Val Asp Glu Lys Gln Trp Tyr Asn Tyr Ala Thr Asn Ser Cys
                080                 085                 090

Ala Ala Gly Lys Val Cys Gly His Tyr Thr Gln Val Val Trp Arg
                095                 100                 105

Ala Thr Thr Ser Ile Gly Cys Ala Arg Val Val Cys Arg Asp Asn
                110                 115                 120

Arg Gly Val Phe Ile Ile Cys Asn Tyr Glu Pro Arg Gly Asn Ile
                125                 130                 135

Ala Gly Met Lys Pro Tyr
```

140                 145                 150

(2) INFORMATION FOR SEQ ID NO:105:

(i) SEQUENCE CHARACTERISTICS:
        (A) LENGTH: 111

(B) TYPE: amino acid (D) TOPOLOGY: linear (ii) MOLECULE TYPE:
        (A) DESCRIPTION: protein (vi) ORIGINAL SOURCE:
        (A) ORGANISM: tobacco (ix) FEATURE: Pathogenesis related protein; Table 17 Row 1

(x) PUBLICATION INFORMATION:
        (A) AUTHORS:

Cutt, J. R.
            Dixon, D. C.
            Carr, J. P.
            Klessig, D. F.
        (B) TITLE: Isolation and nucleotide sequence of cDNA clones
                for the pathogenesis related proteins of
                Nicotiniana tabacum induced by TMV infection.
        (C) JOURNAL: Nucleic Acids Research (D) VOLUME: 16

(F) PAGES: 9861

(G) DATE: 1988

(xi) SEQUENCE DESCRIPTION: SEQ ID NO:105:

Met Ser Trp Asp Ala Asn Leu Ala Ser Arg Ala Gln Asn Tyr Ala
            005                 010                 015

Asn Ser Arg Ala Gly Asp Cys Asn Leu Ile His Ser Gly Ala Gly
            020                 025                 030

Glu Asn Leu Ala Lys Gly Gly Gly Asp Phe Thr Gly Arg Ala Ala
            035                 040                 045

Val Gln Leu Trp Val Ser Glu Arg Pro Ser Tyr Asn Tyr Ala Thr
            050                 055                 060

Asn Gln Cys Val Gly Gly Lys Lys Cys Arg His Tyr Thr Gln Val
            065                 070                 075

Val Trp Arg Asn Ser Val Arg Leu Gly Cys Gly Arg Ala Arg Cys
            080                 085                 090

Asn Asn Gly Trp Trp Phe Ile Ser Cys Asn Tyr Asp Pro Val Gly
            095                 100                 105

Asn Trp Ile Gly Gln Arg
            110                 115                 120

(2) INFORMATION FOR SEQ ID NO:106:

(i) SEQUENCE CHARACTERISTICS:
        (A) LENGTH: 114

(B) TYPE: amino acid (D) TOPOLOGY: linear (ii) MOLECULE TYPE:

(A) DESCRIPTION: protein (vi) ORIGINAL SOURCE:
            (A) ORGANISM: tobacco (ix) FEATURE: Pathogenesis related protein 1a; Table 17 Row 2

(x) PUBLICATION INFORMATION:
            (A) AUTHORS:

Cutt, J. R.
                 Dixon, D. C.
                 Carr, J. P.
                 Klessig, D. F.
            (B) TITLE: Isolation and nucleotide sequence of cDNA clones
                    for the pathogenesis related proteins of
                    Nicotiniana tabacum induced by TMV infection.
            (C) JOURNAL: Nucleic Acids Research (D) VOLUME: 16

(F) PAGES: 9861

(G) DATE: 1988

(xi) SEQUENCE DESCRIPTION: SEQ ID NO:106:

Leu Thr Trp Asp Asp Gln Val Ala Ala Tyr Ala Gln Asn Tyr Ala
                005                 010                 015

Ser Gln Leu Ala Ala Asp Cys Asn Leu Val His Ser His Gly Gln
                020                 025                 030

Tyr Gly Glu Asn Leu Ala Glu Gly Ser Gly Asp Phe Met Thr Ala
                035                 040                 045

Ala Lys Ala Val Glu Met Trp Val Asp Glu Lys Gln Tyr Tyr Asp
                050                 055                 060

His Asp Ser Asn Thr Cys Ala Gln Gly Gln Val Cys Gly His Tyr
                065                 070                 075

Thr Gln Val Val Trp Arg Asn Ser Val Arg Val Gly Cys Ala Arg
                080                 085                 090

Val Gln Cys Asn Asn Gly Gly Tyr Val Val Ser Cys Asn Tyr Asp
                095                 100                 105

Pro Pro Gly Asn Tyr Arg Gly Glu Ser
                110

(2) INFORMATION FOR SEQ ID NO:107:

(i) SEQUENCE CHARACTERISTICS:
            (A) LENGTH: 114

(B) TYPE: amino acid (D) TOPOLOGY: linear (ii) MOLECULE TYPE:
            (A) DESCRIPTION: protein (vi) ORIGINAL SOURCE:
            (A) ORGANISM: tobacco (ix) FEATURE: Pathogenesis related protein 1b; Table 17 Row 3

(x) PUBLICATION INFORMATION:
            (A) AUTHORS:

Cutt, J. R.
                 Dixon, D. C.

```
                    Carr, J. P.
                    Klessig, D. F.
          (B) TITLE: Isolation and nucleotide sequence of cDNA clones
                    for the pathogenesis related proteins of
                    Nicotiniana tabacum induced by TMV infection.
          (C) JOURNAL: Nucleic Acids Research (D) VOLUME: 16

(F) PAGES: 9861

(G) DATE: 1988

(xi) SEQUENCE DESCRIPTION: SEQ ID NO:107:

Leu Thr Trp Asp Asn Gly Val Ala Ala Tyr Ala Gln Asn Tyr Val
            005                 010                 015

Ser Gln Leu Ala Ala Asp Cys Asn Leu Val His Ser His Gly Gln
            020                 025                 030

Tyr Gly Glu Asn Leu Ala Gln Gly Ser Gly Asp Phe Met Thr Ala
            035                 040                 045

Ala Lys Ala Val Glu Met Trp Val Asp Glu Lys Gln Tyr Tyr Asp
            050                 055                 060

His Asp Ser Asn Thr Cys Ala Gln Gly Gln Val Cys Gly His Tyr
            065                 070                 075

Thr Gln Val Val Trp Arg Asn Ser Val Arg Val Gly Cys Ala Arg
            080                 085                 090

Val Lys Cys Asn Asn Gly Gly Tyr Val Val Ser Cys Asn Tyr Asp
            095                 100                 105

Pro Pro Gly Asn Val Ile Gly Gln Ser
            110

(2) INFORMATION FOR SEQ ID NO:108:

(i) SEQUENCE CHARACTERISTICS:
         (A) LENGTH: 114

(B) TYPE: amino acid (D) TOPOLOGY: linear (ii) MOLECULE TYPE:
         (A) DESCRIPTION: protein (vi) ORIGINAL SOURCE:
         (A) ORGANISM: tobacco (ix) FEATURE: Pathogenesis related protein 1c; Table 17 Row 4

(x) PUBLICATION INFORMATION:
         (A) AUTHORS:

Cutt, J. R.
                    Dixon, D. C.
                    Carr, J. P.
                    Klessig, D. F.
         (B) TITLE: Isolation and nucleotide sequence of cDNA clones
                    for the pathogenesis related proteins of
                    Nicotiniana tabacum induced by TMV infection.
         (C) JOURNAL: Nucleic Acids Research (D) VOLUME: 16

(F) PAGES: 9861

(G) DATE: 1988
```

(xi) SEQUENCE DESCRIPTION: SEQ ID NO:108:

Leu Thr Trp Asp Asp Gln Val Ala Ala Tyr Ala Gln Asn T

Asn Ser Asn Ser Cys Val Gly Gly Val Cys Gly His Tyr Thr Gln
            065                 070                 075

Val Val Trp Arg Asn Ser Val Arg Leu Gly Cys Ala Arg Val Arg
            080                 085                 090

Ser Asn Asn Gly Trp Phe Phe Ile Thr Cys Asn Tyr Asp Pro Pro
            095                 100                 105

Gly Asn Phe Ile Gly Gln Arg
            110                 115                 120

(2) INFORMATION FOR SEQ ID NO:110:

(i) SEQUENCE CHARACTERISTICS:
        (A) LENGTH: 137

(B) TYPE: amino acid (D) TOPOLOGY: linear (ii) MOLECULE TYPE:
        (A) DESCRIPTION: protein (vi) ORIGINAL SOURCE:
        (A) ORGANISM: rat (ix) FEATURE: sperm coating glycoprotein; Table 17 Row 6

(x) PUBLICATION INFORMATION:
        (A) AUTHORS:

Brooks, D. E.
            Means, A. R.
            Wright, E. J.
            Singh, S. P.
            Tiver, K. K.
        (B) TITLE: Molecular cloning of the cDNA for androgen-
            dependent sperm coating glycoprotein secreted by
            the rat epidemis.
        (C) JOURNAL: European Journal of Biochemistry (D) VOLUME: 161

(F) PAGES: 13-18

(G) DATE: 1986

(xi) SEQUENCE DESCRIPTION: SEQ ID NO:110:

Leu Arg Val Glu Trp Asp His Asp Ala Tyr Val Asn Ala Gln Lys
            005                 010                 015

Trp Ala Asn Arg Cys Ile Tyr Asn His Ser Pro Leu Gln His Arg
            020                 025                 030

Thr Thr Thr Leu Lys Cys Gly Glu Asn Leu Phe Met Ala Asn Tyr
            035                 040                 045

Pro Ala Ser Trp Ser Ser Val Ile Gln Asp Trp Tyr Asp Glu Ser
            050                 055                 060

Leu Asp Phe Val Phe Gly Phe Gly Pro Lys Lys Val Gly Val Lys
            065                 070                 075

Val Gly His Tyr Thr Gln Val Val Trp Asn Ser Thr Phe Leu Val
            080                 085                 090

Ala Cys Gly Val Ala Glu Cys Pro Asp Gln Pro Leu Lys Tyr Phe
            095                 100                 105

Tyr Val Cys His Tyr Cys Pro Gly Gly Asn Tyr Val Gly Arg Leu
            110                 115                 120

Tyr Ser Pro Tyr Thr Glu Gly Glu Pro Cys Asp Ser Cys Pro Gly
            125                 130                 135

Asn Cys (2) INFORMATION FOR SEQ ID NO:111:

(i) SEQUENCE CHARACTERISTICS:
        (A) LENGTH: 137

(B) TYPE: amino acid (D) TOPOLOGY: linear (ii) MOLECULE TYPE:
        (A) DESCRIPTION: protein (vi) ORIGINAL SOURCE:
        (A) ORGANISM: human (ix) FEATURE: testis specific protein; Table 17 Row 7

(x) PUBLICATION INFORMATION:
        (A) AUTHORS:

Kasahara, M.
            Gutknecht, J.
            Brew, K.
            Spurr, N.
            Goodfellow, P. N.
        (B) TITLE: Cloning and mapping of a testis-specific gene with
                sequence similarity to a sperm coating glycoprotein
                gene
        (C) JOURNAL: Genomics (D) VOLUME: 5

(F) PAGES: 527-534

(G) DATE: 1989

(xi) SEQUENCE DESCRIPTION: SEQ ID NO:111:

Leu Lys Met Glu Trp Ser Ile Gln Ala Thr Thr Asn Ala Gln Lys
            005                 010                 015

Trp Ala Asn Lys Cys Ile Leu Glu His Ser Ser Lys Asp Asp Arg
            020                 025                 030

Lys Ile Asn Ile Arg Cys Gly Glu Asn Leu Tyr Met Ser Thr Asp
            035                 040                 045

Pro Thr Leu Trp Ser Thr Val Ile Gln Ser Trp Tyr Asn Glu Asn
            050                 055                 060

Glu Asp Phe Val Tyr Gly Val Gly Ala Lys Pro Asn Ser Ala Val
            065                 070                 075

Gly His Tyr Thr Gln Leu Val Trp Tyr Ser Ser Phe Lys Ile Gly
            080                 085                 090

Cys Gly Ile Ala Tyr Cys Pro Asn Gln Asp Asn Leu Lys Tyr Phe
            095                 100                 105

Tyr Val Cys His Tyr Cys Pro Met Gly Asn Asn Val Met Lys Lys
            110                 115                 120

Ser Thr Pro Tyr Gln Gln Gly Thr Pro Cys Ala Ser Cys Pro Asn
            125                 130                 135

Asn Cys (2) INFORMATION FOR SEQ ID NO:112:

```
      (i) SEQUENCE CHARACTERISTICS:
          (A) LENGTH: 138

(B) TYPE: amino acid (D) TOPOLOGY: linear (ii) MOLECULE TYPE:
          (A) DESCRIPTION: protein (vi) ORIGINAL SOURCE:
          (A) ORGANISM: human (ix) FEATURE: Testis specific protein; Table 17 Row 8

(x) PUBLICATION INFORMATION:
          (A) AUTHORS:

Kasahara, M.
              Gutknecht, J.
              Brew, K.
              Spurr, N.
              Goodfellow, P. N.
          (B) TITLE: Cloning and mapping of a testis-specific gene with
                  sequence similarity to a sperm coating glycoprotein
                  gene
          (C) JOURNAL: Genomics (D) VOLUME: 5

(F) PAGES: 527-534

(G) DATE: 1989

(xi) SEQUENCE DESCRIPTION: SEQ ID NO:112:

Leu Lys Met Glu Trp Ser Arg Glu Val Thr Thr Asn Ala Gln Arg
                005                 010                 015

Trp Ala Asn Lys Cys Thr Leu Gln His Ser Asp Pro Glu Asp Arg
                020                 025                 030

Lys Thr Ser Thr Arg Cys Gly Glu Asn Leu Tyr Met Ser Ser Asp
                035                 040                 045

Pro Thr Ser Trp Ser Ser Ala Ile Gln Ser Trp Tyr Asp Glu Ile
                050                 055                 060

Leu Asp Phe Val Tyr Gly Val Gly Pro Lys Ser Pro Asn Ala Val
                065                 070                 075

Val Gly His Tyr Thr Gln Leu Val Trp Tyr Ser Thr Tyr Gln Val
                080                 085                 090

Gly Cys Gly Ile Ala Tyr Cys Pro Asn Gln Asp Ser Leu Lys Tyr
                095                 100                 105

Tyr Tyr Val Cys Gln Tyr Cys Pro Ala Gly Asn Asn Met Asn Arg
                110                 115                 120

Lys Asn Thr Pro Tyr Gln Gln Gly Thr Pro Cys Ala Gly Cys Pro
                125                 130                 135

Asp Asp Cys (2) INFORMATION FOR SEQ ID NO:113:

(i) SEQUENCE CHARACTERISTICS:
          (A) LENGTH: 124

(B) TYPE: amino acid (D) TOPOLOGY: linear
```

(ii) MOLECULE TYPE:
            (A) DESCRIPTION: protein (vi) ORIGINAL SOURCE:
            (A) ORGANISM: Dolichovespula maculata (white face hornet)

(ix) FEATURE: venom allergen; Table 17 Row 9

(x) PUBLICATION INFORMATION:
            (A) AUTHORS:

Fang, K. S. Y.
                 Vitale, M.
                 Fehlner, P.
                 King, T. P.
            (B) TITLE: cDNA cloning and primary structure of a white-face
                hornet venom allergen, antigen 5.
            (C) JOURNAL: Proceedings of the National Academy of Sciences,
                U.S.A.
            (D) VOLUME: 85

(F) PAGES: 895-899

(G) DATE: 1988

(xi) SEQUENCE DESCRIPTION: SEQ ID NO:113:

Asn Val Leu Val Trp Asn Asp Glu Leu Ala Lys Ile Ala Gln Thr
                005                 010                 015

Trp Ala Asn Gln Cys Asp Phe Asn His Asp Asp Cys Arg Asn Thr
                020                 025                 030

Ala Lys Tyr Gln Val Gly Gln Asn Ile Ala Ile Ser Ser Thr Thr
                035                 040                 045

Ala Thr Gln Phe Asp Arg Pro Ser Lys Leu Ile Lys Gln Trp Glu
                050                 055                 060

Asp Glu Val Thr Glu Phe Asn Tyr Lys Val Gly Leu Gln Asn Ser
                065                 070                 075

Asn Phe Arg Lys Val Gly His Tyr Thr Gln Met Val Trp Gly Lys
                080                 085                 090

Thr Lys Glu Ile Gly Cys Gly Ser Ile Lys Tyr Ile Glu Asp Asn
                095                 100                 105

Trp Tyr Thr His Tyr Leu Val Cys Asn Tyr Gly Pro Gly Gly Asn
                110                 115                 120

Asp Phe Asn Gln (2) INFORMATION FOR SEQ ID NO:114:

(i) SEQUENCE CHARACTERISTICS:
           (A) LENGTH: 125

(B) TYPE: amino acid (D) TOPOLOGY: linear (ii) MOLECULE TYPE:
            (A) DESCRIPTION: protein (vi) ORIGINAL SOURCE:
            (A) ORGANISM: Dolichovespula maculata (white face hornet)

(ix) FEATURE: Venom allergen; Table 17 Row 10

(x) PUBLICATION INFORMATION:
            (A) AUTHORS:

```
              Fang, K. S. Y.
              Vitale, M.
              Fehlner, P.
              King, T. P.
     (B) TITLE: cDNA cloning and primary structure of a white-face
             hornet venom allergen, antigen 5.
     (C) JOURNAL: Proceedings of the National Academy of Sciences,
                  U.S.A.
     (D) VOLUME: 85

(F) PAGES: 895-899

(G) DATE: 1988

(xi) SEQUENCE DESCRIPTION: SEQ ID NO:114:

Asn Val Leu Val Trp Asn Asp Glu Leu Ala Lys Ile Ala Gln Thr
              005                 010                 015

Trp Ala Asn Gln Cys Ser Phe Gly His Asp Gln Cys Arg Asn Thr
              020                 025                 030

Glu Lys Tyr Gln Val Gly Gln Asn Val Ala Ile Ala Ser Thr Thr
              035                 040                 045

Gly Asn Ser Tyr Ala Thr Met Ser Lys Leu Ile Glu Met Trp Glu
              050                 055                 060

Asn Glu Val Lys Asp Phe Asn Pro Lys Lys Gly Thr Met Gly Asp
              065                 070                 075

Asn Asn Phe Ser Lys Val Gly His Tyr Thr Gln Met Val Trp Gly
              080                 085                 090

Lys Thr Lys Glu Ile Gly Cys Gly Ser Val Lys Tyr Ile Glu Asn
              095                 100                 105

Asn Trp His Thr His Tyr Leu Val Cys Asn Tyr Gly Pro Ala Gly
              110                 115                 120

Asn Tyr Met Asp Gln
              125
```

What is claimed is:

1. A method for predicting the folded structure of proteins that comprises obtaining an alignment of the sequences of a set of homologous proteins, using patterns of conservation and variation of the sequence between proteins with clearly defined evolutionary relationships to assign positions in the alignment to the surface of the folded structure, the inside of the folded structure, active site, or parsing segments, assigning secondary structural units by identifying periodicity in said assignments, and assembling said secondary structural units into a globular form using distance constraints imposed by disulfide bridges, active site assignments, and covariation analysis.

2. A method for predicting the secondary structure of proteins that comprises obtaining an alignment of the sequences of a set of homologous proteins, using patterns of conservation and variation of the sequence between proteins with clearly defined evolutionary relationships to assign positions in the alignment to the surface of the folded structure, the inside of the folded structure, active site, or parsing segments, and assigning secondary structural units by identifying periodicity in said assignments.

* * * * *